(12) United States Patent
Markwalder et al.

(10) Patent No.: US 9,765,018 B2
(45) Date of Patent: Sep. 19, 2017

(54) IDO INHIBITORS

(71) Applicant: BRISTOL-MYERS SQUIBB COMPANY, Princeton, NJ (US)

(72) Inventors: Jay A. Markwalder, Lahaska, PA (US); Steven P. Seitz, Swarthmore, PA (US); James Aaron Balog, Lambertville, NJ (US); Audris Huang, New Hope, PA (US); Sunil Kumar Mandal, Bangalore (IN); David K. Williams, Delran, NJ (US); Amy C. Hart, Ewing, NJ (US); Jennifer Inghrim, Plainsboro, NJ (US)

(73) Assignees: Bristol-Myers Squibb Company, Princeton, NJ (US); Syngene International Limited, Bangalore, Karnataka (IN); Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/897,668

(22) PCT Filed: Jul. 1, 2014

(86) PCT No.: PCT/US2014/044992
§ 371 (c)(1),
(2) Date: Dec. 11, 2015

(87) PCT Pub. No.: WO2015/002918
PCT Pub. Date: Jan. 8, 2015

(65) Prior Publication Data
US 2016/0137595 A1    May 19, 2016

Related U.S. Application Data

(60) Provisional application No. 61/841,448, filed on Jul. 1, 2013.

(51) Int. Cl.
| | | |
|---|---|---|
| C07C 275/42 | (2006.01) |
| C07C 311/51 | (2006.01) |
| C07D 213/75 | (2006.01) |
| C07D 257/04 | (2006.01) |
| C07D 401/04 | (2006.01) |
| A61K 31/18 | (2006.01) |
| A61K 31/41 | (2006.01) |
| A61K 31/44 | (2006.01) |
| C07D 213/79 | (2006.01) |
| C07D 307/86 | (2006.01) |
| A61K 31/196 | (2006.01) |
| A61K 31/277 | (2006.01) |
| A61K 31/343 | (2006.01) |
| A61K 31/4418 | (2006.01) |
| A61K 31/444 | (2006.01) |
| A61K 45/06 | (2006.01) |

(Continued)

(52) U.S. Cl.
CPC ............ *C07C 275/42* (2013.01); *A61K 31/18* (2013.01); *A61K 31/196* (2013.01); *A61K 31/277* (2013.01); *A61K 31/343* (2013.01); *A61K 31/41* (2013.01); *A61K 31/444* (2013.01); *A61K 31/4418* (2013.01); *A61K 45/06* (2013.01); *C07C 311/09* (2013.01); *C07C 311/51* (2013.01); *C07D 213/75* (2013.01); *C07D 213/79* (2013.01); *C07D 257/04* (2013.01); *C07D 307/79* (2013.01); *C07D 307/86* (2013.01); *C07D 401/04* (2013.01); *C07C 2101/02* (2013.01); *C07C 2101/14* (2013.01); *C07C 2102/08* (2013.01); *C07C 2102/10* (2013.01)

(58) Field of Classification Search
None
See application file for complete search history.

(56) References Cited

U.S. PATENT DOCUMENTS

| | | |
|---|---|---|
| 2007/0259910 A1 | 11/2007 | Halley et al. |
| 2016/0060237 A1 | 3/2016 | Balog et al. |
| 2016/0137595 A1 | 5/2016 | Markwalder et al. |

FOREIGN PATENT DOCUMENTS

| | | |
|---|---|---|
| WO | WO 01/98268 A2 * | 12/2001 |
| WO | WO2008/058178 A1 | 5/2008 |

(Continued)

OTHER PUBLICATIONS

Allen, L.V. Jr. et al., *Remington: The Science and Practice of Pharmacy* (2 Volumes) 22,d Edition (2012) Pharmaceutical Press.
(Continued)

*Primary Examiner* — Zinna Northington Davis
(74) *Attorney, Agent, or Firm* — Serena Farquharson-Torres; Elliott Korsen

(57) ABSTRACT

There are disclosed compounds of formula (I) that modulate or inhibit the enzymatic activity of indoleamine 2,3-dioxygenase (IDO), pharmaceutical compositions containing said compounds and methods of treating proliferative disorders, such as cancer, viral infections and/or inflammatory disorders utilizing the compounds of the invention.

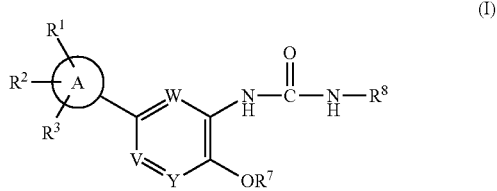

11 Claims, No Drawings

(51) Int. Cl.
C07C 311/09 (2006.01)
C07D 307/79 (2006.01)

(56) References Cited

FOREIGN PATENT DOCUMENTS

| WO | WO2014/150646 A1 | 9/2014 |
|----|------------------|--------|
| WO | WO2015/002918 A1 | 1/2015 |
| WO | WO2015/069310 A1 | 5/2015 |

OTHER PUBLICATIONS

Buchwald, Stephen et al., "Me$_3$(OMe)tBuXPhos: A Surrogate Ligand for Me$_4$tBuXPhos in Palladium-Catalyzed C—N and C—O Bond-Forming Reactions", The Journal of Organic Chemistry, vol. 77, pp. 2543-2547 (2012).
Bundgaard, Hans et al., "Glycolamide Esters as Biolabile Prodrugs of Carboxylic Acid Agents: Synthesis, Stability, Bioconversion, and Physicochemical Properties", Journal of Pharmaceutical Sciences, vol. 77(4), p. 285 (1988).
Bundgaard, Hans, Editor, Design of Prodrugs, Elsevier (1985).
Bundgaard, Hans, "Means to Enhance Penetration, Prodrugs as a means to improve the delivery of peptide drugs", Advanced Drug Delivery Reviews, vol. 8, pp. 1-38 (1992).
Bundgaard, Hans, Editor, Chapter 5, "Design and Application of Prodrugs", *A Textbook of Drug Design and Development*, pp. 113-119 (1991).
Dolusic, E. et al., Indoleamine 2,3-dioxygenase inhibitors: a patent review (2008-2012), Expert Opinion on Therapeutic Patents, vol. 23(10), pp. 1367-1381 (2013).
Goldstein, N. et al., "Biological Efficacy of a Chimeric Antibody to the Epidermal Growth Factor Receptor in a Human Tumor Xenograft Model", Clinical Cancer Research, vol. 1, pp. 1311-1318 (1995).
Greene, T.W. et al., *Protective Groups in Organic Synthesis*, Third Edition, Wiley—Interscience, NY (1999).
Gross, E., *The Peptides: Analysis, Synthesis, Biology*, vol. 3, Academic Press, NY (1981).
Heck, R.F. et al., "Organophosphinepalladium Complexes as Catalysts for Vinylic Hydrogen Substitution Reactions", J. Am. Chem. Soc., vol. 96(4), pp. 1133-1136 (1974).
House, H.O., Modern Synthetic Reactions, Second Edition, W.A. Benjamin Inc., Menlo Park CA, (1972).
Kakeya, N. et al., "Studies on Prodrugs of Cephalosporins. I. Synthesis and Biological Properties of Glycyloxbenzoyloxymethyl and Glycylaminobenzoyloxymethyl Esters of 7β-[2-(2-Aminothiazol-4-yl)-(Z)-2-methoxyiminoacetamido]-3-methyl-3-cephem-4-carboxylic Acid", Chem. Phar. Bull., vol. 32(2), pp. 692-698 (1984).
King, F. D., ed., *Medicinal Chemistry: Principles and Practice*, The Royal Society of Chemistry, Cambridge, UK 2$^{nd}$ Edition, (2006).
Kinzel, Tom et al., "A New Palladium Precatalyst Allows for the Fast Suzuki-Miyaura Coupling Reactions of Unstable Polyfluorophenyl and 2-Heteroaryl Boronic Acids", J. American Chemistry Society, vol. 132, pp. 14073-14075 (2010).
Kohl, Nancy E. et al., "Inhibition of farnesyltransferase induces regression of mammary and salivary carcinomas in ras transgenic mice", Nature Medicine, vol. 1(8), pp. 792-797 (1995).
Kotha, S. et al., "Recent applications of the Suzuki-Miyaura cross-coupling reaction in organic synthesis", Tetrahedron, vol. 58, pp. 9633-9695 (2002).
Lancellotti, S. et al., "Biochemical Properties of Indoleamine 2,3-dioxygenase: From Structure to Optimized Design of Inhibitors", Current Medicinal Chemistry, vol. 18, pp. 2205-2214 (2011).
Mitchell, Terence N., "Palladium-Catalysed Reactions of Organotin Compounds", Synthesis, pp. 803-815 (1992).
Negishi, E. et al., "Palladium-Catalyzed Alkenylation by the Nehishi Coupling", Aldrichimica Acta, vol. 38(3), pp. 71-78 (2005).
Rautio, J. (Editor). *Prodrugs and Targeted Delivery (Methods and Principles in Medicinal Chemistry)*, vol. 47, Wiley—VCH, (2011).
Sausville, Edward A., "Cyclin-Dependent Kinase Modulators Studied at the NCI: Pre-Clinical and Clinical Studies", Current Med. Chemistry-Anti-Cancer Agents, vol. 3, pp. 47-56 (2003).
Scheller, B. et al., "Paclitaxel Balloon Coating, a Novel Method for Prevention and Therapy of Restenosis", Circulation, vol. 110, pp. 810-814 (2004).
Sekulić, A. et al., "A Direct Linkage between the Phosphoinositide 3-Kinase-AKT Signaling Pathway and the Mammalian Target of Rapamycin in Mitogen-stimulated and Transformed Cells", Cancer Research, vol. 60, pp. 3504-3513 (2000).
Smith, M.B. et al., *"March's Advanced Organic Chemistry Reactions, Mechanisms, and Structure"*, Fifth Edition, Wiley-Interscience, NY (2001).
Sonogashira, K. et al., "A Convenient Synthesis of Acetylenes: Catalytic Substitutions of Acetylenic Hydrogen with Bromoalkenes, Iodoarenes, and Bromopyridines", Tetrahedron Letters, vol. 50, pp. 4467-4470 (1975).
Still, W. Clark et al., "Rapid Chromatographic Technique for Preparative Separations with Moderate Resolution", J. Org. Chem. vol. 43(14), pp. 2923-2925 (1978).
Swamy, K.C. Kumara, et al., "Mitsunobu and Related Reactions: Advances and Applications", Chem. Rev., vol. 109, pp. 2551-2651 (2009).
Testa, B. et al., *Hydrolysis in Drug and Prodrug Metabolism, Chemistry, Biochemistry and Enzymology*, VCHA and Wiley—VCH, Zurich, Switzerland (2003).
Vlahos, C. et al., "A Specific Inhibitor of Phosphatidylinositol 3-Kinase, 2-(4-Morpholinyl)-8-phenyl-4H-1-benzopyran-4-one (LY294002)", The J. of Biological Chemistry, vol. 269(7), pp. 5241-5248 (1994).
Wermuth, C.G. (Editor), *The Practice Medicinal Chemistry*, 3$^{rd}$ Edition, Academic Press, San Diego, CA (2008).
Widder, K. et al., Editor, *"Methods in Enzymology"*, vol. 112, pp. 309-396, Academic Press, (1985).
Wuts, P.G.M. and Greene, T. W. *Protecting Groups in Organic Synthesis*, 4$^{th}$ Edition, Wiley (2007).
Jackson, Alan E. et al., "Rapid, Selective Removal of Benzyloxycarbonyl Groups from Peptides by Catalytic Transfer Hydrogenation", Synthesis, Issue 10, pp. 685-687, (Oct. 1976).

* cited by examiner

IDO INHIBITORS

CROSS-REFERENCE TO RELATED APPLICATIONS

This application claims the benefit of U.S. Provisional Application No. 61/841,448, filed Jul. 1, 2013, the disclosure of which is incorporated herein by reference in its entirety.

FIELD OF THE INVENTION

The invention relates generally to compounds that modulate or inhibit the enzymatic activity of indoleamine 2,3-dioxygenase (IDO), pharmaceutical compositions containing said compounds and methods of treating proliferative disorders, such as cancer, viral infections and/or autoimmune diseases utilizing the compounds of the invention.

BACKGROUND OF THE INVENTION

Tryptophan is an amino acid which is essential for cell proliferation and survival. It is required for the biosynthesis of the neurotransmitter serotonin, the synthesis of the cofactor nicotinamide adenine dinucleotide (NAD), and is an important component in the immune system response ("immune escape") to tumors. Depletion of levels of tryptophan is associated with adverse effects on the proliferation and function of lymphocytes and diminished immune system response.

The enzyme indoleamine-2,3-deoxygenase (IDO) is overexpressed in many human tumors. IDO catalyzes the initial, rate-limiting step in the conversion of tryptophan to N-formylkynurenime. Moreover, IDO has been implicated in neurologic and psychiatric disorders including mood disorders as well as other chronic diseases characterized by IDO activation and tryptophan degradation such as viral infections, for example, AIDS, Alzheimer's disease, cancers including T-cell leukemia and colon cancer, autoimmune diseases, diseases of the eye such as cataracts, bacterial infections such as Lyme disease, and streptococcal infections.

Accordingly, an agent which is safe and effective in inhibiting the function of IDO would be an important addition for the treatment of patients with diseases or conditions affected by the activity of the enzyme.

SUMMARY OF THE INVENTION

The present invention provides compounds and/or pharmaceutically acceptable salts thereof, stereoisomers thereof or tautomers thereof, methods of modulating or inhibiting the enzymatic activity of IDO, and methods for treating various medical conditions using said compounds.

The present invention also provides processes and intermediates for making the compounds of the present invention and/or pharmaceutically acceptable salts thereof or stereoisomers thereof or tautomers thereof.

The present invention also provides pharmaceutical compositions comprising a pharmaceutically acceptable carrier and one or more of the compounds of the present invention and/or pharmaceutically acceptable salts thereof or stereoisomers thereof or tautomers thereof.

The compounds of the invention and/or pharmaceutically acceptable salts thereof or stereoisomers thereof or tautomers thereof may be used in the treatment and/or prophylaxis of multiple diseases or disorders associated with enzymatic activity of IDO inhibition, such as cancer, viral infections, autoimmune diseases, and other maladies.

The compounds of the invention and/or pharmaceutically acceptable salts thereof or stereoisomers thereof or tautomers thereof may be used in therapy.

The compounds of the invention and/or pharmaceutically acceptable salts thereof or stereoisomers thereof or tautomers thereof may be used for the manufacture of a medicament for the treatment and/or prophylaxis of multiple diseases or disorders associated with enzymatic activity of IDO.

The compounds of the invention and/or pharmaceutically acceptable salts thereof or stereoisomers thereof or tautomers thereof can be used alone, in combination with other compounds of the present invention and/or pharmaceutically acceptable salts thereof or stereoisomers thereof or tautomers thereof, or in combination with one or more other agent(s).

Other features and advantages of the invention will be apparent from the following detailed description and claims.

DETAILED DESCRIPTION OF THE INVENTION

I. Compounds of the Invention

In a first aspect, the present invention provides compounds of Formula (I)

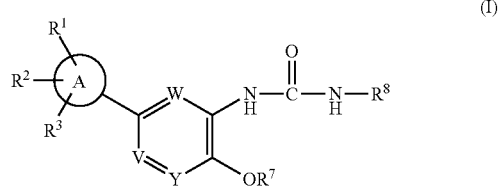

wherein:
W is $CR^4$ or N,
V is $CR^5$ or N, and
Y is $CR^6$ or N;
Ⓐ is optionally substituted phenyl or optionally substituted 5 to 7-membered monocyclic heteroaryl;
$R^1$ is COOH, tetrazol-5-yl, $-NHSO_2R^{20}$,

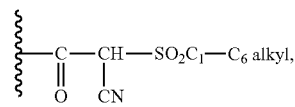

$-CONHSO_2R^{21}$, $-CONHCOOR^{22}$, or $-SO_2NHCOR^{23}$;
$R^2$ and $R^3$ are independently H, hydroxy, optionally substituted $C_1$-$C_6$ alkyl, halo, $N(C_1$-$C_6$ alkyl$)_2$, optionally substituted $C_1$-$C_6$ alkoxy;
$R^4$, $R^5$ and $R^6$ are independently H, optionally substituted $C_1$-$C_6$ alkyl, optionally substituted aryl, $C_1$-$C_6$ alkanoyl, halo, CN, $C_2$-$C_6$ alkenyl, $C_2$-$C_6$ alkynyl, $C_2$-$C_6$ alkenyl, optionally substituted $C_3$-$C_8$ cycloalkyl, $C_2$-$C_6$-alken-dienyl, dihydroindenyl, optionally substituted $C_1$-$C_6$ alkoxy, or OH,
wherein the optional substituents, where possible, are 1-3 groups selected from halo, $C_3$-$C_8$ cycloalkyl, aryl, optionally substituted $C_1$-$C_6$ alkyl, $C_1$-$C_6$ alkoxy, di-$C_1$-$C_6$-alkylamino or cyano;

$R^7$ is H, optionally substituted aryl, optionally substituted bicyclic carbocyclyl, optionally substituted 5 to 7-membered monocyclic heteroaryl, optionally substituted 5 to 7-membered monocyclic heterocyclic, optionally substituted $C_1$-$C_6$ alkoxy, optionally substituted arylalkyl, optionally substituted $C_1$-$C_9$ alkyl, optionally substituted $C_2$-$C_6$ alkenyl, optionally substituted $C_2$-$C_6$ alkynyl, optionally substituted $C_3$-$C_8$ cycloalkyl, or optionally substituted $C_5$-$C_8$ cycloalkenyl, wherein the optional substituents, where possible, are 1-3 groups selected from H, $C_1$-$C_6$ alkyl, aryl, $C_2$-$C_6$ alkenyl, $C_2$-$C_6$ alkynyl, $C_3$-$C_8$ cycloalkyl, 5 to 7-membered monocyclic heterocyclic, $C_2$-$C_6$ alkynyloxy($C_1$-$C_6$ alkyl)$_{0-1}$, halo, halo substituted aryl, oxo, trihalo-$C_1$-$C_6$-alkyl, or $OR^{19}$, where $R^{19}$ is H, $C_1$-$C_6$ alkyl, $C_2$-$C_6$ alkyl, or $C_2$-$C_6$ alkynyl;

$R^8$ is optionally substituted aryl, optionally substituted $C_3$-$C_8$ cycloalkyl, optionally substituted $C_1$-$C_6$ alkyl, optionally substituted 5 to 7-membered monocyclic heterocyclic, optionally substituted 5 to 7-membered monocyclic heteroaryl, optionally substituted 8- to 10-membered bicyclic heteroaryl, optionally substituted $C_1$-$C_6$ alkoxycarbonyl 5- to 7-membered monocyclic heteroaryl, $R^{24}CO$—, optionally substituted $C_2$-$C_6$ alkenyl, optionally substituted $C_2$-$C_6$ alkynyl, or optionally substituted $C_5$-$C_5$ cycloalkenyl, wherein the optional substituents, where possible, are 1-2 groups selected from H, optionally substituted $C_1$-$C_6$ alkyl, $C_2$-$C_6$ alkenyl, $C_2$-$C_6$ alkynyl, $C_3$-$C_8$ cycloalkyl, halo, optionally substituted $C_1$-$C_6$-alkoxy, cyano, 5 to 7-membered monocyclic heteroaryl, $NH_2CO$—, di $C_1$-$C_6$ alkylamino, aminosulfonyl, 5 to 7-membered monocyclic heterocyclo, hydroxy, $C_1$-$C_6$ alkylsulfonyl, azido, or aryl;

$R^{19}$ is H, $C_1$-$C_6$ alkyl, $C_2$-$C_6$ alkenyl, or $C_2$-$C_6$ alkynyl;

$R^{20}$ is optionally substituted $C_1$-$C_6$ alkyl, optionally substituted phenyl, $CF_3$, $CF_2CF_3$ or $CH_2CF_3$;

$R^{21}$ is optionally substituted $C_1$-$C_6$ alkyl, or optionally substituted $C_3$-$C_8$ cycloalkyl;

$R^{22}$ is $C_1$-$C_6$ alkyl, $C_3$-$C_8$ cycloalkyl, $C_2$-$C_6$ alkenyl, or $C_2$-$C_6$ alkynyl;

$R^{23}$ is $C_1$-$C_6$ alkyl, $C_3$-$C_8$ cycloalkyl, $C_2$-$C_6$ alkenyl, or $C_2$-$C_6$ alkynyl;

$R^{24}$ is optionally substituted aryl-$C_1$-$C_6$-alkyl, $C_1$-$C_6$ alkylaryl, aryl $C_1$-$C_6$ alkyl (hydroxy), or optionally substituted $C_1$-$C_6$ alkyl;

and/or a stereoisomer, a tautomer or a pharmaceutically acceptable salt thereof.

In a second aspect, the invention provides a compound of Formula (I) within the scope of the first aspect wherein:

W is $CR^4$;
V is $CR^5$;
Y is $CR^6$ or N;
$R^4$ is H;
$R^5$ is H; and
$R^6$ is H, halo, optionally substituted $C_1$-$C_6$-alkyl, optionally substituted $C_2$-$C_6$-alkenyl, optionally substituted $C_2$-$C_6$ alken-dienyl, $C_3$-$C_8$ cycloalkyl or $C_3$-$C_8$-cycloalkyl-$C_1$-$C_6$-alkyl;

and/or a stereoisomer, a tautomer or a pharmaceutically acceptable salt thereof.

In a third aspect, the invention provides a compound of Formula (I) within the scope of the first and second aspects wherein Ⓐ is phenyl, and/or a pharmaceutically acceptable salt thereof, a tautomer thereof, or a stereoisomer thereof.

In a fourth aspect, the invention provides a compound of Formula (I) within the scope of the previously mentioned aspects wherein:

$R^1$ is COOH, tetrazol-5-yl, —$NHSO_2R^{20}$ or —$CONHSO_2R^{21}$;

$R^2$ is H, halo, hydroxy, optionally substituted $C_1$-$C_6$-alkyl, $C_1$-$C_6$ alkoxy; and $R^3$ is H or $C_1$-$C_6$ alkoxy;

and/or a stereoisomer, a tautomer or a pharmaceutically acceptable salt thereof.

In a fifth aspect, the invention provides a compound of Formula (I) within the scope of the previously mentioned aspects wherein:

$R^7$ is aryl, optionally substituted $C_1$-$C_9$ alkyl, optionally substituted $C_1$-$C_6$ alkylaryl, $C_3$-$C_8$-cycloalkyl-$C_1$-$C_6$-alkyl, $C_3$-$C_8$ cycloalkylaryl, optionally substituted $C_3$-$C_8$-cycloalkyl or optionally substituted aryl $C_1$-$C_6$-alkyl, and/or a stereoisomer, a tautomer or a pharmaceutically acceptable salt thereof.

In a sixth aspect, the invention provides a compound of Formula (I) within the scope of the previously mentioned aspects wherein:

$R^8$ is optionally substituted $C_1$-$C_6$ alkylaryl, optionally substituted aryl, optionally substituted $C_3$-$C_8$ cycloalkylaryl, optionally substituted $C_3$-$C_8$-cycloalkyl-$C_1$-$C_6$ alkyl, optionally substituted 5 to 7-membered heterocyclic, optionally substituted $C_1$-$C_6$ alkyl, optionally substituted aryl-$C_1$-$C_6$-alkyl, $C_1$-$C_6$ alkoxyaryl, $C_1$-$C_6$-alkoxy($C_1$-$C_6$-alkyl)aryl, $C_3$-$C_8$ cycloalkyl, optionally substituted $C_1$-$C_6$-alkyl-$C_3$-$C_8$-cycloalkyl, optionally substituted $C_1$-$C_6$ alkanoyl, di-$C_1$-$C_6$-alkylaminophenyl or $C_2$-$C_6$ alkenyl, and/or a stereoisomer, a tautomer or a pharmaceutically acceptable salt thereof.

In a seventh aspect, the invention provides a compound of Formula (II)

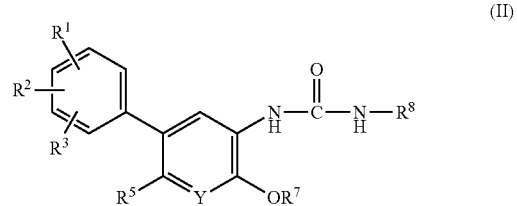

wherein:
Y is $CR^6$ or N;

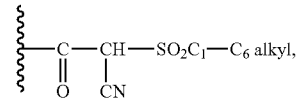

$R^1$ is COOH, tetrazol-5-yl, or

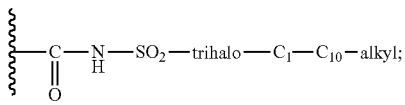

$R^2$ is H, optionally substituted $C_1$-$C_6$ alkyl, OH, optionally substituted $C_1$-$C_6$ alkoxy or $CF_3$;
$R^3$ is H, $C_1$-$C_6$ alkyl, or $C_1$-$C_6$ alkoxy;
$R^4$ is H;
$R^5$ is H;

R⁶ is H, optionally substituted aryl $C_1$-$C_6$-alkyl, optionally substituted aryl-$C_2$-$C_6$-alkenyl, optionally substituted $C_1$-$C_6$ alkyl, optionally substituted $C_2$-$C_6$ alkenyl or optionally substituted $C_2$-$C_6$-alken-dienyl, R⁷ is selected from optionally substituted aryl, optionally substituted $C_1$-$C_6$ alkylaryl, optionally substituted $C_3$-$C_8$ cycloalkyl, optionally substituted $C_1$-$C_8$ alkyl, optionally substituted aryl-$C_1$-$C_6$-alkyl, $C_3$-$C_8$ cycloalkylaryl, 2,2-$C_1$-$C_6$-dialkyldihydrobenzofuran

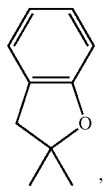

optionally substituted $C_1$-$C_6$-alkyl(aryl)-$C_1$-$C_6$-alkyl, $C_2$-$C_6$ alkynyloxy($C_1$-$C_6$ alkyl)aryl, optionally substituted 5 to 7-membered monocyclic heterocyclic or optionally substituted $C_3$-$C_8$-cycloalkyl-$C_1$-$C_6$-alkyl;

R⁸ is optionally substituted $C_1$-$C_6$ alkylaryl, optionally substituted $C_1$-$C_6$ alkyl, optionally substituted aryl, optionally substituted aryl-$C_1$-$C_6$-alkyl, optionally substituted $C_1$-$C_6$ alkoxyaryl, optionally substituted $C_1$-$C_6$-alkoxy($C_1$-$C_6$-alkyl)aryl, optionally substituted $C_3$-$C_8$ cycloalkyl, optionally substituted $C_3$-$C_8$ cycloalkylaryl, optionally substituted $C_3$-$C_8$-cycloalkyl-$C_1$-$C_6$-alkyl, optionally substituted 5- to 7-membered monocyclic heterocyclic, optionally substituted $C_1$-$C_6$-alkyl-$C_3$-$C_8$-cycloalkyl, optionally substituted $C_1$-$C_6$ alkanoylaryl, $C_1$-$C_6$ dialkylaminoaryl, dihydroindenyl, optionally substituted $C_2$-$C_6$ alkenyl, or optionally substituted $C_2$-$C_6$ alkynyl;

and/or a pharmaceutically acceptable salt thereof, a tautomer thereof, or a stereoisomer thereof.

In another aspect, the invention provides a compound of Formula (II) within the scope of the seventh aspect wherein:
R⁴ is H;
R⁵ is H; and
R⁶ is

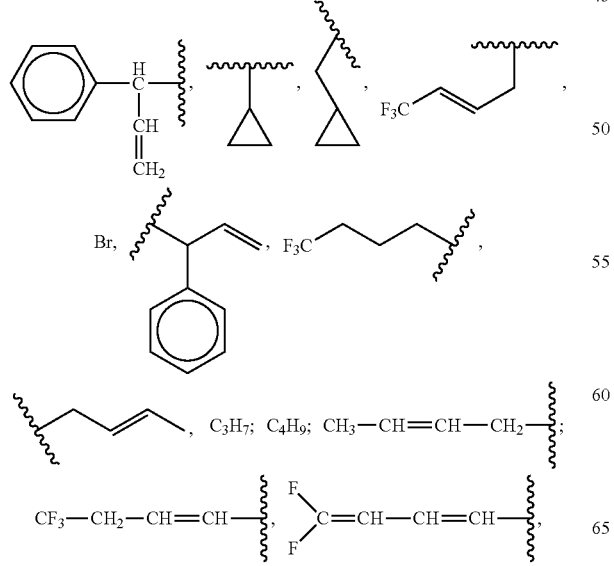

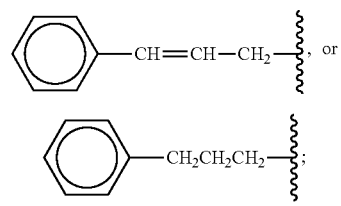

R⁷ is

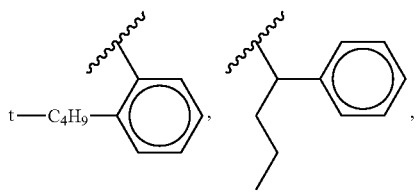

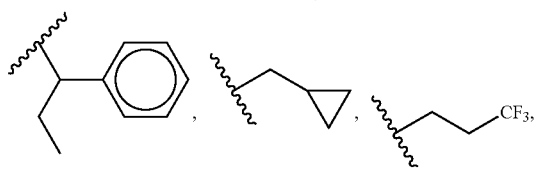

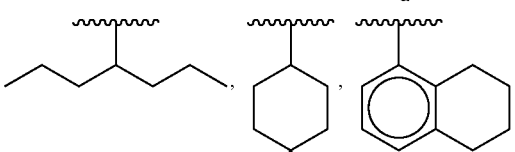

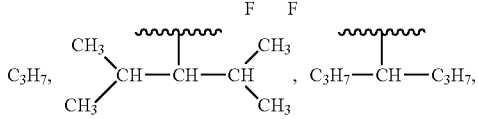

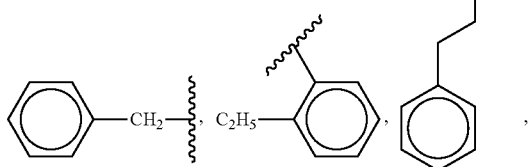

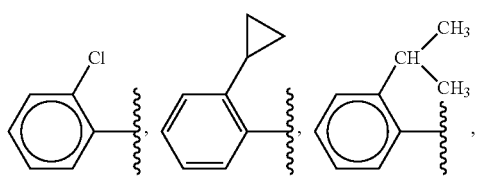

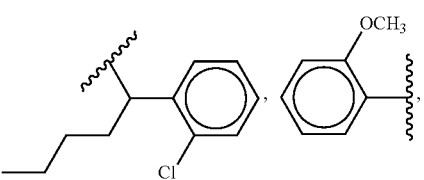

-continued
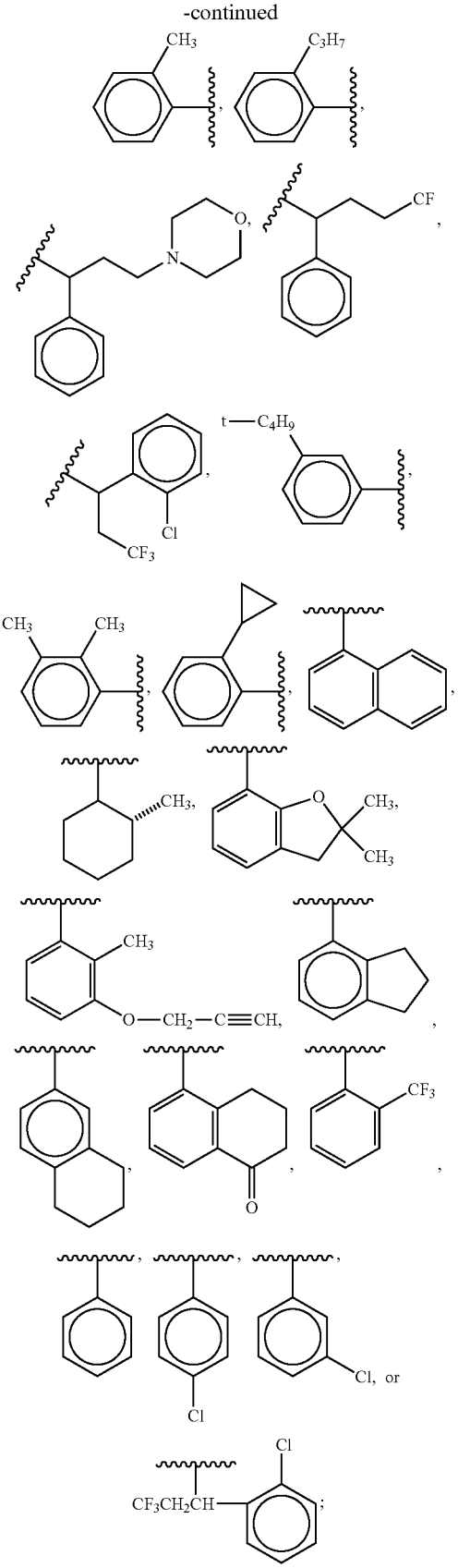
and
R[8] is
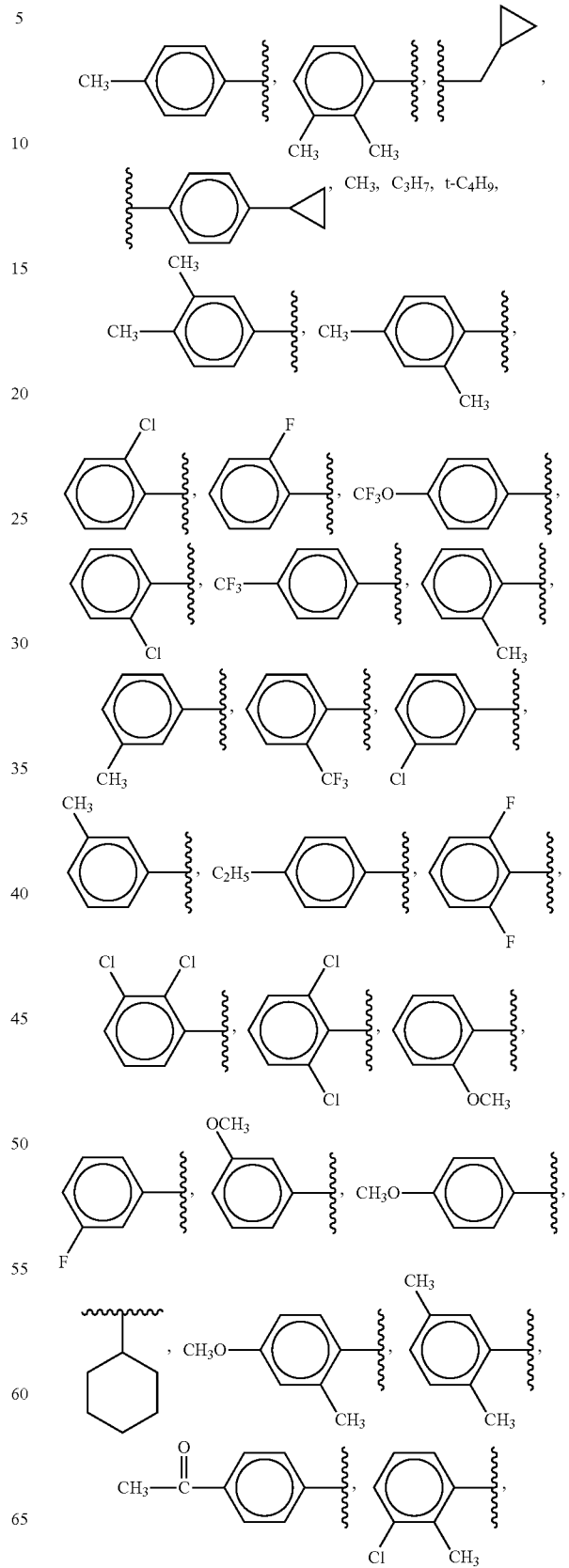

-continued

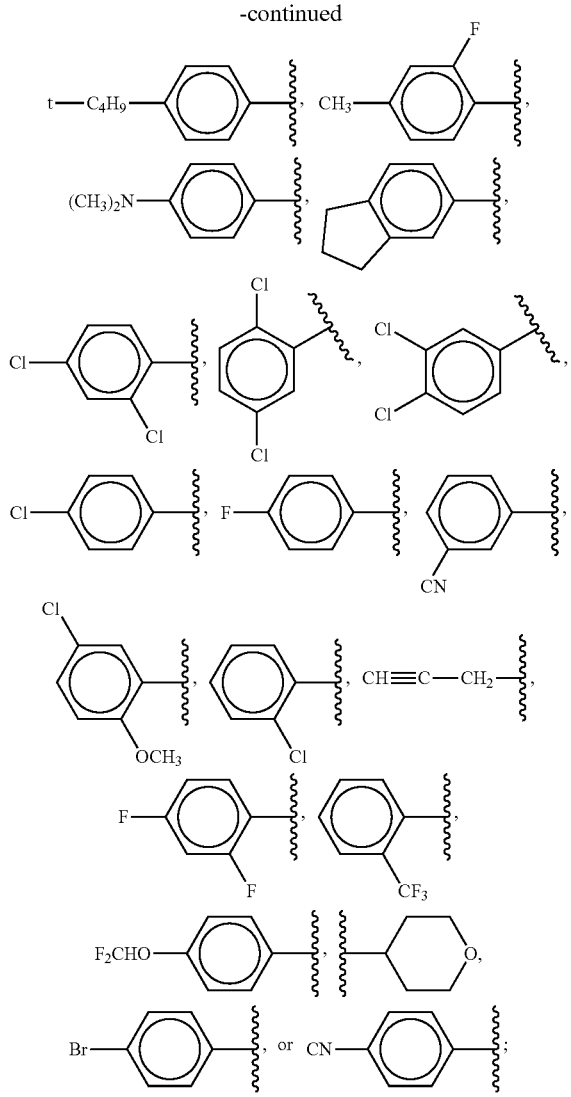

and/or a pharmaceutically acceptable salt thereof, a tautomer thereof, or a stereoisomer thereof.

In another aspect, the invention provides a compound of Formula (II) within the scope of the seventh aspect wherein:
R$^1$ is COOH, tetrazol-5-yl, CONHSO$_2$CH$_3$ or —NHSO$_2$CH$_3$;
R$^2$ is H, Cl, F, OH, or CH$_3$O; and R$^3$ is H or CH$_3$O;
and/or a pharmaceutically acceptable salt thereof, a tautomer thereof, or a stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have human IDO IC$_{50}$ values ≤250 nM.

In another embodiment, the compounds of the invention have human IDO IC$_{50}$ values ≤50 nM.

In another embodiment, the compounds of the invention have human IDO IC$_{50}$ values ≤20 nM.

In another embodiment, the compounds of the invention have human IDO IC$_{50}$ values ≤10 nM.

II. Other Embodiments of the Invention

In another embodiment, the present invention provides a composition comprising one or more compounds of the present invention and/or a pharmaceutically acceptable salt thereof, a stereoisomer thereof, a tautomer thereof, or a solvate thereof.

In another embodiment, the present invention provides a pharmaceutical composition comprising a pharmaceutically acceptable carrier and at least one of the compounds of the present invention and/or a pharmaceutically acceptable salt thereof, a stereoisomer thereof, a tautomer thereof, or a solvate thereof.

In another embodiment, the present invention provides a pharmaceutical composition, comprising: a pharmaceutically acceptable carrier and a therapeutically effective amount of at least one of the compounds of the present invention and/or a pharmaceutically acceptable salt thereof, a stereoisomer thereof, a tautomer thereof, or a solvate thereof.

In another embodiment, the present invention provides a process for making a compound of the present invention and/or a pharmaceutically acceptable salt thereof, a stereoisomer thereof, a tautomer thereof, or a solvate thereof.

In another embodiment, the present invention provides an intermediate for making a compound of the present invention and/or a pharmaceutically acceptable salt thereof, a stereoisomer thereof, a tautomer thereof, or a solvate thereof.

In another embodiment, the present invention provides a method for the treatment and/or prophylaxis of various types of cancer, viral infections and/or autoimmune diseases, comprising administering to a patient in need of such treatment and/or prophylaxis a therapeutically effective amount of one or more compounds of the present invention and/or a pharmaceutically acceptable salt thereof, a stereoisomer thereof or a tautomer thereof, alone, or, optionally, in combination with another compound of the present invention and/or at least one other type of therapeutic agent, such as a chemotherapeutic agent or a signal transductor inhibitor.

In another embodiment, the present invention provides a compound of the present invention, and/or a pharmaceutically acceptable salt thereof, a stereoisomer thereof or a tautomer thereof, for use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in therapy.

In another embodiment, the present invention provides a combined preparation of a compound of the present invention, and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with the enzymatic activity of IDO.

In another aspect, the invention provides a method of treating a patient suffering from or susceptible to a medical condition that is sensitive to enzymatic activity of IDO. A number of medical conditions can be treated. The method comprises administering to the patient a therapeutically effective amount of a composition comprising a compound described herein and/or a pharmaceutically acceptable salt thereof, a stereoisomer thereof or a tautomer thereof. For example, the compounds described herein may be used to treat or prevent viral infections, proliferative diseases (e.g., cancer), and autoimmune diseases.

III. Therapeutic Applications

The compounds and pharmaceutical compositions of the present invention are useful in treating or preventing any disease or conditions that are sensitive to enzymatic activity of IDO. These include viral and other infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the patient. In certain embodiments, the compound or pharmaceutical composition is administered orally. In other embodiments, the compound or pharmaceutical composition is administered parenterally.

Compounds of the invention can modulate activity of the enzyme indoleamine-2,3-dioxygenase (IDO). The term "modulate" is meant to refer to an ability to increase or decrease activity of an enzyme or receptor. Accordingly, compounds of the invention can be used in methods of modulating IDO by contacting the enzyme with any one or more of the compounds or compositions described herein. In some embodiments, compounds of the present invention can act as inhibitors of IDO. In further embodiments, the compounds of the invention can be used to modulate activity of IDO in cell or in an individual in need of modulation of the enzyme by administering a modulating (e.g., inhibiting) amount of a compound of the invention.

Compounds of the invention can inhibit activity of the enzyme indoleamine-2,3-dioxygenase (IDO). For example, the compounds of the invention can be used to inhibit activity of IDO in cell or in an individual in need of modulation of the enzyme by administering an inhibiting amount of a compound of the invention.

The present invention further provides methods of inhibiting the degradation of tryptophan in a system containing cells expressing IDO such as a tissue, living organism, or cell culture. In some embodiments, the present invention provides methods of altering (e.g., increasing) extracellular tryptophan levels in a mammal by administering an effective amount of a compound of composition provided herein. Methods of measuring tryptophan levels and tryptophan degradation are routine in the art.

The present invention further provides methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, viral infection, and viral replication.

The present invention further provides methods of treating diseases associated with activity or expression, including abnormal activity and/or overexpression, of IDO in an individual (e.g., patient) by administering to the individual in need of such treatment a therapeutically effective amount or dose of a compound of the present invention or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity. Examples of IDO-associated diseases include cancer, viral infection such as HIV infection, HCV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, allergic inflammation, inflammatory bowel disease, psoriasis and systemic lupus erythematosus.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound of the invention includes the administration of a compound of the present invention to an individual or patient, such as a human, having IDO, as well as, for example, introducing a compound of the invention into a sample containing a cellular or purified preparation containing the IDO enzyme.

The term "IDO inhibitor" refers to an agent capable of inhibiting the activity of indoleamine 2,3-dioxygenase (IDO) and thereby reversing IDO-mediated immunosuppression. The IDO inhibitor may inhibit IDO1 and/or IDO2 (INDOL1). An IDO inhibitor may be a reversible or irreversible IDO inhibitor. "A reversible IDO inhibitor" is a compound that reversibly inhibits IDO enzyme activity either at the catalytic site or at a non-catalytic site and "an irreversible IDO inhibitor" is a compound that irreversibly destroys IDO enzyme activity by forming a covalent bond with the enzyme.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as pemphigus vulgaris, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, malaria and Chagas disease.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of the present invention for treatment of IDO-associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of the present invention include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide, YERVOY™ or Nivolumab. Compounds according to the invention may also be combined with immunotherapy drugs, including cytokines such as interferon alpha, interleukin 2, and tumor necrosis factor (TNF) in the treatment of melanoma.

Compounds of the invention may also be used in combination with vaccine therapy in the treatment of melanoma. Anti-melanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of the invention, using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 102° to 104° F. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-10 or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.*, 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.*, 1(8):792-797 (1995)); (iv) inhibitors of Akt family kinases or the Akt pathway, such as, for example, rapamycin (see, for example, Sekulic et al., *Cancer Res.*, 60:3504-3513 (2000)); (v) cell cycle kinase inhibitors such as, for example, flavopiridol and UCN-01 (see, for example, Sausville, *Curr. Med. Chem. Anti-Canc. Agents*, 3:47-56 (2003)); and (vi) phosphatidyl inositol kinase inhibitors such as, for example, LY294002 (see, for example, Vlahos et al., *J. Biol. Chem.*, 269:5241-5248 (1994)). Alternatively, at least one STI and at least one IDO inhibitor may be in separate pharmaceutical compositions. In a specific embodiment of the present invention, at least one IDO inhibitor and at least one STI may be administered to the patient concurrently or sequentially. In other words, at least one IDO inhibitor may be administered first, at least one STI may be administered first, or at least one IDO inhibitor and at least one STI may be administered at the same time. Additionally, when more than one IDO inhibitor and/or STI is used, the compounds may be administered in any order.

The present invention further provides a pharmaceutical composition for the treatment of a chronic viral infection in a patient comprising at least one IDO inhibitor, optionally, at least one chemotherapeutic drug, and, optionally, at least one antiviral agent, in a pharmaceutically acceptable carrier. The pharmaceutical compositions may include at least one IDO inhibitor of the instant invention in addition to at least one established (known) IDO inhibitor. In a specific embodiment, at least one of the IDO inhibitors of the pharmaceutical composition is selected from the group consisting of compounds of formulas (I) and (II).

Also provided is a method for treating a chronic viral infection in a patient by administering an effective amount of the above pharmaceutical composition.

In a specific embodiment of the present invention, at least one IDO inhibitor and at least one chemotherapeutic agent may be administered to the patient concurrently or sequentially. In other words, at least one IDO inhibitor may be administered first, at least one chemotherapeutic agent may be administered first, or at least one IDO inhibitor and the at least one STI may be administered at the same time. Additionally, when more than one IDO inhibitor and/or chemotherapeutic agent is used, the compounds may be administered in any order. Similarly, any antiviral agent or STI may also be administered at any point in comparison to the administration of an IDO inhibitor.

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

In yet another embodiment, the pharmaceutical compositions comprising at least one IDO inhibitor of the instant invention may be administered to a patient to prevent arterial restenosis, such as after balloon endoscopy or stent placement. In a particular embodiment, the pharmaceutical composition further comprises at least one taxane (e.g., paclitaxel (Taxol); see e.g., Scheller et al., *Circulation*, 110:810-814 (2004)).

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-I0652; emitricitabine [(−)-FTC]; beta-L-FD4 (also called beta-L-D4C and named beta-L-2',3'-dicleoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

Definitions

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

When a substituent is noted as "optionally substituted", the substituents are selected from, for example, substituents such as alkyl, cycloalkyl, aryl, heterocyclo, halo, hydroxy, alkoxy, oxo, alkanoyl, aryloxy, alkanoyloxy, amino, alkylamino, arylamino, arylalkylamino, disubstituted amines in which the 2 amino substituents are selected from alkyl, aryl or arylalkyl; alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, arylalkylthiono, alkylsulfonyl, arylsulfonyl, arylalkylsulfonyl, sulfonamido, e.g. —SO$_2$NH$_2$, substituted sulfonamido, nitro, cyano, carboxy, carbamyl, e.g. —CONH$_2$, substituted carbamyl e.g. —CONHalkyl, —CONHaryl, —CONHarylalkyl or cases where there are two substituents on the nitrogen selected from alkyl, aryl or arylalkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl, unless otherwise defined.

For purposes of clarity and in accordance with standard convention in the art, the symbol

is used in formulas and tables to show the bond that is the point of attachment of the moiety or substituent to the core/nucleus of the structure.

Additionally, for purposes of clarity, where a substituent has a dash (-) that is not between two letters or symbols; this is used to indicate a point of attachment for a substituent. For example, —CONH$_2$ is attached through the carbon atom.

Additionally, for purposes of clarity, when there is no substituent shown at the end of a solid line, this indicates that there is a methyl (CH$_3$) group connected to the bond.

As used herein, the term "alkyl" or "alkylene" is intended to include both branched and straight-chain saturated aliphatic hydrocarbon groups having the specified number of carbon atoms. For example, "C$_1$-C$_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkenyl" denotes a straight- or branch-chained hydrocarbon radical containing one or more double bonds and typically from 2 to 20 carbon atoms in length. For example, "C$_2$-C$_8$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" denotes a straight- or branch-chained hydrocarbon radical containing one or more triple bonds and typically from 2 to 20 carbon atoms in length. For example, "C$_2$-C$_8$ alkenyl" contains from two to eight carbon atoms. Representative alkynyl groups include, but are not limited to, for example, ethynyl, 1-propynyl, 1-butynyl, heptynyl, octynyl and the like.

The term "alkoxy" or "alkyloxy" refers to an —O-alkyl group. "C$_{1-6}$ alkoxy" (or alkyloxy), is intended to include C$_1$, C$_2$, C$_3$, C$_4$, C$_5$, and C$_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or as part of a larger moiety such as "aralkyl", "aralkoxy", or "aryloxyalkyl", refers to monocyclic, bicyclic and tricyclic ring systems having a total of five to 15 ring members, wherein at least one ring in the system is aromatic and wherein each ring in the system contains three to seven ring members. In certain embodiments of the invention, "aryl" refers to an aromatic ring system which includes, but not limited to phenyl, biphenyl, indanyl, 1-naphthyl, 2-naphthyl and terahydronaphthyl. The term "aralkyl" or "arylalkyl" refers to an alkyl residue attached to an aryl ring. Non-limiting examples include benzyl, phenethyl and the like. The fused aryls may be connected to another group either at a suitable position on the cycloalkyl ring or the aromatic ring. For example:

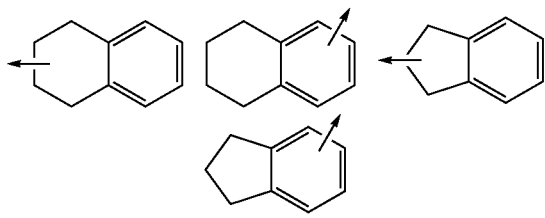

Arrowed lines drawn from the ring system indicate that the bond may be attached to any of the suitable ring atoms.

The term "cycloalkyl" refers to cyclized alkyl groups. C$_{3-6}$ cycloalkyl is intended to include C$_3$, C$_4$, C$_5$, and C$_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. C$_{4-6}$ cycloalkenyl is intended to include C$_4$, C$_5$, and C$_6$ cycloalkenyl groups. Example cycloalkenyl groups include, but are not limited to, cyclobutenyl, cyclopentenyl, and cyclohexenyl.

The term "cycloalkylalkyl" refers to a cycloalkyl or substituted cycloalkyl bonded to an alkyl group connected to the carbazole core of the compound.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "C$_{1-6}$ haloalkoxy", is intended to include C$_1$, C$_2$, C$_3$, C$_4$, C$_5$, and C$_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

The term "benzyl," as used herein, refers to a methyl group on which one of the hydrogen atoms is replaced by a phenyl group.

As used herein, the term "heterocycle," "heterocyclyl," or "heterocyclic group" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and S(O)$_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more, preferably one to three, atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "heterocyclylalkyl" refers to a heterocyclyl or substituted heterocyclyl bonded to an alkyl group connected to the carbazole core of the compound.

The term "counter ion" is used to represent a negatively charged species such as chloride, bromide, hydroxide, acetate, and sulfate or a positively charged species such as sodium (Na+), potassium (K+), ammonium ($R_nNH_m$+ where n=0-4 and m=0-4) and the like.

The term "electron withdrawing group" (EWG) refers to a substituent which polarizes a bond, drawing electron density towards itself and away from other bonded atoms. Examples of EWGs include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl)$_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a disubstituted hydrazine, R4-M and R7-M, a nucleophile, a hydrazine reducing agent, an activator, a strong base, a hindered amine base and a cyclizing agent. Such amine protecting groups fitting these criteria include those listed in Wuts, P. G. M. and Greene, T. W. *Protecting Groups in Organic Synthesis,* 4th Edition, Wiley (2007) and *The Peptides: Analysis, Synthesis, Biology,* Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington: The Science and Practice of Pharmacy*, $22^{nd}$ Edition, Allen, L. V. Jr., Ed.; Pharmaceutical Press, London, UK (2012), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs," *A Textbook of Drug Design and Development*, pp. 113-191, Krosgaard-Larsen, P. et al., eds., Harwood Academic Publishers (1991);

c) Bundgaard, H., *Adv. Drug Deliv. Rev.*, 8:1-38 (1992);

d) Bundgaard, H. et al., *J. Pharm. Sci.*, 77:285 (1988);

e) Kakeya, N. et al., *Chem. Pharm. Bull.*, 32:692 (1984); and f) Rautio, J (Editor). *Prodrugs and Targeted Delivery (Methods and Principles in Medicinal Chemistry)*, Vol 47, Wiley-VCH, 2011.

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art. Preparation of prodrugs is well known in the art and described in, for example, King, F. D., ed., *Medicinal Chemistry: Principles and Practice*, The Royal Society of Chemistry, Cambridge, UK ($2^{nd}$ edition, reproduced, 2006); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, $3^{rd}$ edition, Academic Press, San Diego, Calif. (2008).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably refers to humans.

As used herein, the term "effective amount" means that amount of a drug or pharmaceutical agent, i.e., a compound of the invention, that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. An effective amount can be administered in one or more administrations, applications or dosages and is not intended to be limited to a particular formulation or administration route. The term also includes within its scope amounts effective to enhance normal physiological function As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

VI. Methods of Preparation

The compounds of the present invention may be prepared by methods such as those illustrated in the following Schemes utilizing chemical transformations known to those skilled in the art. Solvents, temperatures, pressures, and other reaction conditions may readily be selected by one of ordinary skill in the art. Starting materials are commercially available or readily prepared by one of ordinary skill in the art. These Schemes are illustrative and are not meant to limit the possible techniques one skilled in the art may use to manufacture compounds disclosed herein. Different methods may be evident to those skilled in the art. Additionally, the various steps in the synthesis may be performed in an alternate sequence or order to give the desired compound(s). Further, the representation of the reactions in these Schemes as discrete steps does not preclude their being performed in tandem, either by telescoping multiple steps in the same reaction vessel or by performing multiple steps without purifying or characterizing the intermediate(s). In addition, many of the compounds prepared by the methods below can be further modified using conventional chemistry well known to those skilled in the art. All documents cited herein are incorporated herein by reference in their entirety.

References to many of these chemical transformations employed herein can be found in Smith, M. B. et al., *March's Advanced Organic Chemistry Reactions, Mechanisms, and Structure*, Fifth Edition, Wiley-Interscience, New York (2001), or other standard texts on the topic of synthetic organic chemistry. Certain transformations may require that reactive functional groups be masked by protecting group(s). A convenient reference which provides conditions for introduction, removal, and relative susceptibility to reaction conditions of these groups is Greene, T. W. et al., *Protective Groups in Organic Synthesis*, Third Edition, Wiley-Interscience, New York (1999)

Referring to Scheme 1 below, Compounds (i) where X is Cl, Br or I, and Q is a halogen are commercially available or can be prepared using standard transformations known to those of ordinary proficiency in the art of organic/medicinal chemistry. Treatment of an alcohol or phenol $R^7OH$ and a base of suitable strength to deprotonated it, ideally in a solvent such as THF, DMF, NMP followed by (i), affords adducts (ii). Depending on the steric requirements and the degree of nucleophilicity of the alkoxide, heating may be required. Suitable bases for alcohols include, but are not limited to, sodium hydride, alkali metal dialkylamides and the related hexamethyldisilylazides and organometallics such as Grignard or alkyllithium reagents. Typically, phenols are deprotonated with bases like sodium or potassium carbonate. Reduction of the nitro group in compounds (ii) to afford anilines (iii) can be effected by various means including catalytic hydrogenation and dissolving metal reductions both in their various forms. See House, H. O., *Modern Synthetic Reactions*, Second Edition, W. A. Benjamin, Inc., Menlo Park, Calif., publ. (1972). A preferred method for effecting this reduction without removal of the halogen substituent X involves stirring a solution of (ii) in a wet alcoholic solvent with an acid such as ammonium chloride and finely divided zinc. Treatment of anilines (iii) with an isocyanate $R^8N=C=O$ (iva), affords urea compounds (iv). Typically, this reaction is performed in a solvent such as THF at a temperature between ambient and the boiling point of the solvent. Coupling of (iv) with arylboronic acids (ivb), preferably under the conditions of Suzuki (see Kotha, S. et al., *Tetrahedron*, 58:9633-9695 (2002)) affords compounds of the invention I. Typically, this reaction is performed by heating the halide and the boronic acid or ester to from about 90 to about 98° C. with a base such as aqueous tribasic sodium or potassium phosphate or sodium or potassium carbonate in a solvent such as dioxane, DMF, THF, or NMP using a catalyst such as tetrakis(triphenylphosphine)palladium or $Cl_2Pd(dppf)$. Many variations on this reaction involving the use of different temperatures, solvents, bases, anhydrous conditions, catalysts, boronate derivatives, and halide surrogates such as triflates are known to those skilled in the art of organic/medicinal chemistry. Recently, mild conditions have been reported for the coupling of sensitive boronic acid derivatives. See Kinzel, T. et al., *J. Am. Chem. Soc.*, 132(40):14073-14075 (2010). Related coupling reactions for the conversion of (iv) and other aryl halide intermediates described in later Schemes into compounds of the invention include the Heck (olefin) (*J. Am. Chem. Soc.*, 96(4):1133-1136 (1974)), Stille (organostannane) (*Synthesis*, 803-815 (1992)), Sonogashira (acetylene) (Sonogashira, K. et al., *Tetrahedron Lett.*, 16(50):4467-4470 (1975)), and Negishi (organozinc) (*Aldrichimica Acta*, 38(3):71-78 (2005)) coupling reactions.

Scheme 1

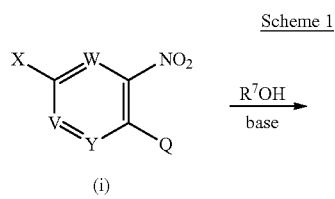

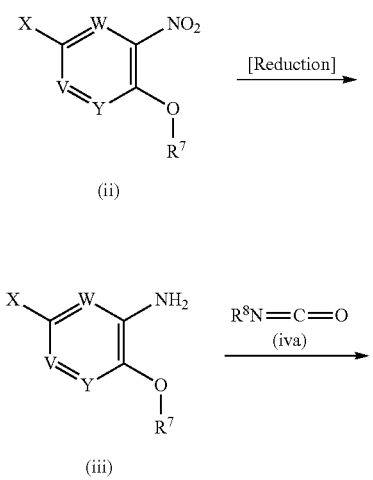

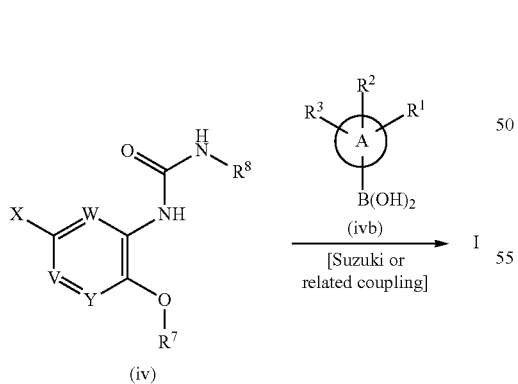

Scheme 2 describes a preparation of compounds of the invention I similar to that of Scheme 1 but with the transformations performed in a different order. In this Scheme, the Suzuki or related coupling is performed on intermediate (iii) to afford aniline (v) which is derivatized by reaction of an isocyanate (iva) to afford compounds of formula I.

Scheme 2

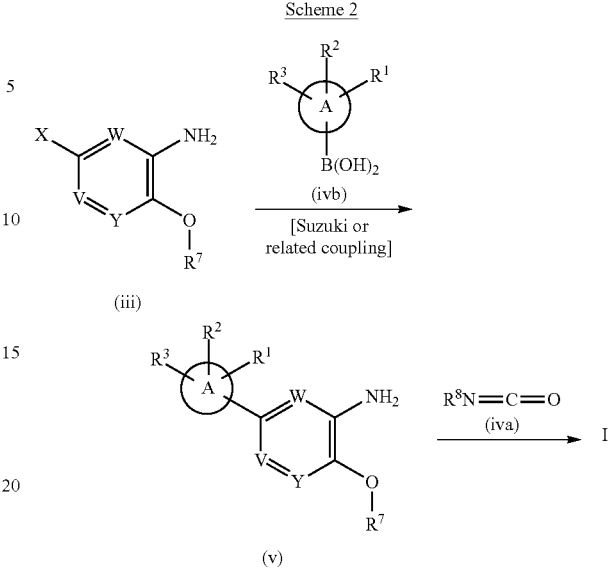

Scheme 3 illustrates a route to compounds of formula I in which the Suzuki or related coupling is performed on intermediates (ii) to afford intermediates (vi). Reduction under the conditions described above provides anilines (v) which react with isocyanates to afford compounds of formula I.

Scheme 3

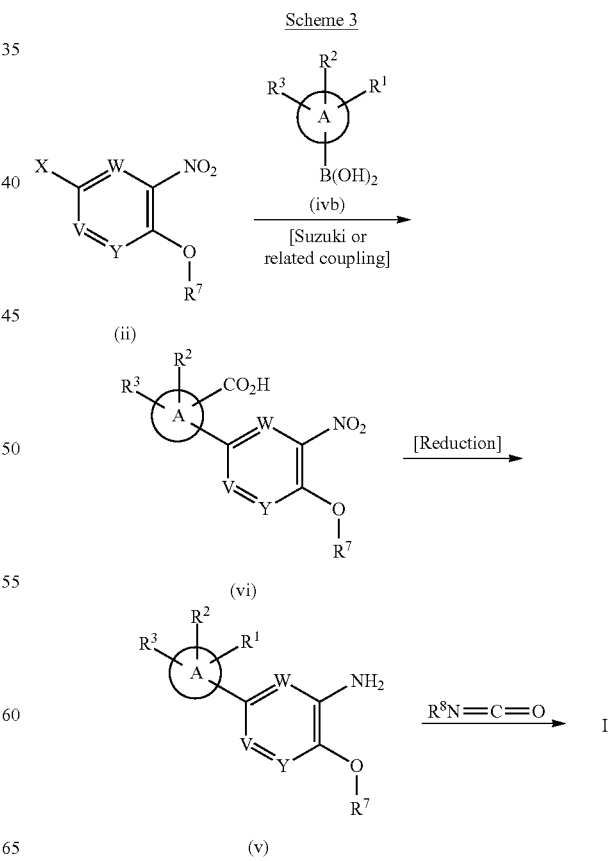

Scheme 4 illustrates a method suitable for preparation of compounds of the invention for which the boronic acid/ester or related derivatives of the (A) group do not readily undergo coupling reactions or are not commercially available or readily accessible. Derivatives (iii) can be coupled with boronate ester dimers such as bis(neopentylglycolato)diboron (ivc) by heating in a solvent such as DMSO, dioxane, toluene or DMF in the presence of a base such as potassium acetate and a catalyst such as $Cl_2Pd(dppf)$ to give aryl boronate esters (vii). These esters can undergo Suzuki or related couplings as described above, to afford intermediates (v). Functionalization as above by treatment with $R^8N{=}C{=}O$ affords compounds of formula I.

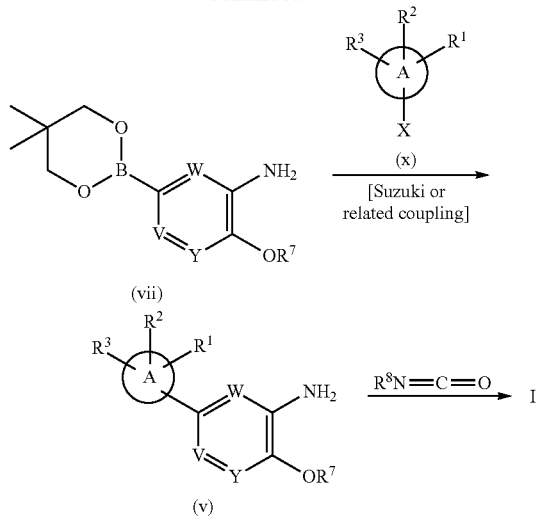

Scheme 4

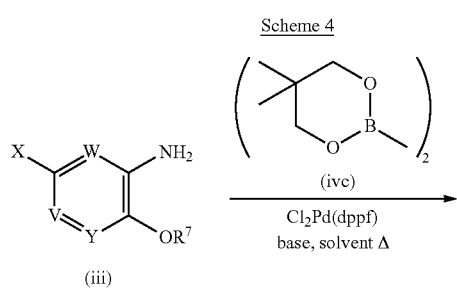

In Scheme 5 the order of synthetic steps is changed from that shown in Scheme 4. Accordingly, aryl boronate esters (vii) are functionalized by treatment with $R^8N{=}C{=}O$ to give ureas (ix). Alternatively, (ix) could be prepared by the conditions shown in Scheme 4 on (iv), or some other intermediate which bears a urea substituent

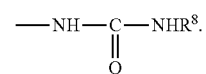

These derivatives undergo Suzuki or related coupling reactions to afford compounds of formula I.

Scheme 5

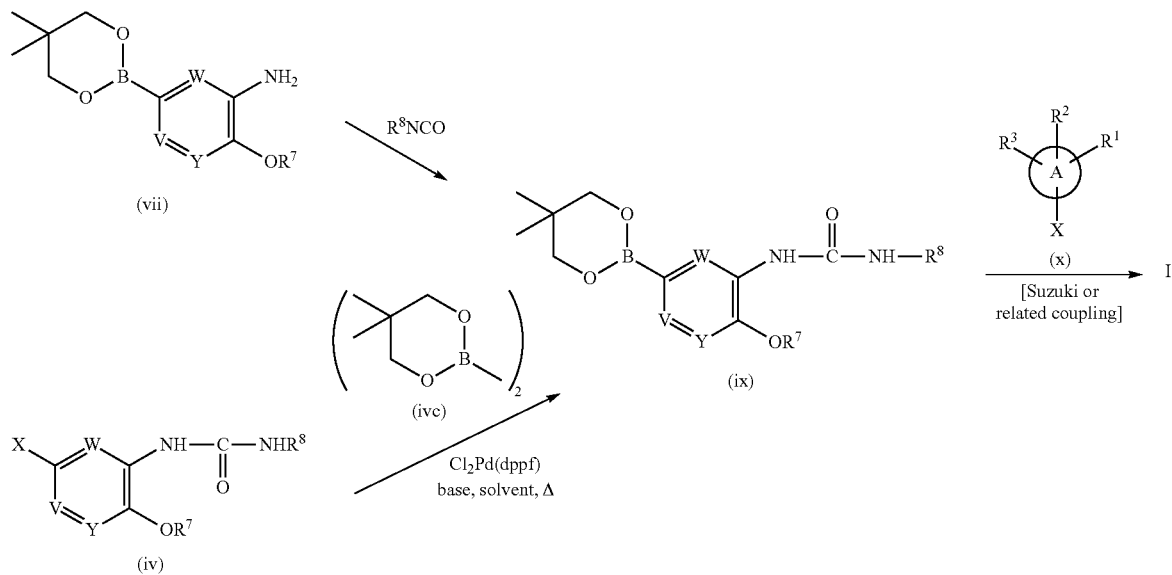

Scheme 6 describes an additional method for the preparation of compounds of formula I. Treatment of an alcohol or phenol $R^7OH$ and a base of suitable strength to deprotonate it, ideally in a solvent such as DMF or NMP followed by heating with an acid or ester (xvi), affords adducts (xvii) or (xviii). Suitable bases for alcohols include, but are not be limited to, sodium hydride and organometallics such as Grignard or alkyllithium reagents. Typically, phenols are deprotonated with bases like sodium or potassium carbonate. Esters (xvii) may be converted to the corresponding carboxylic acids (xviii) under various conditions familiar to those of ordinary skill in the art. Generally this is effected using an alkali metal hydroxide (MOH) in aqueous solution, preferably with an organic co-solvent such as methanol or THF. Carboxylic acids (xviii) can be converted (by treatment with DPPA and a tertiary amine base) to acyl azides which rearrange (Curtius rearrangement) upon heating to form isocyanates which can be trapped by alcohols $R^aOH$ to furnish carbamates (xix). Many variations on the Curtius rearrangement are familiar to those skilled in the art of organic/medicinal chemistry which have utility for the transformation of carboxylic acids such as (xviii) into carbamates (xix) or the related amines (iii). Transformation of carbamates (xix) into the corresponding amine (iii) is effected in a manner which depends upon the nature of the $R^a$ group. Typically, acidic conditions (~4M HCl in dioxane or ~1:1 TFA-CH$_2$Cl$_2$) are used for acid-labile carbamates ($R^a$=t-Bu). Benzylic carbamates are generally cleaved to the corresponding anilines by exposure to hydrogen gas in the presence of a noble metal catalyst such as Pd or Pt or by phase transfer hydrogenolysis. (*Synthesis*, 685 (1976).) Methods for transformation of amines (iii) into compounds of formula I are described in the other Schemes.

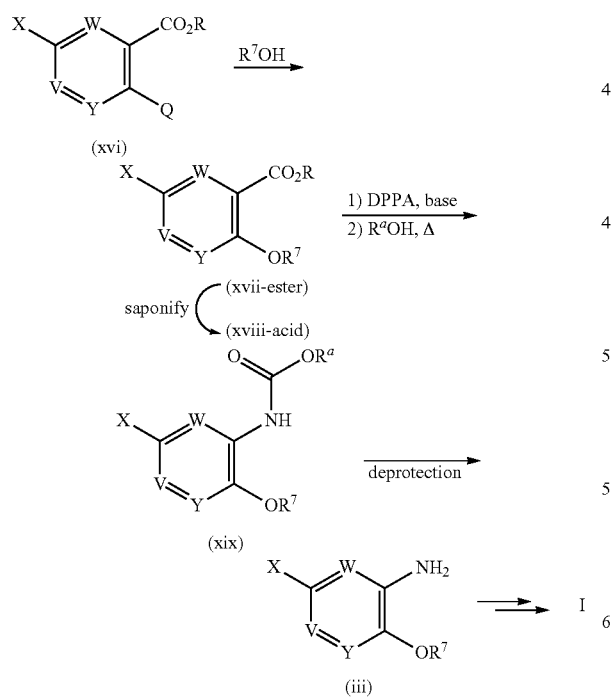

Scheme 6

Scheme 7 describes a preparation of compounds of the invention I similar to that of Scheme 6 in which the intermediate acid (xviii) is intercepted by an amine $R^8NH_2$ to generate urea intermediate (iv). Intermediate (iv) is further transformed using the Suzuki or related coupling into compounds of formula I.

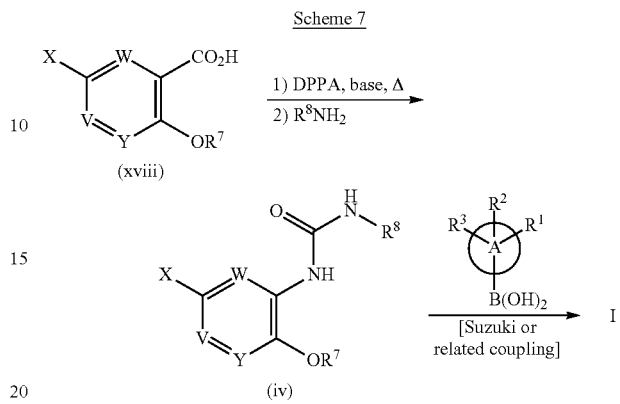

Scheme 7

Intermediates (v) are useful for preparation of further compounds of the invention as shown in Scheme 8. Treatment with a phenyl chloroformate derivative and a suitable base, generally in a solvent such as dichloromethane provides phenyl carbamate derivatives (xxiii). Where greater reactivity than that available with derivatives of phenyl chloroformate (R═H) is required, the related carbamates where R is an electron-withdrawing substituent such as a p-nitro group may be employed. Suitable bases include but are not limited to pyridines and aliphatic tertiary amines. These derivatives may be isolated or used in the next reaction without isolation. In any event, they react with amines $R^8NH_2$ to give compounds of formula I.

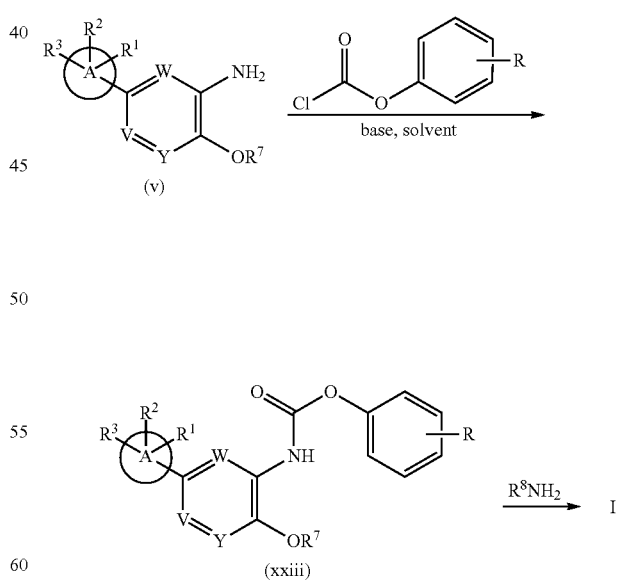

Scheme 8

In Scheme 9, an earlier aniline intermediate (iii) is converted into the corresponding urea derivative (iv) by the method shown in Scheme 8. Suzuki or related coupling reactions serve to transform this intermediate into compounds of formula I.

Scheme 9

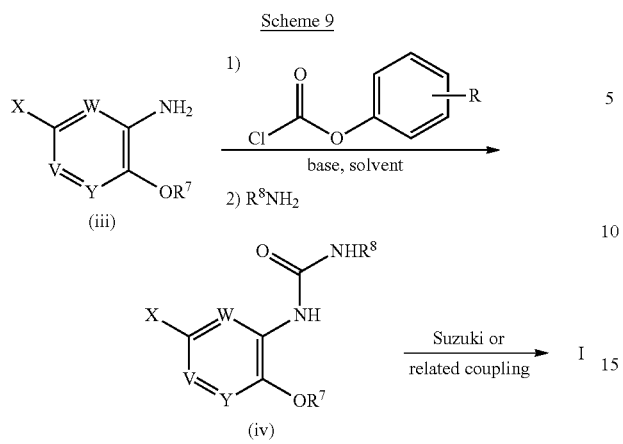

Scheme 10 describes a preparation of compounds of the invention starting from dibromoaniline or related dihaloheterocycles (xxv). Introduction of the RNHC=ONH group is accomplished as in the above Schemes to provide dibromourea (xxvi). This intermediate can undergo Suzuki or related coupling at the less hindered bromide to afford intermediate (xxvii). Finally, treatment with alcohol or phenol R⁷OH, preferably using the conditions of Buchwald, (Buchwald, Stephen L. *J. Org. Chem.* 2012, 77(5), 2543 and references therein) affords compounds of formula I.

Scheme 10

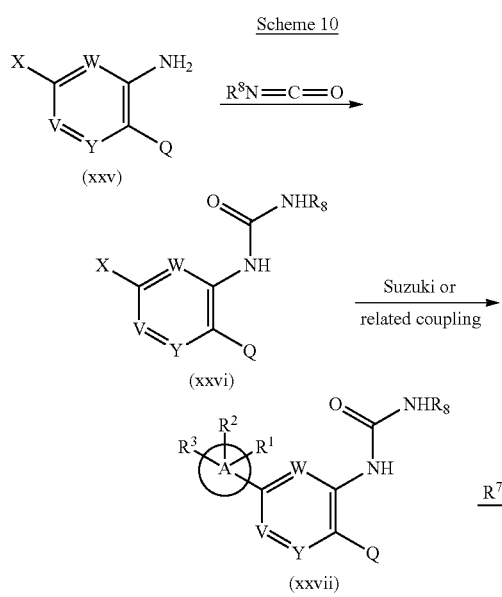

Intermediates prepared in the above Schemes may require further elaboration in order to be converted into compounds of the invention. Examples of this are provided in the following Schemes.

Scheme 11 illustrates the conversion of nitriles (xxviii) into tetrazoles of the invention (xxix). Typically, the nitrile is prepared by chemistry described above (often Suzuki coupling on an intermediate such as (iv) or (iii)) and heating with an azide such as tributyltinazide in a solvent such as toluene at or near the boiling point. This methodology may be used to prepare heteroaromatic tetrazole derivatives in addition to the phenyl derivatives shown.

Scheme 11

Scheme 12 illustrates the transformation of intermediates or compounds of the invention into further intermediates or compounds of the invention by functional group interconversions. Accordingly, alkyl ethers can be converted to phenols by treatment with Lewis acids such as BBr₃, preferably in a solvent such as CH₂Cl₂ or CH₂ClCH₂Cl. Re-alkylation affords new ether derivatives (xxx) in which the carboxylic acid has also been alkylated. Alternatively, phenols may be alkylated using the Mitsunobu reaction. (Reviewed in: Kumara Swamy, K. C. et al., "Mitsunobu and Related Reactions: Advances and Applications", *Chem. Rev.*, 109:2551-2651 (2009).). Further transformation affords carboxylic acids derivatives (xxxi) which may be compounds of formula I or protected intermediates which could be further transformed into compounds of formula I. The saponification reaction is generally accomplished by the use of an alkali metal hydroxide in aqueous or mixed aqueous/organic solvents. This methodology could be used to prepare heteroaromatic carboxylate derivatives in addition to the phenyl derivatives shown.

Scheme 12

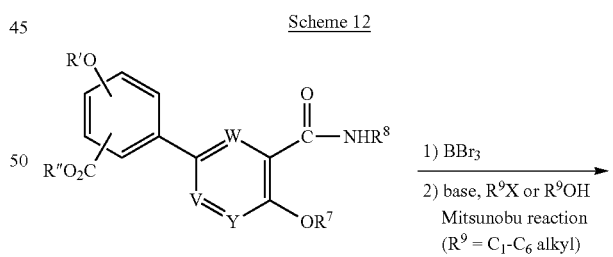

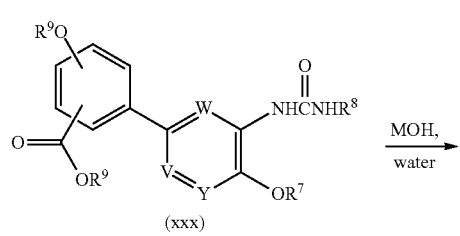

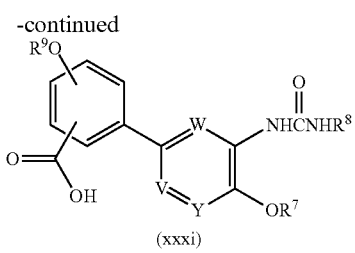

(xxxi)

These carboxylic acids can be derivatized (Scheme 13) to provide acylsulfonamides (xxxiii) which may be compounds of formula I or which may be transformed into compounds of formula I using chemistry described in the schemes above. Generally, the conversion of carboxylic acids to acylsulfonamides is accomplished using a coupling reagent such as CDI and a base such as DBU in a solvent such as DMF or THF. This methodology could be used to prepare heteroaromatic acylsulfonamide derivatives in addition to the phenyl derivatives shown.

Scheme 13

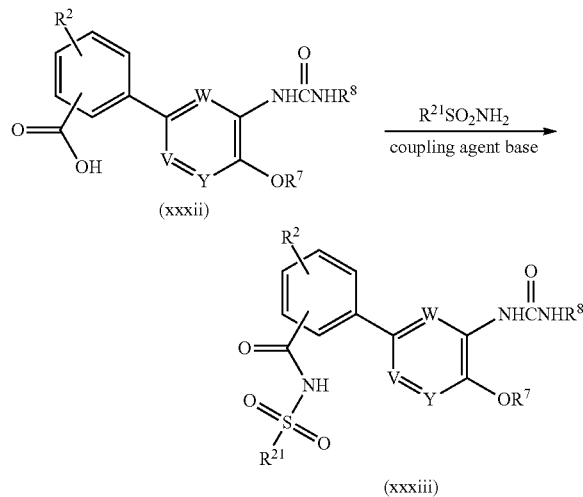

The methods described in the Schemes above can be used to prepare amine derivatives (xxxiv) which may be further elaborated by treatment with a base and an electrophile such as an acyl or sulfonyl chloride or a carboxylic or sulfonic acid anhydride or activated esters or the like to prepare carboxamide or sulfonamide compounds of formula I (Scheme 14). Alternatively, this derivitazation could be performed on an earlier intermediate which could be transformed into compounds of formula I using reactions described in the schemes above. This methodology could be used to prepare heteroaromatic amine derivatives in addition to the aniline derivatives shown.

Scheme 14

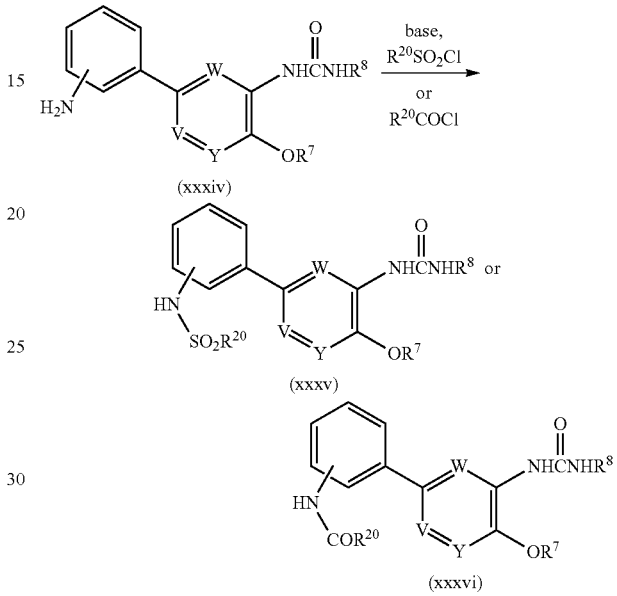

Scheme 15 describes a preparation of compounds of formula I in which Y is $CR^6$. Allylic ethers (iia), prepared as in Scheme 1 or by alkylation of a nitrophenol with an allylic halide, rearrange upon heating to afford C-alkylated phenols (xl). Typically this reaction is done in a high-boiling solvent such as xylene, mesitylene, digylme, or the like. Alternatively, ethers (iia) can be prepared from phenols and alcohols by the Mitsunobu reaction. Phenols (xl) can be realkylated to afford ethers (ii). Reduction affords anilines (iii), which can be processed into compounds of formula I by coupling under Suzuki or related conditions followed by treatment with an isocyanate. Alternatively, the order of the final two steps can be reversed.

Scheme 15

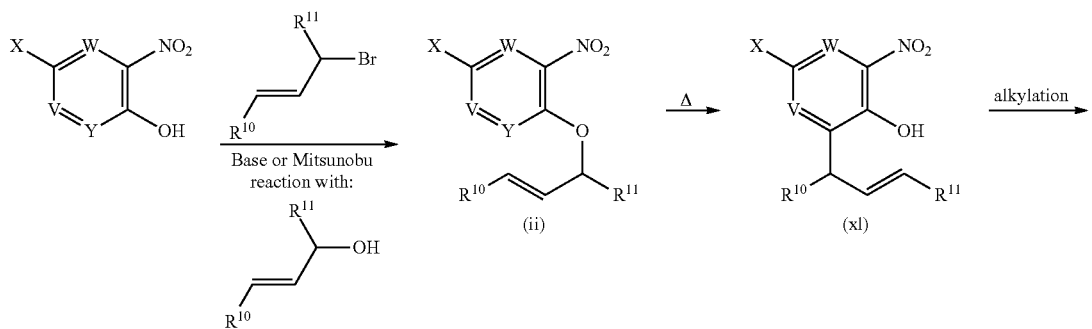

-continued

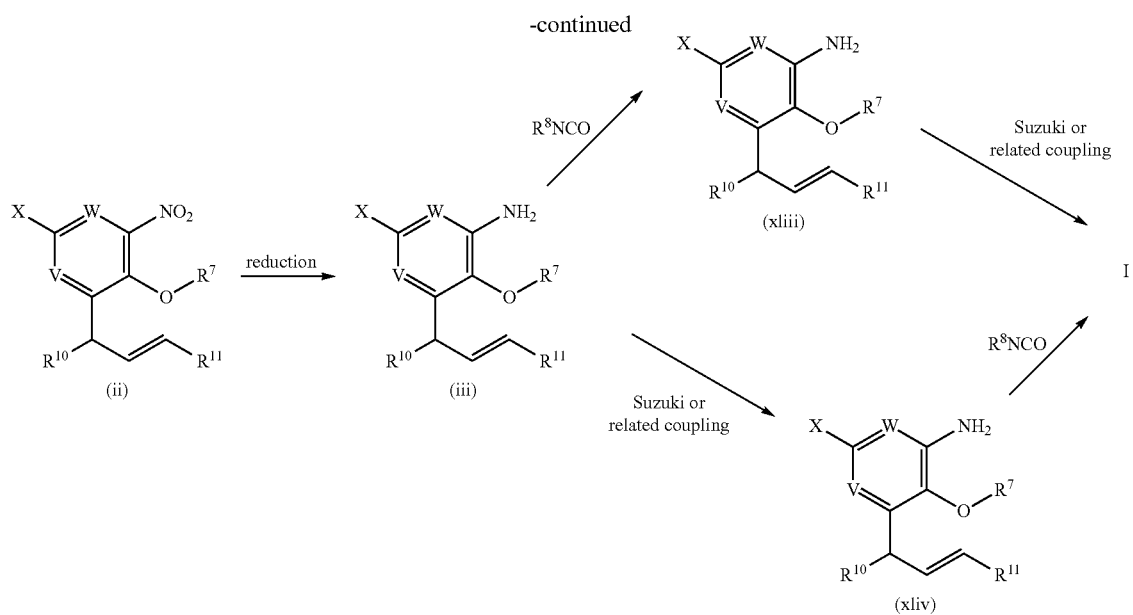

EXAMPLES

The invention is now described with reference to the following Examples. These Examples are provided for the purpose of illustration only and the invention should in no way be construed as being limited to these Examples but rather should be construed to encompass any and all variations which become evident as a result of the teaching provided herein.

General Experimental

Air- or moisture-sensitive reactions were generally performed under an atmosphere of nitrogen or argon in anhydrous solvents (EMD DRISOLV®). Zinc (−325 mesh) for nitro group reduction was obtained from Alfa Aesar. Reaction concentrations indicated in the tables and procedures are given in units of molar and are approximate. Temperatures are given in degrees Celsius. Reactions were monitored for completeness by thin layer chromatography (TLC) or tandem liquid chromatography-mass spectroscopy (LCMS). For TLC, 0.25 mm plates coated with Silica60/F254 were used with visualization by UV light at ~254 nM, exposure to iodine vapor, or heating with PMA (phosphomolybdic acid solution), ninhydrin in ethanol, anisaldehyde solution, or ceric ammonium molybdate solution.

Unless otherwise specified, "dried" refers to the addition of anhydrous $MgSO_4$ followed by filtration and rinsing the residual solids with an appropriate organic solvent. "Stripped" means concentration under reduced pressure, generally on a rotary evaporator. "Silica gel chromatography", "flash chromatography", or "chromatographed on silica gel" refers to glass column chromatography performed in a manner similar to that described by Still (J. Org. Chem., 43:2923 (1978)). Typically silica gel 60 (EMD, 230-400 mesh ASTM) is used with solvents from JT Baker or Mallinckrodt. HPLC refers to purification by reverse-phase high-performance liquid chromatography generally on C18 columns using the stated mobile phases. Analytical HPLC runs were performed using the columns, flow rates, and mobile phases indicated. It is understood that analytical HPLC retention times ($T_r$) are reported in minutes, and may be dependent on temperature, pH, and other factors. ISCO refers to chromatography on pre-packed silica gel cartridges using automated systems marketed by Teledyne Isco. For all chromatographic purifications the isolation of product by concentration of the appropriate fractions by evaporation at or below ambient pressure is implied. Melting points were determined on a Thomas-Hoover Uni-Melt apparatus and are uncorrected. Generally, mass spectral results are reported as the $(M+H)^+$ value. For halogenated compounds where two or more peaks are significant, m/z for one peak in the cluster, generally the most intense, is reported. $^1$H NMR spectra were recorded on dilute solutions at 400 or 500 MHz on VARIAN® or JEOL® instruments in the solvents indicated. Chemical shifts are reported in parts per million (ppm) downfield from internal tetramethylsilane (TMS) or from the position of TMS inferred by the deuterated NMR solvent. Apparent multiplicities are reported as: singlet-s, doublet-d, triplet-t, quartet-q, or multiplet-m. Peaks which exhibit broadening are further denoted as br. Integrations are approximate. It should be noted that integration intensities, peak shapes, chemical shifts and coupling constants can be dependent on solvent, concentration, temperature, pH, and other factors. Further, peaks which overlap with or exchange with water or solvent peaks in the NMR spectrum may not provide reliable integration intensities.

Unless otherwise specified, the various substituents of the compounds as employed herein are defined in the same manner as compounds of the invention of Formula (I).

For ease of reference, the following abbreviations are used herein.

| Abbreviations | |
|---|---|
| AcOH, HOAc | acetic acid |
| ACN | acetonitrile |
| $Ac_2O$ | acetic anhydride |
| ADDP | 1,1'-(azodicarbonyl)dipiperidine |
| aq. | aqueous |
| Bn | benzyl |
| Boc | t-butyl carbamate |

Abbreviations

| | |
|---|---|
| Boc₂O | di-t-butyl dicarbonate |
| Bu | butyl |
| Cbz | benzyl carbamate |
| conc. | concentrated |
| DCE | dichloroethane |
| DCM | dichloromethane |
| DIAD | diisopropyl azodicarboxylate |
| DIEA | N,N-diisopropylethylamine |
| DMAP | 4-N,N-dimethylaminopyridine |
| DMF | dimethylformamide |
| DMSO | dimethylsulfoxide |
| DMT-MM | 4-(4,6-dimethoxy-1,3,5-triazin-2-yl)-4-methylmorpholinium chloride |
| EDC | 1-(3-(dimethylamino)propyl)-3-ethylcarbodiimide hydrochloride |
| Et | ethyl |
| EtOAc | ethyl acetate |
| EtOH | ethanol |
| Et₂O | diethyl ether |
| Et₃N | triethylamine |
| Fmoc | 9-fluorenylmethyl carbamate |
| h | hour(s) |
| HATU | O-(7-azabenzotriazol-1-yl)-N,N,N',N'-tetramethyluronium hexafluorophosphate |
| HOAt | 1-hydroxy-7-azabenzotriazole |
| HPLC | high performance liquid chromatography |
| i-PrOH | isopropanol |
| KOAc | potassium acetate |
| LAH | Lithium aluminum hydride |
| min | minute(s) |
| Me | methyl |
| MeCN | acetonitrile |
| MeOH | methanol |
| Me₂NH | dimethylamine |
| NaHMDS | sodium bis(trimethylsilyl)amide |
| Na(OAc)₃BH | sodium triacetoxyborohydride |
| n-BuLi | n-butyllithium |
| NCS | N-chlorosuccinimide |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| Pd(dppf)₂Cl₂ | [1,1'-bis(diphenylphosphino)ferrocene]dichloropalladium(II) |
| Pd(OAc)₂ | palladium acetate |
| Pd(PPh₃)₄ | tetrakis(triphenylphosphine)palladium |
| Pd₂(dba)₃ | tris(dibenzylideneacetone)dipalladium(0) |
| PE | Petroleum ether |
| Ph | phenyl |
| PhMe | toluene |
| Ph₂TfN | 1,1,1-trifluoro-N-phenyl-N-(trifluoromethyl)sulfonyl methanesulfonamide |
| PPh₃ | triphenyl phosphine |
| RB | Round-bottom flask |
| rt | room temperature |
| sat. | saturated |
| t-Bu | tertiary butyl |
| t-BuOH | tertiary butanol |
| TFA | trifluoroacetic acid |
| Tf₂O | trifluoromethylsulfonic anhydride |
| THF | tetrahydrofuran |
| TMS | trimethylsilyl |
| TsO | p-toluenesulfonyl |

Analytical HPLC Conditions:

[a]Waters Sunfire C18 4.6×150 mm 3.5μ. 1 mL/min, 10-90% methanol-water 0.2% H₃PO₄, gradient over 15 min.

[b]Waters Sunfire C18 4.6×150 mm 3.5μ. 1 mL/min, 10-90% methanol-water 0.2% H₃PO₄, gradient over 10 min.

[c]YMC S5 ODS, 4.6×50 mm. 4 mL/min, 10-90% methanol-water 0.2% H₃PO₄, gradient over 12 min.

[d]Waters X-Bridge Phenyl 4.6×150 mm 3.5μ, 1 mL/min, 10-90% methanol-water 0.2% H₃PO₄, gradient over 10 min.

[e]YMC S5 ODS, 4.6×50 mm. 4 mL/min, 10-90% methanol-water 0.2% H₃PO₄, gradient over 4 min.

[f]YMC S5 ODS, 4.6×50 mm. 1 mL/min, 10-90% methanol-water 0.2% H₃PO₄, gradient over 15 min.

[g]Sunfire C18 3.0×150 mm 3.5μ. 0.5 mL/min, 14-95% acetonitrile-water, 0.05% TFA, gradient over 12 min.

[h]YMC pro c18 S5 ODS, 4.6×50 mm. 4 mL/min, 10-90% methanol-water 0.2% H₃PO₄, gradient over 12 min.

[i]SUPELCO® Ascentis 4.6×50 mm, 2.7 μC18, 4 mL/min, 5-95% acetonitrile-water, 10 mM NH₄OAc, gradient over 4 min. (Column temp.=35° C.)

[j]Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

[k]Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[l]Luna C18, 4.6×30 mm, 3-μm particles; 10-90% MeOH-water (0.1% TFA in both phases) gradient over 5 min. Flow: 4 mL/min.

[m]ZORBAX® SB C18, 4.6×75 mm, 50-90% MeOH-water (0.1% TFA in both phases) gradient over 8 min. Flow: 2.5 mL/min.

[n]YMC S5 ODS, 4.6×50 mm. 4 mL/min, 10-90% methanol-water 0.05% TFA, gradient over 4 min.

[o]Luna C18, 4.6×30 mm, 3-μm particles; 10-86% CH₃CN-water (10 mM NH₄OAc in both phases) gradient over 2 min. Flow: 4 mL/min.

[p]Luna C18, 4.6×30 mm, 3-μm particles; 10-85.5% MeOH-water (0.1% TFA in both phases) gradient over 2 min. Flow: 4 mL/min.

[q]Luna C18, 4.6×30 mm, 3-μm particles; 10-90% MeOH-water (0.1% TFA in both phases) gradient over 3.5 min. Flow: 4 mL/min.

[r]PHENOMENEX®, 2.0×30 mm, 2.5-μm particles; 26-90% MeOH-water (0.1% TFA in both phases) gradient over 3 min. Flow: 1 mL/min.

[s]Waters Acquity UPLC BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Temperature: 50° C.; Gradient: 0-100% B over 3 minutes, then a 0.75-minute hold at 100% B; Flow: 1.11 mL/min.

[t]Column: Xbridge (150×4.6 mm), 3.5μ; Method: 0.05% TFA in water pH2.5; Mobile Phase A: Buffer: acetonitrile (95:5) Mobile Phase B: acetonitrile: Buffer (95:5) Flow: 1.0 ml/min.

[u]Column: Sunfire (150×4.6 mm), Method: 0.05% TFA in water pH2.5 Mobile Phase A: Buffer: acetonitrile (95:5) Mobile Phase B: acetonitrile: Buffer (95:5) Flow: 1.0 ml/min.

[v]Column: Ascentis Express C8 (5×2.1 mm) 2.7 μM particles, 10 mM in ammonium formate. 98:2 to 2:98 water-acetonitrile gradient over 1.5 min. Flow: 1.0 ml/min.

Example 1

4'-(2-tert-Butylphenoxy)-4-chloro-3'-(3-p-tolylureido)biphenyl-3-carboxylic acid

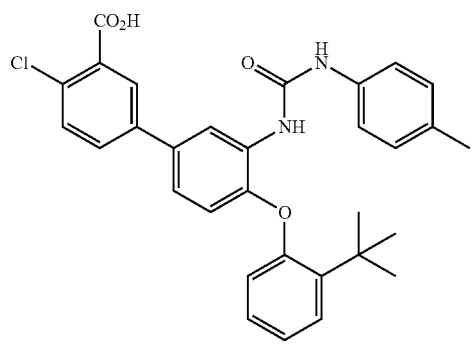

1A. 4-Bromo-1-(2-tert-butylphenoxy)-2-nitrobenzene

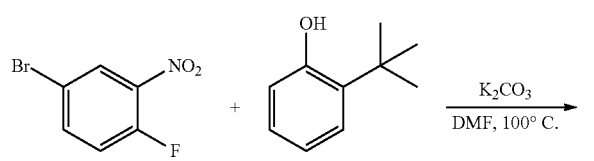

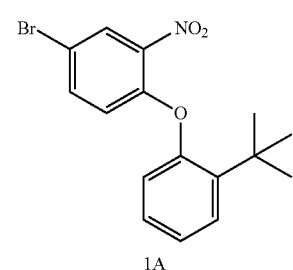

1A

To a stirred solution of 4-bromo-1-fluoro-2-nitrobenzene (4.40 g, 20 mmol) and 2-tert-butylphenol (3.06 g, 20.40 mmol) in DMF (Volume: 20 mL) was added potassium carbonate (5.53 g, 40.0 mmol). The mixture was heated to 100° C. and stirred for 4 h. The reaction was cooled, diluted with water, and extracted with 1:1 EtOAc-hexanes. The organic extract was dried and stripped to afford 6.9 g (99%) of 4-bromo-1-(2-tert-butylphenoxy)-2-nitrobenzene (1A) as an oil which solidified on the pump to give large crystals with a bit of residual oil. mp. 59-61° C. HPLC $T_r$: 15.4 min.[b] 1H NMR (400 MHz, DMSO-$d_6$) δ ppm 8.29 (d, 1H, J=2.4 Hz); 7.81 (dd, 1H, J=8.9, 2.3 Hz); 7.46 (dd, 1H, J=7.8, 1.9 Hz); 7.18-7.47 (m, 2H); 6.94 (dd, 1H, J=8.1, 1.6 Hz); 6.89 (d, 1H, J=8.9 Hz); 1.33 (s, 9H).

1B. 5-Bromo-2-(2-tert-butylphenoxy)aniline

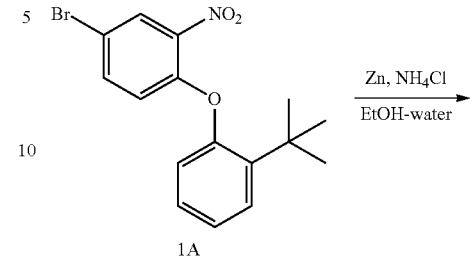

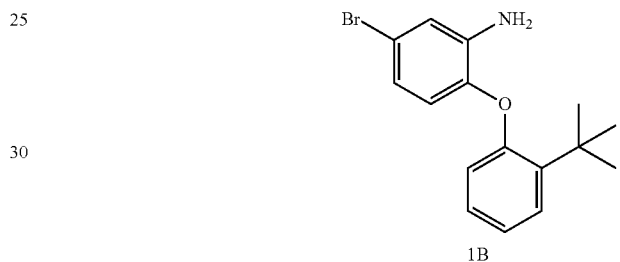

To a stirred solution of 4-bromo-1-(2-tert-butylphenoxy)-2-nitrobenzene (6 g, 17.13 mmol) in ethanol (Volume: 30 mL) was added zinc (11.21 g, 171 mmol) and ammonium chloride (9.16 g, 171 mmol) followed by 10 mL of water. The mixture was brought to reflux briefly then cooled to RT over 1 h with stirring. The reaction was diluted with chloroform, filtered, and the filtrate was washed with water, dried, and stripped to afford 8.6 g (99%) of 5-bromo-2-(2-tert-butylphenoxy)aniline (1B), as a waxy tan solid, mp. 91-92° C. MS(ES): m/z=322 [M+H]+. 1H NMR (400 MHz, DMSO-$d_6$) δ ppm 7.36 (1H, dd, J=7.9, 1.5 Hz), 7.15 (1H, td, J=7.7, 1.5 Hz), 7.03 (1H, td, J=7.5, 1.3 Hz), 6.96 (1H, d, J=2.4 Hz), 6.65 (1H, dd, J=8.0, 1.2 Hz), 6.61 (1H, dd, J=8.4, 2.4 Hz), 6.46 (1H, d, J=8.6 Hz), 5.18 (2H, s), 1.39 (9H, s).

1C. 1-(5-Bromo-2-(2-tert-butylphenoxy)phenyl)-3-p-tolylurea

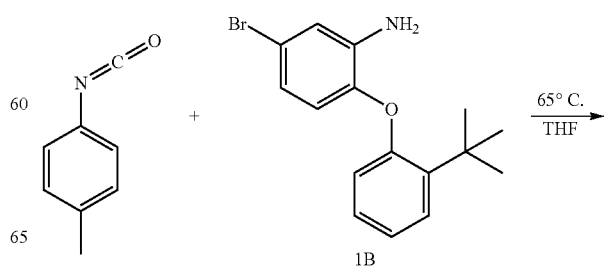

-continued

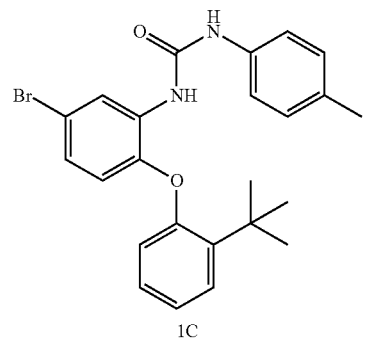

1C

To a stirred solution of 5-bromo-2-(2-tert-butylphenoxy) aniline (0.17 g, 0.531 mmol) in THF (3 mL) was added 1-isocyanato-4-methylbenzene (0.141 g, 1.062 mmol). The solution was stirred 22 h at 65° C. then cooled and treated with 0.2 mL of N,N-dimethylethylenediamine. The reaction was diluted with aq. HCl and extracted twice with chloroform. The combined organic extracts were dried and stripped to afford an oil. The crude product was purified by flash chromatography (gradient elution with EtOAc-hexanes) to afford 0.24 g (95%) of 1-(5-bromo-2-(2-tert-butylphenoxy)phenyl)-3-p-tolylurea (1C) as an oil which solidified upon standing. $^1$H NMR (400 MHz, DMSO-$d_6$) δ ppm 9.36 (1H, s), 8.56 (1H, s), 8.50 (1H, d, J=2.4 Hz), 7.47 (1H, dd, J=7.8, 1.7 Hz), 7.34 (2H, d, J=8.6 Hz), 7.22-7.30 (1H, m), 7.14-7.21 (1H, m), 7.10 (2H, d, J=8.1 Hz), 7.07 (1H, dd, J=8.6, 2.4 Hz), 6.85 (1H, dd, J=8.0, 1.4 Hz), 6.52 (1H, d, J=8.8 Hz), 2.25 (3H, s), 1.39 (9H, s). MS(ES): m/z=455 [M+H]$^+$.

1. 4'-(2-tert-Butylphenoxy)-4-chloro-3'-(3-p-tolylureido)biphenyl-3-carboxylic acid

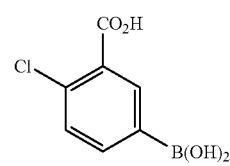

+

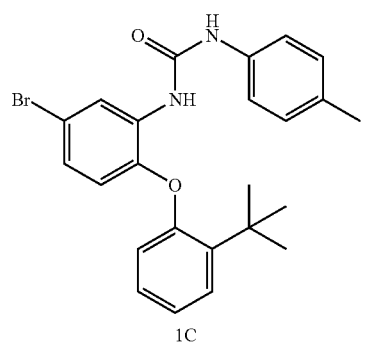

1C

Pd(Ph$_3$P)$_4$
K$_2$CO$_3$, 100° C.
DMF, water,

-continued

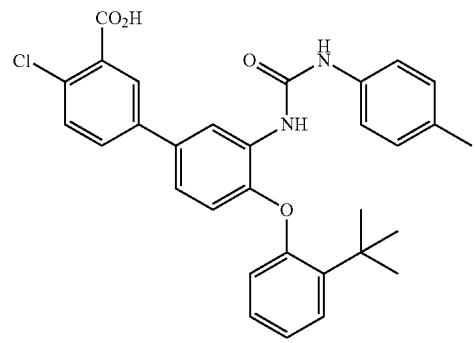 [SMILES: Cc1ccc(NC(=O)Nc2cc(-c3ccc(Cl)c(C(=O)O)c3)ccc2Oc2ccccc2C(C)(C)C)cc1]

1

A suspension of 5-borono-2-chlorobenzoic acid (0.027 g, 0.132 mmol) and 1-(5-bromo-2-(2-tert-butylphenoxy)phenyl)-3-p-tolylurea (0.03 g, 0.066 mmol) and tetrakis(triphenylphosphine)palladium(0) (7.65 mg, 6.62 μmol) in degassed DMF (1 mL) was treated with aq. potassium carbonate (0.22 mL, 0.331 mmol). The mixture was placed under nitrogen, heated at 100° C. for 2 h, then cooled. The reaction was diluted with aq. HOAc and extracted twice with chloroform. The combined organic extract was dried, stripped, and purified by Prep. HPLC (Axia Luna 21×100 mm column, MeOH-water-TFA gradient). The appropriate fraction was partially concentrated, and product was precipitated by addition of a little water. The resulting solid was filtered, rinsed with water and air-dried to afford 0.007 g (20%) of 4'-(2-tert-butylphenoxy)-4-chloro-3'-(3-p-tolylureido)biphenyl-3-carboxylic acid (1) as a white powder. $^1$H NMR (400 MHz, DMSO-$d_6$) δ ppm 9.34 (1H, s), 8.62 (1H, d, J=2.2 Hz), 8.52 (1H, s), 7.90-7.97 (1H, m), 7.70-7.78 (1H, m), 7.58-7.64 (1H, m), 7.48 (1H, dd, J=7.9, 1.5 Hz), 7.36 (2H, d, J=8.4 Hz), 7.22-7.31 (2H, m), 7.14-7.21 (1H, m), 7.10 (2H, d, J=8.4 Hz), 6.90 (1H, d, J=1.1 Hz), 6.68 (1H, d, J=8.6 Hz), 2.25 (3H, s), 1.42 (9H, s). MS(ES): m/z=529 [M+H]$^+$.

Using the methods described for the preparation of 1B, the aniline intermediates iii shown in Table 1 were prepared.

TABLE 1

| | X | W | V | Y | R$^7$ | (M + H)$^+$ | HPLC T$_r^{method}$ |
|---|---|---|---|---|---|---|---|
| iiia | Br | CH | CH | CH | phenyl | 266 | 3.70[1] |
| iiib | Br | CH | CH | CH | 3-chlorophenyl | 300 | 4.24[1] |

TABLE 1-continued

X-W=N-V-Y with NH₂ and OR⁷ substituents

| | X | W | V | Y | R⁷ | (M+H)⁺ | HPLC T_r^method |
|---|---|---|---|---|---|---|---|
| iiic | Br | CH | CH | CH | 4-chlorophenyl | 300 | 4.19¹ |
| iiid | Br | CH | CH | CH | 2-(trifluoromethyl)phenyl | 334 | 4.23¹ |
| iiie | Br | CH | CH | CH | 2,6-dichlorophenyl | 334 | 4.01¹ |
| iiif | Br | CH | CH | CH | 2-ethylphenyl | 294 | 4.25¹ |
| iiig | Br | CH | CH | CH | 2-tert-butyl-6-methylphenyl | 336 | 4.76¹ |
| iiih | Br | CH | CH | CH | 2-isopropylphenyl | 308 | 4.43¹ |
| iiii | Br | CH | CH | CH | 2-chlorophenyl | 300 | 4.03¹ |
| iiij | Br | CH | CH | CH | 2-methoxyphenyl | 296 | 3.47¹ |
| iiik | Br | CH | CH | CH | 2-propylphenyl | 308 | 3.77¹ |
| iiil | Br | CH | CH | CH | 2-cyanophenyl | 291 | 3.48¹ |
| iiim | Br | CH | CH | CH | 2-methylphenyl | 280 | 3.96¹ |
| iiin | Br | CH | CH | CH | 3-tert-butylphenyl | 322 | 4.59¹ |
| iiio | Br | CH | CH | CH | 5,6,7,8-tetrahydronaphthalen-1-yl | 320 | 4.69¹ |
| iiip | Br | CH | CH | CH | 2,3-dimethylphenyl | 294 | 4.34¹ |
| iiiq | Br | CH | CH | CH | 3-(prop-2-yn-1-yloxy)phenyl | 320 | 4.01¹ |
| iiir | Br | CH | CH | CH | naphthalen-1-yl | 316 | 4.49¹ |
| iiis | Br | CH | CH | CH | 2-cyclopropylphenyl | 304 | 4.34¹ |
| iiiu | Br | CH | CH | CH | 2,3-dihydro-1H-inden-4-yl | 306 | 4.48¹ |

TABLE 1-continued

| | X | W | V | Y | R[7] | (M + H)[+] | HPLC T[r][method] |
|---|---|---|---|---|---|---|---|
| iiiv | Br | CH | CH | CH | (tetrahydronaphthyl) | 320 | 4.73[l] |
| iiix | Br | CH | CH | N | (phenyl) | 267 | 3.13[l] |
| iiiy | Br | CH | CH | N | (2-tert-butylphenyl) | 323 | 4.16[l] |

Example 2

4'-(2-tert-Butylphenoxy)-3'-(3-p-tolylureido)biphenyl-2-carboxylic acid

2A. 3'-Amino-4'-(2-tert-butylphenoxy)biphenyl-2-carboxylic acid

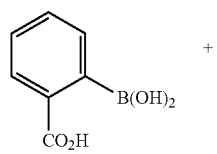

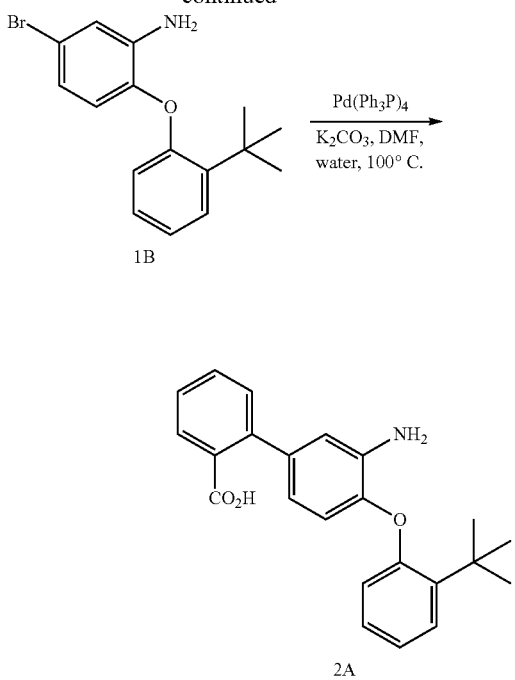

A suspension of 5-bromo-2-(2-tert-butylphenoxy)aniline (1B) (0.5 g, 1.561 mmol) and 2-boronobenzoic acid (0.389 g, 2.342 mmol) and tetrakis(triphenylphosphine)palladium (0) (0.054 g, 0.047 mmol) in degassed DMF (Volume: 8 mL) was treated with aq. potassium carbonate (4.16 mL, 6.25 mmol). The mixture was placed under nitrogen and heated to 100° C. for 2 h. The reaction was cooled, brought to pH 3 with aq. HCl, and extracted twice with dichloromethane. The combined organic extract was dried, stripped, and chromatographed on silica gel (gradient elution with EtOAc-hexanes-1% HOAc) to afford 0.41 g (69%) of 3'-amino-4'-(2-tert-butylphenoxy)biphenyl-2-carboxylic acid (2A) as a yellow glass. $^1$H NMR (400 MHz, DMSO-d$_6$) δ ppm 7.63 (dd, 1H, J=7.7, 1.3 Hz); 7.52 (dd, 1H, J=7.6, 1.5 Hz); 7.33-7.43 (m, 3H); 7.13-7.19 (m, 1H); 6.99-7.04 (m, 1H); 6.81 (d, 1H, J=2.0 Hz); 6.66 (dd, 1H, J=8.1, 1.3 Hz); 6.61 (d, 1H, J=8.1 Hz); 6.48 (dd, 1H, J=8.1, 2.2 Hz); 4.90 (br. s, 2H); 1.43 (s, 9H). MS(ES): m/z=362 [M+H][+].

2. 4'-(2-tert-Butylphenoxy)-3'-(3-p-tolylureido)biphenyl-2-carboxylic acid

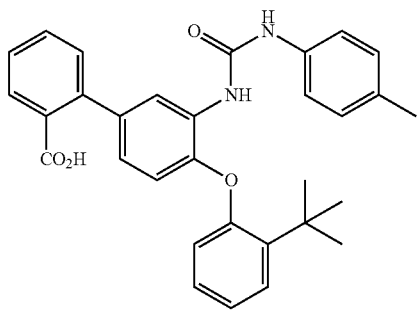 [SMILES: Cc1ccc(NC(=O)Nc2cc(-c3ccccc3C(=O)O)ccc2Oc2ccccc2C(C)(C)C)cc1]

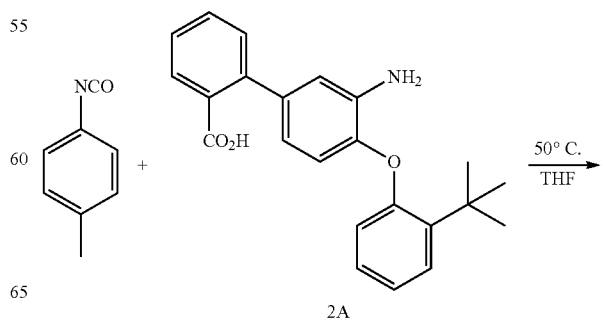

-continued

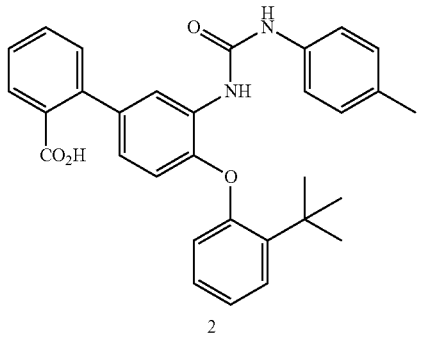

2

To a stirred solution of 3'-amino-4'-(2-tert-butylphenoxy) biphenyl-2-carboxylic acid (2A) (0.015 g, 0.042 mmol) in THF (0.3 mL) was added 1-isocyanato-4-methylbenzene (8.29 mg, 0.062 mmol). The solution was stirred 1 h at 50° C. then cooled and purified by prep. HPLC (Axia Luna 21×100 mm column, MeOH-water-TFA gradient). Concentration of the appropriate fraction afforded 0.015 g (73%) of 4'-(2-tert-butylphenoxy)-3'-(3-p-tolylureido)biphenyl-2-carboxylic acid (2) as a white powder. $^1$H NMR (400 MHz, DMSO-$d_6$) δ ppm 9.30 (s, 1H); 8.43 (s, 1H); 8.31 (d, 1H, J=2.2 Hz); 7.69 (dd, 1H, J=7.5, 0.9 Hz); 7.56 (td, 1H, J=7.5, 1.3 Hz); 7.43-7.48 (m, 2H); 7.40 (td, 1H, J=7.7, 1.0 Hz); 7.33 (2H, d, J=8.6 Hz), 7.26 (td, 1H, J=7.6, 1.8 Hz); 7.15 (td, 1H, J=7.6, 1.3 Hz); 7.08 (d, 2H, J=8.4 Hz); 6.87 (dd, 1H, J=8.4, 2.4 Hz); 6.83 (dd, 1H, J=7.9, 1.3 Hz); 6.63 (1H, d, J=8.4 Hz); 2.23 (s, 3H); 1.43 (s, 9H). MS(ES): m/z=495 [M+H]$^+$.

Using the method described for the conversion of 1B into 1C, the urea intermediates iv shown in Table 2 were prepared.

TABLE 2

| | X | W | V | Y | R$^8$ | R$^7$ | (M + H)$^+$ | HPLC T$_r^{method}$ |
|---|---|---|---|---|---|---|---|---|
| iva | Br | CH | CH | CH | -C$_6$H$_4$-OCF$_3$ (para) | 2-tert-butylphenyl | 525 | 5.00$^l$ |
| ivb | Br | CH | CH | CH | -C$_6$H$_4$-OCF$_3$ (para) | 2-chlorophenyl | 503 | 5.05$^l$ |
| ivc | Br | CH | CH | CH | 2-chlorophenyl | 2-trifluoromethylphenyl | 487 | 2.77$^q$ |
| ivd | Br | CH | CH | N | 4-methylphenyl | phenyl | 400 | 2.67$^q$ |

Example 3

5-(5-(3-(2-Chlorophenyl)ureido)-4-methyl-6-(5,6,7,8-tetrahydronaphthalen-1-yloxy)pyridin-3-yl)-2-methoxybenzoic acid

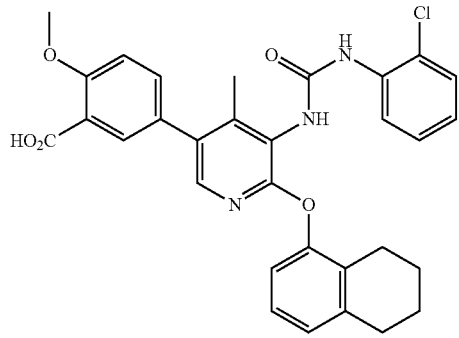 [SMILES: COc1ccc(-c2cnc(Oc3cccc4c3CCCC4)c(NC(=O)Nc3ccccc3Cl)c2C)cc1C(=O)O]

3A. 5-Bromo-4-methyl-3-nitro-2-(5,6,7,8-tetrahydronaphthalene-1-yloxy)pyridine

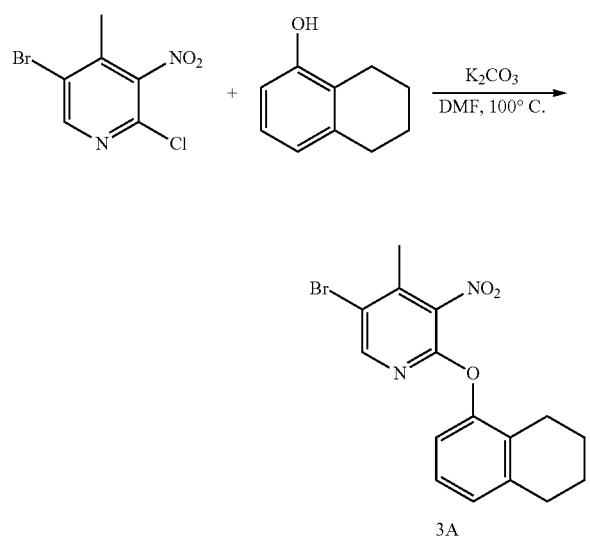

To a solution of 5,6,7,8-tetrahydronaphthalen-1-ol (0.148 g, 1.000 mmol) and 5-bromo-2-chloro-4-methyl-3-nitropyridine (0.251 g, 1 mmol) in DMF (Volume: 4 mL) was added potassium carbonate (0.276 g, 2.000 mmol). The mixture was warmed to 100° C. for 4 h then cooled and diluted with water. This dark suspension was extracted twice with dichloromethane, and the combined organic extract dried and stripped to afford a dark oil. Chromatography on silica gel (gradient elution with ether-hexanes) afforded 0.2 g (50%) of 5-bromo-4-methyl-3-nitro-2-(5,6,7,8-tetrahydronaphthalen-1-yloxy)pyridine (3A) as an oily solid. $^1$H NMR (400 MHz, DMSO-$d_6$) δ ppm 8.46 (s, 1H); 7.15 (t, 1H, J=7.7 Hz); 7.01 (d, 1H, J=7.5 Hz); 6.93 (d, 1H, J=7.5 Hz); 2.72-2.77 (m, 2H); 2.37-2.42 (m, 5H); 1.63-1.71 (m, 4H). MS(ES): m/z=365 [M+H]$^+$.

3B. 2-Methoxy-5-(4-methyl-5-nitro-6-(5,6,7,8-tetrahydronaphthalen-1-yloxy)pyridin-3-yl)benzoic acid

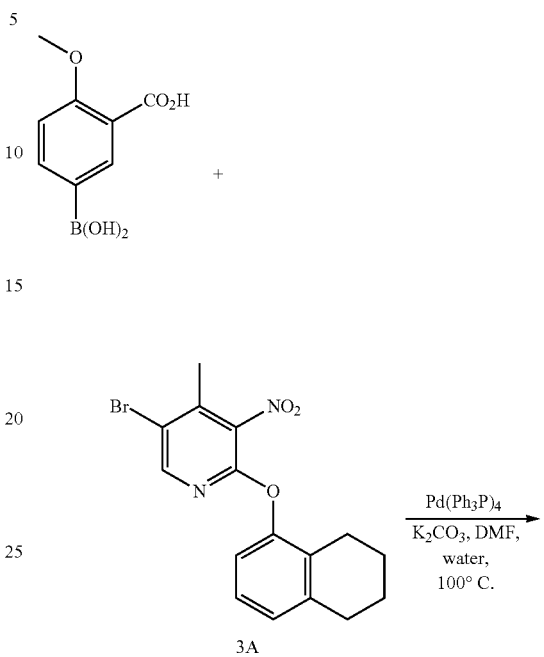

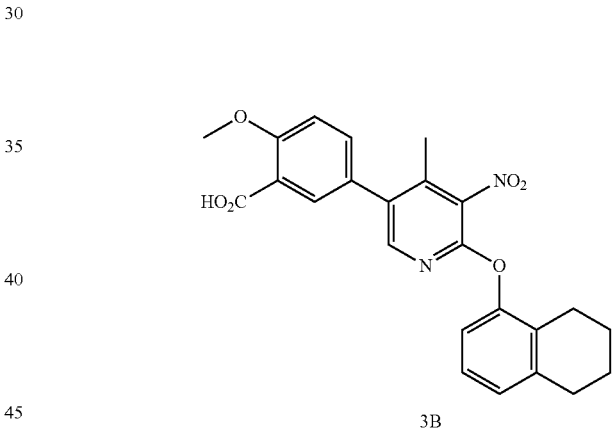

To a suspension of 5-borono-2-methoxybenzoic acid (0.067 g, 0.340 mmol) and 5-bromo-4-methyl-3-nitro-2-(5,6,7,8-tetrahydronaphthalen-1-yloxy)pyridine (3A) (0.073 g, 0.2 mmol) and tetrakis(triphenylphosphine)palladium (0) (0.012 g, 10.00 µmol) in degassed DMF (Volume: 2 mL) was added aq. potassium carbonate (0.667 mL, 1.000 mmol). The mixture was placed under nitrogen and heated to 100° C. for 2 h. The reaction was cooled, brought to pH 3 with aq. HOAc, and extracted twice with dichloromethane. The combined organic extract was dried and stripped to afford an oily yellow solid. Chromatography on silica gel (gradient elution with EtOAc-hexanes-1% HOAc) afforded 0.08 g (92%) of 2-methoxy-5-(4-methyl-5-nitro-6-(5,6,7,8-tetrahydronaphthalen-1-yloxy)pyridin-3-yl)benzoic acid (3B) as a tan foam. $^1$H NMR (400 MHz, DMSO-$d_6$) δ ppm 8.12 (s, 1H); 7.63 (d, 1H, J=2.2 Hz); 7.57 (dd, 1H, J=8.6, 2.4 Hz); 7.23 (d, 1H, J=8.6 Hz); 7.16 (t, 1H, J=7.7 Hz); 7.01 (d, 1H, J=7.3 Hz); 6.94 (d, 1H, J=7.7 Hz); 3.86 (s, 3H); 2.73-2.79 (m, 2H); 2.42-2.46 (m, 2H); 2.24 (s, 3H); 1.65-1.73 (m, 4H). MS(ES): m/z=435 [M+H]$^+$.

3C. 5-(5-Amino-4-methyl-6-(5,6,7,8-tetrahydronaphthalen-1-yloxy)pyridin-3-yl)-2-methoxybenzoic acid

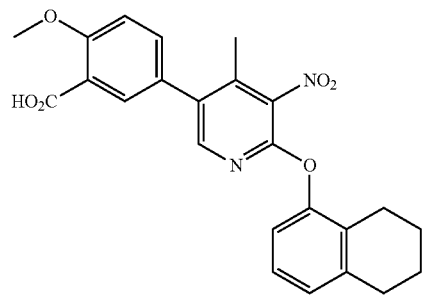

3. 5-(5-(3-(2-Chlorophenyl)ureido)-4-methyl-6-(5,6,7,8-tetrahydronaphthalen-1-yloxy)pyridin-3-yl)-2-methoxybenzoic acid

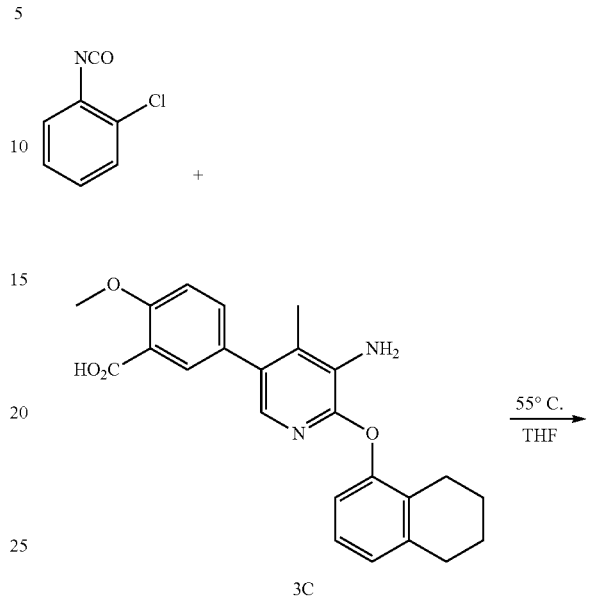

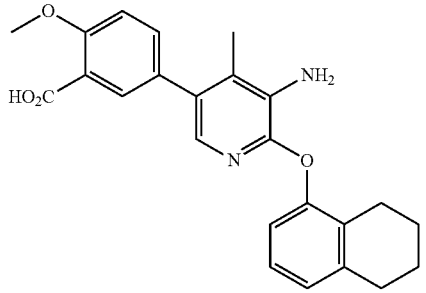

To a stirred solution of 2-methoxy-5-(4-methyl-5-nitro-6-(5,6,7,8-tetrahydronaphthalen-1-yloxy)pyridin-3-yl)benzoic acid (3B) (0.08 g, 0.184 mmol) in ethanol (Volume: 4 mL) was added 1 mL of water. The mixture was brought to reflux then treated with zinc (0.120 g, 1.841 mmol) and ammonium chloride (0.099 g, 1.841 mmol). This mixture was stirred 1 h, cooling to RT then diluted with dichloromethane and filtered. The filtrate was washed with water, dried, and stripped to afford 0.063 g (80%) 5-(5-amino-4-methyl-6-(5,6,7,8-tetrahydronaphthalen-1-yloxy)pyridin-3-yl)-2-methoxybenzoic acid (3C) as an off-white foam. $^1$H NMR (400 MHz, DMSO-$d_6$) δ ppm 7.46 (br. s, 1H); 7.32-7.42 (br. m, 1H); 7.05-7.16 (m, 3H); 6.90 (d, 1H, J=7.5 Hz); 6.79 (d, 1H, J=7.5 Hz); 5.03 (br. s, 2H); 3.82 (s, 3H); 2.72-2.78 (m, 2H); 2.48-2.56 (m, integration not determined); 2.05 (s, 3H); 1.66-1.73 (m, 4H). MS(ES): m/z=405 [M+H]$^+$.

To a stirred solution of 5-(5-amino-4-methyl-6-(5,6,7,8-tetrahydronaphthalen-1-yloxy)pyridin-3-yl)-2-methoxybenzoic acid (3C) (0.012 g, 0.030 mmol) in THF (Volume: 0.3 mL) was added 1-chloro-2-isocyanatobenzene (9.11 mg, 0.059 mmol). The solution was stirred 1 h at 55° C. then cooled and purified by prep. HPLC (Axia 21×100 mm column, MeOH-water-TFA gradient). Concentration of the appropriate fraction afforded 0.012 g (69%) of 5-(5-(3-(2-chlorophenyl)ureido)-4-methyl-6-(5,6,7,8-tetrahydronaphthalen-1-yloxy)pyridin-3-yl)-2-methoxybenzoic acid (3) as a white powder. $^1$H NMR (400 MHz, DMSO-$d_6$) δ ppm 12.70 (br. s, 1H); 8.87 (s, 1H); 8.58 (s, 1H); 8.18 (dd, 1H, J=8.4, 1.3 Hz); 7.77 (s, 1H); 7.57 (d, 1H, J=2.4 Hz); 7.50 (dd, 1H, J=8.6, 2.4 Hz); 7.45 (dd, 1H, J=7.9, 1.3 Hz); 7.28 (td, 1H, J=7.8, 1.3 Hz); 7.22 (d, 1H, J=8.8 Hz); 7.11 (t, 1H, J=7.8 Hz); 7.01 (td, 1H, J=7.7, 1.5 Hz); 6.94 (d, 1H, J=7.7 Hz); 6.87 (d, 1H, J=7.9 Hz); 3.86 (s, 3H); 2.71-2.78 (m, 2H); 2H not accounted for-likely under solvent peak; 2.18 (s, 3H); 1.63-1.72 (m, 4H). MS(ES): m/z=558 [M+H]$^+$.

Using the methods described for the preparation of 1C, the biaryl intermediates v shown in Table 3 were prepared.

TABLE 3

Reaction scheme: Compound (iii) with X=Br reacts with A-B(OH)$_2$ reagent (bearing R$^1$, R$^2$, R$^3$ substituents), K$_2$CO$_3$, DMF-water, 95-100° C. to give compound (v).

| | W | V | Y | A (with R$^1$, R$^2$, R$^3$) | R$^7$ | (M + H)$^+$ | HPLC Tr |
|---|---|---|---|---|---|---|---|
| va | CH | CH | CH | 3-(CO$_2$H)phenyl | 2-tert-butylphenyl | 362 | 4.03$^l$ |
| vb | CH | CH | CH | 3-(CO$_2$H)phenyl | phenyl | 306 | 3.43$^l$ |
| vc | CH | CH | CH | 3-(CO$_2$H)-5-chlorophenyl | 2-tert-butylphenyl | 396 | 4.81$^l$ |
| vd | CH | CH | CH | 3-(CO$_2$H)phenyl | 3-chlorophenyl | 340 | 3.96$^l$ |
| ve | CH | CH | CH | 3-(CO$_2$H)phenyl | 4-chlorophenyl | 340 | 3.90$^l$ |
| vf | CH | CH | N | 3-(CO$_2$H)-5-chlorophenyl | 2-tert-butylphenyl | 397 | 4.38$^l$ |

TABLE 3-continued
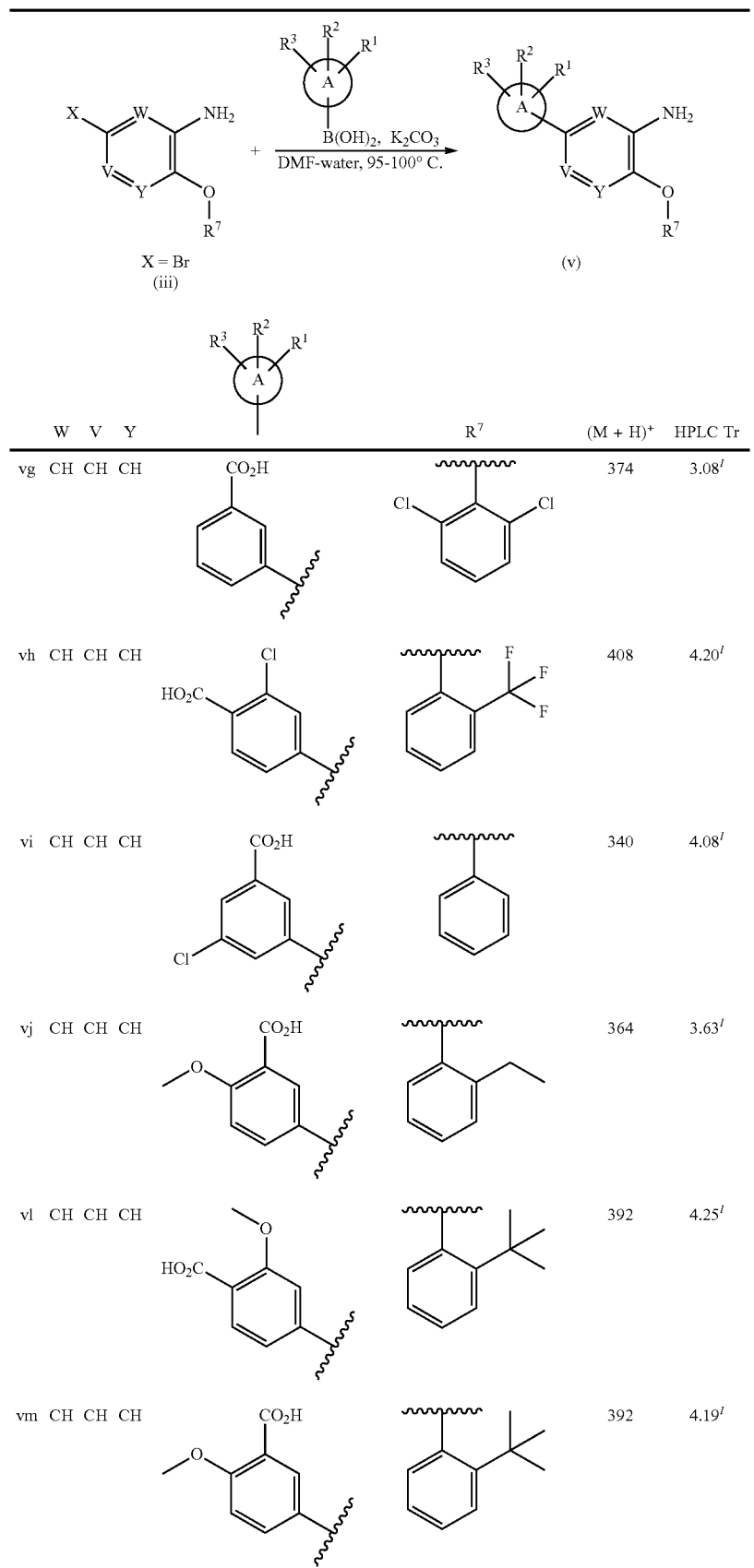
| | W | V | Y | A (with R1, R2, R3) | R7 | (M + H)+ | HPLC Tr |
|---|---|---|---|---|---|---|---|
| vg | CH | CH | CH | 3-CO2H-phenyl | 2,6-dichlorophenyl | 374 | 3.08[l] |
| vh | CH | CH | CH | 3-Cl-4-CO2H-phenyl | 2-CF3-phenyl | 408 | 4.20[l] |
| vi | CH | CH | CH | 3-Cl-5-CO2H-phenyl | phenyl | 340 | 4.08[l] |
| vj | CH | CH | CH | 3-OMe-4-CO2H-phenyl | 2-ethylphenyl | 364 | 3.63[l] |
| vl | CH | CH | CH | 3-OMe-4-CO2H-phenyl | 2-tert-butylphenyl | 392 | 4.25[l] |
| vm | CH | CH | CH | 3-OMe-4-CO2H-phenyl | 2-tert-butylphenyl | 392 | 4.19[l] |

TABLE 3-continued

| | W | V | Y | A (with R1, R2, R3) | R7 | (M + H)+ | HPLC Tr |
|---|---|---|---|---|---|---|---|
| vn | CH | CH | CH | 3-(CO2H), 4-OMe-phenyl | 2-Cl-phenyl | 370 | 3.40[I] |
| vo | CH | CH | CH | 3-(CO2H), 4-OMe-phenyl | 2-tBu-6-Me-phenyl | 406 | 4.08[I] |
| vp | CH | CH | CH | 4-(CO2H), 3-Cl-phenyl | 2-tBu-phenyl | 396 | 4.81[I] |
| vq | CH | CH | CH | 3-(CO2H), 4-OMe-phenyl | 2-iPr-phenyl | 378 | 3.81[I] |
| vr | CH | CH | CH | 3-(CO2H), 5-F-phenyl | 2-tBu-phenyl | 380 | 4.60[I] |
| vs | CH | CH | CH | 3-(CO2H), 4-OMe-phenyl | 2-OMe-phenyl | 366 | 3.08[I] |

TABLE 3-continued
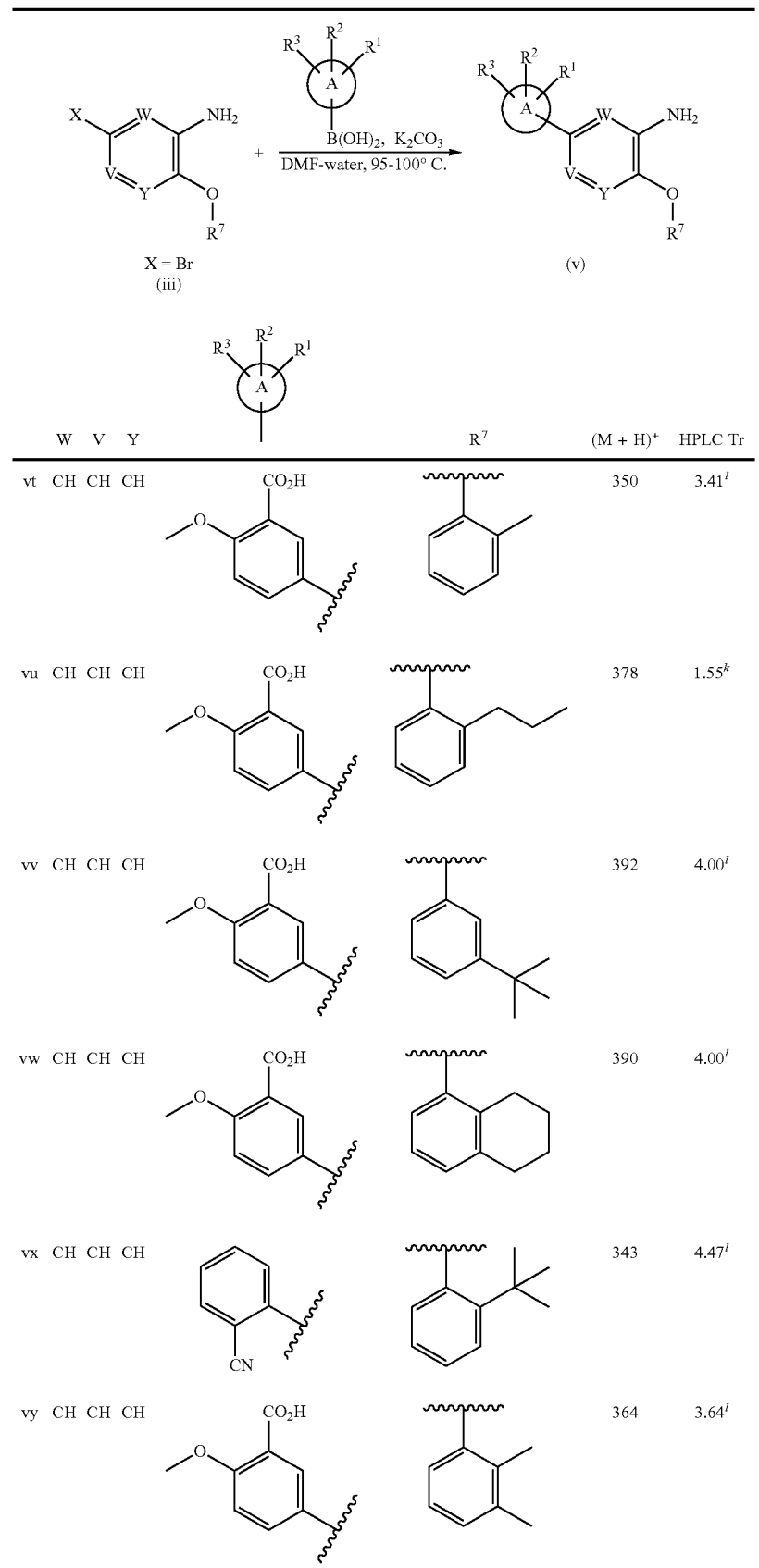

TABLE 3-continued

| | W | V | Y | A substituent | R[7] | (M + H)[+] | HPLC Tr |
|---|---|---|---|---|---|---|---|
| vz | CH | CH | CH | 2-CN-phenyl | 5,6,7,8-tetrahydronaphthalen-1-yl | 341 | 4.24[l] |
| vaa | CH | CH | CH | 3-CO₂H-4-methoxyphenyl | 2-cyclopropylphenyl | 376 | 3.68[l] |
| vab | CH | CH | CH | 2-(1H-tetrazol-5-yl)phenyl | 5,6,7,8-tetrahydronaphthalen-1-yl | 384 | 3.59[l] |
| vac | CH | CH | CH | 4-CO₂H-phenyl | 2-tert-butylphenyl | 362 | 4.33[l] |
| vad | CH | CH | CH | 4-CO₂H-3-F-phenyl | 2-tert-butylphenyl | 380 | 4.41[l] |
| vae | CH | CH | N | 3-CO₂H-4-methoxyphenyl | 2-tert-butylphenyl | 393 | 0.98[k] |

TABLE 3-continued

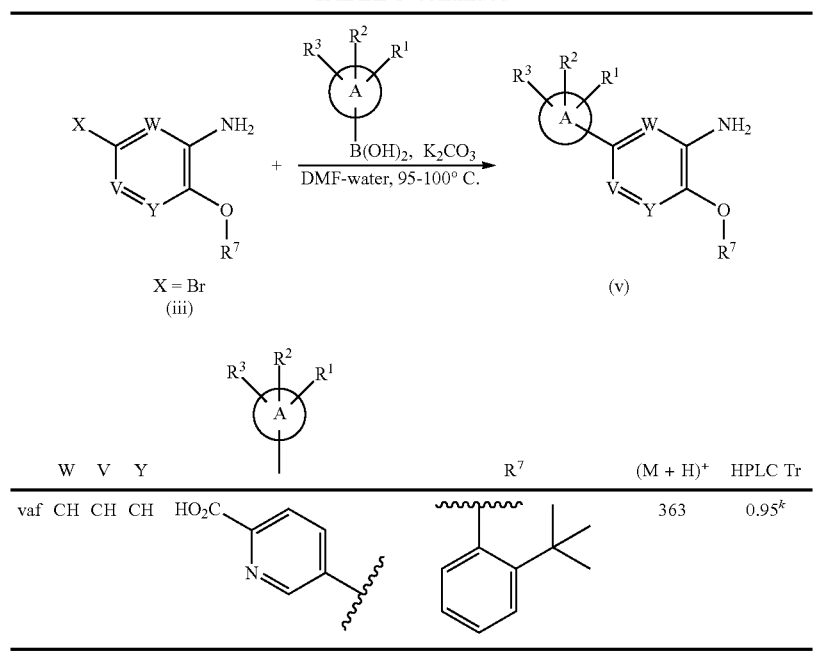

| W | V | Y | | R⁷ | (M + H)⁺ | HPLC Tr |
|---|---|---|---|---|---|---|
| vaf | CH | CH | CH HO₂C-pyridyl | 2-tert-butylphenyl | 363 | 0.95ᵏ |

Example 4

1-(4-(2-tert-Butylphenoxy)-2'-(1H-tetrazol-5-yl)biphenyl-3-yl)-3-p-tolylurea

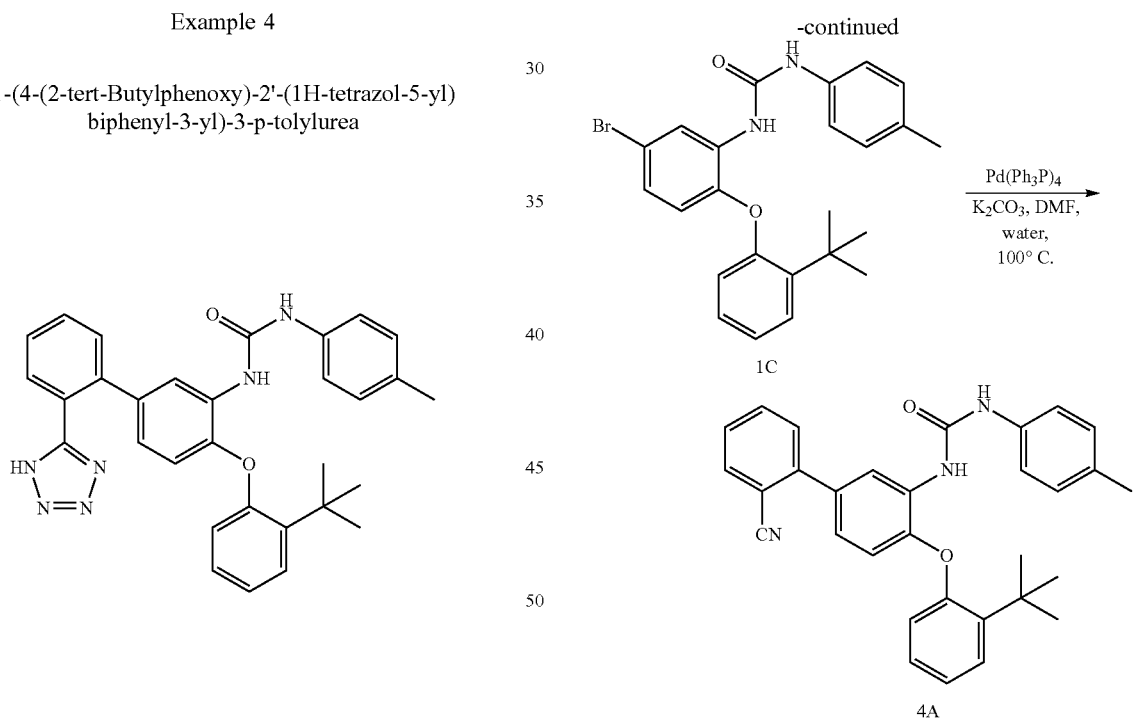

4A. 1-(4-(2-tert-Butylphenoxy)-2'-cyanobiphenyl-3-yl)-3-p-tolylurea

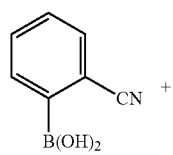

To a suspension of 1-(5-bromo-2-(2-tert-butylphenoxy)phenyl)-3-p-tolylurea (0.1 g, 0.221 mmol) and 2-cyanophenylboronic acid (0.065 g, 0.441 mmol) in degassed DMF (3 mL) was added aq. potassium carbonate (0.368 mL, 0.551 mmol). The mixture was placed under nitrogen and heated at 100° C. for 3 h then cooled. The mixture was diluted with aq. HOAc and extracted twice with chloroform. The combined organic extract was dried, stripped, and purified by prep. HPLC (Axia Luna 30×100 mm column, MeOH-water-TFA gradient) to afford 1-(4-(2-tert-butylphenoxy)-2'-cyanobiphenyl-3-yl)-3-p-tolylurea (0.043 g, 41% yield). ¹H NMR (400 MHz, DMSO-d$_6$) δ ppm 9.35 (s, 1H); 8.58 (s, 1H); 8.53 (d, 1H, J=2.2 Hz); 7.95 (dd, 1H, J=7.7, 0.9 Hz); 7.80 (td, 1H, J=7.7, 1.3 Hz); 7.52-7.67 (m, 2+H); 7.50 (dd, 1H, J=7.9, 1.5 Hz); 7.35 (d, 2H, J=8.4 Hz); 7.30 (td, 1H, J=7.6, 1.7 Hz); 7.19 (td, 1H, J=7.6, 1.3 Hz); 7.14 (dd, 1H, J=8.2, 2.4); 7.09 (d, 2H, J=8.1 Hz); 6.93 (dd, 1H, J=7.9, 1.3 Hz); 6.72 (d, 1H, J=8.4 Hz); 2.25 (s, 3H); 1.43 (s, 9H). MS(ES): m/z=476 [M+H]$^+$.

4. 1-(4-(2-tert-Butylphenoxy)-2'-(1H-tetrazol-5-yl)biphenyl-3-yl)-3-p-tolylurea

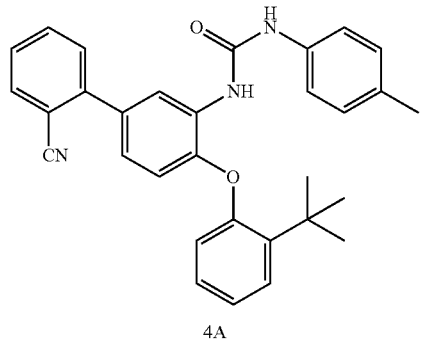

4A n-Bu$_3$SnN$_3$
PhCH$_3$,
110° C.

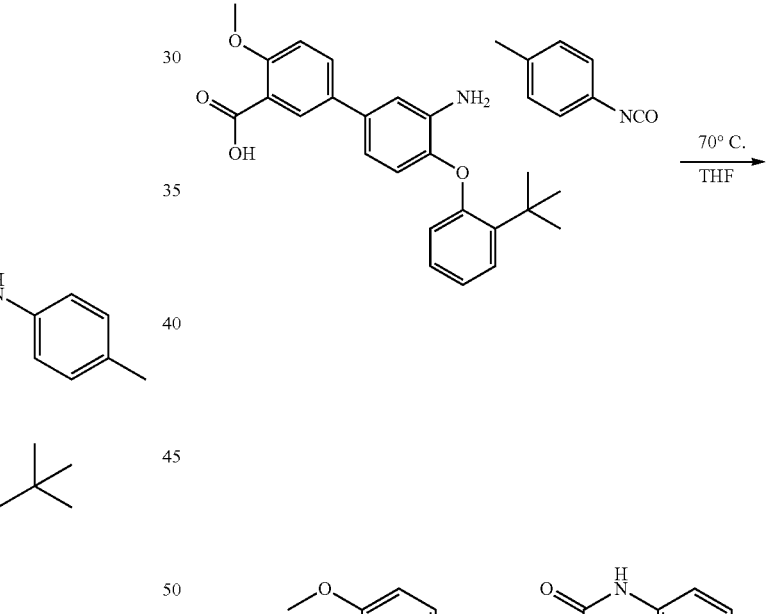

4

To a solution of 1-(4-(2-tert-butylphenoxy)-2'-cyanobiphenyl-3-yl)-3-p-tolylurea (4A) (0.036 g, 0.076 mmol) in toluene (0.5 mL) was added azidotributyltin (0.145 mL, 0.530 mmol). The solution was placed under nitrogen and heated at 110° C. for 20 h. Prep. HPLC (Axia Luna 30×100 mm column, MeOH-water-TFA gradient) afforded 1-(4-(2-tert-butylphenoxy)-2'-(1H-tetrazol-5-yl)biphenyl-3-yl)-3-p-tolylurea (0.009 g, 23% yield) as a white powder. $^1$H NMR (400 MHz, DMSO-d$_6$) δ ppm 9.35 (s, 1H); 8.34 (s, 1H); 8.14 (s, 1H); 7.64-7.72 (m, 2H); 7.50-7.60 (m, 2H); 7.45 (dd, 1H, J=7.9, 1.5 Hz); 7.31 (d, 2H, J=8.4 Hz); 7.26 (td, 1H, J=7.7, 1.8 Hz); 7.15 (td, 1H, J=7.6, 1.3 Hz); 7.08 (d, 2H, J=8.1 Hz); 6.79 (dd, 1H, J=8.1, 1.3 Hz); 6.60 (dd, 1H, J=8.4, 2.2 Hz); 6.52 (d, 1H, J=8.6 Hz); 2.24 (s, 3H); 1.41 (s, 9H). MS(ES): m/z=519 [M+H]$^+$.

Example 5

4'-(2-tert-Butylphenoxy)-4-ethoxy-3'-(3-p-tolylureido)biphenyl-3-carboxylic acid

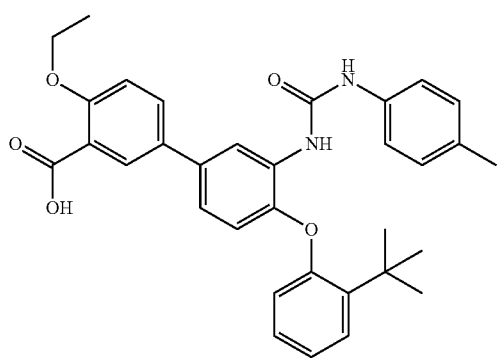 [SMILES: CCOc1ccc(-c2ccc(Oc3ccccc3C(C)(C)C)c(NC(=O)Nc3ccc(C)cc3)c2)cc1C(=O)O]

5A. 4'-(2-tert-butylphenoxy)-4-methoxy-3'-(3-p-tolylureido)biphenyl-3-carboxylic acid

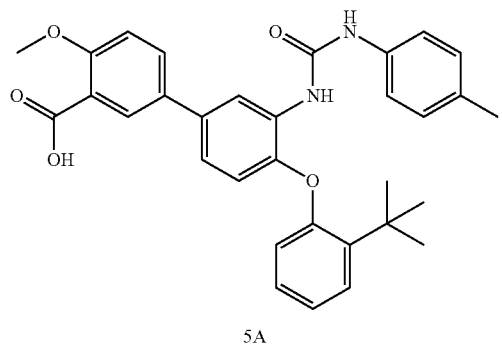

5A

The title compound was prepared from aniline vm and 4-methylphenylisocyanate at 70° C. by the procedure used to prepare Example 2. HPLC T$_r$: 4.37 min.$^1$ MS(ES): m/z=525 [M+H]$^+$.

5B. 4'-(2-tert-Butylphenoxy)-4-hydroxy-3'-(3-p-tolylureido)biphenyl-3-carboxylic acid

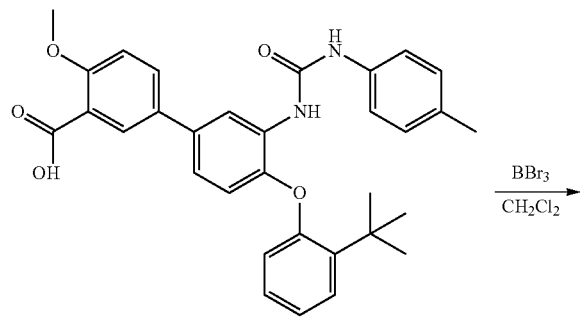

5A

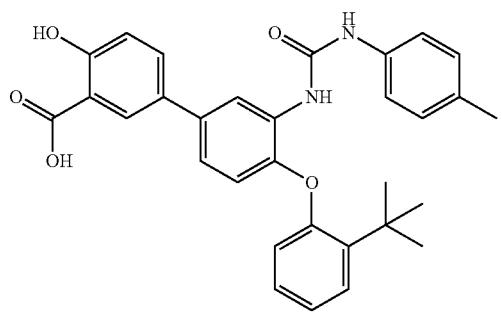

5B

To a stirred solution of 4'-(2-tert-butylphenoxy)-4-methoxy-3'-(3-p-tolylureido)biphenyl-3-carboxylic acid (0.088 g, 0.17 mmol) in dichloromethane (0.5 mL) was added a 2M solution of boron tribromide (0.839 mL, 1.677 mmol) in dichloromethane. The solution was stirred 15 min. at RT. then most of the solvent was removed under a stream of nitrogen. The reaction was quenched with water and extracted twice with chloroform. The combined organic extract was dried and stripped to afford 4'-(2-tert-butylphenoxy)-4-hydroxy-3'-(3-p-tolylureido)biphenyl-3-carboxylic acid (0.082 g, 96% yield). HPLC $T_r$: 16.89 min.[a] MS(ES): m/z=511 [M+H]+.

5C. Ethyl 4'-(2-tert-butylphenoxy)-4-ethoxy-3'-(3-p-tolylureido)biphenyl-3-carboxylate

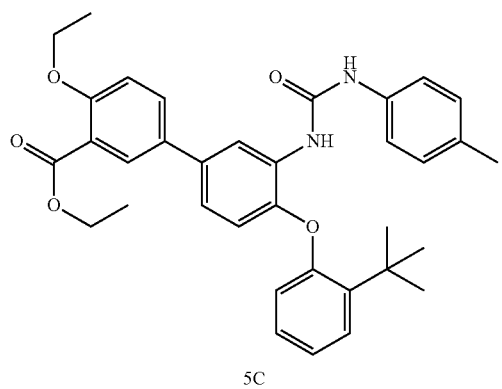

5C

To a stirred solution of 4'-(2-tert-butylphenoxy)-4-hydroxy-3'-(3-p-tolylureido)biphenyl-3-carboxylic acid (5A) (0.024 g, 0.047 mmol) in DMF (0.2 mL) was added potassium carbonate (0.019 g, 0.141 mmol) followed by iodoethane (0.015 mL, 0.188 mmol). The mixture was warmed to 50° C. and stirred for 4 h. The reaction was treated with one drop of water and 50 μl of glacial HOAc to decompose remaining carbonates. The mixture was diluted with ethanol, filtered, and purified by prep. HPLC (Axia 21×100 mm column, MeOH-water-TFA gradient) to afford ethyl 4'-(2-tert-butylphenoxy)-4-ethoxy-3'-(3-p-tolylureido)biphenyl-3-carboxylate (0.017 g, 63.8% yield) as a white powder. $^1$H NMR (400 MHz, DMSO-$d_6$) δ ppm 9.34 (s, 1H); 8.57 (d, 1H, J=2.2 Hz); 8.48 (s, 1H); 7.83 (d, 1H, J=2.6 Hz); 7.76 (dd, 1H, J=8.8, 2.4 Hz); 7.50 (dd, 1H, J=7.9, 1.5 Hz); 7.38 (d, 2H, J=8.4 Hz); 7.25-7.39 (m, 2H); 7.17-7.22 (m, 2H); 7.12 (d, 2H, J=8.4 Hz); 6.89 (dd, 1H, J=7.9, 1.3 Hz); 6.69 (d, 1H, J=8.6 Hz); 4.32 (q, 2H, J=7.1 Hz); 4.17 (q, 2H, J=6.9 Hz); 2.28 (s, 3H); 1.46 (s, 9H); 1.39 (t, 3H, J=6.9 Hz); 1.34 (t, 3H, J=7.0 Hz). MS(ES): m/z=567 [M+H]+.

5. 4'-(2-tert-Butylphenoxy)-4-ethoxy-3'-(3-p-tolylureido)biphenyl-3-carboxylic acid

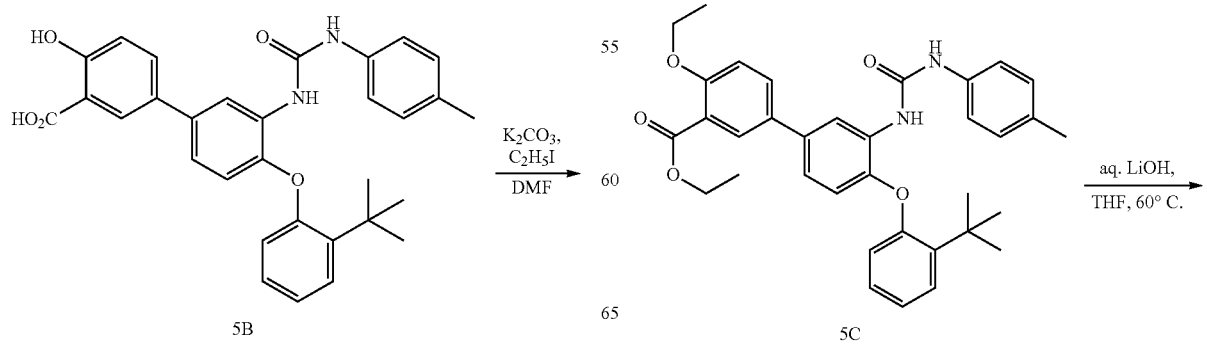

-continued

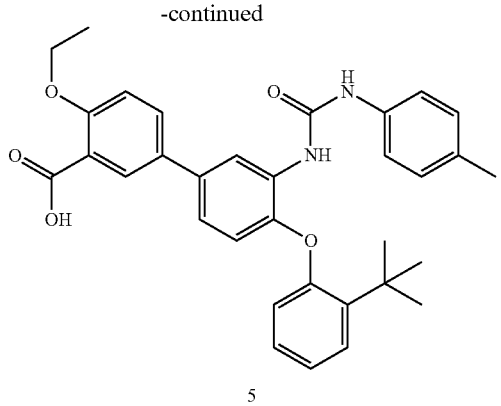

5

To a stirred solution of ethyl 4'-(2-tert-butylphenoxy)-4-ethoxy-3'-(3-p-tolylureido)biphenyl-3-carboxylate (0.011 g, 0.019 mmol) in THF (0.3 mL) was added lithium hydroxide (9.30 mg, 0.388 mmol) in water (0.300 mL). The mixture was treated with 0.1 mL of MeOH to give a single phase and heated at 60° C. for 3 h. The reaction was cooled, and most of the THF was removed under a stream of nitrogen. The reaction was diluted with 1 mL of water, and product was precipitated by the dropwise addition of conc. HCl. Filtration afforded 4'-(2-tert-butylphenoxy)-4-ethoxy-3'-(3-p-tolylureido)biphenyl-3-carboxylic acid (0.010 g, 96% yield). $^1$H NMR (400 MHz, DMSO-$d_6$) δ ppm 12.67 (br. s, 1H); 9.31 (s, 1H); 8.56 (d, 1H, J=2.2 Hz); 8.45 (s, 1H); 7.83 (d, 1H, J=2.4 Hz); 7.72 (dd, 1H, J=8.8, 2.4 Hz); 7.47 (dd, 1H, J=7.9, 1.5 Hz); 7.36 (d, 2H, J=8.4 Hz); 7.13-7.29 (m, 4H); 7.10 (d, 2H, J=8.4 Hz); 6.87 (dd, 1H, J=8.1, 1.1 Hz); 6.66 (d, 1H, J=8.6 Hz); 4.15 (q, 2H, J=7.0 Hz); 2.25 (s, 3H); 1.43 (s, 9H); 1.36 (t, 3H, J=6.9 Hz). MS(ES): m/z=539 [M+H]$^+$.

Example 6

4'-(2-tert-Butylphenoxy)-N-(methylsulfonyl)-3'-(3-p-tolylureido)biphenyl-2-carboxamide

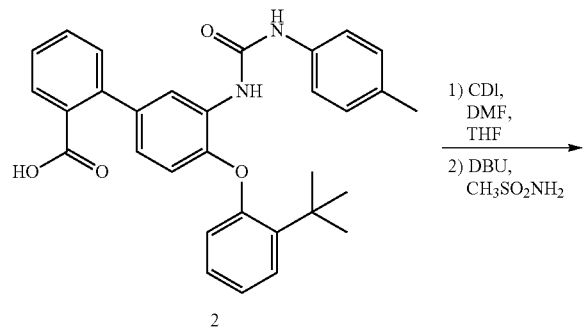

-continued

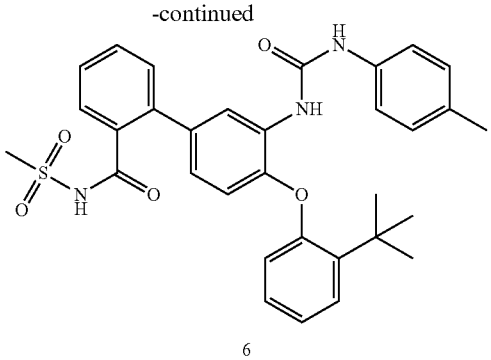

6

To a stirred solution of 4'-(2-tert-butylphenoxy)-3'-(3-p-tolylureido)biphenyl-2-carboxylic acid (Example 2) (0.045 g, 0.091 mmol) in THF (0.2 mL)-DMF (0.1 mL) was added CDI (0.022 g, 0.136 mmol). The solution was stirred 30 min. at 60° C. then cooled to RT and treated with methanesulfonamide (0.013 g, 0.136 mmol) and DBU (0.025 mL, 0.164 mmol). The resulting mixture was stirred overnight at RT then purified by prep. HPLC (Axia Luna 21×100 mm column, MeOH-water-TFA gradient) to afford 4'-(2-tert-butylphenoxy)-N-(methylsulfonyl)-3'-(3-p-tolylureido)biphenyl-2-carboxamide (0.037 g, 71% yield) as a white powder. $^1$H NMR (400 MHz, DMSO-$d_6$) δ ppm 12.18 (br. s, 1H); 9.33 (s, 1H); 8.47 (s, 1H); 8.42 (d, 1H, J=2.2 Hz); 7.59 (t, 1H, J=7.4 Hz); 7.44-7.54 (m, 4H); 7.33 (d, 2H, J=8.4 Hz); 7.27 (td, 1H, J=7.6, 1.8 Hz); 7.16 (td, 1H, J=7.6, 1.3 Hz); 7.09 (d, 2H, J=8.4 Hz); 6.93 (dd, 1H, J=8.4, 2.4 Hz); 6.84 (dd, 1H, J=7.9, 1.3 Hz); 6.66 (d, J=8.4 Hz); 3.15 (br. s, 3H); 2.24 (s, 3H); 1.43 (s, 9H). MS(ES): m/z=572 [M+H]$^+$.

Example 7

N-(4'-(2-tert-Butylphenoxy)-4-methoxy-3'-(3-p-tolylureido)biphenyl-3-yl)-1,1,1-trifluoromethanesulfonamide

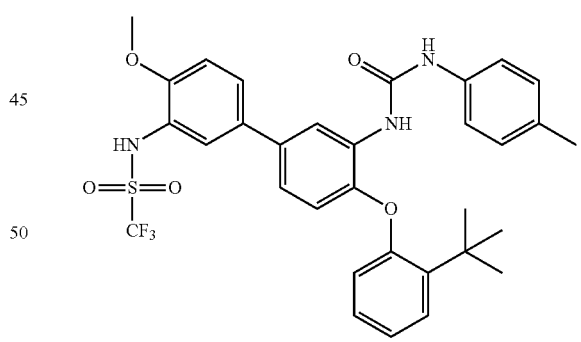

7A. 4-(2-tert-Butylphenoxy)-4'-methoxy-3'-nitrobiphenyl-3-amine

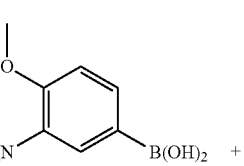

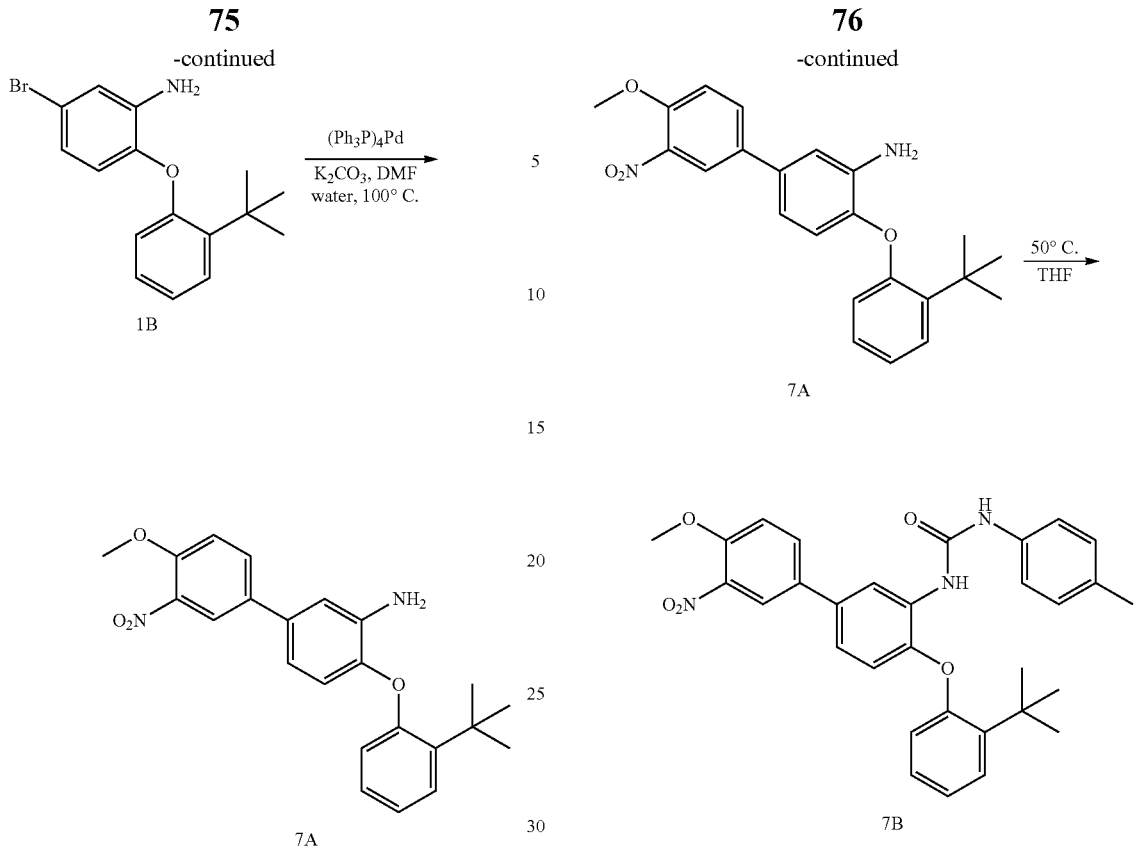

7A

A mixture of 4-methoxy-3-nitrophenylboronic acid (1B) (0.355 g, 1.800 mmol) and 5-bromo-2-(2-tert-butylphenoxy) aniline (0.320 g, 1 mmol) and tetrakis(triphenylphosphine) palladium(0) (0.058 g, 0.050 mmol) in degassed DMF (Volume: 6 mL) was treated with aq. potassium carbonate (2.000 mL, 3.00 mmol) and placed under nitrogen. The mixture was heated to 100° C. for 2 h then cooled. The dark suspension was diluted with water and extracted twice with chloroform. The combined organic extract was dried, stripped, and chromatographed on silica gel (gradient elution with EtOAc-hexanes) to afford, after removal of solvent, 4-(2-tert-butylphenoxy)-4'-methoxy-3'-nitrobiphenyl-3-amine (0.33 g, 80% yield) as a yellow foam. $^1$H NMR (400 MHz, DMSO-$d_6$) δ ppm 8.02 (d, 1H, J=2.4 Hz); 7.85 (dd, 1H, J=8.8, 2.4 Hz); 7.42 (d, 1H, J=8.8 Hz); 7.38 (dd, 1H, J=7.8, 1.7 Hz); 7.12-7.19 (m, 2H); 7.04 (td, 1H, J=7.5, 1.3 Hz); 6.83 (dd, 1H, J=8.4, 2.4 Hz); 6.70 (dd, 1H, J=8.0, 1.2); 6.63 (d, 1H, J=8.4 Hz); 5.00 (br. s, 2H); 3.95 (s, 3H); 1.42 (s, 9H). MS(ES): m/z=393 [M+H]$^+$.

7B. 1-(4-(2-tert-Butylphenoxy)-4'-methoxy-3'-nitro-biphenyl-3-yl)-3-p-tolylurea

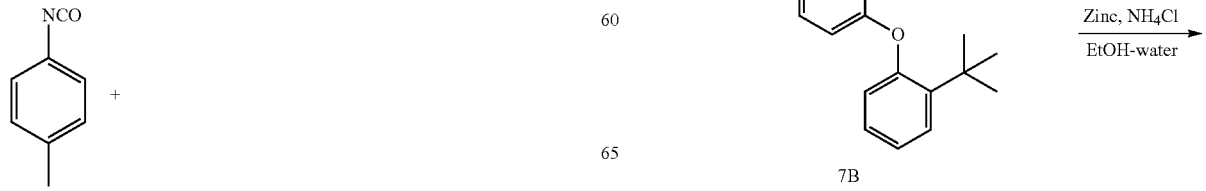

To a stirred solution of 4-(2-tert-butylphenoxy)-4'-methoxy-3'-nitrobiphenyl-3-amine (7A) (0.12 g, 0.306 mmol) in THF (Volume: 1 mL) was added 1-isocyanato-4-methylbenzene (0.061 g, 0.459 mmol). The solution was stirred 1 h at 50° C. then purified by silica gel chromatography (gradient elution with EtOAc-hexanes) to afford 14442-tert-butylphenoxy)-4'-methoxy-3'-nitrobiphenyl-3-yl)-3-p-tolylurea (0.15 g, 89% yield) as a yellow solid. $^1$H NMR (400 MHz, DMSO-$d_6$) δ ppm 9.30 (s, 1H); 8.57 (d, 1H, J=2.2 Hz); 8.47 (s, 1H); 8.05 (d, 1H, J=2.4 Hz); 7.89 (dd, 1H, J=8.8, 2.4 Hz); 7.43-7.49 (m, 2H); 7.35 (d, 2H, J=8.6 Hz); 7.21-7.29 (m, 2H); 7.16 (td, 1H, J=7.6, 1.3 Hz); 7.09 (d, 2H, J=8.1 Hz); 6.87 (dd, 1H, J=7.9, 1.3 Hz); 6.67 (d, 1H, J=8.4 Hz); 3.96 (s, 3H); 2.24 (s, 3H); 1.41 (s, 9H). MS(ES): m/z=526 [M+H]$^+$.

7C. 1-(3'-Amino-4-(2-tert-butylphenoxy)-4'-methoxybiphenyl-3-yl)-3-p-tolylurea

-continued

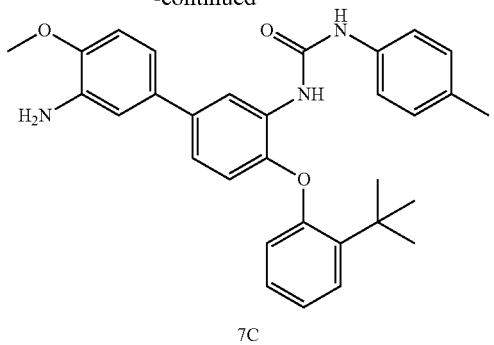

7C

To a stirred solution of 1-(4-(2-tert-butylphenoxy)-4'-methoxy-3'-nitrobiphenyl-3-yl)-3-p-tolylurea (0.12 g, 0.228 mmol) in ethanol (Volume: 5 mL) was added zinc (0.149 g, 2.283 mmol) and ammonium chloride (0.122 g, 2.283 mmol). The mixture was treated with 1 mL of water and heated to reflux. The reaction was allowed to cool to RT with stirring over 1 h then diluted with dichloromethane and filtered. The filtrate was washed with water, dried, and concentrated under reduced pressure to afford 1-(3'-amino-4-(2-tert-butylphenoxy)-4'-methoxybiphenyl-3-yl)-3-p-tolylurea (0.1 g, 84% yield) as a yellow solid. $^1$H NMR (400 MHz, DMSO-$d_6$) δ ppm 9.27 (s, 1H); 8.47 (d, 1H, J=2.2 Hz); 8.35 (s, 1H); 7.44 (dd, 1H, J=7.9, 1.5 Hz); 7.35 (d, 2H, J=8.4 Hz); 7.23 (td, 1H, J=7.7, 1.7 Hz); 7.04-7.16 (m, 4H); 6.90 (d, 1H, J=2.2 Hz); 6.81-6.87 (m, 2H); 6.75 (dd, 1H, J=8.1, 2.2 Hz); 6.62 (d, 1H, J=8.4 Hz); 4.80 (s, 2H); 3.79 (s, 3H); 2.24 (s, 3H); 1.42 (s, 9H). MS(ES): m/z=496 [M+H]$^+$.

7. 1 N-(4'-(2-tert-Butylphenoxy)-4-methoxy-3'-(3-p-tolylureido)biphenyl-3-yl)-1,1,1-trifluoromethanesulfonamide

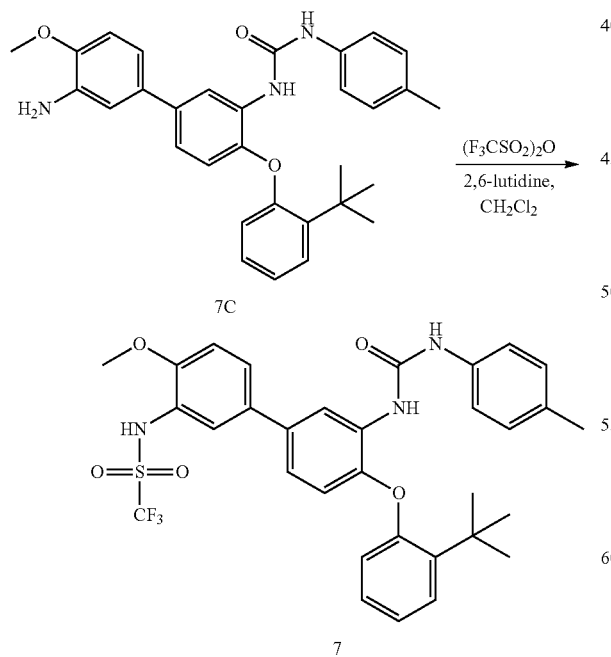

To a stirred solution of 1-(3'-amino-4-(2-tert-butylphenoxy)-4'-methoxybiphenyl-3-yl)-3-p-tolylurea (0.025 g, 0.050 mmol) in dichloromethane (Volume: 1 mL) was added 2,6-lutidine (0.012 mL, 0.101 mmol) followed by trifluoromethanesulfonic anhydride (0.013 mL, 0.076 mmol). The solution was stirred 30 min. at RT then purified by silica gel chromatography (gradient elution with EtOAc-hexanes). Concentration of the appropriate fraction afforded N-(4'-(2-tert-butylphenoxy)-4-methoxy-3'-(3-p-tolylureido)biphenyl-3-yl)-1,1,1-trifluoromethanesulfonamide (0.017 g, 51.0% yield) as a white powder. $^1$H NMR (400 MHz, DMSO-$d_6$) δ ppm 9.29 (s, 1H); 8.51 (d, 1H, J=2.2 Hz); 8.46 (s, 1H); 7.57 (br. d, 1H, J=8.8 Hz); 7.40-7.48 (m, 2H); 7.35 (d, 2H, J=8.4 Hz); 7.19-7.27 (m, 2H); 7.11-7.18 (m, 2H); 7.09 (d, 2H, J=8.1 Hz); 6.85 (dd, 1H, J=6.6, 1.3 Hz); 6.66 (d, 1H, J=8.4 Hz); 3.87 (s, 3H); 2.24 (s, 3H); 1.42 (s, 9H). MS(ES): m/z=628 [M+H]$^+$.

Example 8

1-(5-(1-Phenylallyl)-4-propoxy-2'-(1H-tetrazol-5-yl)-[1,1'-biphenyl]-3-yl)-3-(p-tolyl)urea

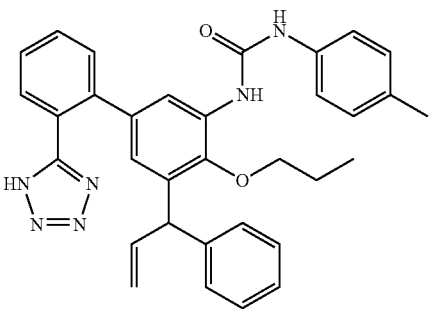 [SMILES: C=CC(c1ccccc1)c1cc(-c2ccccc2-c2nnn[nH]2)cc(NC(=O)Nc2ccc(C)cc2)c1OCCC]

8A. 4-Bromo-1-(cinnamyloxy)-2-nitrobenzene

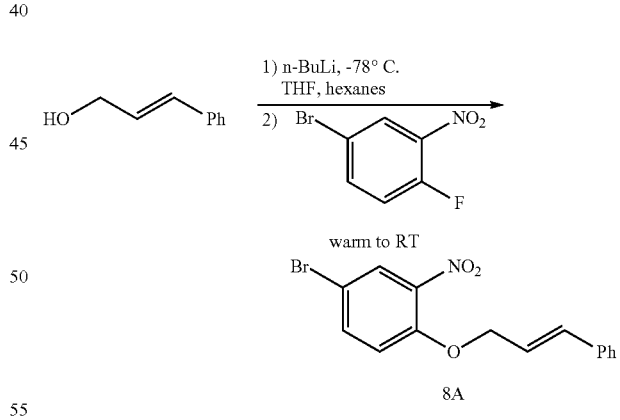

8A

To a stirred, cooled (−78° C.) solution of (E)-3-phenyl-prop-2-en-1-ol (2.415 g, 18.00 mmol) in THF (3 mL) was added n-butyllithium (5.76 mL, 14.40 mmol), dropwise over 4-5 min. The solution was stirred for 5 min. at −78° C. then treated with 4-bromo-1-fluoro-2-nitrobenzene (2.64 g, 12 mmol) and allowed to warm to RT with stirring. Stirring at RT was continued for 30 min, after which time the reaction was transferred into aq. HCl, and this mixture was extracted with ether. The organic extract was dried, stripped, and chromatographed on silica gel (gradient elution with ether-hexanes). Concentration of the appropriate fractions afforded an oily yellow solid. This was triturated with heptane to afford 4-bromo-1-(cinnamyloxy)-2-nitrobenzene (2.2 g, 52.1% yield) as a pale yellow powder, mp 95-97° C. $^1$H NMR (400 MHz, DMSO-d$_6$) δ ppm 8.13 (d, 1H, J=2.4 Hz); 7.84 (dd, 1H, J=9.0, 2.4 Hz); 7.47 (d, 2H, J=7.3 Hz); 7.42 (d, 1H, J=9.2 Hz); 7.35 (t, 2H, J=7.4 Hz); 7.28 (t, 1H, J=7.8 Hz); 6.78 (d, 1H, J=16.1 Hz); 6.46 (dt, 1H, J=16.1, 5.8 Hz); 4.92 (d, 2H, J=5.9 Hz).

8B. (+/−)-4-Bromo-2-nitro-6-(1-phenylallyl)phenol

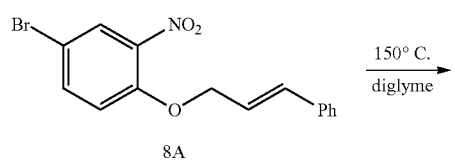

A solution of 4-bromo-1-(cinnamyloxy)-2-nitrobenzene (8A) (1.5 g, 4.49 mmol) in diglyme (3 mL) was placed under nitrogen and heated to 150° C. for 36 h. The reaction was cooled and purified by flash chromatography (gradient elution with hexanes up to 15% ether-hexanes). Concentration of the appropriate fractions afforded 4-bromo-2-nitro-6-(1-phenylallyl)phenol (1.08 g, 68.4% yield) as an oily yellow solid. $^1$H NMR (400 MHz, DMSO-d$_6$) δ ppm 10.73 (br. s, 1H); 8.04 (d, 1H, J=2.4 Hz); 7.62 (d, 1H, J=2.4 Hz); 7.31 (t, 2H, J=7.4 Hz); 7.16-7.25 (m, 3H); 6.39 (ddd, 1H, J=17.1, 10.1, 7.5 Hz); 5.23 (d, 1H, J=10.1 Hz); 5.15 (d, 1H, J=7.3 Hz); 5.00 (d, 1H, J=17.2 Hz).

8C. (+/−)-5-Bromo-1-nitro-3-(1-phenylallyl)-2-propoxybenzene

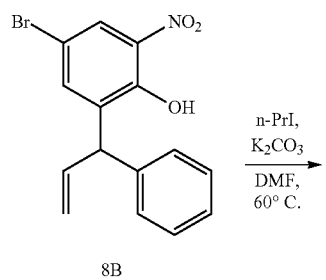

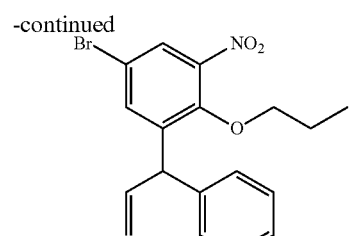

To a solution of 4-bromo-2-nitro-6-(1-phenylallyl)phenol (8B) (0.3 g, 0.898 mmol) in DMF (2 mL) was added potassium carbonate (0.372 g, 2.69 mmol) followed by 1-iodopropane (0.763 g, 4.44 mmol). This mixture was brought to 60° C. and stirred for 2 h. The reaction was cooled, quenched with glacial HOAc, and purified by flash chromatography (gradient elution with ether-hexanes). Concentration of the appropriate fractions afforded 2-(allyloxy)-5-bromo-1-nitro-3-(1-phenylallyl)benzene (0.32 g, 95% yield) as a colorless oil. $^1$H NMR (400 MHz, DMSO-d$_6$) δ ppm 8.10 (d, 1H, J=2.6 Hz); 7.71 (d, 1H, J=2.4 Hz); 7.36 (t, 2H, J=7.7 Hz); 7.27 (t, 1H, J=7.4 Hz); 7.21 (d, 2H, J=7.3 Hz); 6.42 (ddd, 1H, J=17.0, 10.1, 1.1 Hz); 5.29 (dd, 1H, J=10.1, 1.1 Hz); 5.15 (d, 1H, J=7.5 Hz); 5.04 (d, 1H, J=17 Hz); 3.63-3.83 (m, 2H); 1.60-1.71 (m, 2H); 0.91 (t, 3H, J=7.4 Hz).

8D. (+/−)-5-Bromo-3-(1-phenylallyl)-2-propoxyaniline

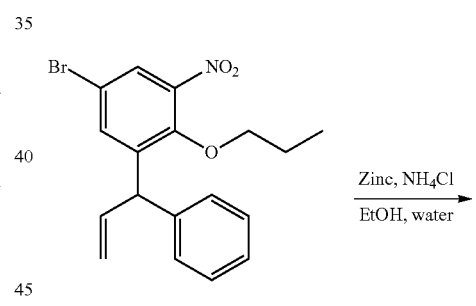

To a solution of 5-bromo-1-nitro-3-(1-phenylallyl)-2-propoxybenzene (8C) (0.02 g, 0.053 mmol) in ethanol (4 mL) was added 0.5 mL of water followed by ammonium chloride (0.043 g, 0.797 mmol). This mixture was stirred 5 min. then treated with zinc (0.052 g, 0.797 mmol). The reaction was stirred 15 min. then diluted with dichloromethane and filtered. The filtrate was washed with water, dried, and stripped to afford an amber oil. MS(ES): m/z=346 [M+H]$^+$. HPLC T$_r$: 4.65$^l$.

8E. (+/−)-1-(5-Bromo-3-(1-phenylallyl)-2-propoxy-phenyl)-3-(p-tolyl)urea

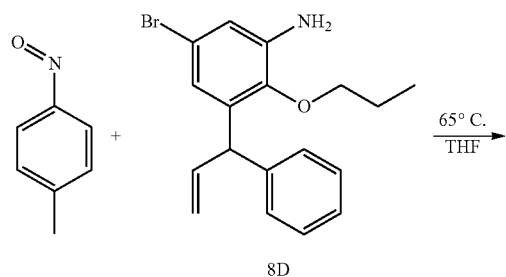

8D

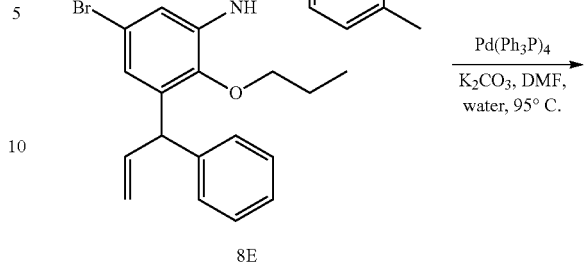

8E

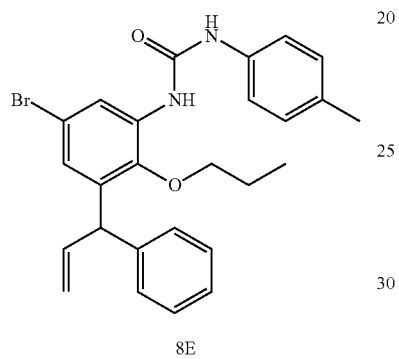

8E

The crude material from step 8D was dissolved in 0.5 mL of THF and treated with 1-isocyanato-4-methylbenzene (0.014 g, 0.106 mmol). The solution was heated to 65° C. for 1 h then cooled and stirred at RT. The reaction was treated with 0.01 mL of N,N-dimethylethylenediamine and purified by flash chromatography (gradient elution with ether-heptane). Concentration of the appropriate fractions afforded 1-(5-bromo-3-(1-phenylallyl)-2-propoxyphenyl)-3-(p-tolyl)urea (0.02 g, 74.6% yield) as a white powder. $^1$H NMR (400 MHz, DMSO-$d_6$) δ ppm 9.24 (1H, s); 8.22 (1H, d, J=2.4 Hz); 8.17 (1H, s); 7.29-7.35 (m, 4H); 7.16-7.24 (m, 3H); 7.09 (d, 2H, J=8.4 Hz); 6.94 (d, 1H, J=2.6 Hz); 6.35 (ddd, 1H, J=17.2, 10.1, 7.3 Hz); 5.23 (d, 1H, J=10.1 Hz); 5.06 (d, 1H, J=7.5 Hz); 4.97 (d, H, J=17.0 Hz); 3.55-3.71 (m, 2H); 2.24 (s, 3H); 1.75-1.86 (m, 2H), 0.93 (t, 3H, J=7.5 Hz). MS(ES): m/z=479 [M+H]$^+$.

8. (+/−)-1-(5-(1-Phenylallyl)-4-propoxy-2'-(1H-tetrazol-5-yl)-[1,1'-biphenyl]-3-yl)-3-(p-tolyl)urea

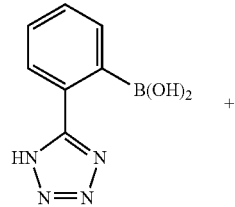 +

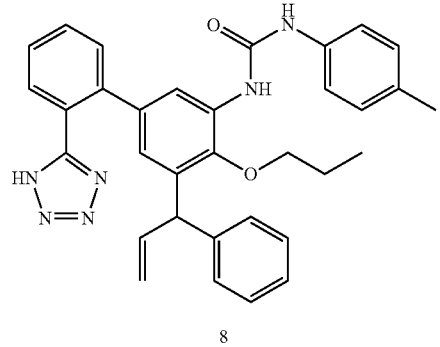

8

A suspension of (2-(1H-tetrazol-5-yl)phenyl)boronic acid (0.016 g, 0.083 mmol) and 1-(5-bromo-3-(1-phenylallyl)-2-propoxyphenyl)-3-(p-tolyl)urea (8E) (0.02 g, 0.042 mmol) and tetrakis(triphenylphosphine)palladium(0) (4.82 mg, 4.17 μmol) in degassed DMF (1 mL) was treated with aq. potassium carbonate (0.139 mL, 0.209 mmol). This mixture was placed under nitrogen and heated at 95° C. for 2 h. The reaction was cooled, brought to pH4 with glacial HOAc, filtered, and purified by prep. HPLC (Axia Luna C18 30×100 mm column, MeOH-water-TFA gradient). Concentration of the appropriate fraction afforded 1-(5-(1-phenylallyl)-4-propoxy-2'-(1H-tetrazol-5-yl)-[1,1'-biphenyl]-3-yl)-3-(p-tolyl)urea (0.013 g, 54.4% yield) as a white powder. $^1$H NMR (400 MHz, DMSO-$d_6$) δ ppm 9.2 (s, 1H); 8.07 (m, 2H); 7.50-7.69 (m, 4H); 7.32 (d, 2H, J=7.3 Hz); 7.26 (t, 2H, J=7.4 Hz); 7.17 (t, 1H, J=7.3 Hz); 7.08 (d, 2H, J=8.4 Hz); 6.93 (d, 2H, J=7.3 Hz); 6.30 (d, 1H, J=2.2 Hz); 5.97 (ddd, 1H, J=17.0, 10.1, 6.8 Hz); 5.08 (d, 1H, J=10.1 Hz); 4.98 (d, 1H, J=6.6 Hz); 4.72 (d, H, J=17.0 Hz); 3.45-3.68 (m, 2H); 2.23 (s, 3H); 1.74-1.83 (m, 2H), 0.90 (t, 3H, J=7.4 Hz). MS(ES): m/z=545 [M+H]$^+$.

Example 9

1-(4-((2,4-Dimethylpentan-3-yl)oxy)-2'-(1H-tetrazol-5-yl)-[1,1'-biphenyl]-3-yl)-3-(p-tolyl)urea

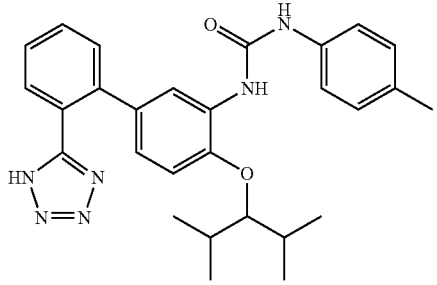 [SMILES: Cc1ccc(NC(=O)Nc2cc(-c3ccccc3-c3nnn[nH]3)ccc2OC(C(C)C)C(C)C)cc1]

9A.
5-Bromo-2-((2,4-dimethylpentan-3-yl)oxy)aniline

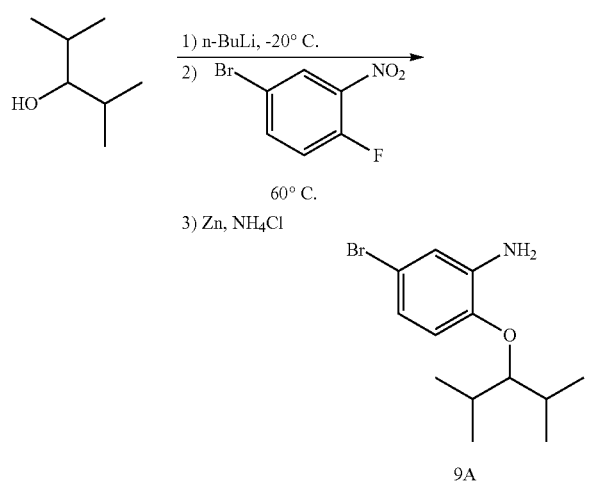

To a stirred, cooled (−20° C.) solution of 2,4-dimethylpentan-3-ol (0.523 g, 4.50 mmol) in THF (4 mL) was added n-BuLi (1.680 mL, 4.20 mmol) over 1 min. The solution was stirred 10 min. at −20° C. then warmed to 40° C. and treated with 4-bromo-1-fluoro-2-nitrobenzene (0.660 g, 3 mmol). This resulted in either an exotherm or a release of gas because there was sufficient volume in the vial everything was contained. The solution was warmed to 60° C. and stirred 30 min. The reaction was diluted with 3:1 ether-heptane and washed sequentially with 10% aq. HOAc and sat. aq. sodium bicarbonate. The organic phase was dried and stripped to afford 4-bromo-1-((2,4-dimethylpentan-3-yl)oxy)-2-nitrobenzene (0.94 g, 94% yield) as a pale yellow oil. A 0.90 g sample of this material was dissolved in ethanol (8 mL) and treated with 2 mL of water followed by ammonium chloride (0.914 g, 17.08 mmol). The resulting mixture was stirred 5 min. at RT then treated with zinc (1.117 g, 17.08 mmol). This mixture was stirred vigorously for 30 min. then diluted with dichloromethane and filtered. The filtrate was washed with water, dried, and stripped to afford 5-bromo-2-((2,4-dimethylpentan-3-yl)oxy)aniline (0.81 g, 99% yield) as a pale yellow oil. MS(ES): m/z=286 [M+H]$^+$. HPLC T$_r$: 2.51$^q$.

9B. 1-(5-Bromo-2-((2,4-dimethylpentan-3-yl)oxy)phenyl)-3-(p-tolyl)urea

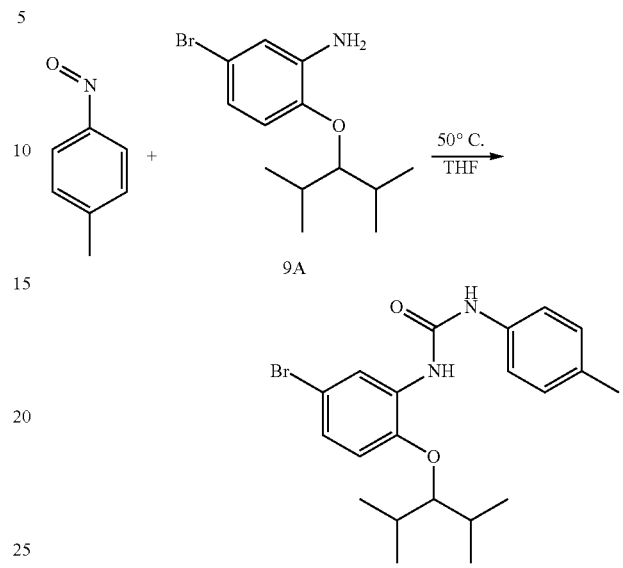

To a solution of 5-bromo-2-((2,4-dimethylpentan-3-yl)oxy)aniline (9A) (0.16 g, 0.559 mmol) in THF (0.4 mL) was added 1-isocyanato-4-methylbenzene (0.089 g, 0.671 mmol). The solution was stirred 1 h at 50° C. then cooled and quenched with 0.02 mL of N,N-dimethylethylenediamine. The reaction was partially concentrated purified by ISCO chromatography (hexanes-EtOAc gradient). Concentration of the appropriate fractions afforded 0.18 g (72%) of 1-(5-bromo-2-((2,4-dimethylpentan-3-yl)oxy)phenyl)-3-(p-tolyl)urea as a colorless foam. MS(ES): m/z=421 [M+H]$^+$. HPLC T$_r$: 2.82$^q$.

9. 1-(4-((2,4-Dimethylpentan-3-yl)oxy)-2'-(1H-tetrazol-5-yl)-[1,1'-biphenyl]-3-yl)-3-(p-tolyl)urea

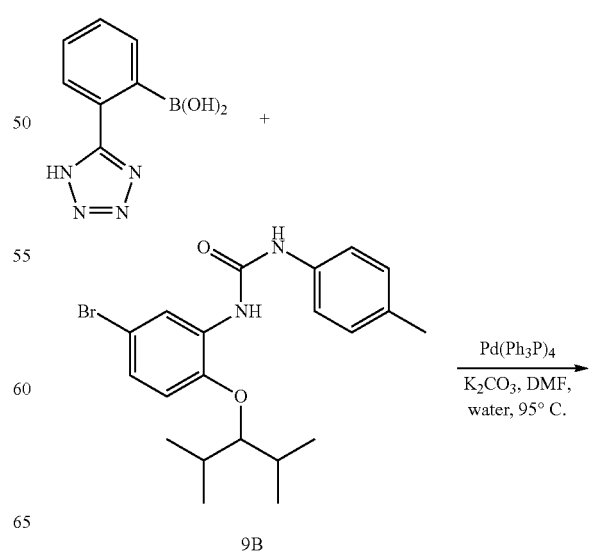

-continued

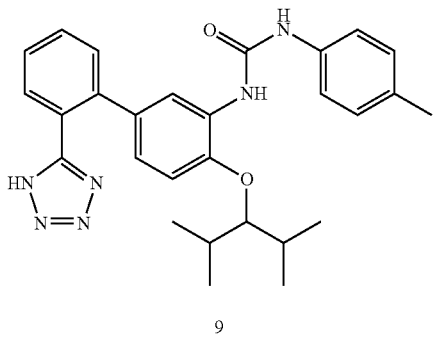

9

The title compound was prepared from 9B using the procedure for the conversion of 8E to 8. MS(ES): m/z=485 [M+H]+. HPLC T$_r$: 2.64$^q$.

Example 10

4'-((2,4-Dimethylpentan-3-yl)oxy)-3'-(3-(p-tolyl)ureido)-[1,1'-biphenyl]-2-carboxylic acid

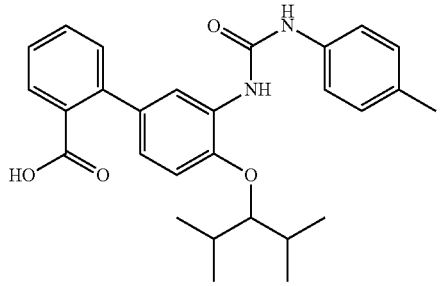 [SMILES: Cc1ccc(NC(=O)Nc2cc(-c3ccccc3C(=O)O)ccc2OC(C(C)C)C(C)C)cc1]

The title compound was prepared from 9B and 2-carboxyphenylboronic acid using the procedure for the conversion of 8E to 8. MS(ES): m/z=461 [M+H]+. HPLC T$_r$: 2.67$^q$.

Example 11

1-(4-((2,4-Dimethylpentan-3-yl)oxy)-2'-(1H-tetrazol-5-yl)-[1,1'-biphenyl]-3-yl)-3-(2-fluorophenyl)urea

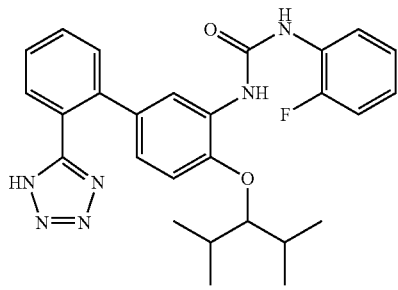 [SMILES: CC(C)C(Oc1ccc(-c2ccccc2-c2nnn[nH]2)cc1NC(=O)Nc1ccccc1F)C(C)C]

11A. 1-(5-Bromo-2-((2,4-dimethylpentan-3-yl)oxy)phenyl)-3-(2-fluorophenyl)urea

The title compound was prepared from 9A and 2-fluorophenylisocyanate using the procedure for the conversion of 9A to 9B. MS(ES): m/z=423 [M+H]+. HPLC T$_r$: 2.80$^q$.

11. 1-(4-((2,4-Dimethylpentan-3-yl)oxy)-2'-(1H-tetrazol-5-yl)-[1,1'-biphenyl]-3-yl)-3-(2-fluorophenyl)urea The title compound was prepared from 11A using the procedure for the conversion of 9B to 9. MS(ES): m/z=489 [M+H]+. HPLC T$_r$: 2.59$^q$.

Example 12

4'-((2,4-Dimethylpentan-3-yl)oxy)-3'-(3-(2-fluorophenyl)ureido)-4-methoxy-[1,1'-biphenyl]-3-carboxylic acid

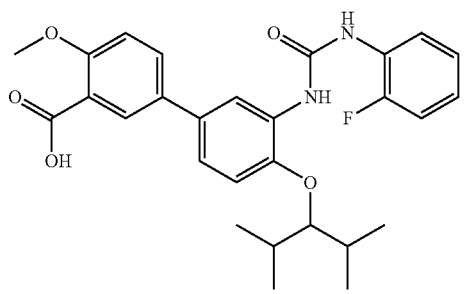 [SMILES: COc1ccc(-c2ccc(OC(C(C)C)C(C)C)c(NC(=O)Nc3ccccc3F)c2)cc1C(=O)O]

The title compound was prepared from 11A and 3-carboxy-4-methoxyphenylboronic acid using the procedure for the conversion of 8E to 8. MS(ES): m/z=495 [M+H]+. HPLC T$_r$: 2.65$^q$.

Example 13

1-(4-(Heptan-4-yloxy)-2'-(1H-tetrazol-5-yl)-[1,1'-biphenyl]-3-yl)-3-(p-tolyl)urea

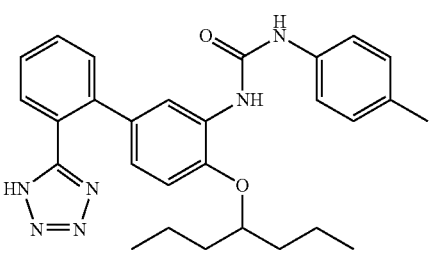 [SMILES: CCCC(CCC)Oc1ccc(-c2ccccc2-c2nnn[nH]2)cc1NC(=O)Nc1ccc(C)cc1]

13A. 5-Bromo-2-(heptan-4-yloxy)aniline

The title compound was prepared from 2-fluoro-5-bromonitrobenzene and 4-heptanol using the procedure for the preparation of 9A. MS(ES): m/z=397 [M+H]+. HPLC T$_r$: 1.67$^q$.

13B. 1-(5-Bromo-2-(heptan-4-yloxy)phenyl)-3-(p-tolyl)urea

The title compound was prepared from 13A at 45° C. using the procedure for the conversion of 9A to 9B. MS(ES): m/z=421 [M+H]⁺. HPLC T$_r$: 3.28$^r$.

13. 1-(4-(Heptan-4-yloxy)-2'-(1H-tetrazol-5-yl)-[1,1'-biphenyl]-3-yl)-3-(p-tolyl)urea The title compound was prepared from 13B using the procedure for the conversion of 8E to 8. MS(ES): m/z=485 [M+H]⁺. HPLC T$_r$: 2.69$^q$.

Example 14

4'-(Heptan-4-yloxy)-3'-(3-(p-tolyl)ureido)-[1,1'-biphenyl]-2-carboxylic acid

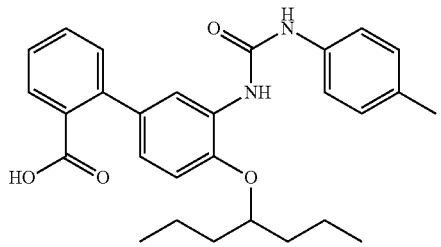 [SMILES: CCCC(CCC)Oc1ccc(-c2ccccc2C(=O)O)cc1NC(=O)Nc1ccc(C)cc1]

The title compound was prepared from 13B and 2-carboxyphenylboronic acid using the procedure for the conversion of 8E to 8. MS(ES): m/z=461 [M+H]⁺. HPLC T$_r$: 2.73$^q$.

Example 15

5-Fluoro-4'-(heptan-4-yloxy)-3'-(3-(p-tolyl)ureido)-[1,1'-biphenyl]-2-carboxylic acid

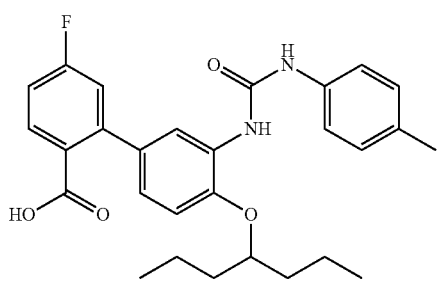 [SMILES: CCCC(CCC)Oc1ccc(-c2cc(F)ccc2C(=O)O)cc1NC(=O)Nc1ccc(C)cc1]

The title compound was prepared from 13B and 5-fluoro-2-carboxyphenylboronic acid using the procedure for the conversion of 8E to 8. MS(ES): m/z=479 [M+H]⁺. HPLC T$_r$: 2.79$^q$.

Example 16

1-(5-(1-Phenylallyl)-4-propoxy-2'-(1H-tetrazol-5-yl)-[1,1'-biphenyl]-3-yl)-3-(p-tolyl)urea

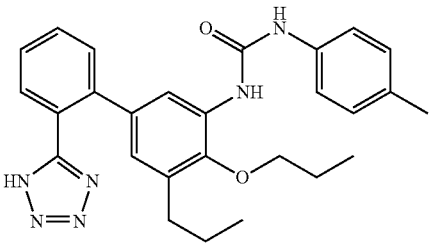 [SMILES: CCCOc1c(CCC)cc(-c2ccccc2-c2nnn[nH]2)cc1NC(=O)Nc1ccc(C)cc1]

16A. 1-(Allyloxy)-4-bromo-2-nitrobenzene

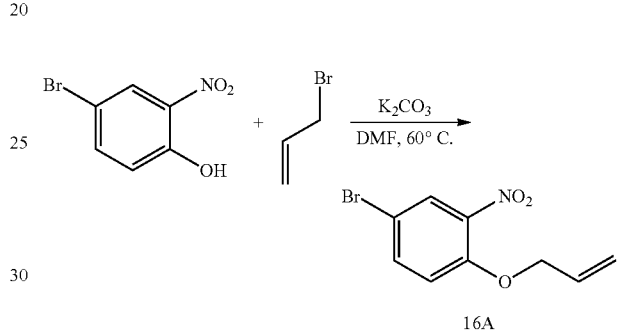

To a solution of 4-bromo-2-nitrophenol (2.180 g, 10 mmol) in warm (60° C.) DMF (10 mL) was added potassium carbonate (2.76 g, 20.00 mmol). The mixture was stirred for 2-3 min. then treated with 3-bromoprop-1-ene (1.298 mL, 15.00 mmol). The reaction was stirred 30 min. at 60° C., gradually changing color from bright orange to pale yellow. The reaction was transferred into 100 mL of water with stirring, and the resulting precipitate was filtered, rinsed with water, and air-dried to afford 1-(allyloxy)-4-bromo-2-nitrobenzene (2.51 g, 92% yield) as a straw-colored powder, mp 64-65° C.

16B. 2-Allyl-4-bromo-6-nitrophenol

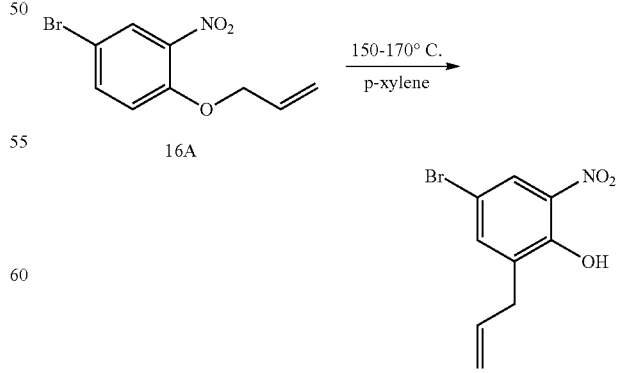

A solution of 1-(allyloxy)-4-bromo-2-nitrobenzene (16A) (0.5 g, 1.937 mmol) in xylene (6 mL) was heated to 150° C. overnight. An aliquot was pumped to dryness and NMR indicated that the Claisen rearrangement product is present at about 10%. The reaction was heated overnight at 160° C. for two more nights and at 170° C. for 6 h the following day. Chromatography on silica gel (gradient elution with 5% to 20% ether-hexanes) afforded 2-allyl-4-bromo-6-nitrophenol (0.25 g, 50% yield) as a pale yellow oil. $^1$H NMR (400 MHz, DMSO-$d_6$) δ ppm 10.62 (br. s, 1H); 8.00 (d, 1H, J=2.4 Hz) 7.66 (d, 1H, J=2.6 Hz); 5.90-6.00 (m, 1H); 5.05-5.12 (m, 2H); 3.39-3.44 (m, 2H).

16C. 1-Allyl-2-(allyloxy)-5-bromo-3-nitrobenzene

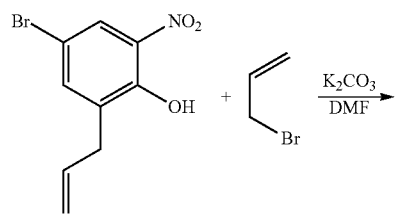

To a solution of 2-allyl-4-bromo-6-nitrophenol (16B) (0.2 g, 0.775 mmol) in DMF (3 mL) was added potassium carbonate (0.214 g, 1.550 mmol) followed by allyl bromide (0.101 mL, 1.162 mmol). The mixture was stirred 64 h at RT then diluted with water and extracted with ether. The organic extract was dried and stripped to afford 1-allyl-2-(allyloxy)-5-bromo-3-nitrobenzene-diethyl ether solvate (0.24 g, 91% yield) as a pale yellow oil. $^1$H NMR (400 MHz, DMSO-$d_6$) δ ppm 8.06 (d, 1H, J=2.6 Hz) 7.72 (d, 1H, J=2.6 Hz); 5.92-6.08 (m, 2H); 5.26-5.43 (m, 2H); 5.10-5.18 (m, 2H); 4.47-4.51 (m, 2H); 3.48 (br.s, 2H, J=6.4 Hz). (Resonances from ether solvate ignored in interpretation.)

16D. 5-Bromo-1-nitro-2-propoxy-3-propylbenzene

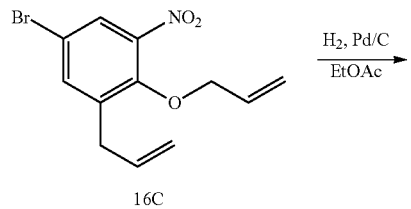

To a solution of 1-allyl-2-(allyloxy)-5-bromo-3-nitrobenzene (16C) (0.1 g, 0.335 mmol) in ethyl acetate (5 mL) was added palladium on carbon (0.018 g, 0.017 mmol). The mixture was stirred under an atmosphere of hydrogen for 1.5 h. LCMS is uninformative, although the lack of strong ion currents suggests that the nitro group is not being reduced. The reaction was treated with MgSO$_4$, filtered and stripped to afford 5-bromo-1-nitro-2-propoxy-3-propylbenzene (0.095 g, 94% yield) as brown oil. $^1$H NMR (400 MHz, DMSO-$d_6$) δ ppm 7.97 (d, 1H, J=2.4 Hz) 7.72 (d, 1H, J=2.6 Hz); 5.92-6.08 (m, 2H); 5.26-5.43 (m, 2H); 5.10-5.18 (m, 2H); 4.47-4.51 (m, 2H); 3.48 (br.s, 2H, J=6.4 Hz).

16E. 1-(5-Bromo-2-propoxy-3-propylphenyl)-3-(p-tolyl)urea

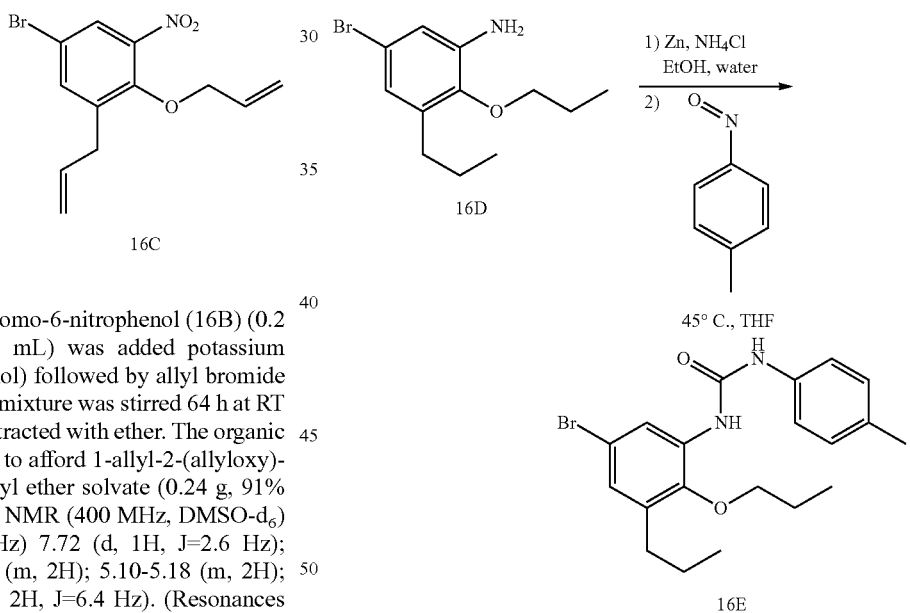

A solution of 5-bromo-1-nitro-2-propoxy-3-propylbenzene (16D) (0.09 g, 0.298 mmol) in ethanol (4 mL) was treated with ammonium chloride (0.239 g, 4.47 mmol), and the mixture was stirred 5 min. at RT. Zinc (0.292 g, 4.47 mmol) was added in two portions, 2 min. apart, and the mixture was stirred 30 min. at RT then diluted with dichloromethane and filtered. The filtrate was washed with water, dried, and stripped to afford 5-bromo-2-propoxy-3-propylaniline as a brown oil. This material was dissolved in tetrahydrofuran (0.5 mL) and treated with 1-isocyanato-4-methylbenzene (0.055 g, 0.411 mmol). The solution was stirred 2 h at 45° C. then purified by flash chromatography (gradient elution with ether-hexanes). Concentration of the appropriate fractions afforded 1-(5-bromo-2-propoxy-3-propylphenyl)-3-(p-tolyl)urea (0.08 g) as an off-white powder. MS(ES): m/z=405 [M+H]$^+$. T$_r$: 5.08$^l$.

16. 1-(4-Propoxy-5-propyl-2'-(1H-tetrazol-5-yl)-[1,1'-biphenyl]-3-yl)-3-(p-tolyl)urea

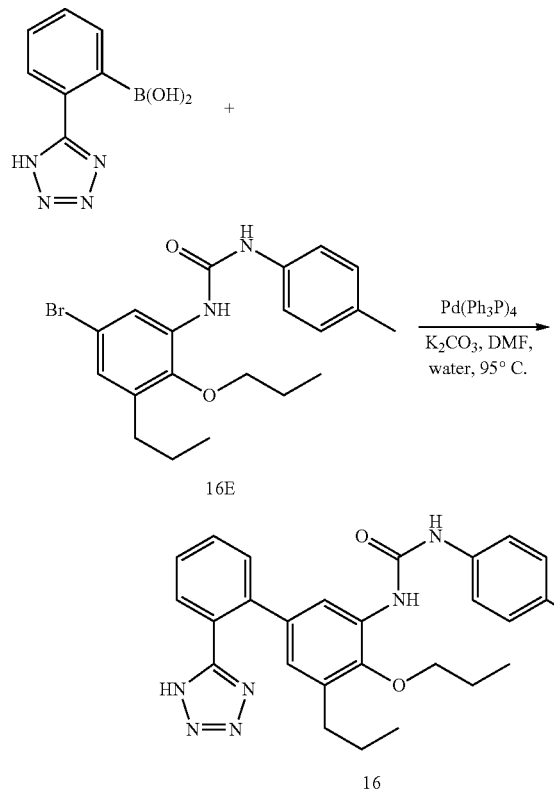

The title compound was prepared from 16E using the procedure for the conversion of 8E to 8. MS(ES): m/z=471 [M+H]$^+$. HPLC T$_r$: 2.16$^k$.

Example 17

4'-Propoxy-3'-propyl-5'-(3-(p-tolyl)ureido)-[1,1'-biphenyl]-2-carboxylic acid

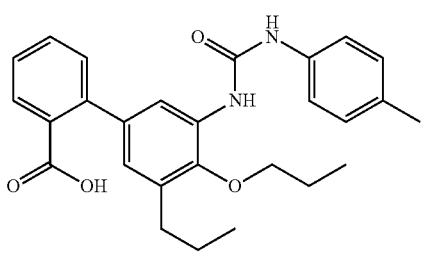

The title compound was prepared from 16E and 2-carboxyphenylboronic acid using the procedure for the conversion of 8E to 8. MS(ES): m/z=447 [M+H]$^+$. HPLC T$_r$: 2.23$^k$.

Example 18

5-Fluoro-4'-propoxy-3'-propyl-5'-(3-(p-tolyl)ureido)-[1,1'-biphenyl]-2-carboxylic acid

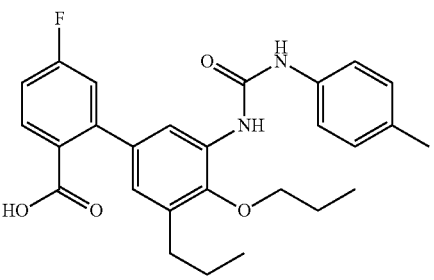 [SMILES: CCCOc1c(CCC)cc(-c2cc(F)ccc2C(=O)O)cc1NC(=O)Nc1ccc(C)cc1]

The title compound was prepared from 16E and 2-borono-4-fluorobenzoic acid using the procedure for the conversion of 8E to 8. MS(ES): m/z=465 [M+H]$^+$. HPLC T$_r$: 2.29$^k$.

Example 19

(E)-1-(5-(But-2-en-1-yl)-4-propoxy-2'-(1H-tetrazol-5-yl)-[1,1'-biphenyl]-3-yl)-3-(p-tolyl)urea

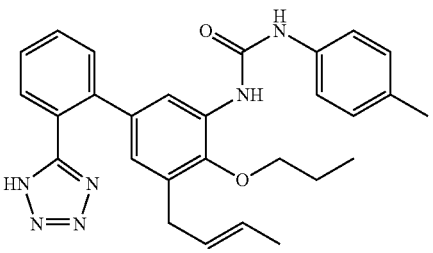 [SMILES: C/C=C/Cc1cc(-c2ccccc2-c2nnn[nH]2)cc(NC(=O)Nc2ccc(C)cc2)c1OCCC]

19A. 4-Bromo-1-(but-3-en-2-yloxy)-2-nitrobenzene

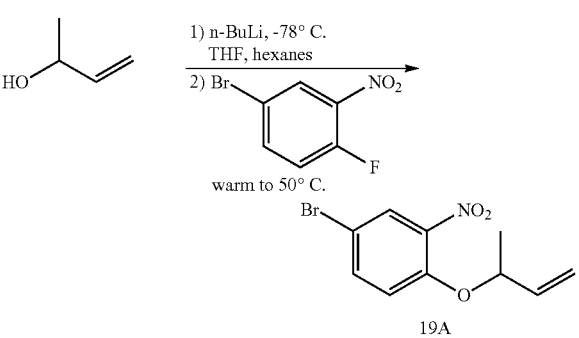

To a stirred, cooled (−78° C.) solution of but-3-en-2-ol (0.721 g, 10.00 mmol) in THF (7 mL) was added N-butyllithium (3.00 mL, 7.50 mmol), dropwise over 2-3 min. The solution was stirred for 2-3 min., warming to 0° C., and it was then re-cooled to −78° C. The solution was treated with 4-bromo-1-fluoro-2-nitrobenzene (1.100 g, 5 mmol) then allowed to warm to RT with stirring. Stirring at RT was continued for 10 min, after which time the reaction was heated to 50° C. for 20 min. The reaction was cooled to RT, transferred into aq. HCl, and this mixture was extracted with ether. The organic extract was dried, stripped, and chromatographed on silica gel (gradient elution with ether-hexanes) to afford 4-bromo-1-(but-3-en-2-yloxy)-2-nitrobenzene (1.3 g, 91% yield) as an amber oil. $^1$H NMR (400 MHz, DMSO-$d_6$) δ ppm 8.08 (d, 1H, J=2.4 Hz); 7.77 (dd, 1H, J=9.0, 2.4 Hz); 7.32 (d, 2H, J=9.0 Hz); 5.87 (ddd, 1H, J=17.0, 10.9, 6.1 Hz); 5.31 (d, 1H, J=17.4 Hz); 5.13-5.22 (m, 2H); 1.36 (d, 3H, J=6.4 Hz).

19B. (E)-4-Bromo-2-(but-2-en-1-yl)-6-nitrophenol

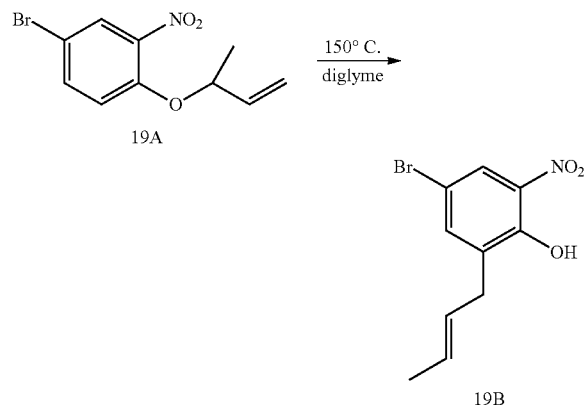

The title compound was prepared from 19A using the procedure for the conversion of 8A to 8B. $^1$H NMR (400 MHz, DMSO-$d_6$) δ ppm 10.59 (br. s, 1H); 7.98 (d, 1H, J=2.6 Hz) 7.63 (d, 1H, J=2.4 Hz); 5.46-5.61 (m, 2H); 3.30-3.36 (m, 2H); 1.64 (d, 3H, J=4.8 Hz).

19C. 2-(Allyloxy)-5-bromo-1-nitro-3-(1-phenylallyl)benzene

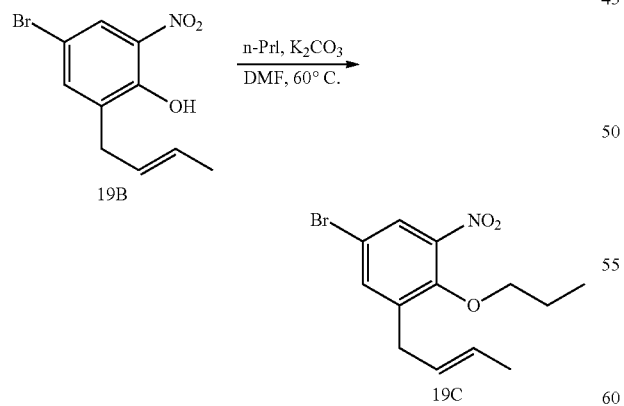

The title compound was prepared from 19B using the procedure for the conversion of 8B to 8C. $^1$H NMR (400 MHz, DMSO-$d_6$) δ ppm 7.99 (d, 1H, J=2.6 Hz) 7.70 (d, 1H, J=2.4 Hz); 5.51-5.60 (m, 2H); 3.85 (t, 2H, J=6.5 Hz); 3.35-3.39 (m, 2H); 1.63-1.74 (m, 5H) 0.95 (t, 3H, J=7.4 Hz).

19D. (E)-1-(5-Bromo-3-(but-2-en-1-yl)-2-propoxyphenyl)-3-(p-tolyl)urea

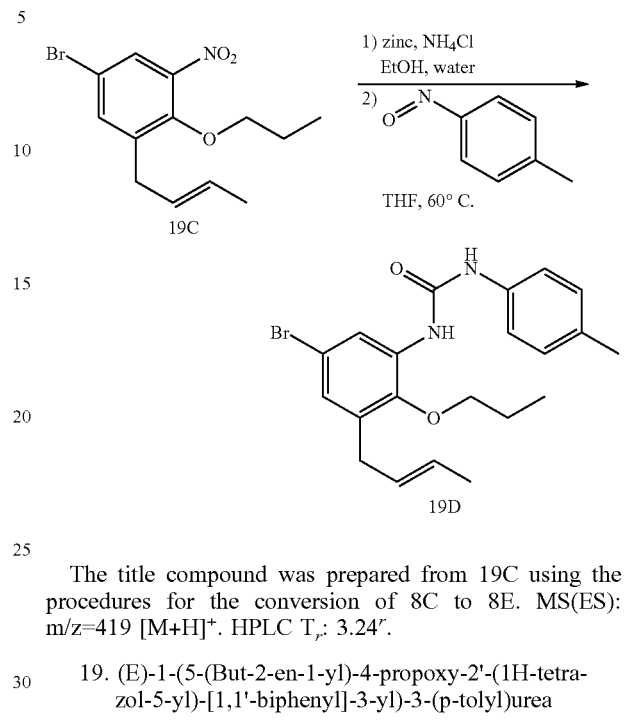

The title compound was prepared from 19C using the procedures for the conversion of 8C to 8E. MS(ES): m/z=419 [M+H]$^+$. HPLC T$_r$: 3.24$^r$.

19. (E)-1-(5-(But-2-en-1-yl)-4-propoxy-2'-(1H-tetrazol-5-yl)-[1,1'-biphenyl]-3-yl)-3-(p-tolyl)urea

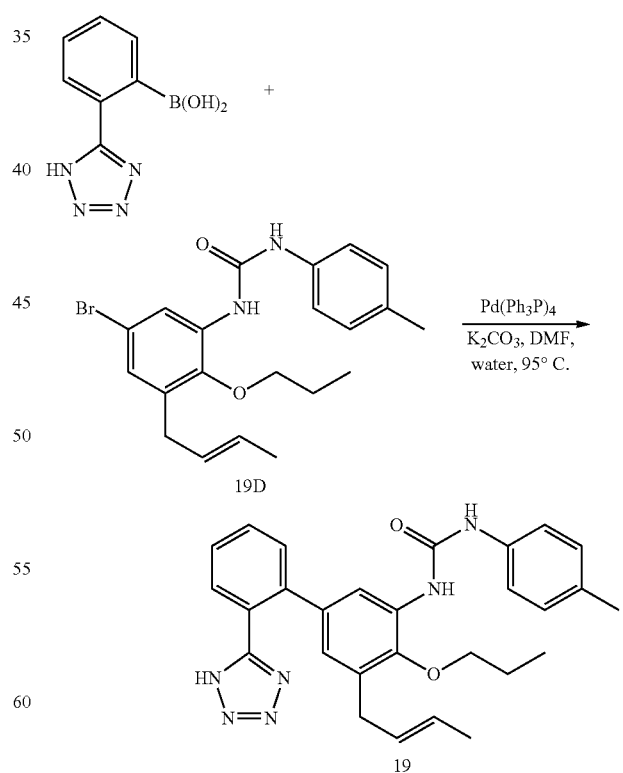

The title compound was prepared from 19D using the procedures for the conversion of 8E to 8. MS(ES): m/z=483 [M+H]$^+$. HPLC T$_r$: 2.87$^r$.

Example 20

(E)-3'-(But-2-en-1-yl)-4'-propoxy-5'-(3-(p-tolyl)ureido)-[1,1'-biphenyl]-2-carboxylic acid

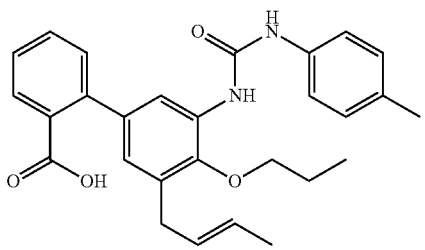 [SMILES: C/C=C/Cc1cc(-c2ccccc2C(=O)O)cc(NC(=O)Nc2ccc(C)cc2)c1OCCC]

The title compound was prepared from 19D and 2-carboxyphenylboronic acid using the procedure for the conversion of 8E to 8. MS(ES): m/z=459 [M+H]$^+$. HPLC T$_r$: 12.69$^d$.

Example 21

(E)-3'-(But-2-en-1-yl)-5-fluoro-4'-propoxy-5'-(3-(p-tolyl)ureido)-[1,1'-biphenyl]-2-carboxylic acid

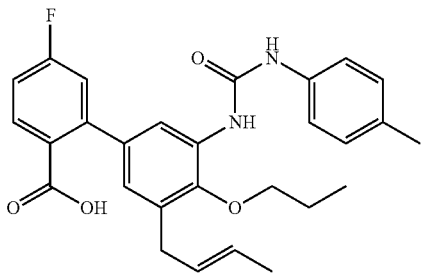 [SMILES: C/C=C/Cc1cc(-c2cc(F)ccc2C(=O)O)cc(NC(=O)Nc2ccc(C)cc2)c1OCCC]

The title compound was prepared from 19D and 2-carboxy-5-fluorophenylboronic acid using the procedure for the conversion of 8E to 8. MS(ES): m/z=477 [M+H]$^+$. HPLC T$_r$: 12.93$^d$.

Example 22

1-(5-Butyl-4-propoxy-2'-(1H-tetrazol-5-yl)-[1,1'-biphenyl]-3-yl)-3-(p-tolyl)urea

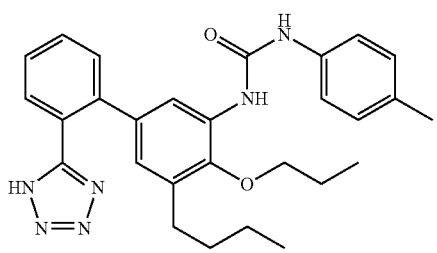

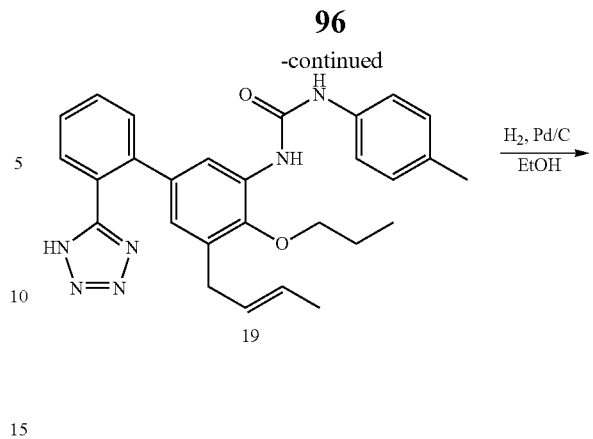

A suspension of (E)-1-(5-(but-2-en-1-yl)-4-propoxy-2'-(1H-tetrazol-5-yl)-[1,1'-biphenyl]-3-yl)-3-(p-tolyl)urea (19) (0.02 g, 0.041 mmol) and palladium on carbon (4.41 mg, 0.041 mmol) was placed under an atmosphere of H$_2$ and stirred for 18 h. The catalyst was removed by filtration, and the resulting solution concentrated. The residue was lyophilized from benzene to afford 1-(5-butyl-4-propoxy-2'-(1H-tetrazol-5-yl)-[1,1'-biphenyl]-3-yl)-3-(p-tolyl)urea (0.018 g, 85% yield) as a white powder. MS(ES): m/z=485 [M+H]$^+$. HPLC T$_r$: 12.72$^d$.

Example 23

3'-Butyl-4'-propoxy-5'-(3-(p-tolyl)ureido)-[1,1'-biphenyl]-2-carboxylic acid

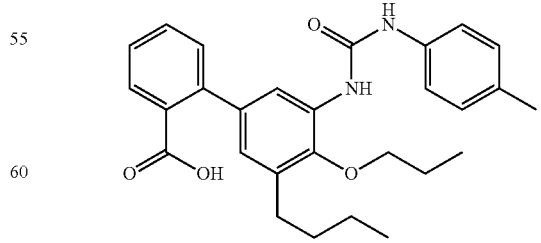

The title compound was prepared from 20 using the procedure for the conversion of 19 to 22. MS(ES): m/z=461 [M+H]$^+$. HPLC T$_r$: 12.84$^d$.

Example 24

(E)-3'-(But-2-en-1-yl)-5-fluoro-4'-propoxy-5'-(3-(p-tolyl)ureido)-[1,1'-biphenyl]-2-carboxylic acid

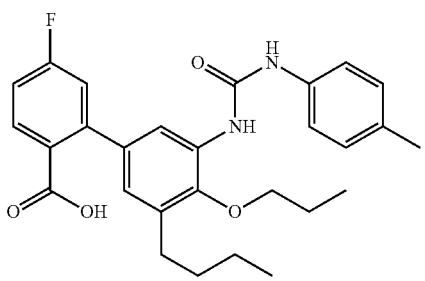 [SMILES: CCCCc1cc(-c2cc(F)ccc2C(=O)O)cc(NC(=O)Nc2ccc(C)cc2)c1OCCC]

The title compound was prepared from 21 using the procedure for the conversion of 19 to 22. MS(ES): m/z=479 [M+H]$^+$. HPLC T$_r$: 13.06$^d$.

Example 25

(E)-1-(4-(Benzyloxy)-5-(but-2-en-1-yl)-2'-(1H-tetrazol-5-yl)-[1,1'-biphenyl]-3-yl)-3-(p-tolyl)urea

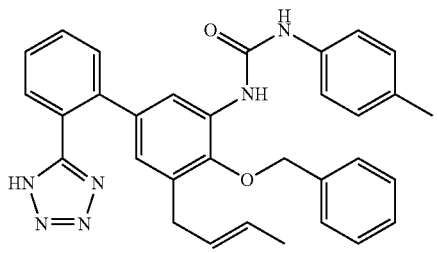 [SMILES: C/C=C/Cc1cc(-c2ccccc2-c2nnn[nH]2)cc(NC(=O)Nc2ccc(C)cc2)c1OCc1ccccc1]

25A. (E)-2-(Benzyloxy)-5-bromo-1-(but-2-en-1-yl)-3-nitrobenzene

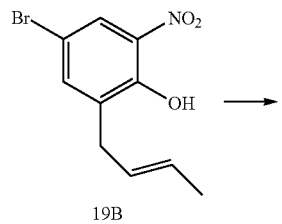

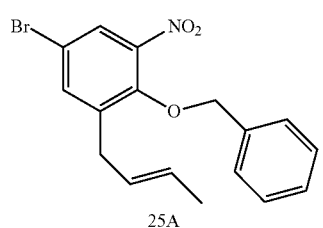

The title compound was prepared from 19B and benzyl bromide using the procedure for the conversion of 8B to 8C. $^1$H NMR (400 MHz, DMSO-d$_6$) δ ppm 8.05 (d, 1H, J=2.6 Hz) 7.73 (d, 1H, J=2.6 Hz); 7.38-7.44 (m, 5H); 5.50-5.55 (m, 2H); 4.97 (s, 2H); 3.36-3.39 (m, 2H); 1.63 (d, 3H, J=4.2 Hz).

25B. (E)-1-(2-(Benzyloxy)-5-bromo-3-(but-2-en-1-yl)phenyl)-3-(p-tolyl)urea

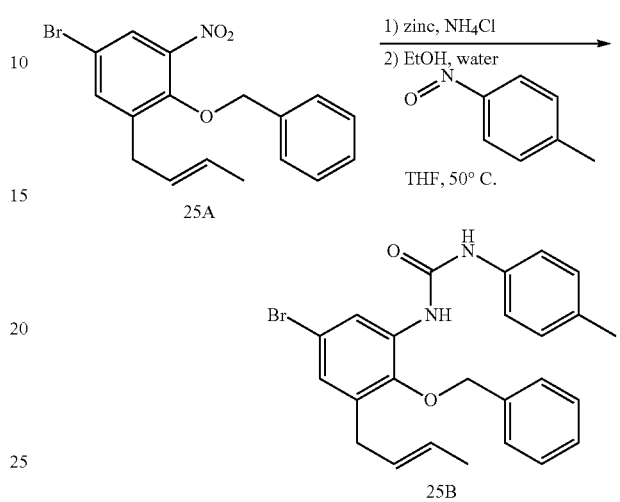

The title compound was prepared from 25A using the procedures for the conversion of 8C to 8E. MS(ES): m/z=467 [M+H]$^+$. HPLC T$_r$: 3.24$^r$.

25. (E)-1-(4-(Benzyloxy)-5-(but-2-en-1-yl)-2'-(1H-tetrazol-5-yl)-[1,1'-biphenyl]-3-yl)-3-(p-tolyl)urea

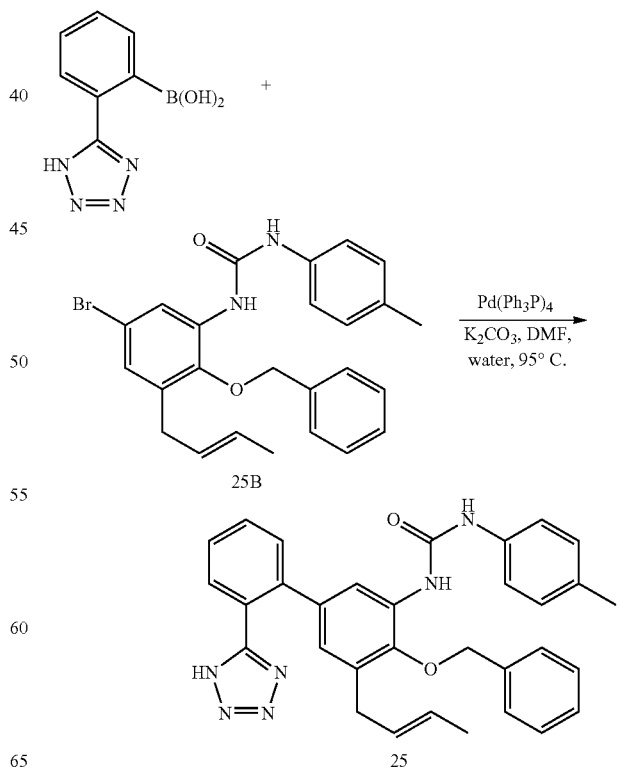

The title compound was prepared from 25B using the procedures for the conversion of 8E to 8. MS(ES): m/z=531 [M+H]⁺. HPLC T$_r$: 12.96$^d$.

Example 26

(E)-4'-(Benzyloxy)-3'-(but-2-en-1-yl)-5'-(3-(p-tolyl)ureido)-[1,1'-biphenyl]-2-carboxylic acid

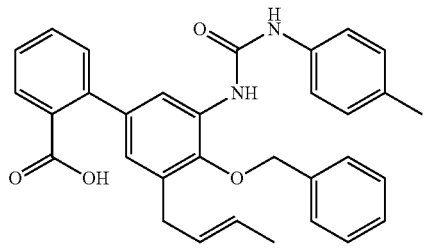 [SMILES: C/C=C/Cc1cc(-c2ccccc2C(=O)O)cc(NC(=O)Nc2ccc(C)cc2)c1OCc1ccccc1]

The title compound was prepared from 25B and 2-carboxyphenylboronic acid using the procedure for the conversion of 8E to 8. MS(ES): m/z=507 [M+H]⁺. HPLC T$_r$: 13.04$^d$.

Example 27

(E)-4'-(Benzyloxy)-3'-(but-2-en-1-yl)-5-fluoro-5'-(3-(p-tolyl)ureido)-[1,1'-biphenyl]-2-carboxylic acid

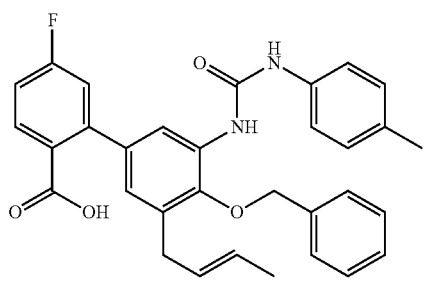 [SMILES: C/C=C/Cc1cc(-c2cc(F)ccc2C(=O)O)cc(NC(=O)Nc2ccc(C)cc2)c1OCc1ccccc1]

The title compound was prepared from 25B and 5-fluoro-2-carboxyphenylboronic acid using the procedure for the conversion of 8E to 8. MS(ES): m/z=525 [M+H]⁺. HPLC T$_r$: 13.27$^d$.

Example 28

1-(4-(Benzyloxy)-2'-(1H-tetrazol-5-yl)-[1,1'-biphenyl]-3-yl)-3-(p-tolyl)urea

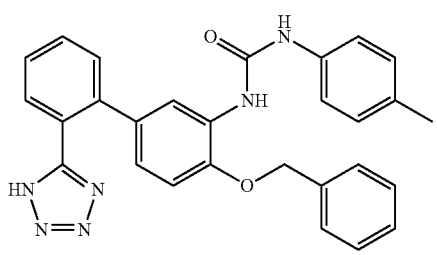 [SMILES: Cc1ccc(NC(=O)Nc2cc(-c3ccccc3-c3nnn[nH]3)ccc2OCc2ccccc2)cc1]

28A. 1-(Benzyloxy)-4-bromo-2-nitrobenzene

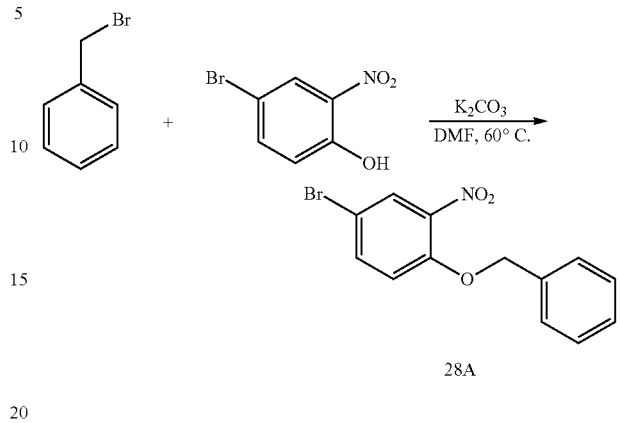

The title compound was prepared from 4-bromo-2-nitrophenol (2.180 g, 10 mmol) and benzyl bromide by the procedure used for the preparation of 16A. ¹H NMR (400 MHz, DMSO-d₆) δ ppm 8.14 (d, 1H, J=2.4 Hz); 7.83 (dd, 1H, J=9.0, 2.4 Hz); 7.31-7.45 (m, 6H,); 5.31 (s, 2H).

28B. 2-(Benzyloxy)-5-bromoaniline

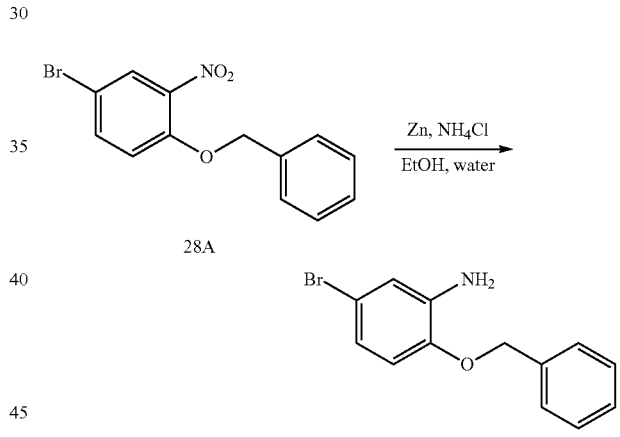

The title compound was prepared from 28A by the procedure used for the conversion of 8C to 8D. MS(ES): m/z=280 [M+H]⁺. HPLC T$_r$: 1.80$^p$.

28C. 1-(2-(Benzyloxy)-5-bromophenyl)-3-(p-tolyl)urea

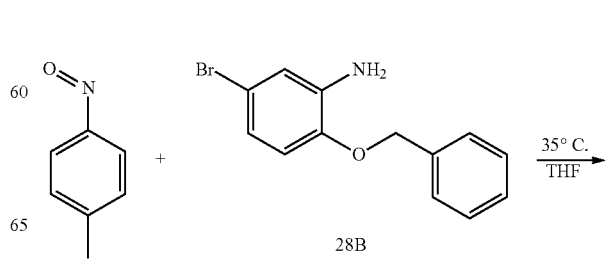

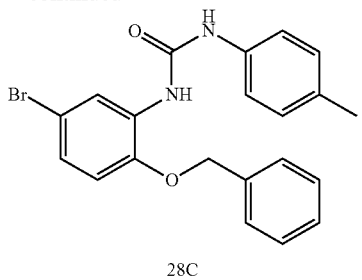

28C

The title compound was prepared from 28B at 35° C. by the procedure used for the conversion of 8D to 8E. MS(ES): m/z=411 [M+H]+. HPLC T$_r$: 2.95$^r$.

28. 1-(4-(Benzyloxy)-2'-(1H-tetrazol-5-yl)-[1,1'-biphenyl]-3-yl)-3-(p-tolyl)urea

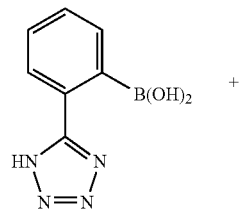 +

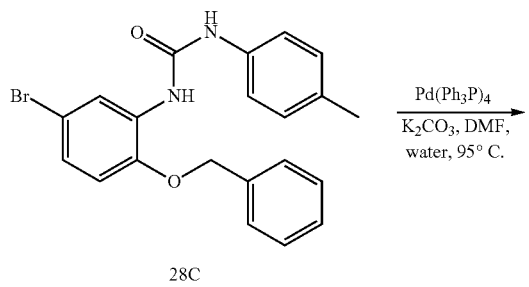

28C

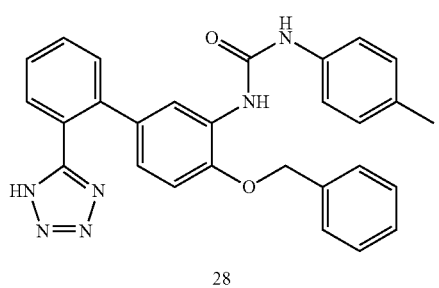

28

The title compound was prepared from 28C using the procedures for the conversion of 8E to 8. MS(ES): m/z=477 [M+H]+. HPLC T$_r$: 12.32$^d$.

Example 29

(E)-1-(4-Propoxy-2'-(1H-tetrazol-5-yl)-5-(4,4,4-trifluorobut-1-en-1-yl)-[1,1'-biphenyl]-3-yl)-3-(p-tolyl)urea

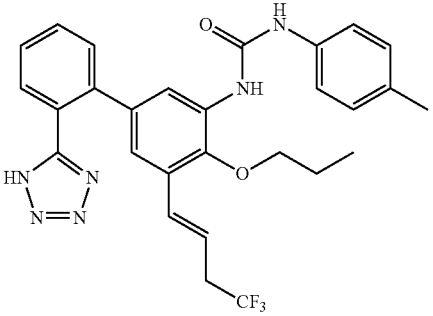 [SMILES: CCCOc1c(/C=C/CC(F)(F)F)cc(-c2ccccc2-c2nnn[nH]2)cc1NC(=O)Nc1ccc(C)cc1]

29A. 4-Bromo-2-nitro-1-((1,1,1-trifluorobut-3-en-2-yl)oxy)benzene

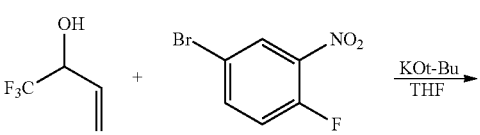

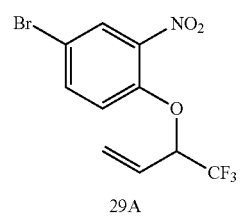

29A

To a solution of 1,1,1-trifluorobut-3-en-2-ol (0.378 g, 3.00 mmol) in THF (3 mL) was added potassium t-butoxide (3.00 mL, 3.00 mmol). The mixture was stirred for 2-3 min. then treated with 4-bromo-1-fluoro-2-nitrobenzene (0.440 g, 2 mmol). The dark solution was stirred for 1 h at RT. The reaction was transferred into aq. HCl, and this mixture was extracted with ether. The organic extract was dried, stripped, and chromatographed on silica gel (gradient elution with ether-hexanes) to afford 4-bromo-2-nitro-1-((1,1,1-trifluorobut-3-en-2-yl)oxy)benzene (0.47 g, 64.9% yield) as an amber oil. $^1$H NMR (400 MHz, DMSO-d$_6$) δ ppm 8.19 (d, 1H, J=2.6 Hz); 7.84 (dd, 1H, J=9.0, 2.4 Hz); 7.43 (d, 1H, J=9.0 Hz); 5.84-6.01 (m, 2H,); 5.74 (d, 1H, J=16.5 Hz); 5.66 (d, 1H, J=9.9 Hz).

29B. (E)-4-Bromo-2-nitro-6-(4,4,4-trifluorobut-2-en-1-yl)phenol

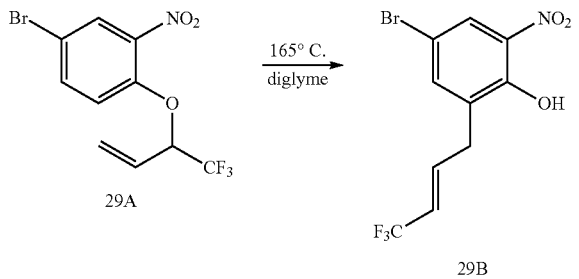 [SMILES: C=CC(Oc1ccc(Br)cc1[N+](=O)[O-])C(F)(F)F ; O=[N+]([O-])c1cc(Br)cc(C/C=C/C(F)(F)F)c1O]

The title compound was prepared from 29A at 165° C. using the procedure for the conversion of 8B to 8C. $^1$H NMR (400 MHz, DMSO-d$_6$) δ ppm 10.73 (br. s, 1H); 8.04 (d, 1H, J=2.4 Hz) 7.74 (d, 1H, J=2.4 Hz); 6.54-6.67 (m, 1H); 5.90-6.00 (m, 1H); 3.55-3.9 (m, 2H).

29C. (E)-5-Bromo-1-nitro-2-propoxy-3-(4,4,4-trifluorobut-1-en-1-yl)benzene, and

29D, (E)-5-Bromo-1-nitro-2-propoxy-3-(4,4,4-trifluorobut-2-en-1-yl)benzene

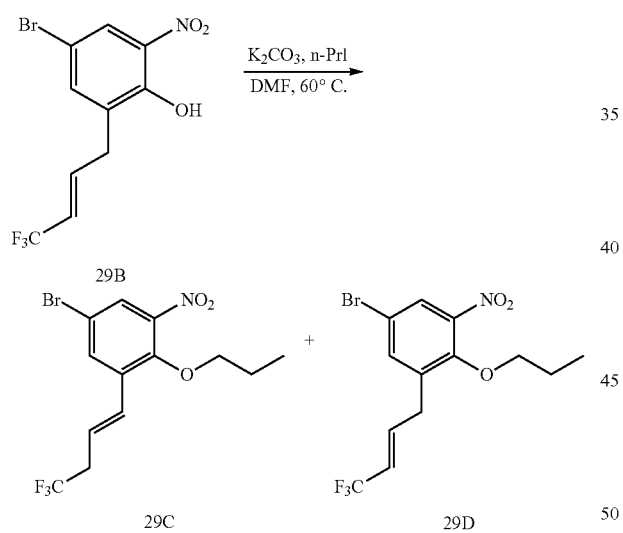

To a solution of (E)-4-bromo-2-nitro-6-(4,4,4-trifluorobut-2-en-1-yl)phenol (29B) (0.14 g, 0.429 mmol) in DMF (1 mL) was added potassium carbonate (0.178 g, 1.288 mmol). The resulting mixture was stirred 10 min. at RT then treated with 1-iodopropane (0.219 g, 1.288 mmol). This mixture was stirred 2 h at 60° C., after which time TLC indicated formation of a new spot at significantly higher Rf, a new spot at slightly higher Rf, and SM. The mixture was treated with 0.05 g more iodide and stirred 7 h longer at 60° C. then overnight at RT. The reaction was chromatographed on silica gel (gradient elution with ether-hexanes). Concentration of the appropriate fractions afforded (E)-5-bromo-1-nitro-2-propoxy-3-(4,4,4-trifluorobut-1-en-1-yl)benzene (0.06 g, 36.1% yield), $^1$H NMR (400 MHz, DMSO-d$_6$) δ ppm 8.14 (d, 1H, J=2.4 Hz) 8.07 (d, 1H, J=2.4 Hz); 6.86 (d, 1H, J=15.9 Hz); 6.50 (dt, 1H, J=16.1, 7.1 Hz); 3.85 (t, 2H, J=6.6 Hz); 3.28-3.39 (m, integration indeterminate due to water peak); 1.66-1.76 (m, 2H); 0.93 (t, 3H, J=7.5 Hz)) and (E)-5-bromo-1-nitro-2-propoxy-3-(4,4,4-trifluorobut-2-en-1-yl)benzene (0.05 g, 30.1% yield, $^1$H NMR (400 MHz, DMSO-d$_6$) δ ppm 8.07 (d, 1H, J=2.4 Hz) 7.80 (d, 1H, J=2.4 Hz); 6.60-6.68 (m, 1H); 5.98-6.09 (m, 1H); 3.86 (t, 2H, J=6.5 Hz); 3.54-3.64 (m, 2H); 1.64-1.74 (m, 2H); 0.93 (t, 3H, J=7.4 Hz).) as pale yellow oils.

29E. (E)-1-(5-Bromo-2-propoxy-3-(4,4,4-trifluorobut-1-en-1-yl)phenyl)-3-(p-tolyl)urea

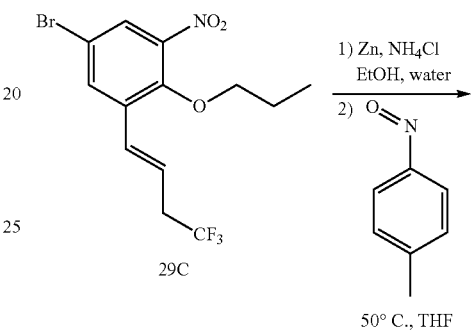

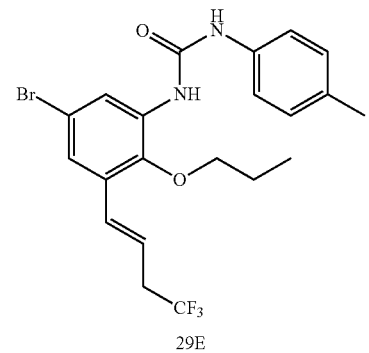

The title compound was prepared from 29C using the procedures for the conversion of 16D to 16E. MS(ES): m/z=473 [M+H]$^+$. HPLC T$_r$: 5.08$^I$.

29. (E)-1-(4-Propoxy-2'-(1H-tetrazol-5-yl)-5-(4,4,4-trifluorobut-1-en-1-yl)-[1,1'-biphenyl]-3-yl)-3-(p-tolyl)urea

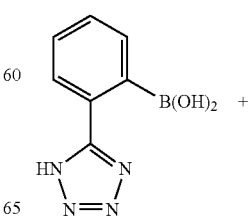

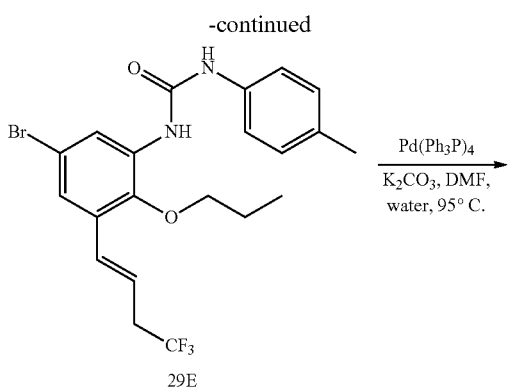

29E

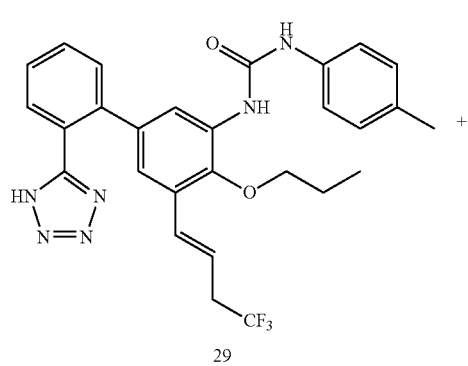

29

Example 30

(E)-1-(5-(4,4-Difluorobuta-1,3-dien-1-yl)-4-propoxy-2'-(1H-tetrazol-5-yl)-[1,1'-biphenyl]-3-yl)-3-(p-tolyl)urea

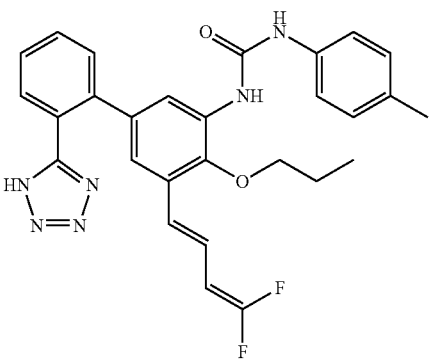 [SMILES: CCCOc1c(/C=C/C=C(F)F)cc(-c2ccccc2-c2nnn[nH]2)cc1NC(=O)Nc1ccc(C)cc1]

The title compound was prepared as a by-product in the conversion of 29E into 29, using the procedure for the conversion of 8E to 8. MS(ES): m/z=517 [M+H]+. HPLC $T_r$: 4.72[i].

Example 31

1-(4-Propoxy-2'-(1H-tetrazol-5-yl)-5-(4,4,4-trifluorobutyl)-[1,1'-biphenyl]-3-yl)-3-(p-tolyl)urea

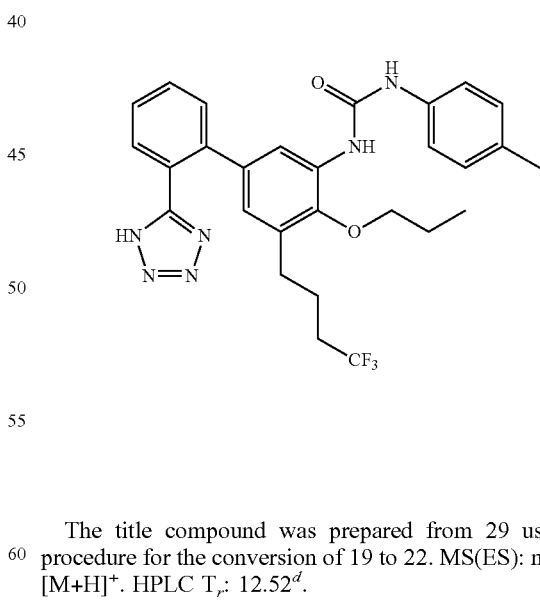

The title compound was prepared from 29 using the procedure for the conversion of 19 to 22. MS(ES): m/z=539 [M+H]+. HPLC $T_r$: 12.52[d].

Example 32

(E)-1-(4-Propoxy-2'-(1H-tetrazol-5-yl)-5-(4,4,4-trifluorobut-2-en-1-yl)-[1,1'-biphenyl]-3-yl)-3-(p-tolyl)urea

30

The title compound was prepared from 29E using the procedure for the conversion of 8E to 8. MS(ES): m/z=537 [M+H]+. HPLC $T_r$: 12.46[d].

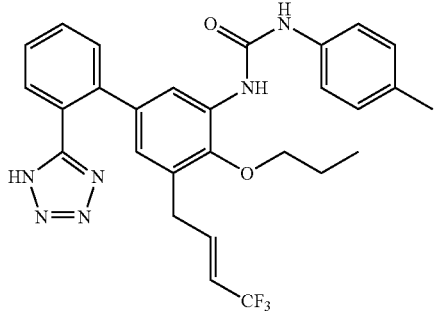

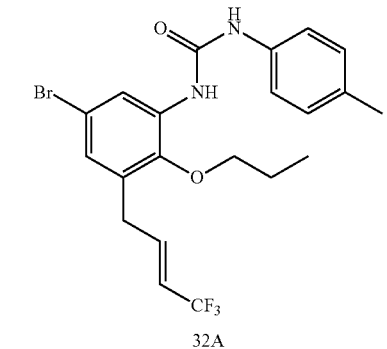

32A. (E)-1-(5-Bromo-2-propoxy-3-(4,4,4-trifluorobut-2-en-1-yl)phenyl)-3-(p-tolyl)urea

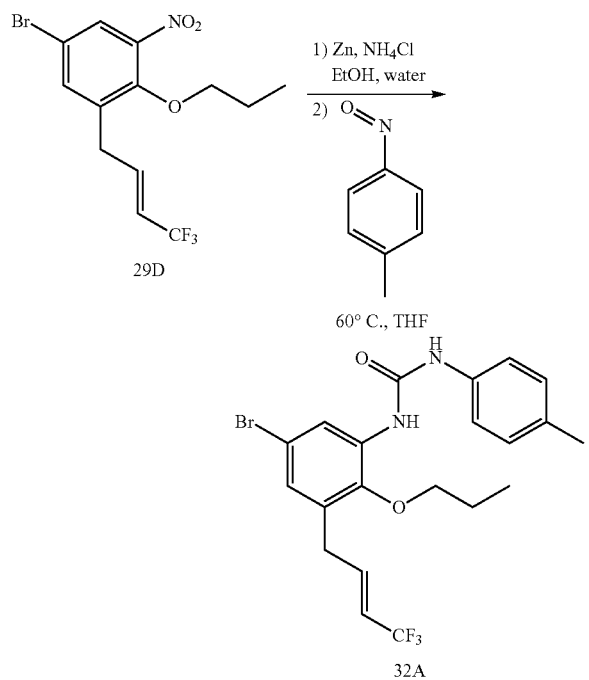

The title compound was prepared from 29D using the procedures for the conversion of 16D to 16E. MS(ES): m/z=473 [M+H]$^+$. HPLC T$_r$: 2.80$^q$.

32. (E)-1-(4-Propoxy-2'-(1H-tetrazol-5-yl)-5-(4,4,4-trifluorobut-2-en-1-yl)-[1,1'-biphenyl]-3-yl)-3-(p-tolyl)urea

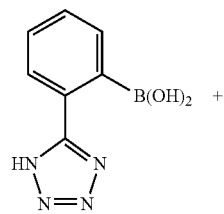

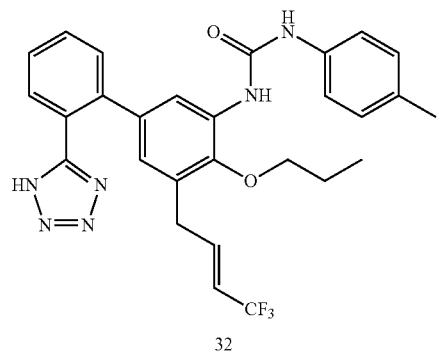

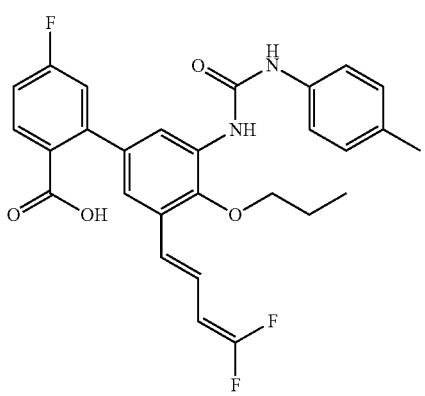 [SMILES: CCCOc1c(/C=C/C=C(F)F)cc(-c2cc(F)ccc2C(=O)O)cc1NC(=O)Nc1ccc(C)cc1]

The title compound was prepared from 32A using the procedure for the conversion of 8E to 8. MS(ES): m/z=537 [M+H]$^+$. HPLC T$_r$: 12.45$^d$.

Example 33

(E)-3'-(4,4-Difluorobuta-1,3-dien-1-yl)-5-fluoro-4'-propoxy-5'-(3-(p-tolyl)ureido)-[1,1'-biphenyl]-2-carboxylic acid The title compound was prepared from 32A and 2-carboxy-5-fluorophenylboronic acid using the procedure for the conversion of 8E to 8. MS(ES): m/z=511 [M+H]$^+$. HPLC T$_r$: 3.07$^r$.

Example 34

(E)-1-(5-Cinnamyl-4-propoxy-2'-(1H-tetrazol-5-yl)biphenyl-3-yl)-3-p-tolylurea

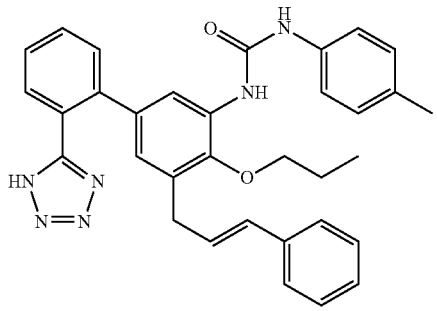 [SMILES: CCCOc1c(C/C=C/c2ccccc2)cc(-c2ccccc2-c2nnn[nH]2)cc1NC(=O)Nc1ccc(C)cc1]

34A. (+/−)-4-Bromo-2-nitro-1-((1-phenylallyl)oxy)benzene

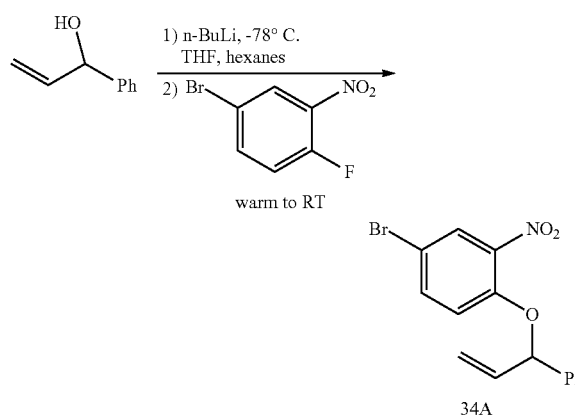

The title compound was prepared from 1-phenylprop-2-en-1-ol and 4-bromo-1-fluoro-2-nitrobenzene by the procedure described in 8A. $^1$H NMR (400 MHz, DMSO-$d_6$) δ ppm 8.10 (d, 1H, J=2.6 Hz); 7.76 (dd, 1H, J=9.0, 2.6 Hz); 7.28-7.44 (m, 6H); 6.20 (br.d, 1H); 6.02 (ddd, 1H, J=17.0, 10.6, 6.4 Hz); 5.42 (dt, 1H, J=17.2, 1.3 Hz); 5.26 (dt, 1H, J=10.3, 1.1 Hz).

34B. 4-Bromo-2-cinnamyl-6-nitrophenol

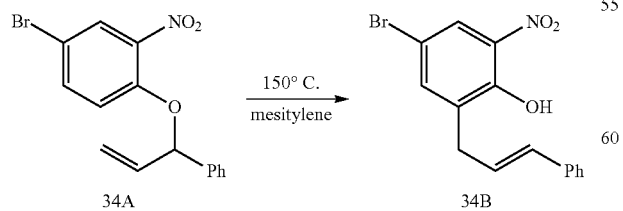

A solution of 4-bromo-2-nitro-1-((1-phenylallyl)oxy)benzene (34A) (0.1 g, 0.299 mmol) in mesitylene (0.5 mL) was heated to 150° C. for 2 h then cooled and purified by flash chromatography (gradient elution with ether-hexanes). Concentration of the appropriate fractions afforded 4-bromo-2-cinnamyl-6-nitrophenol (0.075 g, 71.3% yield) as a yellow oil which solidified upon standing. $^1$H NMR (400 MHz, DMSO-$d_6$) δ ppm 10.68 (br. s, 1H); 8.01 (d, 1H, J=2.6 Hz) 7.73 (d, 1H, J=2.4 Hz); 7.40 (d, 2H, J=7.3 Hz); 7.30 (t, 2H, J=7.7 Hz); 7.21 (t, 1H, J=7.3 Hz); 6.37-6.51 (m, 2H); 3.57 (d, 2H, J=6.2 Hz).

34C. 5-Bromo-1-cinnamyl-3-nitro-2-propoxybenzene

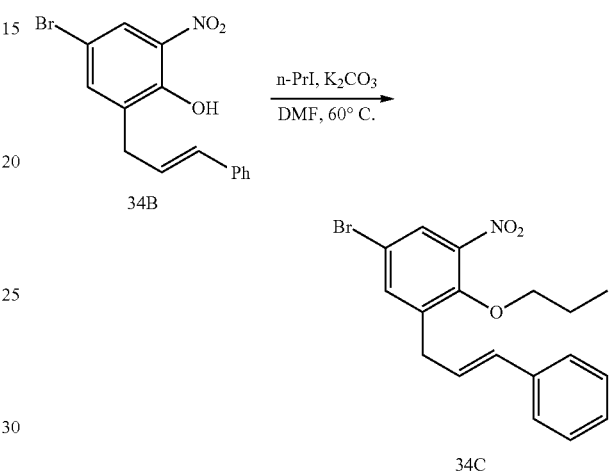

The title compound was prepared from 34B by the procedure described for the conversion of 8B into 8C. $^1$H NMR (400 MHz, DMSO-$d_6$) δ ppm 8.04 (d, 1H, J=2.6 Hz) 7.81 (d, 1H, J=2.4 Hz); 7.42 (d, 2H, J=7.3 Hz); 7.31 (t, 2H, J=7.5 Hz); 7.22 (t, 1H, J=7.3 Hz); 6.52 (d, 1H, J=15.9 Hz); 6.43 (dt, 1H, J=15.9, 6.4 Hz); 3.90 (t, 2H, J=6.4 Hz); 3.62 (d, 2H, J=6.6 Hz); 1.68-1.77 (m, 2H); 0.95 (t, 3H, J=7.5 Hz).

34D. (E)-1-(5-Bromo-3-cinnamyl-2-propoxyphenyl)-3-(p-tolyl)urea

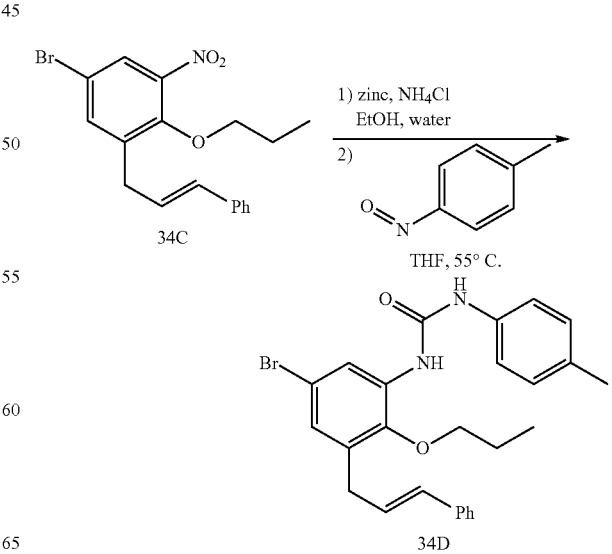

The title compound was prepared from 34C by the procedures described for the conversion of 8C into 8E. MS(ES): m/z=481 [M+H]+. HPLC T$_r$: 2.95$^q$.

34. (E)-1-(5-Cinnamyl-4-propoxy-2'-(1H-tetrazol-5-yl)biphenyl-3-yl)-3-p-tolylurea

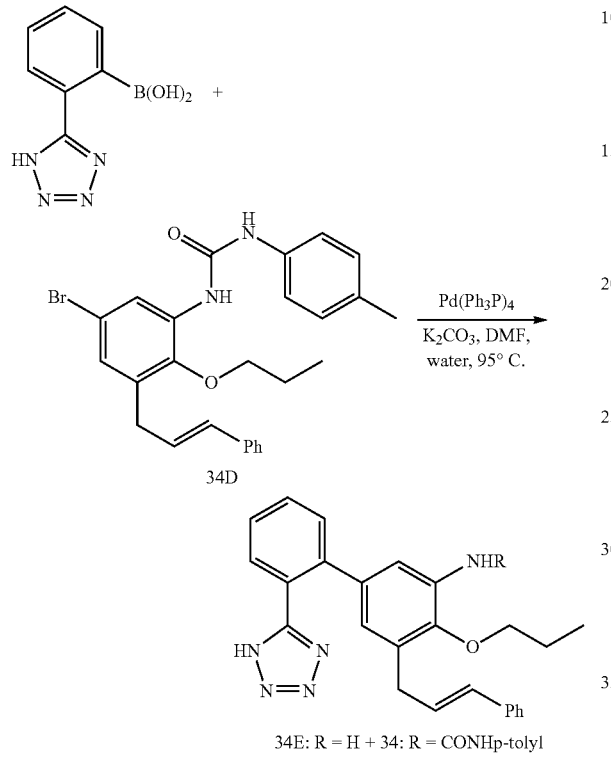

The title compound was prepared from 34D by the procedure described for the conversion of 8E into 8 except that the reaction was run over 18 h. As a result of the extended reaction time some of aniline 34E was isolated in addition to the expected product 34. MS(ES): m/z=545 [M+H]+. HPLC T$_r$: 13.11$^d$. 34E: MS(ES): m/z=412 [M+H]+. HPLC T$_r$: 2.41$^r$.

Example 35

3'-Cinnamyl-4'-propoxy-5'-(3-p-tolylureido)biphenyl-2-carboxylic acid

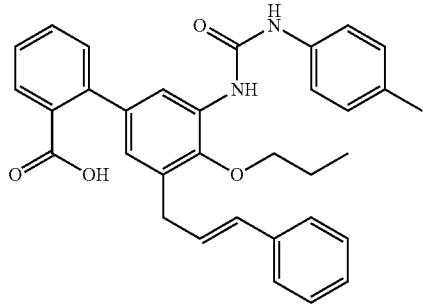 [SMILES: CCCOc1c(C/C=C/c2ccccc2)cc(-c2ccccc2C(=O)O)cc1NC(=O)Nc1ccc(C)cc1]

The title compound was prepared from 34D and 2-carboxyphenylboronic acid by the procedure described for the conversion of 8E into 8. MS(ES): m/z=521 [M+H]+. HPLC T$_r$: 13.22$^d$.

Example 36

3'-(3-Phenylpropyl)-4'-propoxy-5'-(3-p-tolylureido)biphenyl-2-carboxylic acid

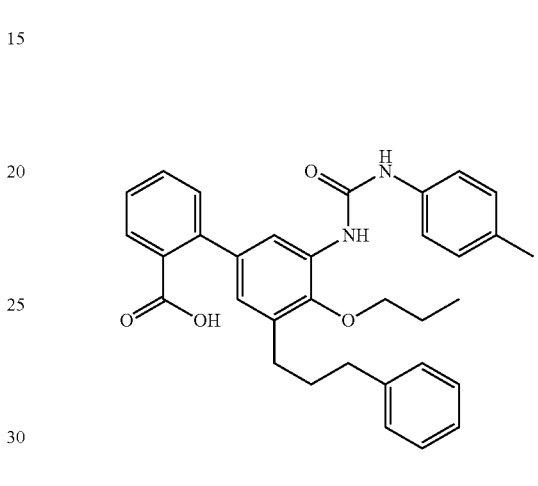

The title compound was prepared from 35 by the procedure described for the conversion of 19 into 22. MS(ES): m/z=523 [M+H]+. HPLC T$_r$: 13.36$^d$.

Example 37

1-(5-(3-Phenylpropyl)-4-propoxy-2'-(1H-tetrazol-5-yl)biphenyl-3-yl)-3-p-tolylurea

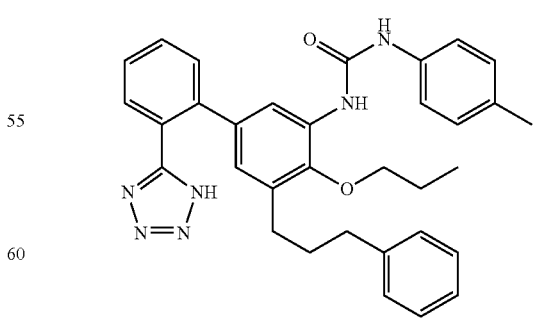

The title compound was prepared from 34 by the procedure described for the conversion of 19 into 22. MS(ES): m/z=547 [M+H]+. HPLC T$_r$: 13.21$^d$.

Example 38

(E)-1-(5-Cinnamyl-4-propoxy-2'-(1H-tetrazol-5-yl)biphenyl-3-yl)-3-(2-fluorophenyl)urea

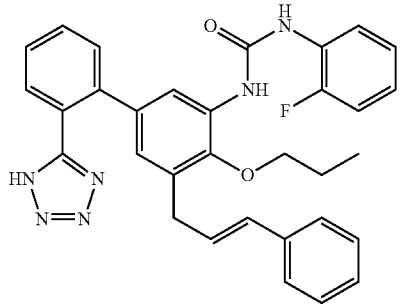 [SMILES: CCCOc1c(C/C=C/c2ccccc2)cc(-c2ccccc2-c2nnn[nH]2)cc1NC(=O)Nc1ccccc1F]

The title compound was prepared at 55° C. from 34E and 2-fluorophenylisocyanate by heating a stirred solution of 34E and the isocyanate at about 50° C. in THF and purifying the resulting solution by prep. HPLC. MS(ES): m/z=549 [M+H]$^+$. HPLC T$_r$: 13.04$^d$.

Example 39

1-(2-Fluorophenyl)-3-(5-(3-phenylpropyl)-4-propoxy-2'-(1H-tetrazol-5-yl)biphenyl-3-yl)urea

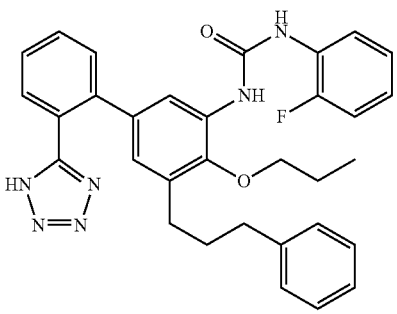 [SMILES: CCCOc1c(CCCc2ccccc2)cc(-c2ccccc2-c2nnn[nH]2)cc1NC(=O)Nc1ccccc1F]

The title compound was prepared from 38 by the procedure described for the conversion of 19 into 22. MS(ES): m/z=551 [M+H]$^+$. HPLC T$_r$: 13.09$^d$.

Example 40

4'-(Benzyloxy)-3'-butyl-5-fluoro-5'-(3-p-tolylureido)biphenyl-2-carboxylic acid

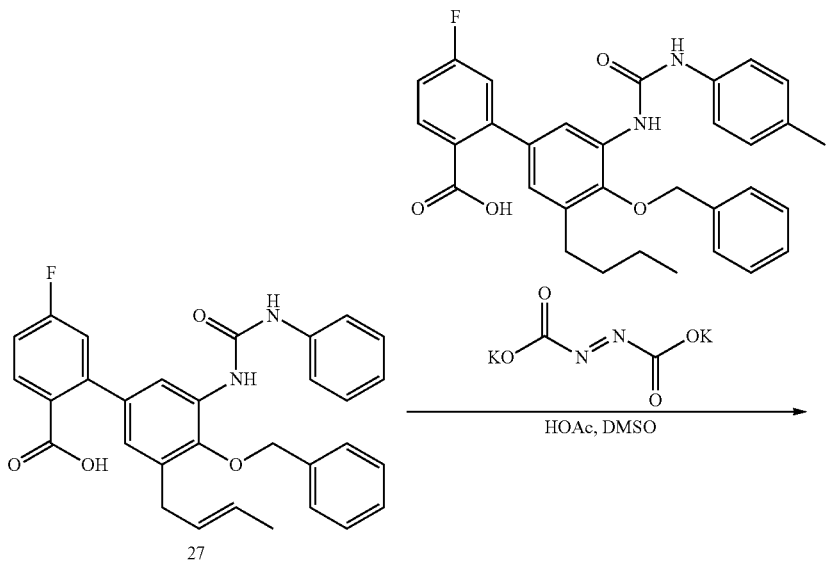

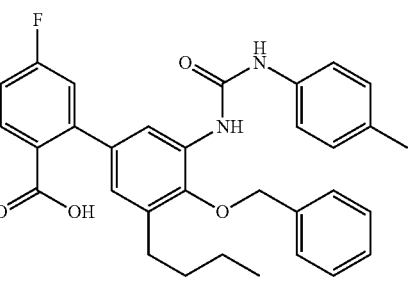

A suspension of (E)-1-(5-(but-2-en-1-yl)-4-propoxy-2'-(1H-tetrazol-5-yl)-[1,1'-biphenyl]-3-yl)-3-(p-tolyl)urea (27) (0.02 g, 0.041 mmol) in DMSO (0.1 mL) was treated with (E)-diazene-1,2-dicarboxylic acid, 2 K+ (0.024 g, 0.124 mmol) followed by acetic acid (0.014 mL, 0.248 mmol). Bubbles formed in the mixture immediately and ceased forming within a few seconds. The additions were repeated twice at 5 min. intervals then LCMS was taken. It appears that product has formed to the extent of about 10%. This suggests that under these conditions diimide is generated immediately and transiently upon HOAc addition. The reaction was stirred 1 day longer with many (~25) small additions of the diimide precursor and HOAc. Also, three additional aliquots of DMSO were added to ensure easier stirring. Reaction is still not complete, but SM and product are resolved on LCMS. The mixture was transferred by pipette into aq. HCl, and this mixture was extracted twice with dichloromethane. The combined organic extracts were dried, stripped, and purified by prep. HPLC (Axia Luna 21×100 mm column, MeOH-water-TFA gradient). Concentration of the appropriate fraction and lyophilization from benzene afforded 4'-(benzyloxy)-3'-butyl-5-fluoro-5'-(3-(p-tolyl)ureido)-[1,1'-biphenyl]-2-carboxylic acid (0.007 g, 51.0% yield) as a white powder. MS(ES): m/z=527 [M+H]+. HPLC $T_r$: 13.46$^d$.

Example 41

4'-(2-tert-butylphenoxy)-4-methoxy-N-(methylsulfonyl)-3'-(3-p-tolylureido)biphenyl-3-carboxamide

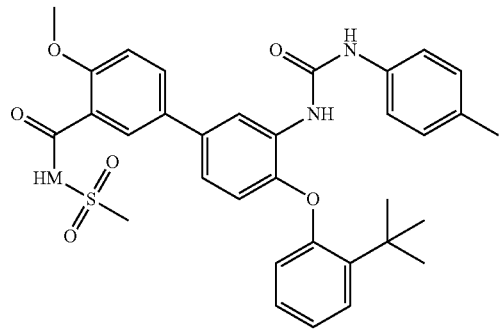

41

The title compound was prepared from 5A using the procedure for the conversion of 2 into 6. MS(ES): m/z=602 [M+H]+. HPLC $T_r$: 13.29$^d$.

Examples 42 to 154

Using the methods described herein (the procedure for the conversion of 2A into 2 is representative), the following compounds of the invention shown in Table 4 were prepared.

TABLE 4

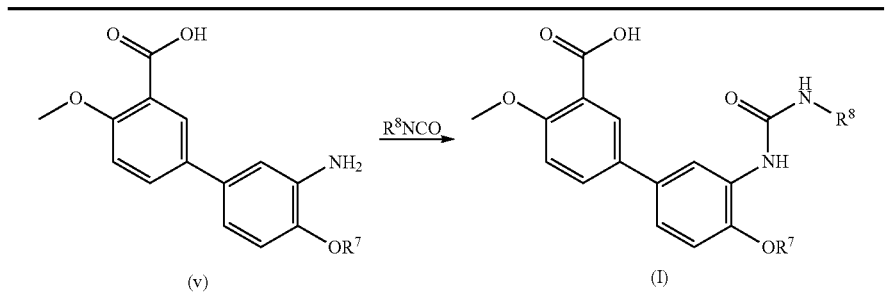

| Ex. No. | Name | R⁸ | —OR⁷ | HPLC $T_r$ | (M + H)+ |
|---|---|---|---|---|---|
| 42 | 4'-(2-tert-butylphenoxy)-3'-(3-(2-chlorophenyl)ureido)-4-methoxybiphenyl-3-carboxylic acid | 2-chlorophenyl | 2-tert-butylphenoxy | 12.22$^f$ | 545 |
| 43 | 4'-(2-tert-butylphenoxy)-4-methoxy-3'-(3-(4-(trifluoromethyl)phenyl)ureido)biphenyl-3-carboxylic acid | 4-(trifluoromethyl)phenyl | 2-tert-butylphenoxy | 13.27$^d$ | 579 |

TABLE 4-continued

| Ex. No. | Name | R[8] | —OR[7] | HPLC T$_r$ | (M + H)[+] |
|---|---|---|---|---|---|
| 44 | 4'-(2-tert-butylphenoxy)-4-methoxy-3'-(3-o-tolylureido)biphenyl-3-carboxylic acid | 2-methylphenyl | 2-tert-butylphenoxy | 13.10[d] | 525 |
| 45 | 4'-(2-tert-butylphenoxy)-4-methoxy-3'-(3-m-tolylureido)biphenyl-3-carboxylic acid | 3-methylphenyl | 2-tert-butylphenoxy | 13.17[d] | 525 |
| 46 | 4'-(2-tert-butylphenoxy)-4-methoxy-3'-(3-(2-(trifluoromethyl)phenyl)ureido)biphenyl-3-carboxylic acid | 2-(trifluoromethyl)phenyl | 2-tert-butylphenoxy | 12.85[d] | 579 |
| 47 | 4'-(2-ethylphenoxy)-4-methoxy-3'-(3-p-tolylureido)biphenyl-3-carboxylic acid | 4-methylphenyl | 2-ethylphenoxy | 12.81[d] | 497 |
| 48 | 4'-(2-ethylphenoxy)-4-methoxy-3'-(3-(4-(trifluoromethyl)phenyl)ureido)biphenyl-3-carboxylic acid | 4-(trifluoromethyl)phenyl | 2-ethylphenoxy | 12.85[d] | 551 |
| 49 | 4'-(2-chlorophenoxy)-3'-(3-(2-chlorophenyl)ureido)-4-methoxybiphenyl-3-carboxylic acid | 2-chlorophenyl | 2-chlorophenoxy | 12.59[d] | 523 |

TABLE 4-continued

| Ex. No. | Name | R8 | —OR7 | HPLC Tr | (M + H)+ |
|---|---|---|---|---|---|
| 50 | 4'-(2-chlorophenoxy)-4-methoxy-3'-(3-m-tolylureido)biphenyl-3-carboxylic acid | 3-methylphenyl | 2-chlorophenoxy | 12.54[d] | 503 |
| 51 | 4'-(2-chlorophenoxy)-4-methoxy-3'-(3-p-tolylureido)biphenyl-3-carboxylic acid | 4-methylphenyl | 2-chlorophenoxy | 12.51[d] | 503 |
| 52 | 4'-(2-chlorophenoxy)-4-methoxy-3'-(3-(2-(trifluoromethyl)phenyl)ureido)biphenyl-3-carboxylic acid | 2-(trifluoromethyl)phenyl | 2-chlorophenoxy | 12.40[d] | 557 |
| 53 | 4'-(2-chlorophenoxy)-4-methoxy-3'-(3-o-tolylureido)biphenyl-3-carboxylic acid | 2-methylphenyl | 2-chlorophenoxy | 12.46[d] | 503 |
| 54 | 4'-(2-tert-butyl-6-methylphenoxy)-3'-(3-(2-chlorophenyl)ureido)-4-methoxybiphenyl-3-carboxylic acid | 2-chlorophenyl | 2-tert-butyl-6-methylphenoxy | 13.17[d] | 559 |
| 55 | 3'-(3-(2-chlorophenyl)ureido)-4'-(2-ethylphenoxy)-4-methoxybiphenyl-3-carboxylic acid | 2-chlorophenyl | 2-ethylphenoxy | 12.83[d] | 517 |

TABLE 4-continued

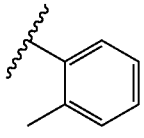 [SMILES: *c1ccccc1C]

| Ex. No. | Name | R⁸ | —OR⁷ | HPLC T$_r$ | (M + H)⁺ |
|---|---|---|---|---|---|
| 56 | 4'-(2-ethylphenoxy)-4-methoxy-3'-(3-o-tolylureido)biphenyl-3-carboxylic acid | 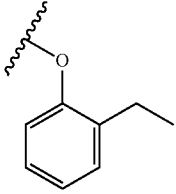 [SMILES: *Oc1ccccc1CC] | 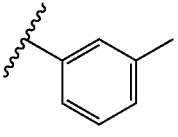 [SMILES: *c1cccc(C)c1] | 12.63$^d$ | 497 |
| 57 | 4'-(2-ethylphenoxy)-4-methoxy-3'-(3-m-tolylureido)biphenyl-3-carboxylic acid | 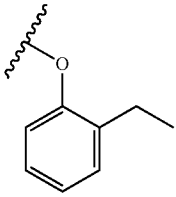 [SMILES: *Oc1ccccc1CC] | 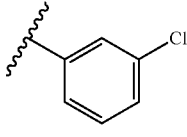 [SMILES: *c1cccc(Cl)c1] | 12.79$^d$ | 497 |
| 58 | 3'-(3-(3-chlorophenyl)ureido)-4'-(2-ethylphenoxy)-4-methoxybiphenyl-3-carboxylic acid | 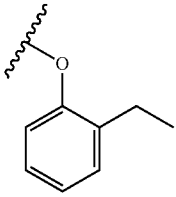 [SMILES: *Oc1ccccc1CC] | 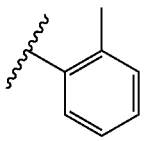 [SMILES: *c1ccccc1C] | 12.96$^d$ | 517 |
| 59 | 4'-(2-tert-butyl-6-methylphenoxy)-4-methoxy-3'-(3-o-tolylureido)biphenyl-3-carboxylic acid | 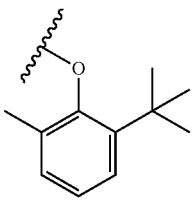 [SMILES: *Oc1c(C)cccc1C(C)(C)C] | 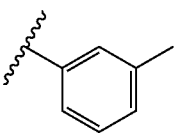 [SMILES: *c1cccc(C)c1] | 13.11$^d$ | 539 |
| 60 | 4'-(2-tert-butyl-6-methylphenoxy)-4-methoxy-3'-(3-m-tolylureido)biphenyl-3-carboxylic acid | 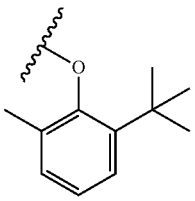 [SMILES: *Oc1c(C)cccc1C(C)(C)C] | 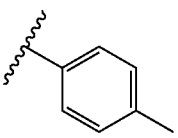 [SMILES: *c1ccc(C)cc1] | 13.13$^d$ | 539 |
| 61 | 4'-(2-tert-butyl-6-methylphenoxy)-4-methoxy-3'-(3-p-tolylureido)biphenyl-3-carboxylic acid | 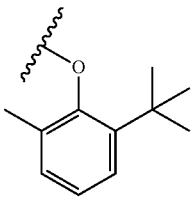 [SMILES: *Oc1c(C)cccc1C(C)(C)C] | | 13.14$^d$ | 539 |

TABLE 4-continued

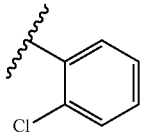 [SMILES: *c1ccccc1Cl]

| Ex. No. | Name | R⁸ | —OR⁷ | HPLC T$_r$ | (M + H)⁺ |
|---|---|---|---|---|---|
| 62 | 3'-(3-(2-chlorophenyl)ureido)-4'-(2-isopropylphenoxy)-4-methoxybiphenyl-3-carboxylic acid | 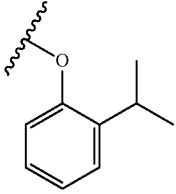 [SMILES: *Oc1ccccc1C(C)C] | 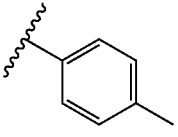 [SMILES: *c1ccc(C)cc1] | 12.96$^d$ | 531 |
| 63 | 4'-(2-isopropylphenoxy)-4-methoxy-3'-(3-p-tolylureido)biphenyl-3-carboxylic acid | 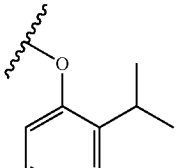 | 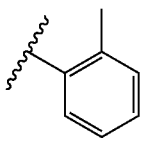 [SMILES: *c1ccccc1C] | 12.89$^d$ | 511 |
| 64 | 4'-(2-isopropylphenoxy)-4-methoxy-3'-(3-o-tolylureido)biphenyl-3-carboxylic acid | 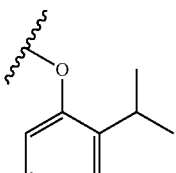 | 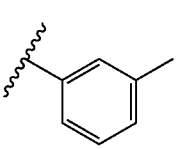 [SMILES: *c1cccc(C)c1] | 12.77$^d$ | 511 |
| 65 | 4'-(2-isopropylphenoxy)-4-methoxy-3'-(3-m-tolylureido)biphenyl-3-carboxylic acid | 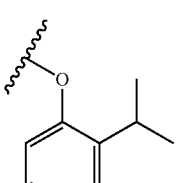 | 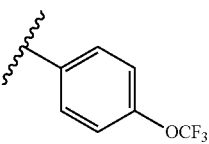 [SMILES: *c1ccc(OC(F)(F)F)cc1] | 12.84$^d$ | 511 |
| 66 | 4'-(2-tert-butylphenoxy)-4-methoxy-3'-(3-(4-(trifluoromethoxy)phenyl)ureido)biphenyl-3-carboxylic acid | 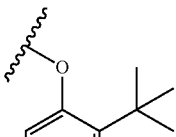 | 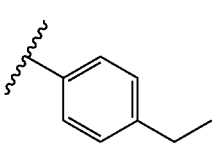 [SMILES: *c1ccc(CC)cc1] | 13.32$^d$ | 595 |
| 67 | 4'-(2-tert-butylphenoxy)-3'-(3-(4-ethylphenyl)ureido)-4-methoxybiphenyl-3-carboxylic acid | 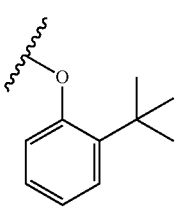 | | 13.36$^d$ | 539 |

TABLE 4-continued

| Ex. No. | Name | R⁸ | —OR⁷ | HPLC T$_r$ | (M + H)⁺ |
|---|---|---|---|---|---|
| 68 | 3'-(3-(2-chlorophenyl)ureido)-4-methoxy-4'-(2-methoxyphenoxy)biphenyl-3-carboxylic acid | 2-chlorophenyl | 2-methoxyphenoxy | 12.37$^d$ | 519 |
| 69 | 4-methoxy-4'-(2-methoxyphenoxy)-3'-(3-p-tolylureido)biphenyl-3-carboxylic acid | m-tolyl | 2-methoxyphenoxy | 12.25$^d$ | 499 |
| 70 | 4-methoxy-4'-(o-tolyloxy)-3'-(3-m-tolylureido)biphenyl-3-carboxylic acid | p-tolyl | o-tolyloxy | 12.54$^d$ | 483 |
| 71 | 3'-(3-(2-chlorophenyl)ureido)-4-methoxy-4'-(o-tolyloxy)biphenyl-3-carboxylic acid | 2-chlorophenyl | o-tolyloxy | 12.64$^d$ | 503 |
| 72 | 4-methoxy-4'-(o-tolyloxy)-3'-(3-o-tolylureido)biphenyl-3-carboxylic acid | o-tolyl | o-tolyloxy | 12.51$^d$ | 483 |
| 73 | 4-methoxy-4'-(o-tolyloxy)-3'-(3-p-tolylureido)biphenyl-3-carboxylic acid | p-tolyl | o-tolyloxy | 12.52$^d$ | 483 |

TABLE 4-continued

| Ex. No. | Name | R⁸ | —OR⁷ | HPLC T$_r$ | (M + H)⁺ |
|---|---|---|---|---|---|
| 74 | 3'-(3-(2-chlorophenyl)ureido)-4-methoxy-4'-(2-propylphenoxy)biphenyl-3-carboxylic acid | 2-chlorophenyl | 2-propylphenoxy | 13.02$^d$ | 531 |
| 75 | 4-methoxy-4'-(2-propylphenoxy)-3'-(3-o-tolylureido)biphenyl-3-carboxylic acid | o-tolyl | 2-propylphenoxy | 12.90$^d$ | 511 |
| 76 | 4-methoxy-4'-(2-propylphenoxy)-3'-(3-m-tolylureido)biphenyl-3-carboxylic acid | m-tolyl | 2-propylphenoxy | 12.96$^d$ | 511 |
| 77 | 4-methoxy-4'-(2-propylphenoxy)-3'-(3-p-tolylureido)biphenyl-3-carboxylic acid | p-tolyl | 2-propylphenoxy | 12.99$^d$ | 511 |
| 78 | 4'-(2-(tert-butyl)phenoxy)-4-methoxy-3'-(3-phenylureido)-[1,1'-biphenyl]-3-carboxylic acid | phenyl | 2-(tert-butyl)phenoxy | 2.41$^i$ | 511 |
| 79 | 4'-(2-(tert-butyl)phenoxy)-3'-(3-(2-fluorophenyl)ureido)-4-methoxy-[1,1'-biphenyl]-3-carboxylic acid | 2-fluorophenyl | 2-(tert-butyl)phenoxy | 2.47$^i$ | 529 |

TABLE 4-continued

| Ex. No. | Name | R⁸ | —OR⁷ | HPLC T_r | (M + H)⁺ |
|---|---|---|---|---|---|
| 80 | 4'-(2-(tert-butyl)phenoxy)-3'-(3-(2,6-difluorophenyl)ureido)-4-methoxy-[1,1'-biphenyl]-3-carboxylic acid | 2,6-difluorophenyl | 2-tert-butylphenoxy | 2.32$^i$ | 547 |
| 81 | 4'-(2-(tert-butyl)phenoxy)-3'-(3-(2,3-dichlorophenyl)ureido)-4-methoxy-[1,1'-biphenyl]-3-carboxylic acid | 2,3-dichlorophenyl | 2-tert-butylphenoxy | 2.77$^i$ | 579 |
| 82 | 4'-(2-(tert-butyl)phenoxy)-3'-(3-(2,6-dichlorophenyl)ureido)-4-methoxy-[1,1'-biphenyl]-3-carboxylic acid | 2,6-dichlorophenyl | 2-tert-butylphenoxy | 2.44$^i$ | 579 |
| 83 | 4'-(2-(tert-butyl)phenoxy)-4-methoxy-3'-(3-(2-methoxyphenyl)ureido)-[1,1'-biphenyl]-3-carboxylic acid | 2-methoxyphenyl | 2-tert-butylphenoxy | 2.46$^i$ | 541 |
| 84 | 4'-(2-(tert-butyl)phenoxy)-3'-(3-(3-fluorophenyl)ureido)-4-methoxy-[1,1'-biphenyl]-3-carboxylic acid | 3-fluorophenyl | 2-tert-butylphenoxy | 2.48$^i$ | 529 |
| 85 | 4'-(2-(tert-butyl)phenoxy)-3'-(3-(3-chlorophenyl)ureido)-4-methoxy-[1,1'-biphenyl]-3-carboxylic acid | 3-chlorophenyl | 2-tert-butylphenoxy | 2.61$^i$ | 545 |

TABLE 4-continued

| Ex. No. | Name | R[8] | —OR[7] | HPLC T$_r$ | (M + H)[+] |
|---|---|---|---|---|---|
| 86 | 4'-(2-(tert-butyl)phenoxy)-3'-(3-(3-methoxyphenyl)ureido)-4-methoxy-[1,1'-biphenyl]-3-carboxylic acid | 3-methoxyphenyl | 2-tert-butylphenoxy | 2.41[i] | 541 |
| 87 | 4'-(2-(tert-butyl)phenoxy)-3'-(3-(4-methoxyphenyl)ureido)-4-methoxy-[1,1'-biphenyl]-3-carboxylic acid | 4-methoxyphenyl | 2-tert-butylphenoxy | 2.35[i] | 541 |
| 88 | 4'-(2-(tert-butyl)phenoxy)-3'-(3-(tert-butyl)ureido)-4-methoxy-[1,1'-biphenyl]-3-carboxylic acid | tert-butyl | 2-tert-butylphenoxy | 2.39[i] | 491 |
| 89 | 4'-(2-(tert-butyl)phenoxy)-3'-(3-(n-propyl)ureido)-4-methoxy-[1,1'-biphenyl]-3-carboxylic acid | n-propyl | 2-tert-butylphenoxy | 2.19[i] | 477 |
| 90 | 4'-(2-(tert-butyl)phenoxy)-3'-(3-(n-butyl)ureido)-4-methoxy-[1,1'-biphenyl]-3-carboxylic acid | n-butyl | 2-tert-butylphenoxy | 2.34[i] | 491 |
| 91 | 4'-(2-(tert-butyl)phenoxy)-3'-(3-(cyclohexyl)ureido)-4-methoxy-[1,1'-biphenyl]-3-carboxylic acid | cyclohexyl | 2-tert-butylphenoxy | 2.49[i] | 517 |

TABLE 4-continued

| Ex. No. | Name | R⁸ | —OR⁷ | HPLC T$_r$ | (M + H)⁺ |
|---|---|---|---|---|---|
| 92 | 4'-(2-(tert-butyl)phenoxy)-3'-(3-(2,3-dimethylphenyl)ureido)-4-methoxy-[1,1'-biphenyl]-3-carboxylic acid | 2,3-dimethylphenyl | 2-(tert-butyl)phenoxy | 2.55$^i$ | 539 |
| 93 | 4'-(2-(tert-butyl)phenoxy)-4-methoxy-3'-(3-(4-methoxy-2-methylphenyl)ureido)-[1,1'-biphenyl]-3-carboxylic acid | 4-methoxy-2-methylphenyl | 2-(tert-butyl)phenoxy | 2.38$^i$ | 555 |
| 94 | 4'-(2-(tert-butyl)phenoxy)-3'-(3-(2,4-dimethylphenyl)ureido)-4-methoxy-[1,1'-biphenyl]-3-carboxylic acid | 2,4-dimethylphenyl | 2-(tert-butyl)phenoxy | 2.58$^i$ | 539 |
| 95 | 4'-(2-(tert-butyl)phenoxy)-3'-(3-(2,5-dimethylphenyl)ureido)-4-methoxy-[1,1'-biphenyl]-3-carboxylic acid | 2,5-dimethylphenyl | 2-(tert-butyl)phenoxy | 2.59$^i$ | 539 |
| 96 | 4'-(2-(tert-butyl)phenoxy)-3'-(3-(3,4-dimethylphenyl)ureido)-4-methoxy-[1,1'-biphenyl]-3-carboxylic acid | 3,4-dimethylphenyl | 2-(tert-butyl)phenoxy | 2.63$^i$ | 539 |
| 98 | 4'-(2-(tert-butyl)phenoxy)-3'-(3-(3-chloro-2-methylphenyl)ureido)-4-methoxy-[1,1'-biphenyl]-3-carboxylic acid | 3-chloro-2-methylphenyl | 2-(tert-butyl)phenoxy | 2.63$^i$ | 559 |

TABLE 4-continued

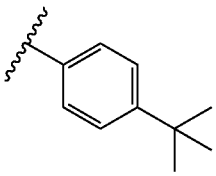

| Ex. No. | Name | R⁸ | —OR⁷ | HPLC $T_r$ | (M + H)⁺ |
|---|---|---|---|---|---|
| 99 | 4'-(2-(tert-butyl)phenoxy)-3'-(3-(4-(tert-butyl)phenyl)ureido)-4-methoxy-[1,1'-biphenyl]-3-carboxylic acid | 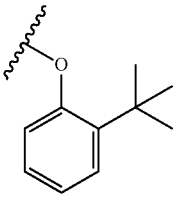 | 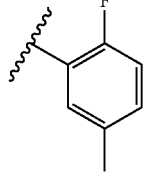 [SMILES: *c1cc(C)ccc1C] | 2.91$^i$ | 567 |
| 100 | 4'-(2-(tert-butyl)phenoxy)-3'-(3-(2-fluoro-4-methylphenyl)ureido)-4-methoxy-[1,1'-biphenyl]-3-carboxylic acid | 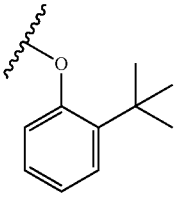 | 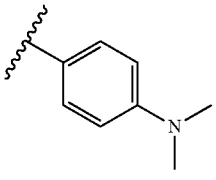 [SMILES: *c1ccc(N(C)C)cc1] | 2.60$^i$ | 543 |
| 101 | 4'-(2-(tert-butyl)phenoxy)-3'-(3-(4-(dimethylamino)phenyl)ureido)-4-methoxy-[1,1'-biphenyl]-3-carboxylic acid | 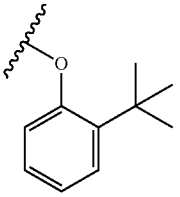 | 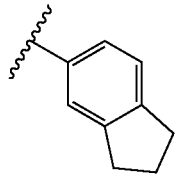 [SMILES: *c1ccc2c(c1)CCC2] | 2.43$^i$ | 554 |
| 102 | 4'-(2-(tert-butyl)phenoxy)-3'-(3-(2,3-dihydro-1H-inden-5-yl)ureido)-4-methoxy-[1,1'-biphenyl]-3-carboxylic acid | 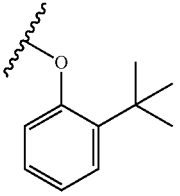 [SMILES: *Oc1ccccc1C(C)(C)C] | 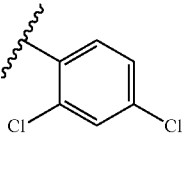 [SMILES: *c1ccc(Cl)cc1Cl] | 2.70$^i$ | 551 |
| 103 | 4'-(2-(tert-butyl)phenoxy)-3'-(3-(2,4-dichlorophenyl)ureido)-4-methoxy-[1,1'-biphenyl]-3-carboxylic acid | 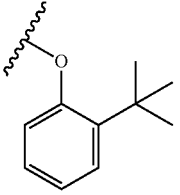 | 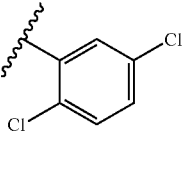 [SMILES: *c1cc(Cl)ccc1Cl] | 2.82$^i$ | 579 |
| 104 | 4'-(2-(tert-butyl)phenoxy)-3'-(3-(2,5-dichlorophenyl)ureido)-4-methoxy-[1,1'-biphenyl]-3-carboxylic acid | 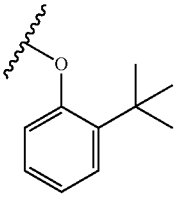 | | 2.81$^i$ | 579 |

TABLE 4-continued

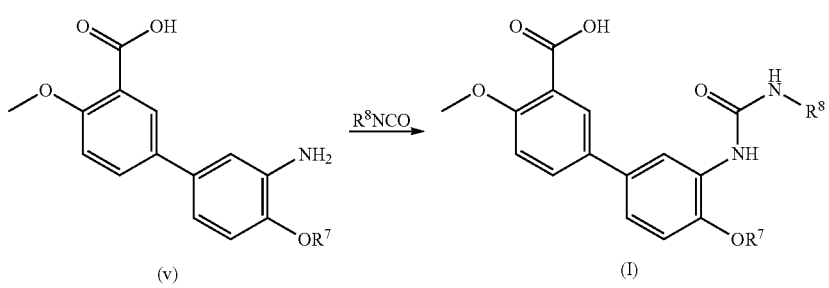

| Ex. No. | Name | R⁸ | —OR⁷ | HPLC T_r | (M + H)⁺ |
|---|---|---|---|---|---|
| 105 | 4'-(2-(tert-butyl)phenoxy)-3'-(3-(3,4-dichlorophenyl)ureido)-4-methoxy-[1,1'-biphenyl]-3-carboxylic acid | 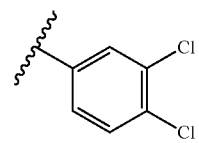 [SMILES: *c1ccc(Cl)c(Cl)c1] | 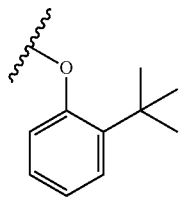 | 2.78$^i$ | 579 |
| 106 | 4'-(2-(tert-butyl)phenoxy)-3'-(3-(4-chlorophenyl)ureido)-4-methoxy-[1,1'-biphenyl]-3-carboxylic acid | 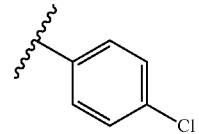 [SMILES: *c1ccc(Cl)cc1] | 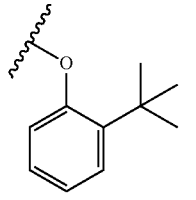 | 2.42$^i$ | 529 |
| 107 | 4'-(2-(tert-butyl)phenoxy)-3'-(3-(4-fluorophenyl)ureido)-4-methoxy-[1,1'-biphenyl]-3-carboxylic acid | 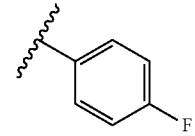 [SMILES: *c1ccc(F)cc1] | 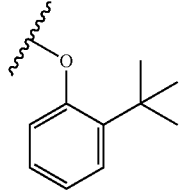 | 2.59$^i$ | 545 |
| 108 | 4'-(2-(tert-butyl)phenoxy)-3'-(3-(3-cyanophenyl)ureido)-4-methoxy-[1,1'-biphenyl]-3-carboxylic acid | 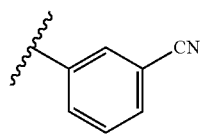 [SMILES: *c1cccc(C#N)c1] | 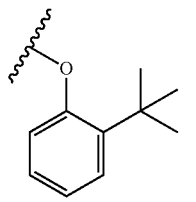 | 2.36$^i$ | 536 |
| 109 | 4'-(2-(tert-butyl)phenoxy)-3'-(3-(5-chloro-2-methoxyphenyl)ureido)-4-methoxy-[1,1'-biphenyl]-3-carboxylic acid | 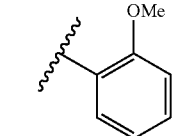 | 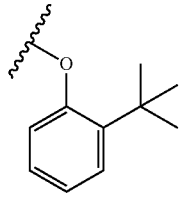 | 2.67$^i$ | 575 |

TABLE 4-continued

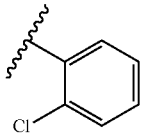 [SMILES: *c1ccccc1Cl]

| Ex. No. | Name | R⁸ | —OR⁷ | HPLC $T_r$ | $(M + H)^+$ |
|---|---|---|---|---|---|
| 110 | 4'-(3-tert-butylphenoxy)-3'-(3-(2-chlorophenyl)ureido)-4-methoxybiphenyl-3-carboxylic acid | 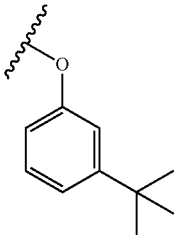 [SMILES: *Oc1cccc(C(C)(C)C)c1] | 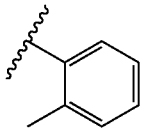 [SMILES: *c1ccccc1C] | 13.33$^d$ | 545 |
| 111 | 4'-(3-tert-butylphenoxy)-4-methoxy-3'-(3-o-tolylureido)biphenyl-3-carboxylic acid | 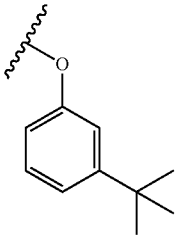 [SMILES: *Oc1cccc(C(C)(C)C)c1] | 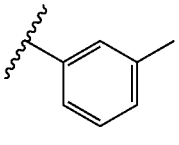 [SMILES: *c1cccc(C)c1] | 13.09$^d$ | 525 |
| 112 | 4'-(3-tert-butylphenoxy)-4-methoxy-3'-(3-m-tolylureido)biphenyl-3-carboxylic acid | 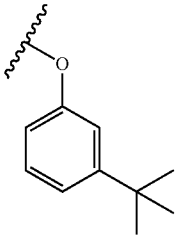 [SMILES: *Oc1cccc(C(C)(C)C)c1] | 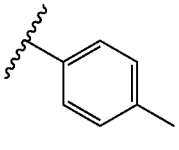 [SMILES: *c1ccc(C)cc1] | 13.21$^d$ | 525 |
| 113 | 4'-(3-tert-butylphenoxy)-4-methoxy-3'-(3-p-tolylureido)biphenyl-3-carboxylic acid | 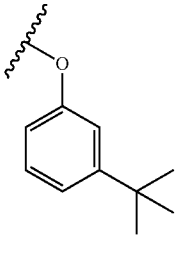 [SMILES: *Oc1cccc(C(C)(C)C)c1] | 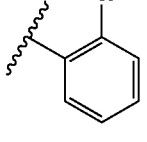 | 13.05$^d$ | 525 |
| 114 | 3'-(3-(2-chlorophenyl)ureido)-4-methoxy-4'-(5,6,7,8-tetrahydronaphthalen-1-yloxy)biphenyl-3-carboxylic acid | 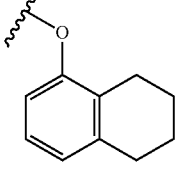 |  | 13.49$^d$ | 543 |

TABLE 4-continued

| Ex. No. | Name | R[8] | —OR[7] | HPLC T$_r$ | (M + H)[+] |
|---|---|---|---|---|---|
| 115 | 4-methoxy-4'-(5,6,7,8-tetrahydronaphthalen-1-yloxy)-3'-(3-o-tolylureido)biphenyl-3-carboxylic acid | 2-methylphenyl | 5,6,7,8-tetrahydronaphthalen-1-yloxy | 13.47[d] | 523 |
| 116 | 4-methoxy-4'-(5,6,7,8-tetrahydronaphthalen-1-yloxy)-3'-(3-m-tolylureido)biphenyl-3-carboxylic acid | 3-methylphenyl | 5,6,7,8-tetrahydronaphthalen-1-yloxy | 13.53[d] | 523 |
| 118 | 4-methoxy-3'-(3-propylureido)-4'-(5,6,7,8-tetrahydronaphthalen-1-yloxy)biphenyl-3-carboxylic acid | propyl | 5,6,7,8-tetrahydronaphthalen-1-yloxy | 12.82[d] | 475 |
| 119 | 4'-(2-tert-butylphenoxy)-4-methoxy-3'-(3-prop-2-ynylureido)biphenyl-3-carboxylic acid | prop-2-ynyl | 2-tert-butylphenoxy | 12.43[d] | 473 |
| 120 | 3'-(3-(2-chlorophenyl)ureido)-4'-(2,3-dimethylphenoxy)-4-methoxybiphenyl-3-carboxylic acid | 2-chlorophenyl | 2,3-dimethylphenoxy | 13.00[d] | 517 |
| 121 | 4'-(2,3-dimethylphenoxy)-4-methoxy-3'-(3-o-tolylureido)biphenyl-3-carboxylic acid | 2-methylphenyl | 2,3-dimethylphenoxy | 12.84[d] | 497 |

TABLE 4-continued

| Ex. No. | Name | R⁸ | —OR⁷ | HPLC $T_r$ | $(M + H)^+$ |
|---|---|---|---|---|---|
| 122 | 4'-(2,3-dimethylphenoxy)-4-methoxy-3'-(3-m-tolylureido)biphenyl-3-carboxylic acid | 3-methylphenyl | 2,3-dimethylphenoxy | 12.93$^d$ | 497 |
| 123 | 4'-(2,3-dimethylphenoxy)-4-methoxy-3'-(3-p-tolylureido)biphenyl-3-carboxylic acid | 4-methylphenyl | 2,3-dimethylphenoxy | 12.82$^d$ | 497 |
| 124 | 3'-(3-(2-chlorophenyl)ureido)-4'-(2-cyclopropylphenoxy)-4-methoxybiphenyl-3-carboxylic acid | 2-chlorophenyl | 2-cyclopropylphenoxy | 13.11$^d$ | 529 |
| 125 | 4'-(2-cyclopropylphenoxy)-4-methoxy-3'-(3-o-tolylureido)biphenyl-3-carboxylic acid | 2-methylphenyl | 2-cyclopropylphenoxy | 12.92$^d$ | 509 |
| 126 | 4'-(2-cyclopropylphenoxy)-4-methoxy-3'-(3-m-tolylureido)biphenyl-3-carboxylic acid | 3-methylphenyl | 2-cyclopropylphenoxy | 13.01$^d$ | 509 |
| 127 | 4'-(2-cyclopropylphenoxy)-4-methoxy-3'-(3-p-tolylureido)biphenyl-3-carboxylic acid | 4-methylphenyl | 2-cyclopropylphenoxy | 12.97$^d$ | 509 |

TABLE 4-continued

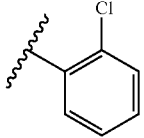 [SMILES: *c1ccccc1Cl]

| Ex. No. | Name | R[8] | —OR[7] | HPLC T[r] | (M + H)[+] |
|---|---|---|---|---|---|
| 128 | 3'-(3-(2-chlorophenyl)ureido)-4-methoxy-4'-(naphthalen-1-yloxy)biphenyl-3-carboxylic acid | 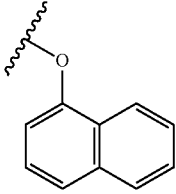 [SMILES: *Oc1cccc2ccccc12] | 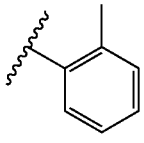 | 12.93[d] | 539 |
| 129 | 4-methoxy-4'-(naphthalen-1-yloxy)-3'-(3-o-tolylureido)biphenyl-3-carboxylic acid | 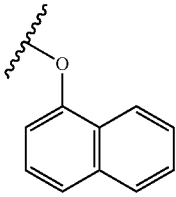 [SMILES: *Oc1cccc2ccccc12] | 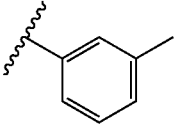 [SMILES: *c1cccc(C)c1] | 13.02[d] | 519 |
| 130 | 4-methoxy-4'-(naphthalen-1-yloxy)-3'-(3-m-tolylureido)biphenyl-3-carboxylic acid | 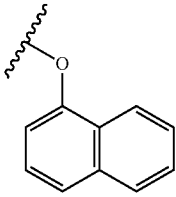 [SMILES: *Oc1cccc2ccccc12] | 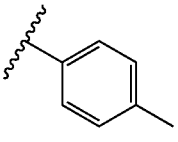 | 13.10[d] | 519 |
| 131 | 4-methoxy-4'-(naphthalen-1-yloxy)-3'-(3-p-tolylureido)biphenyl-3-carboxylic acid | 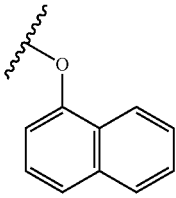 [SMILES: *Oc1cccc2ccccc12] | 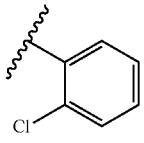 [SMILES: *c1ccccc1Cl] | 13.05[d] | 519 |
| 132 | 3'-(3-(2-chlorophenyl)ureido)-4-methoxy-4'-((trans)-2-methylcyclohexyloxy)biphenyl-3-carboxylic acid | 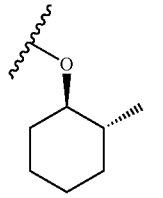 [SMILES: *O[C@@H]1CCCC[C@H]1C] | 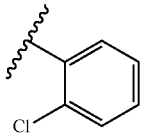 [SMILES: *c1ccccc1Cl] | 12.90[d] | 509 |
| 133 | 3'-(3-(2-chlorophenyl)ureido)-4'-(2,2-dimethyl-2,3-dihydrobenzofuran-7-yloxy)-4-methoxybiphenyl-3-carboxylic acid | | 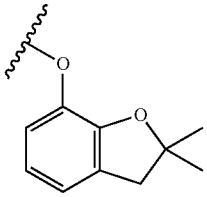 [SMILES: *Oc1cccc2c1OC(C)(C)C2] | 12.95[d] | 559 |

TABLE 4-continued

| Ex. No. | Name | R[8] | —OR[7] | HPLC T$_r$ | (M + H)[+] |
|---|---|---|---|---|---|
| 134 | 4-methoxy-4'-((trans)-2-methylcyclohexyloxy)-3'-(3-p-tolylureido)biphenyl-3-carboxylic acid | 4-methylphenyl | (trans)-2-methylcyclohexyloxy | 12.89[d] | 489 |
| 135 | 4'-(2,2-dimethyl-2,3-dihydrobenzofuran-7-yloxy)-4-methoxy-3'-(3-p-tolylureido)biphenyl-3-carboxylic acid | 4-methylphenyl | 2,2-dimethyl-2,3-dihydrobenzofuran-7-yloxy | 12.79[d] | 539 |
| 136 | 3'-(3-(2-chlorophenyl)ureido)-4-methoxy-4'-(2-methyl-3-(prop-2-ynyloxy)phenoxy)biphenyl-3-carboxylic acid | 2-chlorophenyl | 2-methyl-3-(prop-2-ynyloxy)phenoxy | 12.77[d] | 557 |
| 137 | 4-methoxy-4'-((trans)-2-methylcyclohexyloxy)-3'-(3-o-tolylureido)biphenyl-3-carboxylic acid | 2-methylphenyl | (trans)-2-methylcyclohexyloxy | 12.80[d] | 489 |
| 138 | 4-methoxy-4'-((trans)-2-methylcyclohexyloxy)-3'-(3-m-tolylureido)biphenyl-3-carboxylic acid | 3-methylphenyl | (trans)-2-methylcyclohexyloxy | 12.85[d] | 489 |
| 139 | 4'-(2,2-dimethyl-2,3-dihydrobenzofuran-7-yloxy)-4-methoxy-3'-(3-o-tolylureido)biphenyl-3-carboxylic acid | 2-methylphenyl | 2,2-dimethyl-2,3-dihydrobenzofuran-7-yloxy | 12.69[d] | 539 |

TABLE 4-continued

| Ex. No. | Name | R8 | —OR7 | HPLC T$_r$ | (M + H)$^+$ |
|---|---|---|---|---|---|
| 140 | 4'-(2,2-dimethyl-2,3-dihydrobenzofuran-7-yloxy)-4-methoxy-3'-(3-m-tolylureido)biphenyl-3-carboxylic acid | m-tolyl | 2,2-dimethyl-2,3-dihydrobenzofuran-7-yloxy | 12.80$^d$ | 539 |
| 141 | 4-methoxy-4'-(2-methyl-3-(prop-2-ynyloxy)phenoxy)-3'-(3-p-tolylureido)biphenyl-3-carboxylic acid | p-tolyl | 2-methyl-3-(prop-2-ynyloxy)phenoxy | 12.64$^d$ | 537 |
| 142 | 3'-(3-(2-chlorophenyl)ureido)-4'-(2,3-dihydro-1H-inden-4-yloxy)-4-methoxybiphenyl-3-carboxylic acid | 2-chlorophenyl | 2,3-dihydro-1H-inden-4-yloxy | 13.19$^d$ | 529 |
| 143 | 4'-(2,3-dihydro-1H-inden-4-yloxy)-4-methoxy-3'-(3-o-tolylureido)biphenyl-3-carboxylic acid | o-tolyl | 2,3-dihydro-1H-inden-4-yloxy | 13.05$^d$ | 509 |
| 144 | 4'-(2,3-dihydro-1H-inden-4-yloxy)-4-methoxy-3'-(3-m-tolylureido)biphenyl-3-carboxylic acid | m-tolyl | 2,3-dihydro-1H-inden-4-yloxy | 13.08$^d$ | 509 |
| 145 | 4'-(2,3-dihydro-1H-inden-4-yloxy)-4-methoxy-3'-(3-p-tolylureido)biphenyl-3-carboxylic acid | p-tolyl | 2,3-dihydro-1H-inden-4-yloxy | 13.15$^d$ | 509 |

TABLE 4-continued

| Ex. No. | Name | R[8] | —OR[7] | HPLC T$_r$ | (M + H)[+] |
|---|---|---|---|---|---|
| 146 | 4-methoxy-4'-(5,6,7,8-tetrahydronaphthalen-2-yloxy)-3'-(3-o-tolylureido)biphenyl-3-carboxylic acid | 2-methylphenyl | 5,6,7,8-tetrahydronaphthalen-2-yloxy | 13.36[d] | 523 |
| 147 | 4-methoxy-4'-(5,6,7,8-tetrahydronaphthalen-2-yloxy)-3'-(3-m-tolylureido)biphenyl-3-carboxylic acid | 3-methylphenyl | 5,6,7,8-tetrahydronaphthalen-2-yloxy | 13.50[d] | 523 |
| 148 | 4-methoxy-4'-(5,6,7,8-tetrahydronaphthalen-2-yloxy)-3'-(3-p-tolylureido)biphenyl-3-carboxylic acid | 4-methylphenyl | 5,6,7,8-tetrahydronaphthalen-2-yloxy | 13.46[d] | 523 |
| 149 | 3'-(3-(2-chlorophenyl)ureido)-4-methoxy-4'-(5-oxo-5,6,7,8-tetrahydronaphthalen-1-yloxy)biphenyl-3-carboxylic acid | 2-chlorophenyl | 5-oxo-5,6,7,8-tetrahydronaphthalen-1-yloxy | 12.64[d] | 557 |

TABLE 4-continued

| Ex. No. | Name | R[8] | —OR[7] | HPLC T$_r$ | (M + H)[+] |
|---|---|---|---|---|---|
| 150 | 4-methoxy-4'-(5-oxo-5,6,7,8-tetrahydronaphthalen-1-yloxy)-3'-(3-o-tolylureido)biphenyl-3-carboxylic acid | o-tolyl | 5-oxo-5,6,7,8-tetrahydronaphthalen-1-yloxy | 12.46[d] | 537 |
| 151 | 4-methoxy-3'-(3-phenylureido)-4'-(5,6,7,8-tetrahydronaphthalen-1-yloxy)biphenyl-3-carboxylic acid | phenyl | 5,6,7,8-tetrahydronaphthalen-1-yloxy | 13.07[d] | 509 |
| 152 | 3'-(3-(2-fluorophenyl)ureido)-4-methoxy-4'-(5,6,7,8-tetrahydronaphthalen-1-yloxy)biphenyl-3-carboxylic acid | 2-fluorophenyl | 5,6,7,8-tetrahydronaphthalen-1-yloxy | 13.17[d] | 527 |
| 153 | 3'-(3-(3,4-dimethylphenyl)ureido)-4-methoxy-4'-(5,6,7,8-tetrahydronaphthalen-1-yloxy)biphenyl-3-carboxylic acid | 3,4-dimethylphenyl | 5,6,7,8-tetrahydronaphthalen-1-yloxy | 4.52[n] | 537 |
| 154 | 3'-(3-(2,4-difluorophenyl)ureido)-4-methoxy-4'-(5,6,7,8-tetrahydronaphthalen-1-yloxy)biphenyl-3-carboxylic acid | 2,4-difluorophenyl | 5,6,7,8-tetrahydronaphthalen-1-yloxy | 4.42[n] | 545 |

Examples 155 to 177

Using the methods described herein (the procedure for conversion of 2A to 2 is representative), the following compounds of the invention shown in Table 5 were prepared:

TABLE 5

| Ex. No. | Name | R⁸ | (A ring substituent) | Tr^method | (M + H)⁺ |
|---|---|---|---|---|---|
| 155 | 4'-(2-tert-butylphenoxy)-3'-(3-(2-chlorophenyl)ureido)biphenyl-2-carboxylic acid | 2-chlorophenyl | 2-carboxyphenyl | 13.01^d | 515 |
| 156 | 4'-(2-tert-butylphenoxy)-3'-(3-o-tolylureido)biphenyl-2-carboxylic acid | o-tolyl | 2-carboxyphenyl | 12.95^d | 495 |
| 157 | 4'-(2-tert-butylphenoxy)-3'-(3-m-tolylureido)biphenyl-2-carboxylic acid | m-tolyl | 2-carboxyphenyl | 13.13^d | 495 |
| 158 | 4'-(2-tert-butylphenoxy)-4-chloro-3'-(3-(2-chlorophenyl)ureido)biphenyl-2-carboxylic acid | 2-chlorophenyl | 4-chloro-2-carboxyphenyl | 13.74^d | 549 |
| 159 | 4'-(2-tert-butylphenoxy)-4-chloro-3'-(3-o-tolylureido)biphenyl-2-carboxylic acid | o-tolyl | 4-chloro-2-carboxyphenyl | 13.64^d | 529 |
| 160 | 4'-(2-tert-butylphenoxy)-4-chloro-3'-(3-m-tolylureido)biphenyl-2-carboxylic acid | m-tolyl | 4-chloro-2-carboxyphenyl | 13.83^d | 529 |

TABLE 5-continued

| Ex. No. | Name | R⁸ | (A ring substituent) | Tr$^{method}$ | (M + H)⁺ |
|---|---|---|---|---|---|
| 161 | 4'-(2-tert-butylphenoxy)-4-chloro-3'-(3-p-tolylureido)biphenyl-2-carboxylic acid | p-tolyl | 5-chloro-2-carboxyphenyl | 13.81$^d$ | 529 |
| 162 | 4'-(2-tert-butylphenoxy)-4-methoxy-3'-(3-o-tolylureido)biphenyl-2-carboxylic acid | o-tolyl | 5-methoxy-2-carboxyphenyl | 8.27$^m$ | 525 |
| 163 | 4'-(2-tert-butylphenoxy)-4-methoxy-3'-(3-p-tolylureido)biphenyl-2-carboxylic acid | p-tolyl | 5-methoxy-2-carboxyphenyl | 8.44$^m$ | 525 |
| 164 | 4'-(2-tert-butylphenoxy)-3'-(3-(2-chlorophenyl)ureido)-4-methoxybiphenyl-2-carboxylic acid | 2-chlorophenyl | 5-methoxy-2-carboxyphenyl | 8.44$^m$ | 545 |
| 165 | 4'-(2-tert-butylphenoxy)-4,5-dimethoxy-3'-(3-p-tolylureido)biphenyl-2-carboxylic acid | p-tolyl | 4,5-dimethoxy-2-carboxyphenyl | 8.14$^m$ | 555 |

TABLE 5-continued

| Ex. No. | Name | R⁸ | [A ring] | Tr$^{method}$ | (M + H)⁺ |
|---|---|---|---|---|---|
| 166 | 4'-(2-tert-butylphenoxy)-5-chloro-3'-(3-(2-chlorophenyl)ureido)biphenyl-2-carboxylic acid | 2-chlorophenyl | 4-chloro-2-carboxyphenyl | 9.22$^m$ | 549 |
| 167 | 4'-(2-tert-butylphenoxy)-5-chloro-3'-(3-o-tolylureido)biphenyl-2-carboxylic acid | o-tolyl | 4-chloro-2-carboxyphenyl | 9.07$^m$ | 529 |
| 168 | 4'-(2-tert-butylphenoxy)-5-chloro-3'-(3-p-tolylureido)biphenyl-2-carboxylic acid | p-tolyl | 4-chloro-2-carboxyphenyl | 9.21$^m$ | 529 |
| 169 | 4'-(2-tert-butylphenoxy)-3'-(3-(2-chlorophenyl)ureido)-4-fluorobiphenyl-2-carboxylic acid | 2-chlorophenyl | 5-fluoro-2-carboxyphenyl | 8.77$^m$ | 533 |
| 170 | 4'-(2-tert-butylphenoxy)-4-fluoro-3'-(3-p-tolylureido)biphenyl-2-carboxylic acid | p-tolyl | 5-fluoro-2-carboxyphenyl | 8.63$^m$ | 513 |

TABLE 5-continued

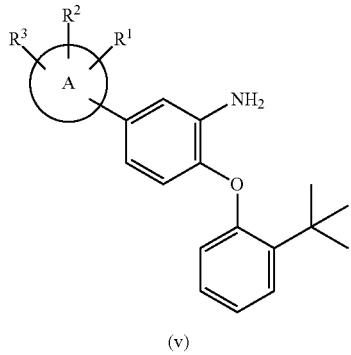

(v) → R⁸NCO → (I)

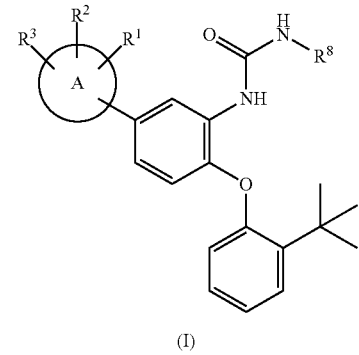

| Ex. No. | Name | R⁸ | [A with R¹,R²,R³] | Tr^method | (M + H)⁺ |
|---|---|---|---|---|---|
| 171 | 4'-(2-tert-butylphenoxy)-3-fluoro-3'-(3-p-tolylureido)biphenyl-2-carboxylic acid | 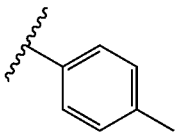 [SMILES: *c1ccc(C)cc1] | 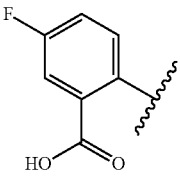 | 8.83^m | 513 |
| 172 | 4'-(2-tert-butylphenoxy)-3-chloro-3'-(3-(2-chlorophenyl)ureido)biphenyl-2-carboxylic acid | 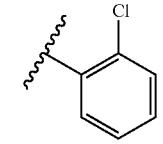 | 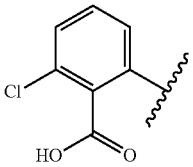 [SMILES: *c1cccc(Cl)c1C(=O)O] | 8.69^m | 549 |
| 173 | 4'-(2-tert-butylphenoxy)-3-chloro-3'-(3-o-tolylureido)biphenyl-2-carboxylic acid | 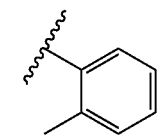 | 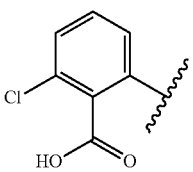 [SMILES: *c1cccc(Cl)c1C(=O)O] | 8.15^m | 529 |
| 174 | 4'-(2-tert-butylphenoxy)-3-chloro-3'-(3-p-tolylureido)biphenyl-2-carboxylic acid | 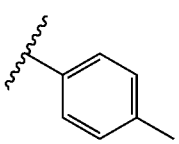 [SMILES: *c1ccc(C)cc1] | 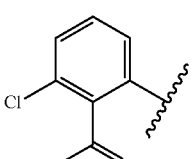 | 8.37^m | 529 |
| 175 | 4'-(2-tert-butylphenoxy)-3-fluoro-3'-(3-o-tolylureido)biphenyl-2-carboxylic acid | 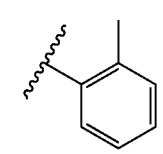 | 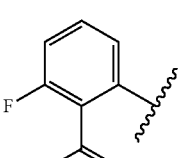 | 8.02^m | 513 |

TABLE 5-continued

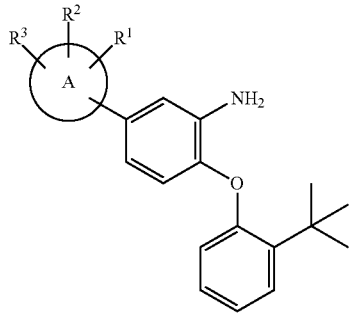

| Ex. No. | Name | R⁸ | [A with R¹,R²,R³] | Tr$^{method}$ | (M + H)⁺ |
|---|---|---|---|---|---|
| 176 | 4'-(2-tert-butylphenoxy)-3-fluoro-3'-(3-p-tolylureido)biphenyl-2-carboxylic acid | p-tolyl | 2-F, 6-(CO₂H)-phenyl | 8.50$^m$ | 513 |
| 177 | 4'-(2-tert-butylphenoxy)-3'-(3-p-tolylureido)-4-(trifluoromethyl)biphenyl-2-carboxylic acid | p-tolyl | 5-CF₃, 2-(CO₂H)-phenyl | 8.63$^m$ | 563 |
| 178 | 5-(4-(2-tert-butylphenoxy)-3-(3-p-tolylureido)phenyl)picolinic acid | p-tolyl | 6-(CO₂H)-pyridin-3-yl | 4.70$^l$ | 496 |

Examples 179 to 199

Using the methods described herein (the procedure for the conversion of 2A to 2 is representative), the following compounds of the invention shown in Table 6 were prepared.

TABLE 6

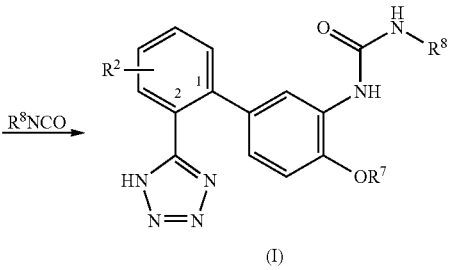

| Ex. No. | Name | R⁸ | —OR⁷ | R² | HPLC T_r | (M + H)⁺ |
|---|---|---|---|---|---|---|
| 179 | 1-(4-(2-tert-butylphenoxy)-2'-(1H-tetrazol-5-yl)biphenyl-3-yl)-3-(2-chlorophenyl)urea | 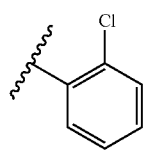 [SMILES: *c1ccccc1Cl] | 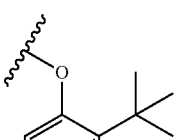 | H | 13.20$^d$ | 539 |
| 180 | 1-(4-(2-tert-butylphenoxy)-2'-(1H-tetrazol-5-yl)biphenyl-3-yl)-3-phenylurea | 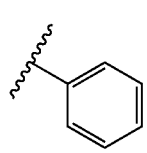 [SMILES: *c1ccccc1] | 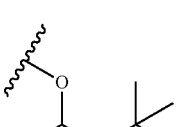 | H | 12.96$^d$ | 505 |
| 181 | 1-(4-(2-tert-butylphenoxy)-2'-(1H-tetrazol-5-yl)biphenyl-3-yl)-3-o-tolylurea | 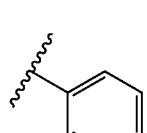 | 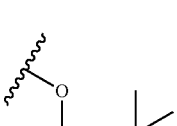 | H | 13.10$^d$ | 519 |
| 182 | 1-(4-(2-tert-butylphenoxy)-2'-(1H-tetrazol-5-yl)biphenyl-3-yl)-3-m-tolylurea | 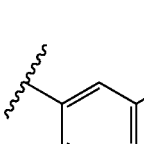 | 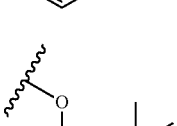 | H | 13.18$^d$ | 519 |
| 183 | 1-(4-(2-tert-butylphenoxy)-2'-(1H-tetrazol-5-yl)biphenyl-3-yl)-3-(2-(trifluoromethyl)phenyl)urea | 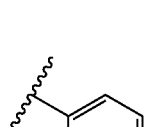 | 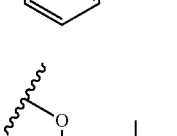 | H | 12.94$^d$ | 573 |
| 184 | 1-phenyl-3-(4-(5,6,7,8-tetrahydronaphthalen-1-yloxy)-2'-(1H-tetrazol-5-yl)biphenyl-3-yl)urea | 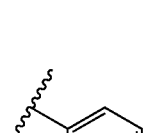 | 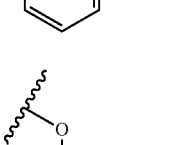 | H | 13.04$^d$ | 503 |

TABLE 6-continued

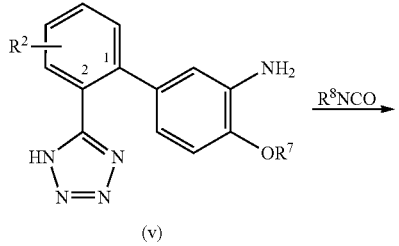

| Ex. No. | Name | R[8] | —OR[7] | R[2] | HPLC T$_r$ | (M + H)[+] |
|---|---|---|---|---|---|---|
| 185 | 1-(4-(5,6,7,8-tetrahydronaphthalen-1-yloxy)-2'-(1H-tetrazol-5-yl)biphenyl-3-yl)-3-p-tolylurea | 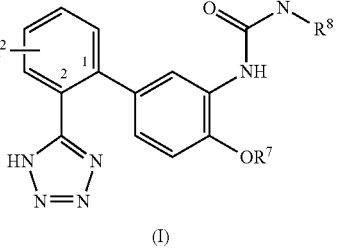 | 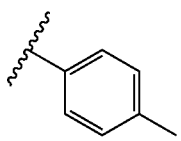 [SMILES: *c1ccc(C)cc1] | H | 4.84[l] | 517 |
| 186 | 1-(2-chlorophenyl)-3-(4-(5,6,7,8-tetrahydronaphthalen-1-yloxy)-2'-(1H-tetrazol-5-yl)biphenyl-3-yl)urea | 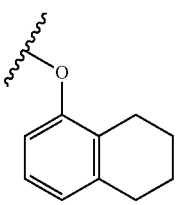 [SMILES: *Oc1cccc2c1CCCC2] | 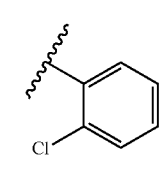 [SMILES: *c1ccccc1Cl] | H | 13.39[d] | 537 |
| 187 | 1-(4-(5,6,7,8-tetrahydronaphthalen-1-yloxy)-2'-(1H-tetrazol-5-yl)biphenyl-3-yl)-3-o-tolylurea | 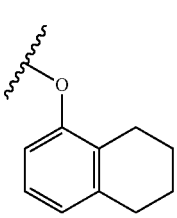 [SMILES: *Oc1cccc2c1CCCC2] | 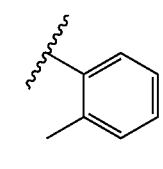 [SMILES: *c1ccccc1C] | H | 13.11[d] | 517 |
| 188 | 1-(2-fluorophenyl)-3-(4-(5,6,7,8-tetrahydronaphthalen-1-yloxy)-2'-(1H-tetrazol-5-yl)biphenyl-3-yl)urea | 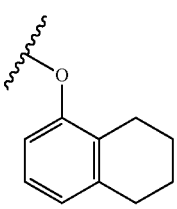 [SMILES: *Oc1cccc2c1CCCC2] | 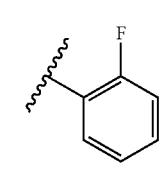 | H | 13.19[d] | 521 |
| 189 | 1-(4-chlorophenyl)-3-(4-(5,6,7,8-tetrahydronaphthalen-1-yloxy)-2'-(1H-tetrazol-5-yl)biphenyl-3-yl)urea | 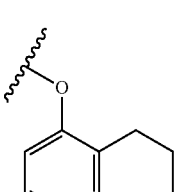 | 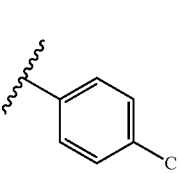 | H | 13.53[d] | 537 |
| 190 | 1-(4-(2-tert-butylphenoxy)-2'-(1H-tetrazol-5-yl)biphenyl-3-yl)-3-(2-fluorophenyl)urea | 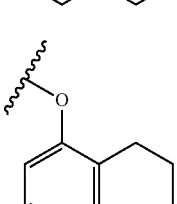 | 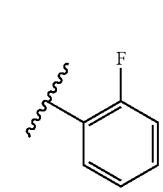 [SMILES: *c1ccccc1F] | H | 12.89[d] | 523 |

TABLE 6-continued

| Ex. No. | Name | R⁸ | —OR⁷ | R² | HPLC T_r | (M + H)⁺ |
|---|---|---|---|---|---|---|
| 191 | 1-butyl-3-(4-(2-tert-butylphenoxy)-2'-(1H-tetrazol-5-yl)biphenyl-3-yl)urea | butyl | 2-tert-butylphenoxy | H | 12.73^d | 485 |
| 192 | 1-(4-(2-tert-butylphenoxy)-4'-methoxy-2'-(1H-tetrazol-5-yl)biphenyl-3-yl)-3-(2-chlorophenyl)urea | 2-chlorophenyl | 2-tert-butylphenoxy | 4-MeO | 7.86^m | 569 |
| 193 | 1-(4-(2-tert-butylphenoxy)-4'-methoxy-2'-(1H-tetrazol-5-yl)biphenyl-3-yl)-3-o-tolylurea | o-tolyl | 2-tert-butylphenoxy | 4-MeO | 8.08^m | 549 |
| 195 | 1-(4-(2-tert-butylphenoxy)-4'-fluoro-2'-(1H-tetrazol-5-yl)biphenyl-3-yl)-3-(2-chlorophenyl)urea | 2-chlorophenyl | 2-tert-butylphenoxy | 4-F | 7.8^m | 577 |
| 197 | 1-(4-(2-tert-butylphenoxy)-4'-fluoro-2'-(1H-tetrazol-5-yl)biphenyl-3-yl)-3-p-tolylurea | p-tolyl | 2-tert-butylphenoxy | 4-F | 7.87^m | 537 |
| 198 | 1-(4-(2-tert-butylphenoxy)-4'-chloro-2'-(1H-tetrazol-5-yl)biphenyl-3-yl)-3-(2-chlorophenyl)urea | 2-chlorophenyl | 2-tert-butylphenoxy | 4-Cl | 8.26^m | 573 |

TABLE 6-continued

| Ex. No. | Name | R[8] | —OR[7] | R[2] | HPLC T$_r$ | (M + H)[+] |
|---|---|---|---|---|---|---|
| 199 | 1-(4-(2-tert-butylphenoxy)-4'-chloro-2'-(1H-tetrazol-5-yl)biphenyl-3-yl)-3-p-tolylurea | 4-methylphenyl | 2-tert-butylphenoxy | 4-Cl | 8.28[m] | 553 |

Examples 200 to 218

Using the methods described herein (the procedure for conversion of 2A to 2 is representative), the following compounds of the invention shown in Table 7 were prepared.

TABLE 7

| Ex. No. | Name | R[8] | —OR[7] | R[2] | HPLC T$_r$ | (M + H)[+] |
|---|---|---|---|---|---|---|
| 200 | 4'-(2-tert-butylphenoxy)-3'-(3-o-tolylureido)biphenyl-4-carboxylic acid | 2-methylphenyl | 2-tert-butylphenoxy | H | 13.29[d] | 495 |
| 201 | 4'-(2-tert-butylphenoxy)-3'-(3-m-tolylureido)biphenyl-4-carboxylic acid | 3-methylphenyl | 2-tert-butylphenoxy | H | 13.34[d] | 495 |

TABLE 7-continued

| Ex. No. | Name | R8 | —OR7 | R2 | HPLC Tr | (M + H)+ |
|---|---|---|---|---|---|---|
| 202 | 4'-(2-tert-butylphenoxy)-3'-(3-(2-chlorophenyl)ureido)biphenyl-4-carboxylic acid | 2-chlorophenyl | 2-tert-butylphenoxy | H | 13.42[d] | 515 |
| 203 | 3-chloro-3'-(3-(2-chlorophenyl)ureido)-4'-(2-(trifluoromethyl)phenoxy)biphenyl-4-carboxylic acid | 2-chlorophenyl | 2-(trifluoromethyl)phenoxy | 3-Cl | 12.77[d] | 561 |
| 204 | 3-chloro-3'-(3-m-tolylureido)-4'-(2-(trifluoromethyl)phenoxy)biphenyl-4-carboxylic acid | 3-methylphenyl | 2-(trifluoromethyl)phenoxy | 3-Cl | 12.71[d] | 541 |
| 205 | 3-chloro-3'-(3-p-tolylureido)-4'-(2-(trifluoromethyl)phenoxy)biphenyl-4-carboxylic acid | 4-methylphenyl | 2-(trifluoromethyl)phenoxy | 3-Cl | 12.68[d] | 541 |
| 206 | 3-chloro-3'-(3-(4-chlorophenyl)ureido)-4'-(2-(trifluoromethyl)phenoxy)biphenyl-4-carboxylic acid | 4-chlorophenyl | 2-(trifluoromethyl)phenoxy | 3-Cl | 12.86[d] | 561 |
| 207 | 3-chloro-4'-(2-(trifluoromethyl)phenoxy)-3'-(3-(4-(trifluoromethyl)phenyl)ureido)biphenyl-4-carboxylic acid | 4-(trifluoromethyl)phenyl | 2-(trifluoromethyl)phenoxy | 3-Cl | 12.74[d] | 595 |

TABLE 7-continued

| Ex. No. | Name | R⁸ | —OR⁷ | R² | HPLC T_r | (M + H)⁺ |
|---|---|---|---|---|---|---|
| 209 | 4'-(2-tert-butylphenoxy)-3'-(3-(4-(trifluoromethyl)phenyl)ureido)biphenyl-4-carboxylic acid | 4-CF₃-phenyl | 2-tert-butylphenoxy | H | 13.24$^d$ | 549 |
| 210 | 4'-(2-tert-butylphenoxy)-3'-(3-(2-(trifluoromethyl)phenyl)ureido)biphenyl-4-carboxylic acid | 2-CF₃-phenyl | 2-tert-butylphenoxy | H | 12.94$^d$ | 549 |
| 211 | 4'-(2-tert-butylphenoxy)-3-methoxy-3'-(3-o-tolylureido)biphenyl-4-carboxylic acid | 2-methylphenyl | 2-tert-butylphenoxy | 3-MeO | 13.14$^d$ | 525 |
| 212 | 4'-(2-tert-butylphenoxy)-3-methoxy-3'-(3-m-tolylureido)biphenyl-4-carboxylic acid | 3-methylphenyl | 2-tert-butylphenoxy | 3-MeO | 13.26$^d$ | 525 |
| 213 | 4'-(2-tert-butylphenoxy)-3-chloro-3'-(3-m-tolylureido)biphenyl-4-carboxylic acid | 3-methylphenyl | 2-tert-butylphenoxy | 3-Cl | 13.40$^d$ | 529 |
| 214 | 4'-(2-tert-butylphenoxy)-3-chloro-3'-(3-(2-(trifluoromethyl)phenyl)ureido)biphenyl-4-carboxylic acid | 2-CF₃-phenyl | 2-tert-butylphenoxy | 3-Cl | 13.10$^d$ | 583 |

TABLE 7-continued

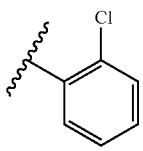 [SMILES: *c1ccccc1Cl]

| Ex. No. | Name | R[8] | —OR[7] | R[2] | HPLC T[r] | (M + H)[+] |
|---|---|---|---|---|---|---|
| 215 | 4'-(2-tert-butylphenoxy)-3-chloro-3'-(3-(2-chlorophenyl)ureido)biphenyl-4-carboxylic acid | 2-chlorophenyl | 2-tert-butylphenoxy | 3-Cl | 13.54[d] | 549 |
| 216 | 4'-(2-tert-butylphenoxy)-3-chloro-3'-(3-o-tolylureido)biphenyl-4-carboxylic acid | o-tolyl | 2-tert-butylphenoxy | 3-Cl | 13.30[d] | 529 |
| 217 | 4'-(2-tert-butylphenoxy)-3'-(3-(2-chlorophenyl)ureido)-3-fluorobiphenyl-4-carboxylic acid | 2-chlorophenyl | 2-tert-butylphenoxy | 3-F | 13.21[d] | 533 |
| 218 | 4'-(2-tert-butylphenoxy)-3-fluoro-3'-(3-p-tolylureido)biphenyl-4-carboxylic acid | p-tolyl | 2-tert-butylphenoxy | 3-F | 13.19[d] | 514 |

Examples 220 to 254

Using the methods described herein (the procedure for conversion of 2A to 2 is representative), the following compounds of the invention shown in Table 8 were prepared:

TABLE 8

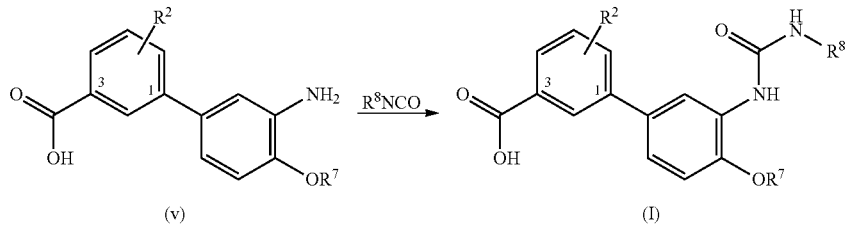

| Ex. No. | Name | R8 | —OR7 | R2 | HPLC Tr | (M + H)+ |
|---|---|---|---|---|---|---|
| 220 | 4'-(2-tert-butylphenoxy)-3'-(3-ethylureido)biphenyl-3-carboxylic acid |  | 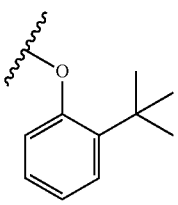 | H | 10.03[h] | 433 |
| 221 | 4'-(2-tert-butylphenoxy)-3'-(3-cyclohexylureido)biphenyl-3-carboxylic acid | 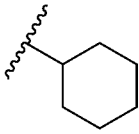 [SMILES: *C1CCCCC1] | 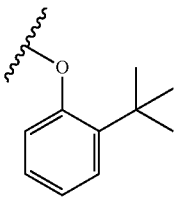 [SMILES: *Oc1ccccc1C(C)(C)C] | H | 10.80[h] | 487 |
| 222 | 4'-(2-tert-butylphenoxy)-5-fluoro-3'-(3-(4-(trifluoromethoxy)phenyl)ureido)biphenyl-3-carboxylic acid | 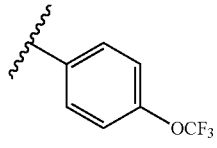 [SMILES: *c1ccc(OC(F)(F)F)cc1] | 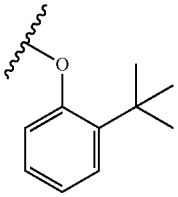 [SMILES: *Oc1ccccc1C(C)(C)C] | 5-F | 11.47[h] | 583 |
| 223 | 4'-(2-tert-butylphenoxy)-3'-(3-(4-(difluoromethoxy)phenyl)ureido)biphenyl-3-carboxylic acid | 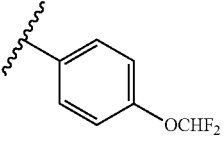 | 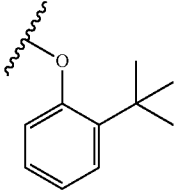 [SMILES: *Oc1ccccc1C(C)(C)C] | H | 10.76[h] | 547 |
| 224 | 4'-(2-tert-butylphenoxy)-3'-(3-o-tolylureido)biphenyl-3-carboxylic acid | 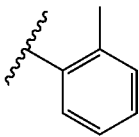 [SMILES: *c1ccccc1C] | 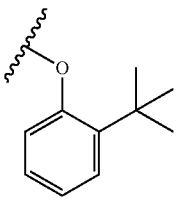 [SMILES: *Oc1ccccc1C(C)(C)C] | H | 13.32[d] | 495 |
| 225 | 4'-(2-tert-butylphenoxy)-3'-(3-m-tolylureido)biphenyl-3-carboxylic acid | 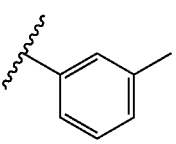 [SMILES: *c1cccc(C)c1] | 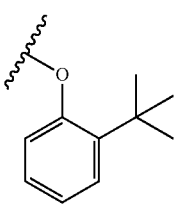 [SMILES: *Oc1ccccc1C(C)(C)C] | H | 13.42[d] | 495 |

TABLE 8-continued

| Ex. No. | Name | R⁸ | —OR⁷ | R² | HPLC T_r | (M + H)⁺ |
|---|---|---|---|---|---|---|
| 226 | 4'-(2-tert-butylphenoxy)-3'-(3-p-tolylureido)biphenyl-3-carboxylic acid | 4-methylphenyl | 2-tert-butylphenoxy | H | 13.39$^d$ | 495 |
| 227 | 4'-(2-tert-butylphenoxy)-3'-(3-(2-methoxyphenyl)ureido)biphenyl-3-carboxylic acid | 2-methoxyphenyl | 2-tert-butylphenoxy | H | 10.63$^h$ | 511 |
| 228 | 4'-(2-tert-butylphenoxy)-3'-(3-(2-chlorophenyl)ureido)biphenyl-3-carboxylic acid | 2-chlorophenyl | 2-tert-butylphenoxy | H | 10.85$^h$ | 515 |
| 229 | 4'-(2-tert-butylphenoxy)-3'-(3-(3-methoxyphenyl)ureido)biphenyl-3-carboxylic acid | 3-methoxyphenyl | 2-tert-butylphenoxy | H | 10.64$^h$ | 511 |
| 230 | 4'-(2-tert-butylphenoxy)-3'-(3-(4-methoxyphenyl)ureido)biphenyl-3-carboxylic acid | 4-methoxyphenyl | 2-tert-butylphenoxy | H | 10.54$^h$ | 511 |
| 231 | 4'-(2-tert-butylphenoxy)-3'-(3-(3-chlorophenyl)ureido)biphenyl-3-carboxylic acid | 3-chlorophenyl | 2-tert-butylphenoxy | H | 11.10$^h$ | 515 |

TABLE 8-continued

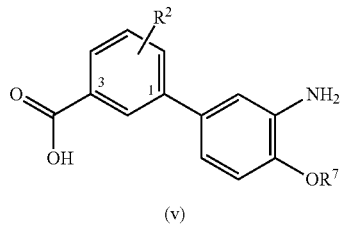

| Ex. No. | Name | R8 | —OR7 | R2 | HPLC T_r | (M + H)+ |
|---|---|---|---|---|---|---|
| 232 | 4'-(2-tert-butylphenoxy)-3'-(3-(4-chlorophenyl)ureido)biphenyl-3-carboxylic acid | 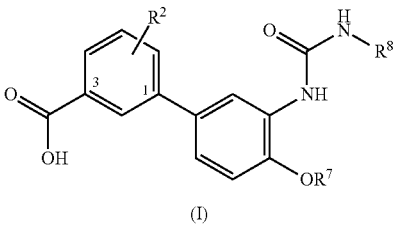 | 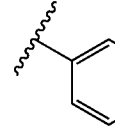 | H | 13.70[d] | 515 |
| 233 | 3'-(3-(4-bromophenyl)ureido)-4'-(2-tert-butylphenoxy)biphenyl-3-carboxylic acid | 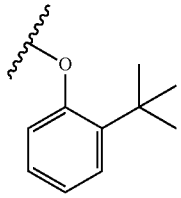 | 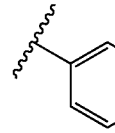 | H | 13.83[d] | 561 |
| 234 | 4'-(2-tert-butylphenoxy)-3'-(3-phenylureido)biphenyl-3-carboxylic acid | 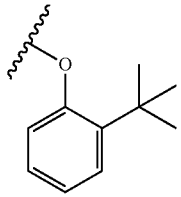 [SMILES: *Oc1ccccc1C(C)(C)C] | 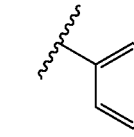 | H | 13.19[d] | 481 |
| 235 | 4'-phenoxy-3'-(3-p-tolylureido)biphenyl-3-carboxylic acid | 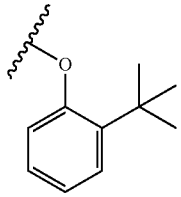 [SMILES: *Oc1ccccc1C(C)(C)C] | 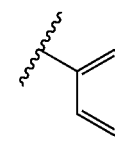 | H | 12.61[d] | 439 |
| 236 | 3'-(3-(4-fluorophenyl)ureido)-4'-phenoxybiphenyl-3-carboxylic acid | 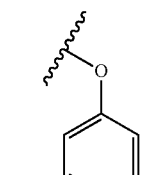 | 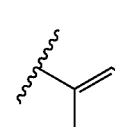 | H | 12.48[d] | 443 |
| 238 | 4'-(2-tert-butylphenoxy)-5-chloro-3'-(3-o-tolylureido)biphenyl-3-carboxylic acid | 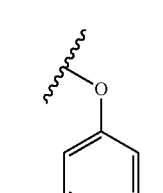 | 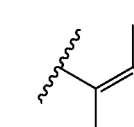 | 5-Cl | 14.31[d] | 529 |

TABLE 8-continued

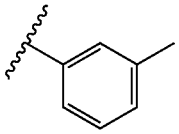 [SMILES: *c1cccc(C)c1]

| Ex. No. | Name | R[8] | —OR[7] | R[2] | HPLC T$_r$ | (M + H)[+] |
|---|---|---|---|---|---|---|
| 239 | 4'-(2-tert-butylphenoxy)-5-chloro-3'-(3-m-tolylureido) biphenyl-3-carboxylic acid | 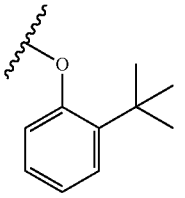 [SMILES: *Oc1ccccc1C(C)(C)C] | 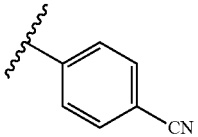 [SMILES: *c1ccc(C#N)cc1] | 5-Cl | 14.38[d] | 529 |
| 240 | 4'-(2-tert-butylphenoxy)-5-chloro-3'-(3-(4-cyanophenyl) ureido)biphenyl-3-carboxylic acid | 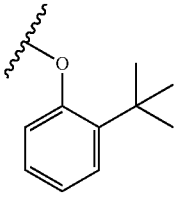 [SMILES: *Oc1ccccc1C(C)(C)C] | 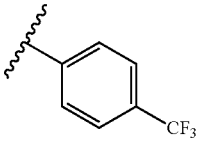 [SMILES: *c1ccc(C(F)(F)F)cc1] | 5-Cl | 14.20[d] | 540 |
| 241 | 4'-(2-tert-butylphenoxy)-5-chloro-3'-(3-(4-(trifluoromethyl) phenyl)ureido) biphenyl-3-carboxylic acid | 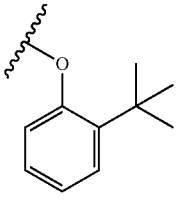 [SMILES: *Oc1ccccc1C(C)(C)C] | 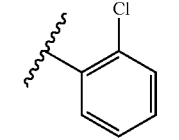 | 5-Cl | 14.43[d] | 583 |
| 242 | 4'-(4-chlorophenoxy)-3'-(3-(2-chlorophenyl) ureido)biphenyl-3-carboxylic acid | 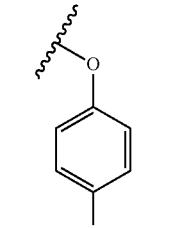 | 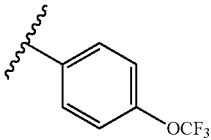 | H | 13.14[d] | 493 |
| 243 | 4'-(4-chlorophenoxy)-3'-(3-(4-(trifluoromethoxy) phenyl)ureido) biphenyl-3-carboxylic acid | 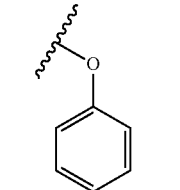 | 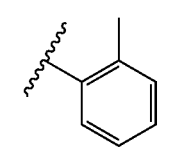 [SMILES: *c1ccccc1C] | H | 13.12[d] | 543 |
| 244 | 4'-(3-chlorophenoxy)-3'-(3-o-tolylureido) biphenyl-3-carboxylic acid | 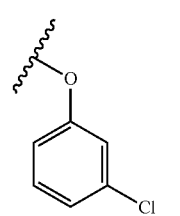 [SMILES: *Oc1cccc(Cl)c1] | | H | 12.86[d] | 473 |

TABLE 8-continued

| Ex. No. | Name | R[8] | —OR[7] | R[2] | HPLC T$_r$ | (M + H)[+] |
|---|---|---|---|---|---|---|
| 245 | 4'-(3-chlorophenoxy)-3'-(3-p-tolylureido)biphenyl-3-carboxylic acid | 4-methylphenyl | 3-chlorophenoxy | H | 12.92[d] | 473 |
| 246 | 4'-(2-tert-butylphenoxy)-5-chloro-3'-(3-p-tolylureido)biphenyl-3-carboxylic acid | 4-methylphenyl | 2-tert-butylphenoxy | 5-Cl | 14.15[d] | 529 |
| 247 | 4'-(2,6-dichlorophenoxy)-3'-(3-p-tolylureido)biphenyl-3-carboxylic acid | 4-methylphenyl | 2,6-dichlorophenoxy | H | 12.59[d] | 507 |
| 248 | 4'-(4-chlorophenoxy)-3'-(3-p-tolylureido)biphenyl-3-carboxylic acid | 4-methylphenyl | 4-chlorophenoxy | H | 12.85[d] | 473 |
| 249 | 4'-(4-chlorophenoxy)-3'-(3-m-tolylureido)biphenyl-3-carboxylic acid | 3-methylphenyl | 4-chlorophenoxy | H | 12.91[d] | 473 |

TABLE 8-continued

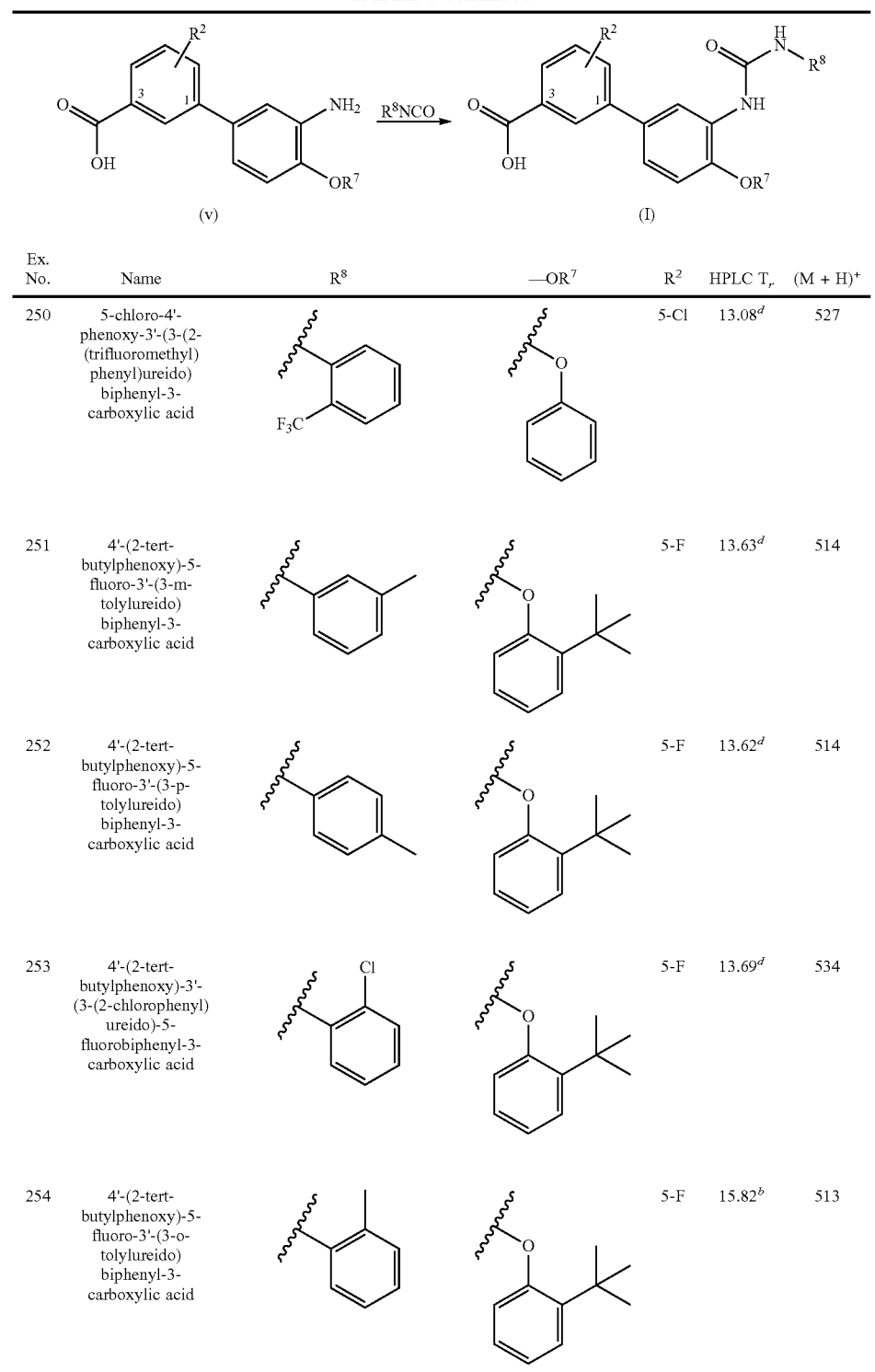

| Ex. No. | Name | R[8] | —OR[7] | R[2] | HPLC T$_r$ | (M + H)[+] |
|---|---|---|---|---|---|---|
| 250 | 5-chloro-4'-phenoxy-3'-(3-(2-(trifluoromethyl)phenyl)ureido)biphenyl-3-carboxylic acid | | | 5-Cl | 13.08[d] | 527 |
| 251 | 4'-(2-tert-butylphenoxy)-5-fluoro-3'-(3-m-tolylureido)biphenyl-3-carboxylic acid | | | 5-F | 13.63[d] | 514 |
| 252 | 4'-(2-tert-butylphenoxy)-5-fluoro-3'-(3-p-tolylureido)biphenyl-3-carboxylic acid | | | 5-F | 13.62[d] | 514 |
| 253 | 4'-(2-tert-butylphenoxy)-3'-(3-(2-chlorophenyl)ureido)-5-fluorobiphenyl-3-carboxylic acid | | | 5-F | 13.69[d] | 534 |
| 254 | 4'-(2-tert-butylphenoxy)-5-fluoro-3'-(3-o-tolylureido)biphenyl-3-carboxylic acid | | | 5-F | 15.82[b] | 513 |

Examples 255 to 266

Using the method described for the conversion of 1C to 1, the following compounds of the invention shown in Table 9 were prepared from bromide intermediates iv and the appropriate boronic acid

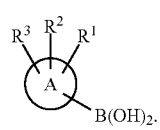

TABLE 9

| Ex. No. | Name | A with R1,R2,R3 | R8 | —OR7 | HPLC Tr | (M + H)+ |
|---|---|---|---|---|---|---|
| 255 | 4'-(2-tert-butylphenoxy)-4-methoxy-3'-(3-p-tolylureido)biphenyl-3-carboxylic acid | 2-methoxy-5-(attachment)-benzoic acid (HO2C, OMe) | p-tolyl | 2-tert-butylphenoxy | 13.09[d] | 525 |
| 256 | 4'-(2-tert-butylphenoxy)-3'-(3-p-tolylureido)biphenyl-4-carboxylic acid | 4-(HO2C)phenyl | p-tolyl | 2-tert-butylphenoxy | 13.37[d] | 495 |
| 257 | 4'-(2-tert-butylphenoxy)-3-chloro-3'-(3-p-tolylureido)biphenyl-4-carboxylic acid | 2-chloro-4-(HO2C)phenyl | p-tolyl | 2-tert-butylphenoxy | 13.47[d] | 529 |
| 258 | 4'-(2-tert-butylphenoxy)-3-methoxy-3'-(3-p-tolylureido)biphenyl-4-carboxylic acid | 2-methoxy-4-(HO2C)phenyl | p-tolyl | 2-tert-butylphenoxy | 13.18[d] | 525 |
| 259 | 3'-(3-(2-chlorophenyl)ureido)-4'-(2-(trifluoromethyl)phenoxy)biphenyl-3-carboxylic acid | 3-(HO2C)phenyl | 2-chlorophenyl | 2-(trifluoromethyl)phenoxy | 12.64[d] | 527 |

TABLE 9-continued

| Ex. No. | Name | A (R1, R2, R3) | R8 | —OR7 | HPLC Tr | (M + H)+ |
|---|---|---|---|---|---|---|
| 260 | 5-chloro-4'-(2-chlorophenoxy)-3'-(3-(4-(trifluoromethoxy)phenyl)ureido)biphenyl-3-carboxylic acid | 3,5-disubstituted (Cl, CO2H) | 4-OCF3-phenyl | 2-chlorophenoxy | 13.71[d] | 577 |
| 261 | 4'-(2-tert-butylphenoxy)-6-fluoro-3'-(3-(4-(trifluoromethoxy)phenyl)ureido)biphenyl-3-carboxylic acid | 3,4-disubstituted (F, CO2H) | 4-OCF3-phenyl | 2-tert-butylphenoxy | 13.61[d] | 583 |
| 262 | 4'-(2-tert-butylphenoxy)-5-chloro-3'-(3-(4-(trifluoromethoxy)phenyl)ureido)biphenyl-3-carboxylic acid | 3,5-disubstituted (Cl, CO2H) | 4-OCF3-phenyl | 2-tert-butylphenoxy | 14.55[d] | 599 |
| 263 | 4'-(2-tert-butylphenoxy)-6-methoxy-3'-(3-(4-(trifluoromethoxy)phenyl)ureido)biphenyl-3-carboxylic acid | 3,4-disubstituted (OMe, CO2H) | 4-OCF3-phenyl | 2-tert-butylphenoxy | 13.35[d] | 595 |
| 265 | 4'-(2-tert-butylphenoxy)-3'-(3-(4-(trifluoromethoxy)phenyl)ureido)biphenyl-4-carboxylic acid | 4-CO2H-phenyl | 4-OCF3-phenyl | 2-tert-butylphenoxy | 13.38[d] | 565 |

TABLE 9-continued

| Ex. No. | Name | R² R¹ / A / (structure) | R⁸ | —OR⁷ | HPLC T_r | (M + H)⁺ |
|---|---|---|---|---|---|---|
| 266 | 5-(4-(2-tert-butylphenoxy)-3-(3-(4-(trifluoromethoxy)phenyl)ureido)phenyl)nicotinic acid | HO₂C-pyridyl | 4-OCF₃-phenyl | 2-tert-butylphenoxy | | |

Example 267

4'-(1-(2-Chlorophenyl)-4,4,4-trifluorobutoxy)-5-fluoro-3'-(3-(p-tolyl)ureido)-[1,1'-biphenyl]-2-carboxylic acid

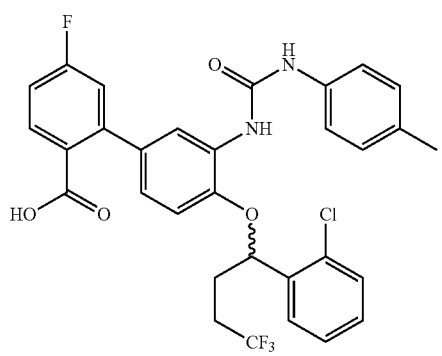 [SMILES: Cc1ccc(NC(=O)Nc2cc(-c3cc(F)ccc3C(=O)O)ccc2OC(CCC(F)(F)F)c2ccccc2Cl)cc1]

267A. 4-Bromo-1-(1-(2-chlorophenyl)-4,4,4-trifluorobutoxy)-2-nitrobenzene

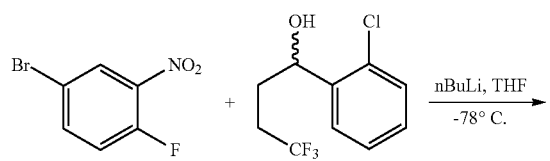

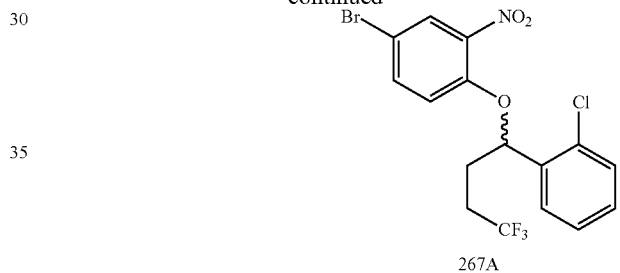

A solution containing 1-(2-chlorophenyl)-4,4,4-trifluorobutan-1-ol (0.529 g, 2.216 mmol) in THF (17.05 ml) at −78° C. under inert atmosphere was treated with nBuLi (0.886 ml, 2.216 mmol). After 20 minutes, a solution containing 4-bromo-1-fluoro-2-nitrobenzene (0.375 g, 1.705 mmol) in 5 mL THF was added and the bath was removed. The vessel was stirred overnight at ambient temperature. The mixture was diluted with water and EtOAc. The layers were separated and the aqueous phase extracted twice with 20 mL EtOAc. The organics were combined, washed with water and brine, then dried over anhydrous sodium sulfate. Filtration and concentration afforded a dark brown oil. The crude product was dissolved in a small amount of DCM and purified by flash chromatography (SiO₂, 0% EtOAc/hexanes to 30% EtOAc/hexanes, 40 g column, 40 mL/min, 20 min gradient, monitoring at 254 nm). The appropriate fractions were pooled and concentrated under reduced pressure revealing 4-bromo-1-(1-(2-chlorophenyl)-4,4,4-trifluorobutoxy)-2-nitrobenzene (0.715 g, 1.614 mmol, 95% yield) as a pale, yellow oil. HPLC Rt=3.198 min$^c$. $^1$H NMR (400 MHz, chloroform-d) δ 7.95 (d, J=2.4 Hz, 1H), 7.50-7.37 (m, 2H), 7.31-7.27 (m, 1H), 6.61 (d, J=9.0 Hz, 1H), 5.84-5.64 (m, 1H), 2.49-2.31 (m, 2H), 2.31-2.16 (m, 2H).

267B. 5-Bromo-2-(1-(2-chlorophenyl)-4,4,4-trifluorobutoxy)aniline

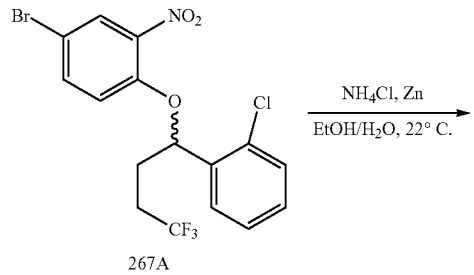

267A

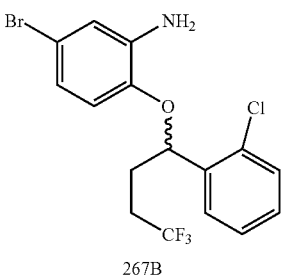

267B

A solution containing 4-bromo-1-(1-(2-chlorophenyl)-4,4,4-trifluorobutoxy)-2-nitrobenzene (267A) (0.715 g, 1.630 mmol) in EtOH (7.41 ml) was treated with ammonium chloride (0.872 g, 16.30 mmol) and water (0.741 ml). Zinc (1.066 g, 16.30 mmol) was added and the mixture stirred 10 min. The slurry was diluted with 40 mL of DCM and then filtered through a pad of CELITE®. The layers of the biphasic mixture were separated and the organics were combined, washed with water and brine, then dried over anhydrous sodium sulfate, affording (0.6 g, 90%). HPLC Rt=3.026 min$^c$ $^1$H NMR (400 MHz, chloroform-d) δ 7.44-7.30 (m, 2H), 7.25-7.21 (m, 2H), 6.82 (d, J=2.4 Hz, 1H), 6.62 (dd, J=8.6, 2.2 Hz, 1H), 6.27 (d, J=8.6 Hz, 1H), 5.57 (dd, J=7.9, 4.2 Hz, 1H), 3.93 (br. s., 2H), 2.50-2.08 (m, 4H).

267C. 1-(5-Bromo-2-(1-(2-chlorophenyl)-4,4,4-trifluorobutoxy)phenyl)-3-(p-tolyl)urea

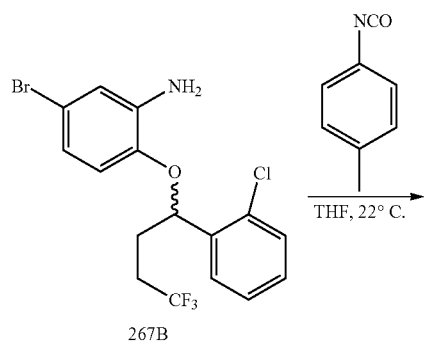

267B

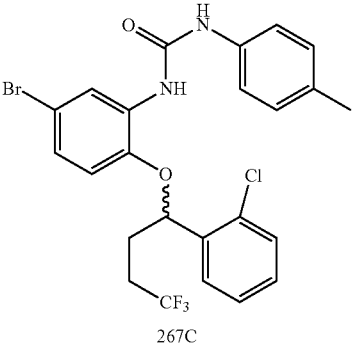

267C

5-Bromo-2-(1-(2-chlorophenyl)-4,4,4-trifluorobutoxy)aniline (267B) (0.3 g, 0.734 mmol) was dissolved in THF (1.835 ml) and treated with 1-isocyanato-4-methylbenzene (0.092 ml, 0.734 mmol). The reaction was stirred overnight. The solvent was removed and the residue was triturated with DCM and filtered, revealing 1-(5-bromo-2-(1-(2-chlorophenyl)-4,4,4-trifluorobutoxy)phenyl)-3-(p-tolyl)urea (0.340 g, 0.628 mmol, 85% yield) as a white solid. The material was used without further manipulation. HPLC Rt=3.263 min$^c$.

267. 4'-(1-(2-Chlorophenyl)-4,4,4-trifluorobutoxy)-5-fluoro-3'-(3-(p-tolyl)ureido)-[1,1'-biphenyl]-2-carboxylic acid 267C + F-phenyl-B(OH)$_2$/CO$_2$H
→ Pd(PPh$_3$)$_4$, K$_2$CO$_3$, DMF/H$_2$O, 100° C.
→ 267

1-(5-Bromo-2-(1-(2-chlorophenyl)-4,4,4-trifluorobutoxy)phenyl)-3-(p-tolyl)urea (267C) (0.050 g, 0.092 mmol), potassium carbonate (0.064 g, 0.461 mmol), and 2-borono-4-fluorobenzoic acid (0.022 g, 0.120 mmol) were suspended in a mixture of DMF (0.8 mL) and water (0.115 mL). The suspension was degassed for 10 minutes by bubbling argon through the solvent. To the degassed mixture was then added tetrakis(triphenylphosphine)palladium(0) (0.021 g, 0.018 mmol). The vessel was purged with argon and heated to 100° C. 2 h. The vessel was cooled and the solution filtered.

The crude material was purified via preparative LC/MS with the following conditions: Column: Waters XBridge C18, 19×150 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 20-100% B over 15 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 0.05% TFA; Mobile Phase B: 95:5 acetonitrile:water with 0.05% TFA; Gradient: 35-75% B over 25 minutes, then a 15-minute hold at 75% B; Flow: 20 mL/min. Fractions containing the desired product were combined and dried via centrifugal evaporation to afford 4'-(1-(2-chlorophenyl)-4,4,4-trifluorobutoxy)-5-fluoro-3'-(3-(p-tolyl)ureido)-[1,1'-biphenyl]-2-carboxylic acid (8.2 mg, 0.014 mmol, 15% yield). HPLC Rt=1.87 min$^j$. MS(ES): m/z=601.0 [M+H]$^+$.

Examples 268 to 331

Using the methods described herein, the following additional compounds of the invention shown in Table 10 were prepared. Examples 276 and 314 are shown in separate examples and are not included in the table.

TABLE 10

| Ex. No. | Structure | HPLC T$_r$ | (M + H)$^+$ |
|---|---|---|---|
| 268 | 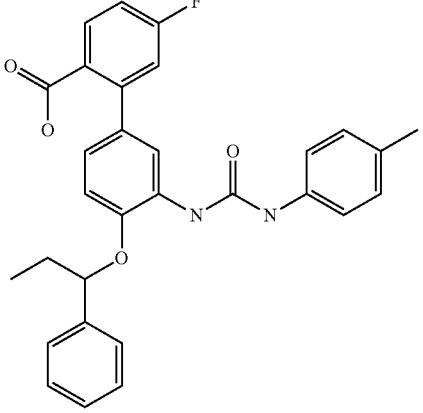 | 1.68$^j$ | 499 |
| 269 | 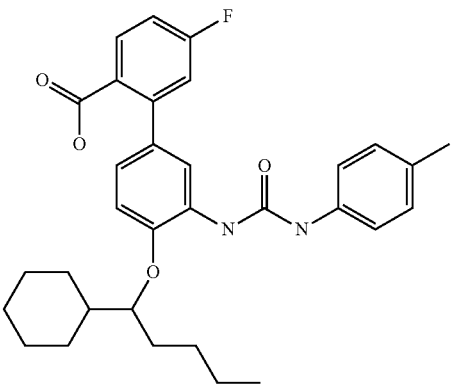 [SMILES: CCCCC(Oc1ccc(-c2cc(F)ccc2C(=O)O)cc1NC(=O)Nc1ccc(C)cc1)C1CCCCC1] | 2.17$^j$ | 533 |

TABLE 10-continued
| Ex. No. | Structure | HPLC $T_r$ | $(M + H)^+$ |
|---|---|---|---|
| 270 | 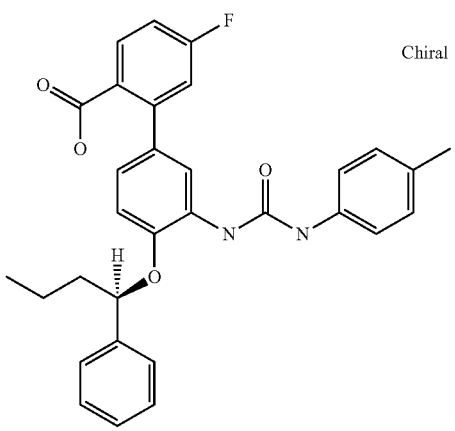 [SMILES: CCC[C@@H](Oc1ccc(-c2cc(F)ccc2C(=O)O)cc1NC(=O)Nc1ccc(C)cc1)c1ccccc1] Chiral | 1.78[j] | 513 |
| 271 | 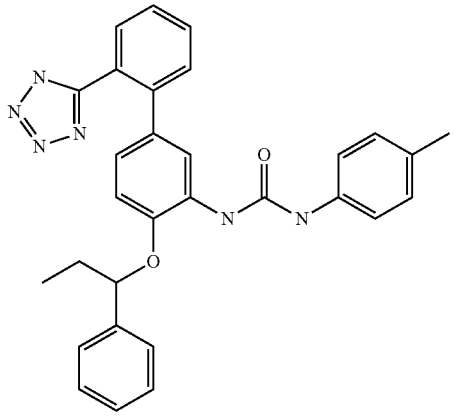 [SMILES: CCC(Oc1ccc(-c2ccccc2-c2nnn[nH]2)cc1NC(=O)Nc1ccc(C)cc1)c1ccccc1] | 1.68[j] | 505 |
| 272 | 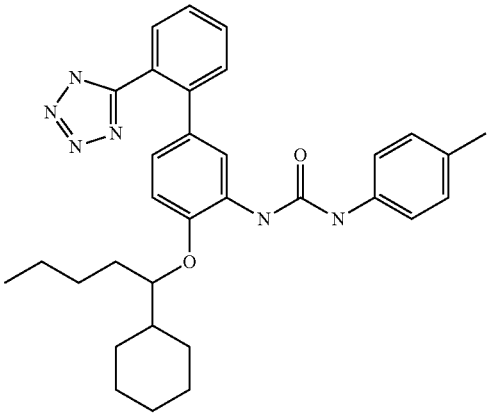 [SMILES: CCCCC(Oc1ccc(-c2ccccc2-c2nnn[nH]2)cc1NC(=O)Nc1ccc(C)cc1)C1CCCCC1] | 2.11[j] | 539 |

TABLE 10-continued
| Ex. No. | Structure | | HPLC T_r | (M + H)+ |
|---|---|---|---|---|
| 273 | 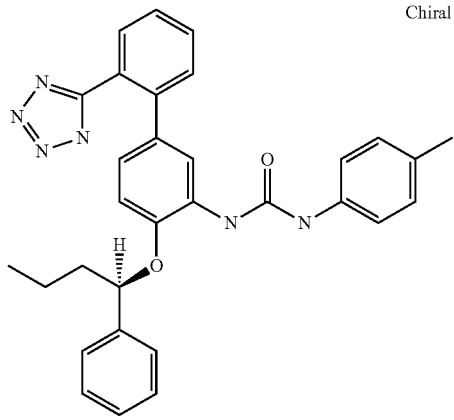 [SMILES: CCC[C@@H](Oc1ccc(-c2ccccc2-c2nnn[nH]2)cc1NC(=O)Nc1ccc(C)cc1)c1ccccc1] | Chiral | 1.80[j] | 519 |
| 274 | 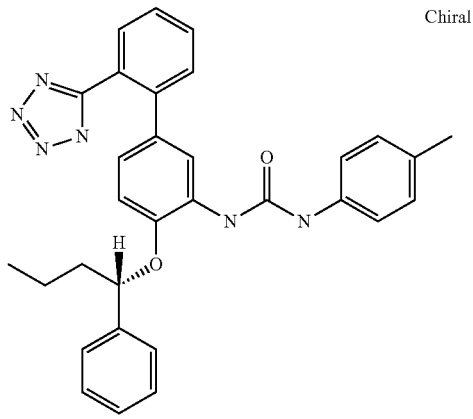 [SMILES: CCC[C@H](Oc1ccc(-c2ccccc2-c2nnn[nH]2)cc1NC(=O)Nc1ccc(C)cc1)c1ccccc1] | Chiral | 2.46[j] | 519 |
| 275 | 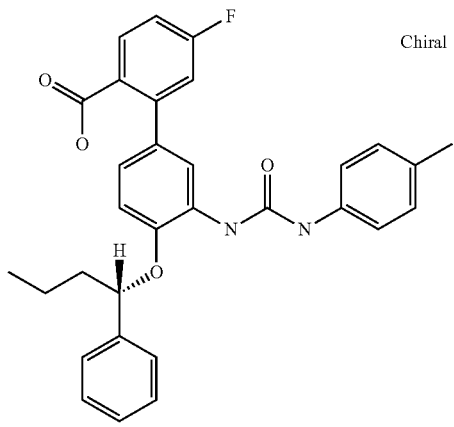 [SMILES: CCC[C@H](Oc1ccc(-c2cc(F)ccc2C(=O)O)cc1NC(=O)Nc1ccc(C)cc1)c1ccccc1] | Chiral | 1.77[j] | 513 |

TABLE 10-continued

| Ex. No. | Structure | HPLC $T_r$ | $(M + H)^+$ |
|---|---|---|---|
| 277 | 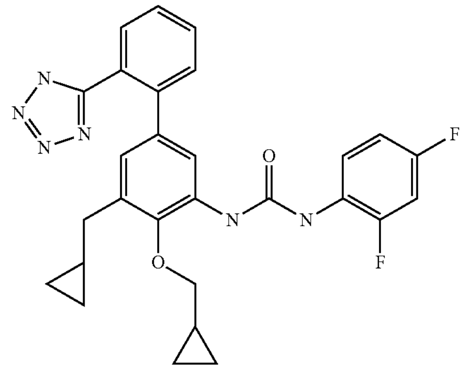 [SMILES: O=C(Nc1ccc(F)cc1F)Nc1cc(-c2ccccc2-c2nnn[nH]2)cc(CC2CC2)c1OCC1CC1] | 1.99[j] | 517.2 |
| 278 | 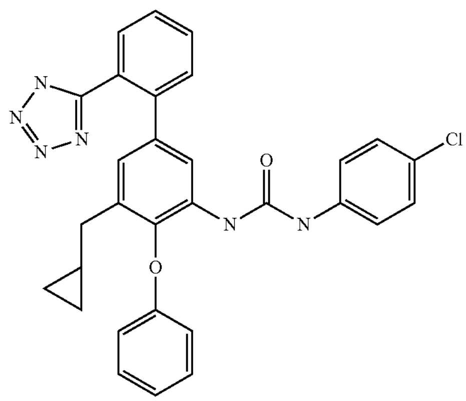 [SMILES: O=C(Nc1ccc(Cl)cc1)Nc1cc(-c2ccccc2-c2nnn[nH]2)cc(CC2CC2)c1Oc1ccccc1] | 1.91[v] | 535.2 |
| 279 | 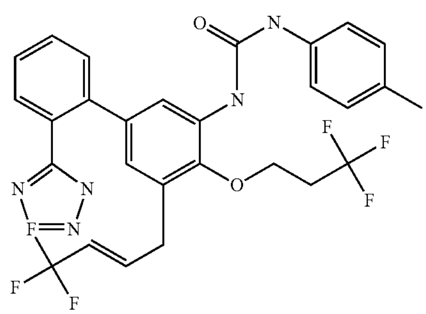 | 2.76[r] | 591 |
| 280 | 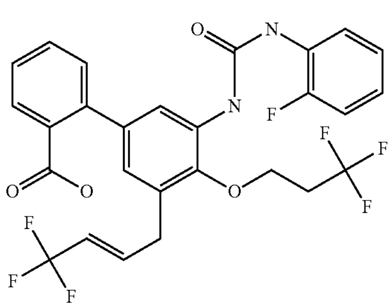 [SMILES: O=C(Nc1ccccc1F)Nc1cc(-c2ccccc2C(=O)O)cc(C/C=C/C(F)(F)F)c1OCCC(F)(F)F] | 4.83[l] | 551.3 |

TABLE 10-continued

| Ex. No. | Structure | HPLC T_r | (M + H)+ |
|---|---|---|---|
| 281 | 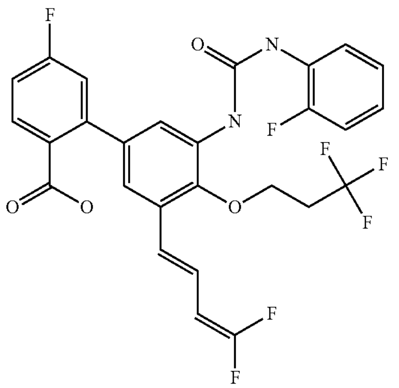 [SMILES: O=C(Nc1ccccc1F)Nc1cc(-c2cc(F)ccc2C(=O)O)cc(/C=C/C=C(F)F)c1OCCC(F)(F)F] | 4.96[l] | 569.3 |
| 282 | 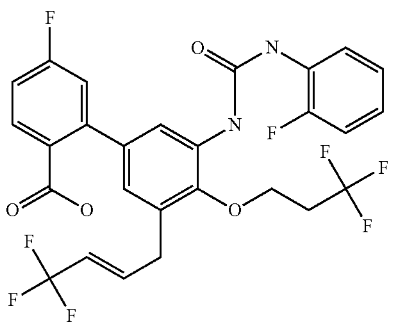 [SMILES: O=C(Nc1ccccc1F)Nc1cc(-c2cc(F)ccc2C(=O)O)cc(C/C=C/C(F)(F)F)c1OCCC(F)(F)F] | 2.91[r] | 589.3 |
| 283 | 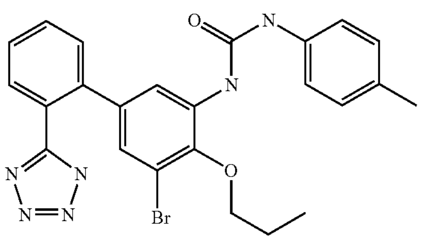 [SMILES: CCCOc1c(Br)cc(-c2ccccc2-c2nnn[nH]2)cc1NC(=O)Nc1ccc(C)cc1] | 2.75[r] | 507 |
| 284 | 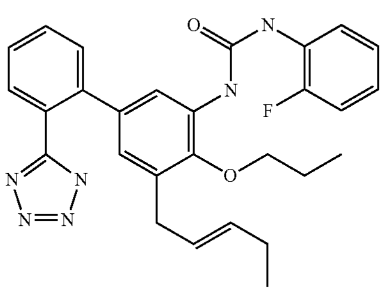 [SMILES: CC/C=C/Cc1cc(-c2ccccc2-c2nnn[nH]2)cc(NC(=O)Nc2ccccc2F)c1OCCC] | 4.75[l] | 501.1 |
| 285 | 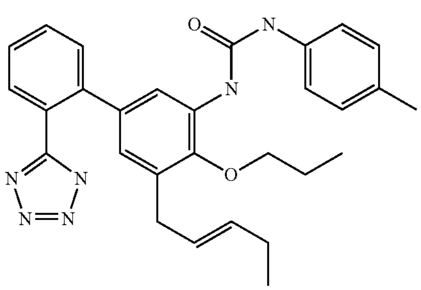 [SMILES: CC/C=C/Cc1cc(-c2ccccc2-c2nnn[nH]2)cc(NC(=O)Nc2ccc(C)cc2)c1OCCC] | 4.85[l] | 497.2 |

TABLE 10-continued

| Ex. No. | Structure | HPLC $T_r$ | $(M + H)^+$ |
|---|---|---|---|
| 286 | 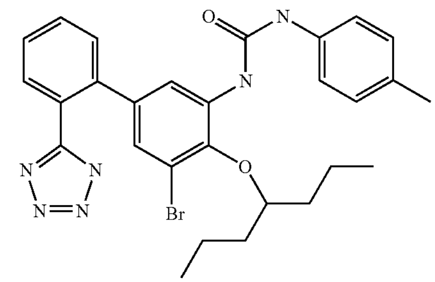 [SMILES: CCCC(CCC)Oc1c(Br)cc(-c2ccccc2-c2nnn[nH]2)cc1NC(=O)Nc1ccc(C)cc1] | $4.97^l$ | 563.1 |
| 287 | 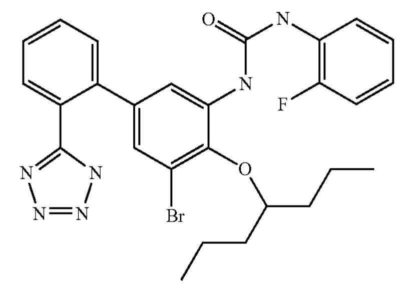 [SMILES: CCCC(CCC)Oc1c(Br)cc(-c2ccccc2-c2nnn[nH]2)cc1NC(=O)Nc1ccccc1F] | $4.86^l$ | 567.1 |
| 288 | 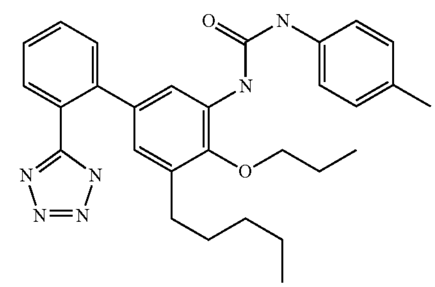 [SMILES: CCCCCc1cc(-c2ccccc2-c2nnn[nH]2)cc(NC(=O)Nc2ccc(C)cc2)c1OCCC] | $4.93^l$ | 503.1 |
| 289 | 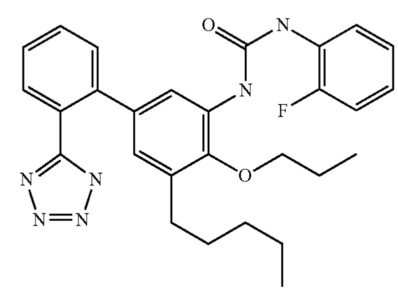 [SMILES: CCCCCc1cc(-c2ccccc2-c2nnn[nH]2)cc(NC(=O)Nc2ccccc2F)c1OCCC] | $4.95^l$ | 503.2 |
| 290 | 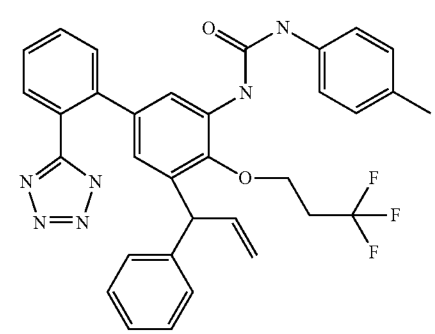 [SMILES: C=CC(c1ccccc1)c1cc(-c2ccccc2-c2nnn[nH]2)cc(NC(=O)Nc2ccc(C)cc2)c1OCCC(F)(F)F] | $1.80^j$ | 599 |

TABLE 10-continued

| Ex. No. | Structure | HPLC $T_r$ | $(M + H)^+$ |
|---|---|---|---|
| 291 | 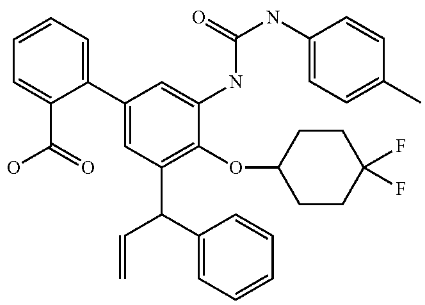 [SMILES: C=CC(c1ccccc1)c1cc(-c2ccccc2C(=O)O)cc(NC(=O)Nc2ccc(C)cc2)c1OC1CCC(F)(F)CC1] | $1.86^j$ | 597 |
| 292 | 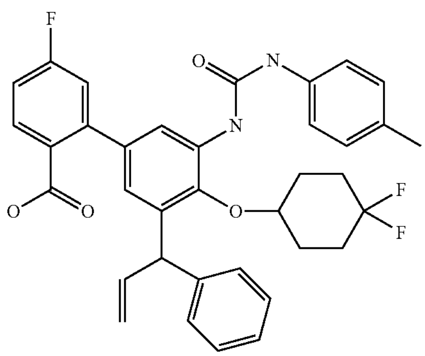 [SMILES: C=CC(c1ccccc1)c1cc(-c2cc(F)ccc2C(=O)O)cc(NC(=O)Nc2ccc(C)cc2)c1OC1CCC(F)(F)CC1] | $1.90^j$ | 615 |
| 293 | 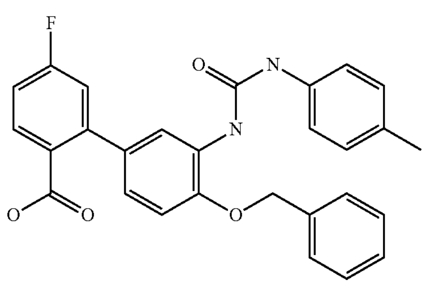 [SMILES: Cc1ccc(NC(=O)Nc2cc(-c3cc(F)ccc3C(=O)O)ccc2OCc2ccccc2)cc1] | $1.60^j$ | 470.2 |
| 294 | 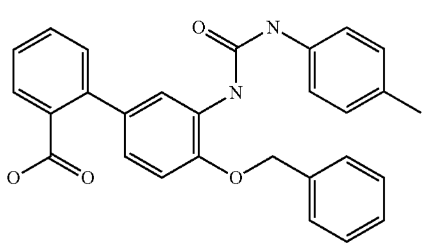 [SMILES: Cc1ccc(NC(=O)Nc2cc(-c3ccccc3C(=O)O)ccc2OCc2ccccc2)cc1] | $1.55^j$ | 453 |
| 295 | 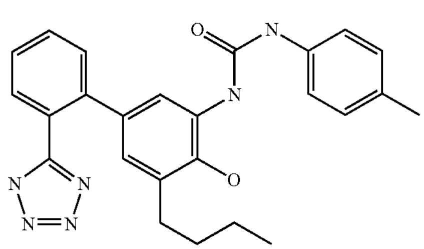 [SMILES: CCCCc1cc(-c2ccccc2-c2nnn[nH]2)cc(NC(=O)Nc2ccc(C)cc2)c1O] | $4.34^l$ | 433.3 |

TABLE 10-continued

| Ex. No. | Structure | HPLC $T_r$ | $(M + H)^+$ |
|---|---|---|---|
| 296 | 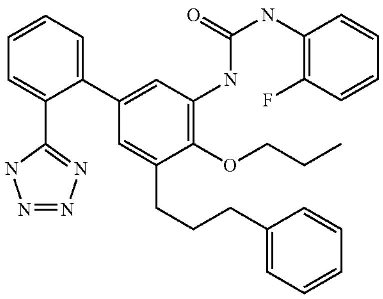 [SMILES: CCCOc1c(CCCc2ccccc2)cc(-c2ccccc2-c2nnn[nH]2)cc1NC(=O)Nc1ccccc1F] | 4.83[l] | 551.4 |
| 298 | 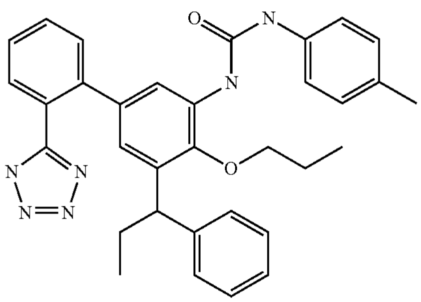 [SMILES: CCCOc1c(NC(=O)Nc2ccc(C)cc2)cc(-c2ccccc2-c2nnn[nH]2)cc1C(CC)c1ccccc1] | 4.82[l] | 547.3 |
| 299 | 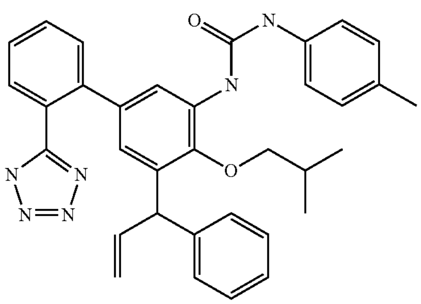 [SMILES: C=CC(c1ccccc1)c1cc(-c2ccccc2-c2nnn[nH]2)cc(NC(=O)Nc2ccc(C)cc2)c1OCC(C)C] | 4.88[l] | 559.5 |
| 300 | 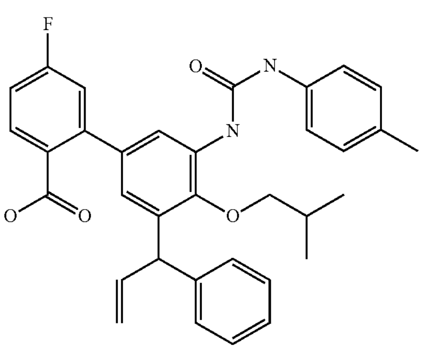 [SMILES: C=CC(c1ccccc1)c1cc(-c2cc(F)ccc2C(=O)O)cc(NC(=O)Nc2ccc(C)cc2)c1OCC(C)C] | 2.40[j] | 551.0 |
| 301 | 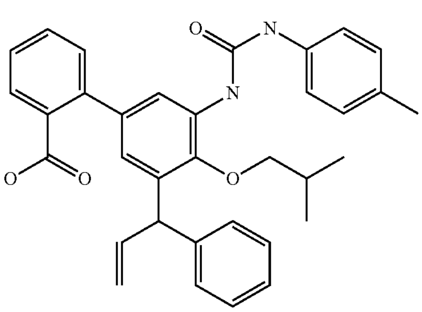 [SMILES: C=CC(c1ccccc1)c1cc(-c2ccccc2C(=O)O)cc(NC(=O)Nc2ccc(C)cc2)c1OCC(C)C] | 2.39[j] | 534.1 |

TABLE 10-continued

| Ex. No. | Structure | HPLC $T_r$ | $(M + H)^+$ |
|---|---|---|---|
| 302 | 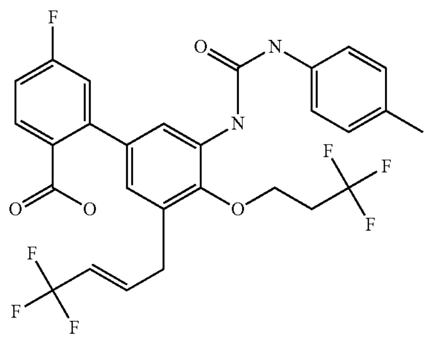 [SMILES: Cc1ccc(NC(=O)Nc2cc(-c3cc(F)ccc3C(=O)O)cc(C/C=C/C(F)(F)F)c2OCCC(F)(F)F)cc1] | 1.77[j] | 585 |
| 303 | 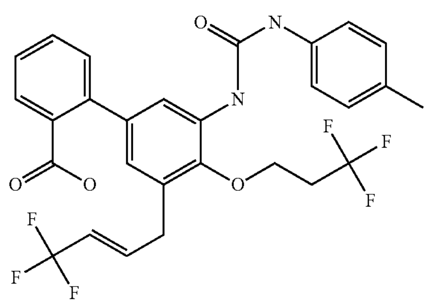 [SMILES: Cc1ccc(NC(=O)Nc2cc(-c3ccccc3C(=O)O)cc(C/C=C/C(F)(F)F)c2OCCC(F)(F)F)cc1] | 1.73[j] | 567 |
| 304 | 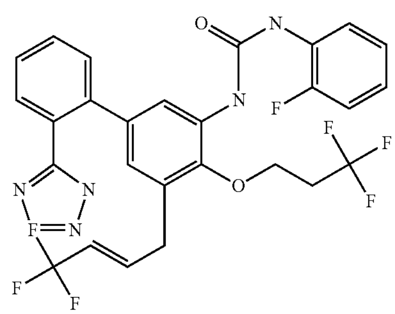 | 4.66[l] | 595.4 |
| 305 | 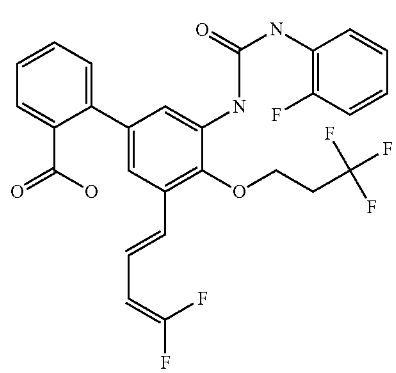 [SMILES: O=C(Nc1ccccc1F)Nc1cc(-c2ccccc2C(=O)O)cc(/C=C/C=C(F)F)c1OCCC(F)(F)F] | 4.83[l] | 551.3 |

TABLE 10-continued

| Ex. No. | Structure | HPLC $T_r$ | $(M + H)^+$ |
|---|---|---|---|
| 306 | 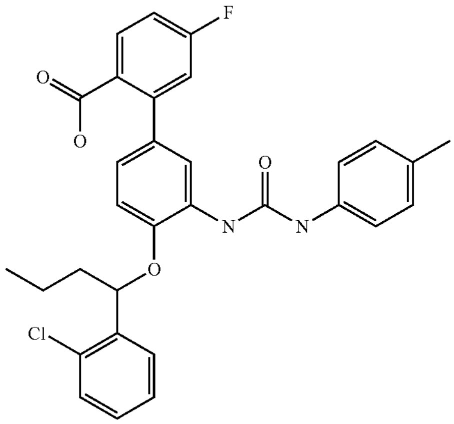 [SMILES: CCCC(Oc1ccc(-c2cc(F)ccc2C(=O)O)cc1NC(=O)Nc1ccc(C)cc1)c1ccccc1Cl] | 1.90$^j$ | 547 |
| 307 | 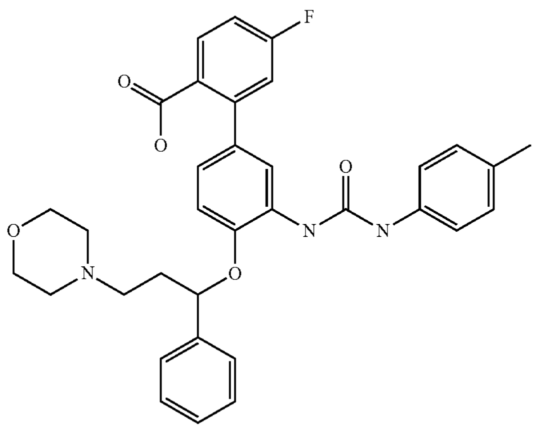 [SMILES: Cc1ccc(NC(=O)Nc2cc(-c3cc(F)ccc3C(=O)O)ccc2OC(CCN2CCOCC2)c2ccccc2)cc1] | 1.58$^j$ | 584 |
| 308 | 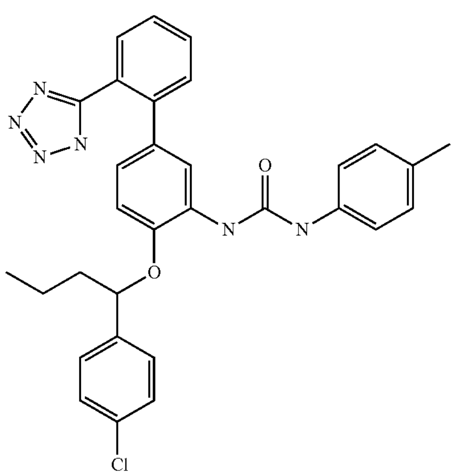 [SMILES: CCCC(Oc1ccc(-c2ccccc2-c2nnn[nH]2)cc1NC(=O)Nc1ccc(C)cc1)c1ccc(Cl)cc1] | 1.91$^j$ | 553 |

TABLE 10-continued

| Ex. No. | Structure | HPLC $T_r$ | $(M + H)^+$ |
|---|---|---|---|
| 309 | 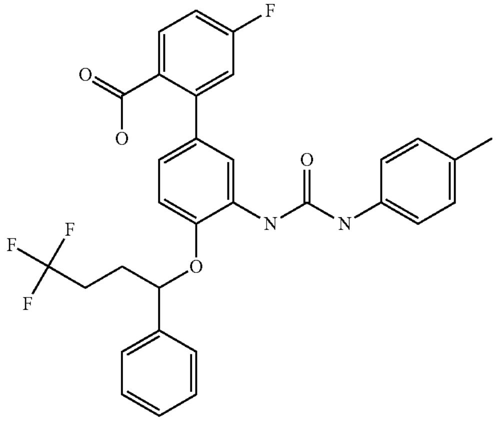 [SMILES: Cc1ccc(NC(=O)Nc2cc(-c3cc(F)ccc3C(=O)O)ccc2OC(CCC(F)(F)F)c2ccccc2)cc1] | 1.77[j] | 567 |
| 310 | 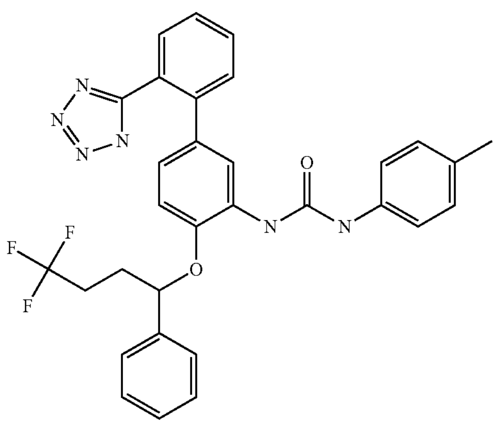 [SMILES: Cc1ccc(NC(=O)Nc2cc(-c3ccccc3-c3nnn[nH]3)ccc2OC(CCC(F)(F)F)c2ccccc2)cc1] | 1.79[j] | 573 |
| 311 | 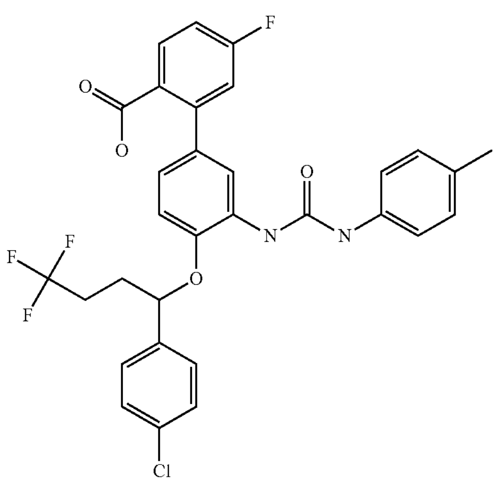 [SMILES: Cc1ccc(NC(=O)Nc2cc(-c3cc(F)ccc3C(=O)O)ccc2OC(CCC(F)(F)F)c2ccc(Cl)cc2)cc1] | 1.91[j] | 601 |

TABLE 10-continued

| Ex. No. | Structure | HPLC $T_r$ | $(M + H)^+$ |
|---|---|---|---|
| 312 | 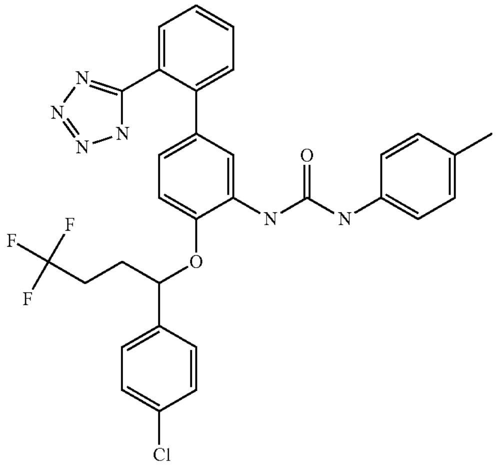 [SMILES: Cc1ccc(NC(=O)Nc2cc(-c3ccccc3-c3nnn[nH]3)ccc2OC(CCC(F)(F)F)c2ccc(Cl)cc2)cc1] | 1.90[j] | 607 |
| 313 | 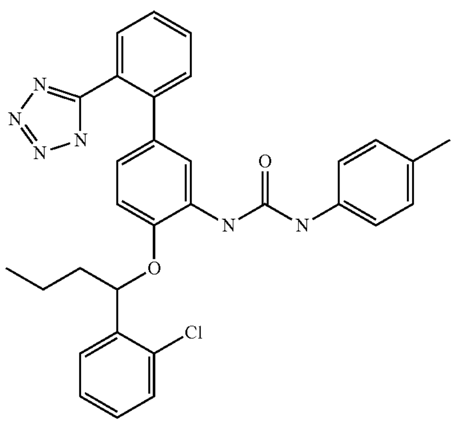 [SMILES: CCCC(Oc1ccc(-c2ccccc2-c2nnn[nH]2)cc1NC(=O)Nc1ccc(C)cc1)c1ccccc1Cl] | 1.90[j] | 553 |
| 315 | 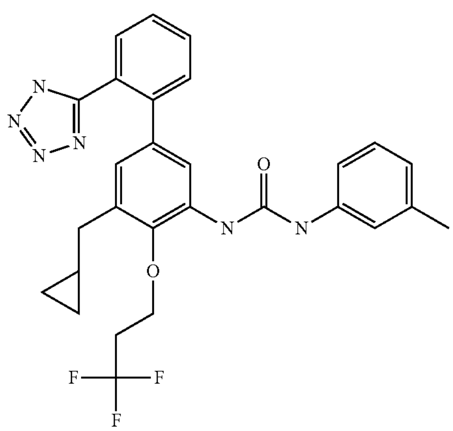 [SMILES: Cc1cccc(NC(=O)Nc2cc(-c3ccccc3-c3nnn[nH]3)cc(CC3CC3)c2OCCC(F)(F)F)c1] | 1.91[v] | 537 |

TABLE 10-continued

| Ex. No. | Structure | HPLC $T_r$ | $(M+H)^+$ |
|---|---|---|---|
| 316 | 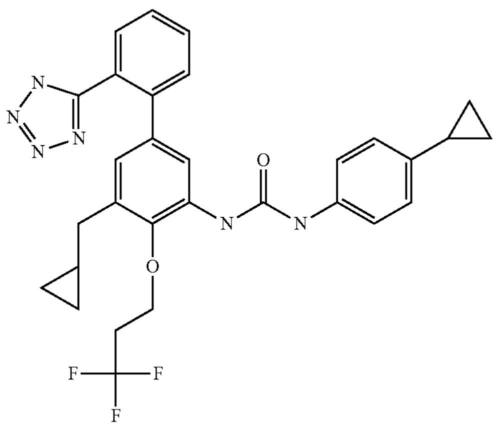 [SMILES: O=C(Nc1ccc(C2CC2)cc1)Nc1cc(-c2ccccc2-c2nnn[nH]2)cc(CC2CC2)c1OCCC(F)(F)F] | 1.94$^v$ | 561.2 (M −H)$^-$ |
| 317 | 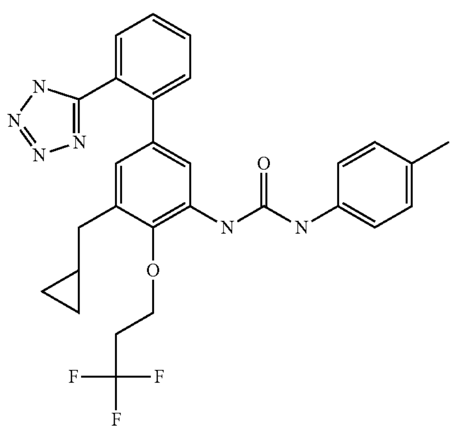 [SMILES: Cc1ccc(NC(=O)Nc2cc(-c3ccccc3-c3nnn[nH]3)cc(CC3CC3)c2OCCC(F)(F)F)cc1] | 1.97$^v$ | 537.2 |
| 318 | 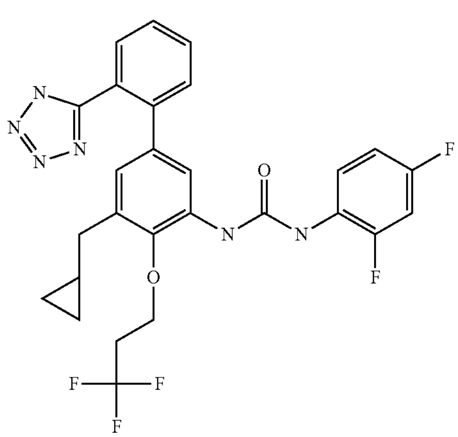 [SMILES: O=C(Nc1ccc(F)cc1F)Nc1cc(-c2ccccc2-c2nnn[nH]2)cc(CC2CC2)c1OCCC(F)(F)F] | 1.96$^v$ | 559.2 |

TABLE 10-continued

| Ex. No. | Structure | HPLC $T_r$ | $(M + H)^+$ |
|---|---|---|---|
| 319 | 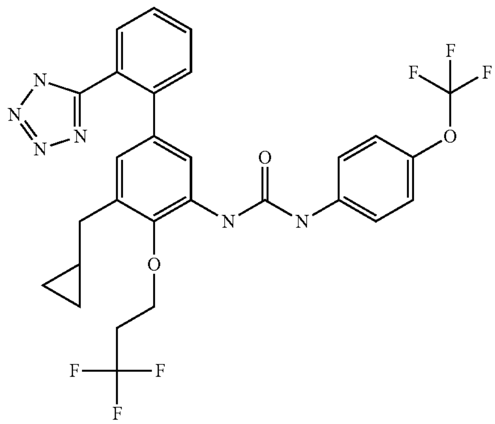 [SMILES: O=C(Nc1ccc(OC(F)(F)F)cc1)Nc1cc(-c2ccccc2-c2nnn[nH]2)cc(CC2CC2)c1OCCC(F)(F)F] | 2.08[v] | 607.2 |
| 320 | 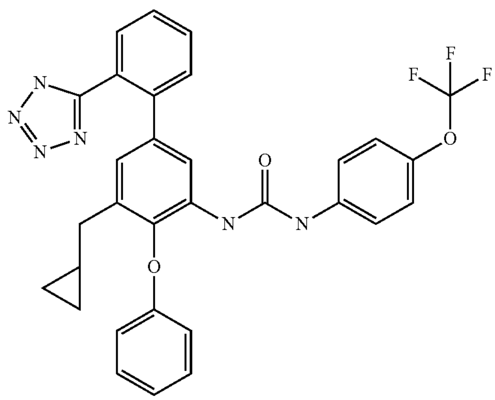 [SMILES: O=C(Nc1ccc(OC(F)(F)F)cc1)Nc1cc(-c2ccccc2-c2nnn[nH]2)cc(CC2CC2)c1Oc1ccccc1] | 1.97[v] | 587.2 |
| 321 | 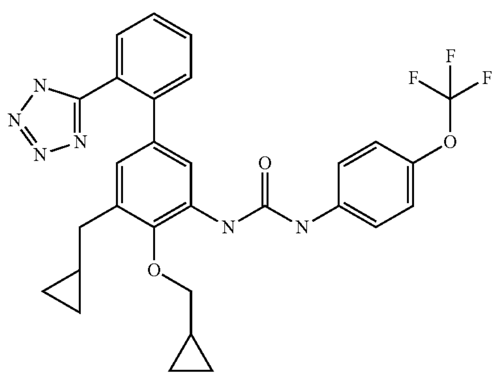 [SMILES: O=C(Nc1ccc(OC(F)(F)F)cc1)Nc1cc(-c2ccccc2-c2nnn[nH]2)cc(CC2CC2)c1OCC1CC1] | 1.93[v] | 565.2 |
| 322 | 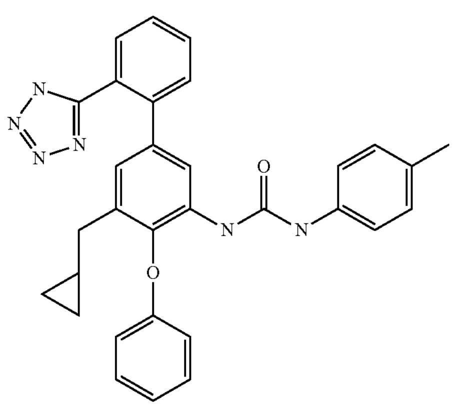 [SMILES: Cc1ccc(NC(=O)Nc2cc(-c3ccccc3-c3nnn[nH]3)cc(CC3CC3)c2Oc2ccccc2)cc1] | 1.92[v] | 517.2 |

TABLE 10-continued

| Ex. No. | Structure | HPLC $T_r$ | $(M + H)^+$ |
|---|---|---|---|
| 323 | 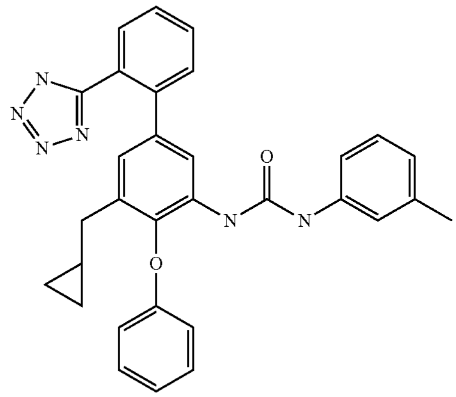 [SMILES: Cc1cccc(NC(=O)Nc2cc(-c3ccccc3-c3nnn[nH]3)cc(CC3CC3)c2Oc2ccccc2)c1] | 1.91$^v$ | 517.2 |
| 324 | 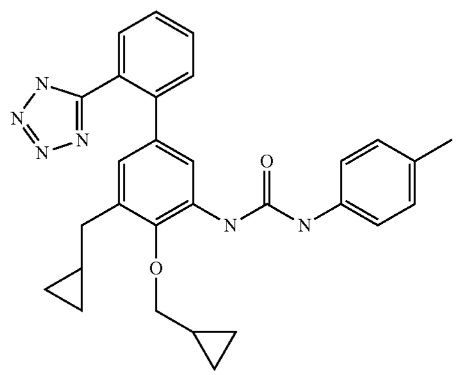 [SMILES: Cc1ccc(NC(=O)Nc2cc(-c3ccccc3-c3nnn[nH]3)cc(CC3CC3)c2OCC2CC2)cc1] | 1.89$^v$ | 495.2 |
| 325 | 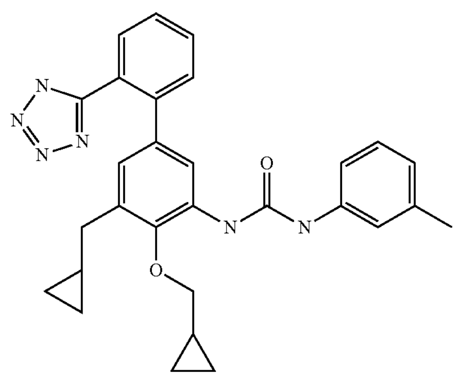 [SMILES: Cc1cccc(NC(=O)Nc2cc(-c3ccccc3-c3nnn[nH]3)cc(CC3CC3)c2OCC2CC2)c1] | 1.90$^v$ | 495.2 |
| 326 | 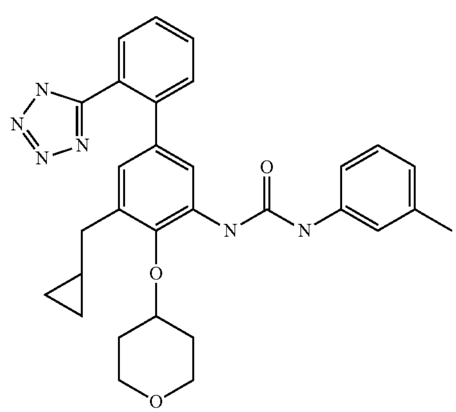 [SMILES: Cc1cccc(NC(=O)Nc2cc(-c3ccccc3-c3nnn[nH]3)cc(CC3CC3)c2OC2CCOCC2)c1] | 1.10$^v$ | 525.4 |

TABLE 10-continued

| Ex. No. | Structure | HPLC T$_r$ | (M + H)$^+$ |
|---|---|---|---|
| 327 | 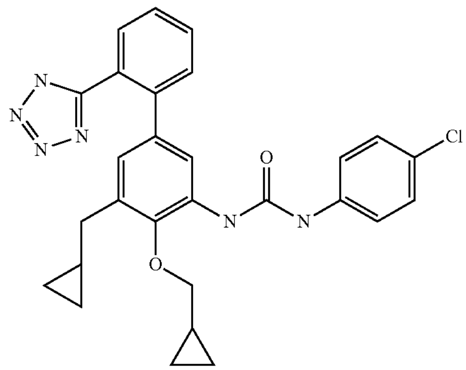 [SMILES: O=C(Nc1ccc(Cl)cc1)Nc1cc(-c2ccccc2-c2nnn[nH]2)cc(CC2CC2)c1OCC1CC1] | 1.91$^v$ | 515.2 |
| 328 | 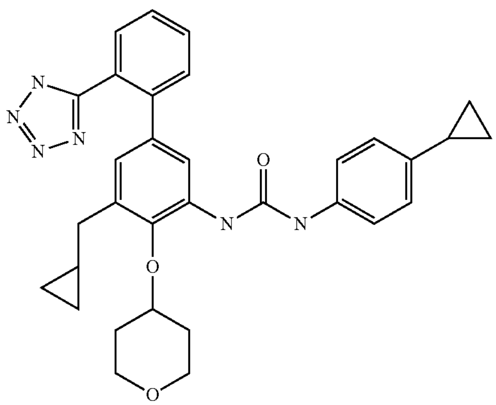 [SMILES: O=C(Nc1ccc(C2CC2)cc1)Nc1cc(-c2ccccc2-c2nnn[nH]2)cc(CC2CC2)c1OC1CCOCC1] | 1.67$^v$ | 551.3 |
| 329 | 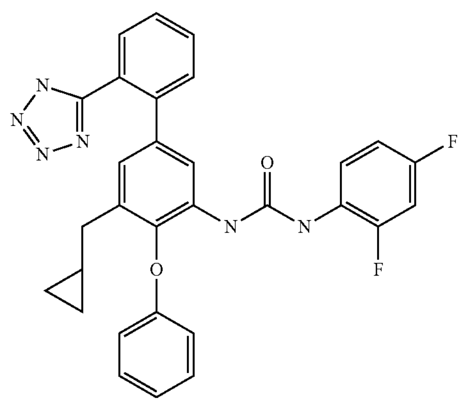 [SMILES: O=C(Nc1ccc(F)cc1F)Nc1cc(-c2ccccc2-c2nnn[nH]2)cc(CC2CC2)c1Oc1ccccc1] | 1.96$^v$ | 537.2 (M − H)$^-$ |
| 330 | 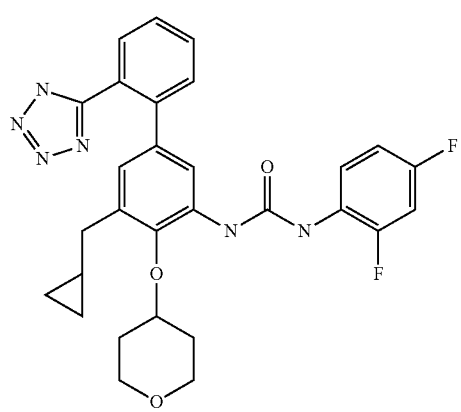 [SMILES: O=C(Nc1ccc(F)cc1F)Nc1cc(-c2ccccc2-c2nnn[nH]2)cc(CC2CC2)c1OC1CCOCC1] | 1.85$^v$ | 545.2 |

TABLE 10-continued

| Ex. No. | Structure | HPLC T_r | (M + H)+ |
|---|---|---|---|
| 331 | 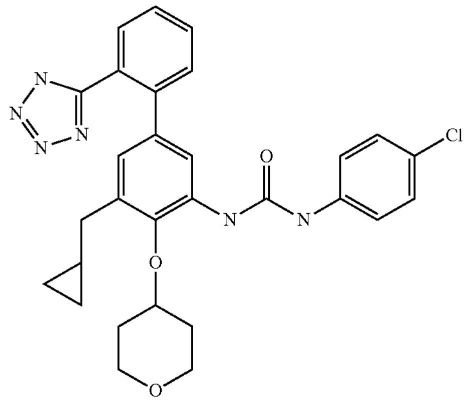 [SMILES: O=C(Nc1ccc(Cl)cc1)Nc1cc(-c2ccccc2-c2nnn[nH]2)cc(CC2CC2)c1OC1CCOCC1] | 1.62^v | 545.2 |
| 332 | | 1.03^k | 496 |
| 333 | | 1.85^j | 621 |
| 334 | 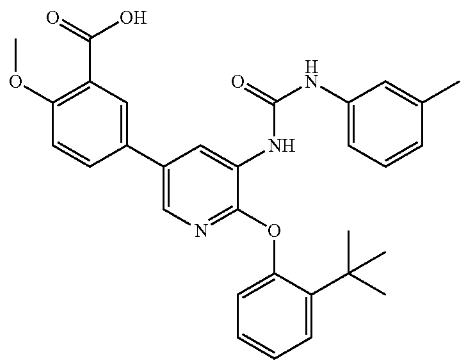 [SMILES: COc1ccc(-c2cnc(Oc3ccccc3C(C)(C)C)c(NC(=O)Nc3cccc(C)c3)c2)cc1C(=O)O] | 4.70^l | 526 |
| 335 | 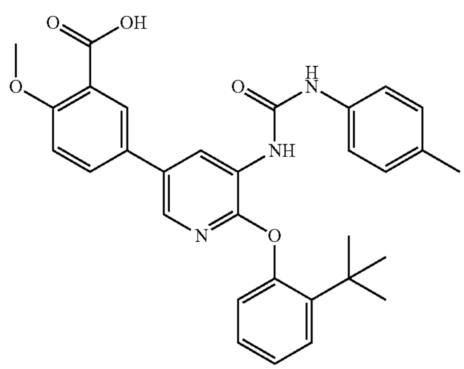 [SMILES: COc1ccc(-c2cnc(Oc3ccccc3C(C)(C)C)c(NC(=O)Nc3ccc(C)cc3)c2)cc1C(=O)O] | 4.69^l | 526 |
| 336 | 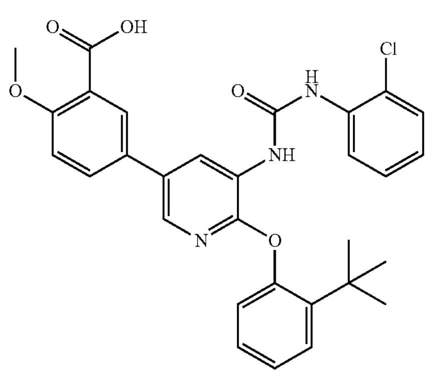 [SMILES: COc1ccc(-c2cnc(Oc3ccccc3C(C)(C)C)c(NC(=O)Nc3ccccc3Cl)c2)cc1C(=O)O] | 4.71^l | 546 |

TABLE 10-continued

| Ex. No. | Structure | HPLC T$_r$ | (M + H)$^+$ |
|---|---|---|---|
| 337 | 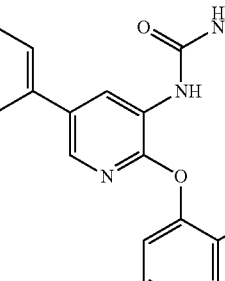 | 5.16$^l$ | 530 |
| 338 | 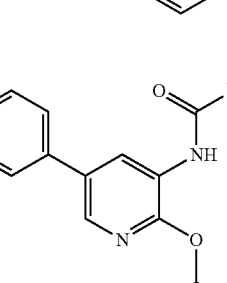 | 4.47$^l$ | 440 |
| 339 | 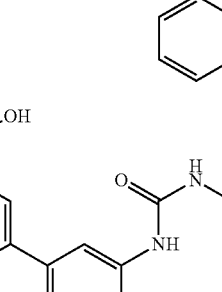 | 4.11$^l$ | 441 |

Example 276

1-(5-cyclopropyl-4-propoxy-2'-(1H-tetrazol-5-yl)-[1,1'-biphenyl]-3-yl)-3-(4-cyclopropylphenyl)urea

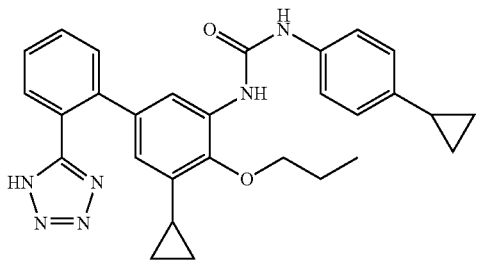 [SMILES: CCCOc1c(NC(=O)Nc2ccc(C3CC3)cc2)cc(-c2ccccc2-c2nnn[nH]2)cc1C1CC1]

276A: 5-bromo-1-nitro-2-propoxy-3-vinylbenzene

276A

To a solution of methyltriphenylphosphonium iodide (9.86 g, 24.39 mmol) in tetrahydrofuran (60 ml) at rt was added sodium bis(trimethylsilyl)amide (50.8 ml, 50.8 mmol). After 3 h of stirring at rt, a solution of 5-bromo-2-hydroxy-3-nitrobenzaldehyde (5 g, 20.32 mmol) was added at −78° C. The mixture was stirred overnight at rt. 1-iodo-propane (2.180 ml, 22.36 mmol) was added and the reaction was allowed to stir at rt overnight. The solvent was evaporated. DMF (20 ml), 1-iodopropane (2.180 ml, 22.36 mmol), and potassium carbonate (4.21 g, 30.5 mmol) were added. After 7 h, the reaction allowed to cool to rt, then quenched with H$_2$O and diluted with ether. Layers were separated. The aqueous phase was extracted with ether (2×). The organic phases were combined, washed with brine (1×), water (2×), dried over Na$_2$SO$_4$, filtered, and concentrated to afford an orange solid. The crude material was dissolved in a minimal amount of CH$_2$Cl$_2$ and chromatographed. Purification of the crude material by silica gel chromatography using an ISCO machine (80 g column, 60 mL/min, 0-20% EtOAc in hexanes over 20 min, t$_r$=12 min) gave the title compound (2.17 g, 7.51 mmol, 36.9% yield) as a yellow solid.

276B:
5-bromo-1-cyclopropyl-3-nitro-2-propoxybenzene

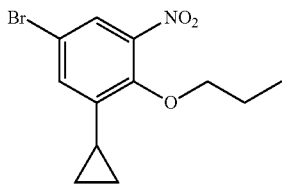

276B 1-methyl-1-nitrosourea (3.60 g, 35.0 mmol) was added in small portions to an ice-cold mixture of potassium hydroxide (9.20 g, 164 mmol) in ethyl ether (29.1 ml) and water (14.56 ml). The resultant yellow mixture was stirred for 15 min at 0° C. The Et$_2$O phase was decanted with a Teflon pipette into a Teflon Erlenmeyer flask containing enough KOH to cover the bottom of the flask. Then the mixture was added to a solution of 276A (0.500 g, 1.748 mmol) and palladium (II) acetate (0.020 g, 0.087 mmol) in dichloromethane (14.56 ml). The reaction mixture was stirred at 0° C. for 1 h. The reaction mixture was filtered through Celite and the filter cake rinsed with CH$_2$Cl$_2$. The solvent was evaporated. NMR showed the title compound (525 mg, 1.662 mmol, 95% yield) as pure yellow solid.

276C: 5-bromo-3-cyclopropyl-2-propoxyaniline

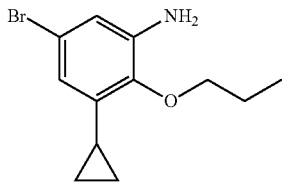

276C

To a solution of ammonium chloride (0.561 g, 10.49 mmol) in water (1.046 ml) was added ethanol (7.32 ml). The reaction vessel was cooled to 0° C., then charged with 942 mg of Zinc flake. The mixture was treated with a solution of 276B (0.525 g, 1.749 mmol) in 1.9 mL of ethanol over 5 min. The reaction mixture was allowed to warm to rt and stirred for 2 h, then filtered through Celite. The filter cake was washed with CH$_2$Cl$_2$. The filtrate was concentrated to one-third volume, then diluted with CH$_2$Cl$_2$ and water. The layers were separated. The organic phase was dried over Na$_2$SO$_4$, filtered, and concentrated to afford a yellow oil. The crude material was dissolved in a minimal amount of CH$_2$Cl$_2$ and chromatographed. Purification of the crude material by silica gel chromatography using an ISCO machine (40 g column, 40 mL/min, 0-30% EtOAc in hexanes over 17 min, t$_r$=13.5 min) gave the title compound (428 mg, 1.568 mmol, 90% yield) as a colorless residue, which turned brown upon standing. MS(ES): m/z=270.1 [M+H]$^+$. HPLC T$_r$: 1.45$^w$.

276D: 1-(5-bromo-3-cyclopropyl-2-propoxyphenyl)-3-(4-cyclopropylphenyl)urea

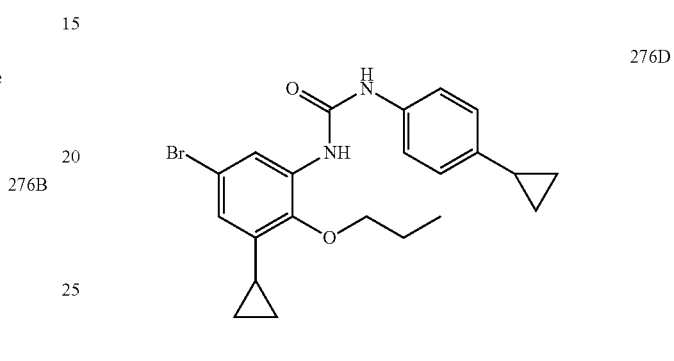

276D

To a solution of 276C (50 mg, 0.185 mmol) in tetrahydrofuran (375 µl) was added 1-cyclopropyl-4-isocyanatobenzene (88 mg, 0.555 mmol). The reaction was heated at 35° C. for 2 h, then allowed to cool to rt. The reaction was diluted with water and extracted with EtOAc (2×). The organic layers were dried over Na$_2$SO$_4$, filtered, and concentrated to afford a white solid. The crude material was dissolved in a minimal amount of CH$_2$Cl$_2$ and chromatographed. Purification of the crude material by silica gel chromatography using an ISCO machine (24 g column, 35 mL/min, 0-20% EtOAc in hexanes over 25 min, t$_r$=20 min) gave the title compound (61 mg, 0.141 mmol, 76% yield) as a white solid. MS(ES): m/z=429.5 [M+H]$^+$. HPLC T$_r$: 1.75$^w$.

276E: 1-(2'-cyano-5-cyclopropyl-4-propoxy-[1,1'-biphenyl]-3-yl)-3-(4-cyclopropylphenyl)urea

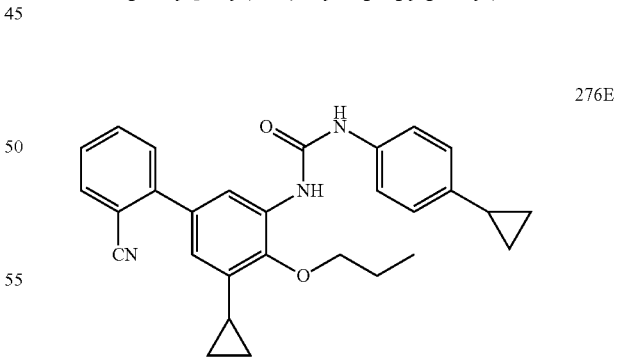

276E

To a solution of 276D (35.7 mg, 0.083 mmol) in dioxane (831 µl) was added 2-(5,5-dimethyl-1,3,2-dioxaborinan-2-yl)benzonitrile (23.25 mg, 0.108 mmol), potassium phosphate, dibasic (43.4 mg, 0.249 mmol). The mixture was degassed with nitrogen for 5 minutes. PdCl$_2$(dppf)-CH$_2$Cl$_2$ adduct (3.40 mg, 4.16 µmol) was then added followed by degassing for an additional 5 minutes. The vial was then sealed and heated at 100° C. for 17 hours. The reaction was allowed to cool to rt, then diluted with EtOAc and H₂O. Layers were separated. The aqueous phase was extracted with EtOAc (2×). The organic phases were combined, dried over Na₂SO₄, filtered and concentrated to give the crude product as a brown oil. The crude material was dissolved in a minimal amount of CH₂Cl₂ and chromatographed. Purification of the crude material by silica gel chromatography using an ISCO machine (24 g column, 35 mL/min, 0-30% EtOAc in hexanes over 25 min, t$_r$=17 min) gave the title compound (13.9 mg, 0.029 mmol, 35.2% yield) as a yellow solid. MS(ES): m/z=452.3 [M+H]⁺. HPLC T$_r$: 1.70$^w$.

1-(5-cyclopropyl-4-propoxy-2'-(1H-tetrazol-5-yl)-[1,1'-biphenyl]-3-yl)-3-(4-cyclopropylphenyl)urea

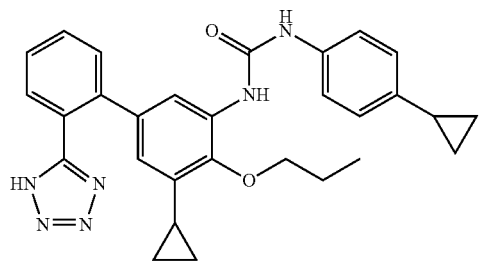

276

To a solution of 276E (13.9 mg, 0.031 mmol) in toluene (123 μl) was added azidotributylstannane (59.0 μl, 0.215 mmol) followed by heating at 105° C. for 20 hours. The reaction was allowed to cool to rt, then concentrated by a stream of N₂. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 25-65% B over 25 minutes, then a 10-minute hold at 65% B; Flow: 20 mL/min. Fractions containing the desired product were combined and dried via centrifugal evaporation to afford the title compound (0.6 mg, 4% yield). MS(ES): m/z=495.2 [M+H]⁺. HPLC T$_r$: 1.29$^w$.

Example 314

1-(4-chlorophenyl)-3-(5-(cyclopropylmethyl)-2'-(1H-tetrazol-5-yl)-4-(3,3,3-trifluoropropoxy)-[1,1'-biphenyl]-3-yl)urea

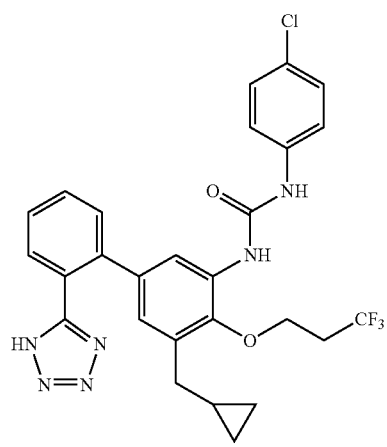 [SMILES: O=C(Nc1ccc(Cl)cc1)Nc1cc(-c2ccccc2-c2nnn[nH]2)cc(CC2CC2)c1OCCC(F)(F)F]

314A. 1-allyl-5-bromo-3-nitro-2-(3,3,3-trifluoropropoxy)benzene

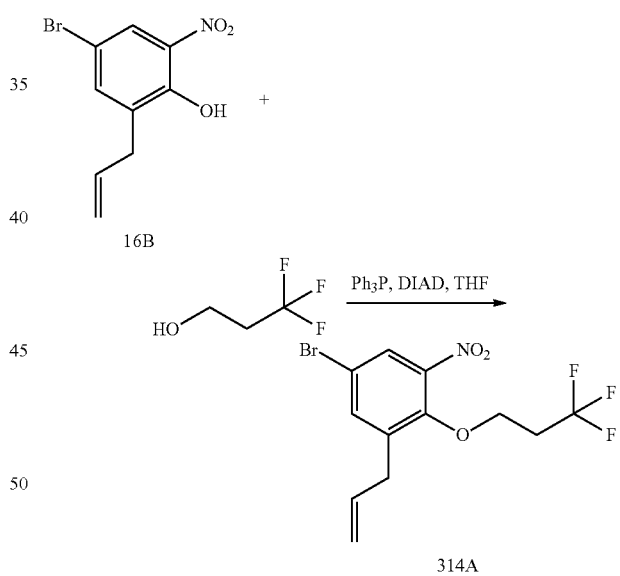

Triphenylphosphine (1.525 g, 5.81 mmol) and diisopropyl azodicarboxylate (1.130 mL, 5.81 mmol) were added to a solution of preparation 16B (1 g, 3.87 mmol) and 3,3,3-trifluoropropan-1-ol (0.663 g, 5.81 mmol) in THF (3 mL). The reaction was stirred overnight, concentrated and the residue was purified by column chromatography (80 g eluted with 0% to 50% EtOAc in Hexane in 25 min to obtain 314A (0.995 g, 2.81 mmol, 72.5% yield).
¹H NMR (400 MHz, METHANOL-d₄) δ 7.93 (d, J=2.4 Hz, 1H), 7.69 (d, J=2.4 Hz, 1H), 6.00 (ddt, J=16.9, 10.3, 6.4 Hz, 1H), 5.29-5.06 (m, 2H), 4.35-4.09 (m, 2H), 3.63-3.40 (m, 2H), 2.73 (qt, J=10.9, 6.1 Hz, 2H)

314B. 5-bromo-1-(cyclopropylmethyl)-3-nitro-2-(3,3,3-trifluoropropoxy)benzene

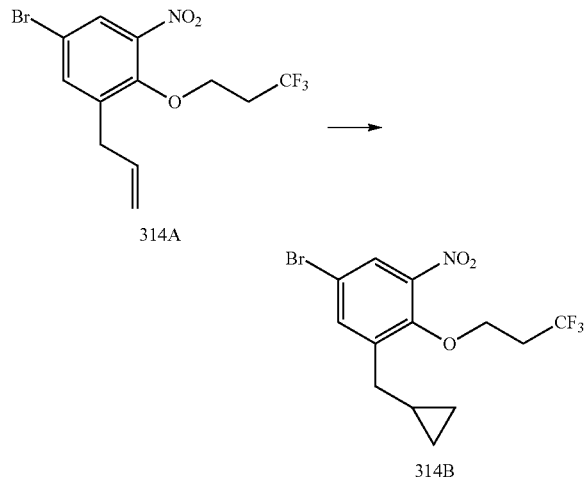

To a solution of 314A (0.5 g, 1.412 mmol) and PdOAc$_2$ (0.079 g, 0.353 mmol) in diethyl ether (15 mL) was added a solution of diazomethane in diethyl ether at 0 deg C. Which was prepared by careful addition of N-nitroso-N-methylurea (1.747 g, 16.94 mmol) into a solution of diethyl ether (15 ml) and 40% KOH (792 mg, 14.12 mmol) solution at −10 deg C., (salt Ice bath). After 30 min $^1$H NMR of an aliquot showed the reaction to be complete. The progress of the reaction was also monitored by TLC.: The reaction mixture was quenched with 20% aqueous acetic acid solution, extracted with ethyl acetate twice, the organic layers were washed with brine, dried over Na$_2$SO$_4$, concentrated to give 314B (450 mg, 1.222 mmol, 87% yield) as pale yellow liquid. $^1$H NMR (400 MHz, CDCl$_3$) δ 7.85 (d, J=2.4 Hz, 1H), 7.78 (d, J=2.4 Hz, 1H), 4.16 (t, J=6.4 Hz, 2H), 2.67 (m, 2H), 2.61 (d, J=7.2 Hz, 2H), 0.97 (m, 1H), 0.63 (m, 2H); 0.26 (m, 2H)

Example 314 can be prepared from preparation 314B by the methods described in Example 16. MS(ES); m/z=558.2 [M+H]$^+$. HPLC T$_r$: 1.95$^v$ min.

Evaluation of Biological Activity

Exemplary compounds were tested for inhibition of IDO activity. Experimental procedures and results are provided below.

IDO Kynurenine Assay with Human IDO1/HEK293 Cells

Human IDO1/HEK293 cells were seeded at 10,000 cells per 50 uL per well with RPMI/phenol red free media contains 10% FBS in a 384-well black wall clear bottom tissue culture plate (Matrix Technologies LLC) 125 nL of certain concentration of compound was then added to each well using ECHO liquid handling systems. The cells were incubated for 20 hours in 37° C. incubator with 5% CO$_2$.

The compound treatments were stopped by adding Trichloroacetic Acid (Sigma-Aldrich) to a final concentration at 0.2%. The cell plate was further incubated at 50° C. for 30 minute. The equal volume supernatant (20 uL) and 0.2% (w/v) Ehrlich reagent (4-dimethylaminobenzaldehyde, Sigma-Aldrich) in glacial acetic acid were mixed in a new clear bottom 384-well plate. This plate was then incubated at room temperature for 30 minute. The absorbance at 490 nm was measured on Envision plate reader.

Compound IC$_{50}$ values were calculated using the counts of 500 nM of a reference standard treatment as one hundred percent inhibition, and counts of no compound but DMSO treatment as zero percent inhibition.

Reagents: Hela cells (ATCC, CCL-2)
IFNg (R&D, 28-IF-100)—resuspend at 10 ug/mL in PBS with 0.1% BSA 30% TCA
Ehrlich reagent (2% w/v p-dimethylaminobenzaldehyde in glacial acetic acid)
Cell Titer 96 Aqueous Non-Radioactive Cell Proliferation Assay, MTS (Promega, Cat # G5430)
Cell Lines and Culture Conditions Hela cancer cell lines were acquired from the American Type Culture Collection. Cells were maintained in phenol red free-RPMI1640 medium containing high glucose and L-glutamine (Invitrogen) supplemented with 10% fetal bovine serum (FBS; Invitrogen). Cell cultures were incubated at 37° C., 5% CO$_2$, and 100% humidity.

Cell Treatment and Kynurenine Assay

Hela cells were seeded on 96-well plates (40,000 cells per well) and allowed to adhere for 5-6 hours. Cells were then treated with vehicle (DMSO) or with IDO inhibitor at a top dose of 30 μM (3-fold dilution all the way down to 1.5 nM). A final concentration of 100 ng/mL of human recombinant IFN-γ (R&D, 28-IF-100) was immediately added to the cells to stimulate IDO expression. Treated cells were then incubated for 20 hours at 37° C. At the end of the 20 h incubation, reactions were terminated by the addition of 30% TCA to each well. Plates were incubated for 30 minutes at 50° C. to hydrolyze N-formylkynurenine to kynurenine. Cells were centrifuged 10 minutes at 2400 rpm. 100 ul of supernatants were transferred to new 96 flat well plates and mixed with 100 ul Ehrlich reagent. The resulting solution was incubated 10 minutes at RT. Absorbance at 490 nM was read using Spectra Max 384 (Molecular Devices).

Results of the IDO assays are shown in the table below.

| Example # | HEK human IDO-1 (IC50, uM) | LLE_IDO_ABS_DR (IC50, uM) | Hela Kyurenine (IC50, uM) |
| --- | --- | --- | --- |
| 1 | 6.18 | | 2.42 |
| 2 | 0.56 | 0.07 | 0.06 |
| 3 | | 4.81 | 3.38 |
| 4 | | | 0.03 |
| 5 | 1.83 | 1.01 | 0.12 |
| 6 | | | 0.73 |
| 7 | 0.75 | 0.32 | 0.11 |
| 8 | 0.03 | 0.01 | |
| 9 | | 0.03 | |
| 10 | | 0.72 | |
| 11 | | 0.16 | |
| 12 | | 0.82 | |
| 13 | | 0.03 | |
| 14 | | 0.60 | |
| 15 | | 0.38 | |
| 16 | 0.03 | 0.03 | |
| 17 | | 0.20 | |
| 18 | | 0.31 | |
| 19 | 0.03 | 0.02 | |
| 20 | | 0.17 | |
| 21 | | 0.15 | |
| 22 | 5.92E−03 | 0.02 | |
| 23 | | 0.13 | |
| 24 | | 0.08 | |
| 25 | | 0.16 | |
| 26 | | 0.65 | |

| Example # | HEK human IDO-1 (IC50, uM) | LLE_IDO_ABS_DR (IC50, uM) | Hela Kyurenine (IC50, uM) |
|---|---|---|---|
| 27 |  | 0.85 |  |
| 28 |  | 0.25 |  |
| 29 | 0.03 | 0.03 |  |
| 30 | 0.02 | 9.95E−03 |  |
| 31 | 0.02 | 0.04 |  |
| 32 | 0.01 | 9.47E−03 |  |
| 33 |  | 0.11 |  |
| 34 |  | 0.17 |  |
| 35 |  | 0.10 |  |
| 36 | 0.02 | 0.03 |  |
| 37 |  | 0.13 |  |
| 38 |  | 0.21 |  |
| 39 |  | 0.05 |  |
| 40 |  | 0.13 |  |
| 41 |  |  | 0.43 |
| 42 | 0.62 | 0.34 | 0.09 |
| 43 |  | 10.00 | 0.44 |
| 44 |  |  | 0.49 |
| 45 |  | 0.39 | 0.15 |
| 46 | 0.54 | 0.32 | 0.05 |
| 47 |  |  | 0.54 |
| 48 |  |  | 1.23 |
| 49 |  | 2.63 | 0.59 |
| 50 |  |  | 0.90 |
| 51 |  |  | 0.83 |
| 52 |  |  | 1.27 |
| 53 |  |  | 2.18 |
| 54 |  | 2.54 | 0.51 |
| 55 |  |  | 0.11 |
| 56 |  |  | 0.13 |
| 57 |  | 0.39 | 0.13 |
| 58 |  | 0.77 | 0.24 |
| 59 |  |  | 0.88 |
| 60 |  | 1.15 | 0.31 |
| 61 |  |  | 0.31 |
| 62 |  | 0.53 | 0.14 |
| 63 | 1.60 | 1.61 | 0.39 |
| 64 |  | 0.64 | 0.18 |
| 65 |  | 0.63 | 0.20 |
| 66 |  | 1.59 | 0.82 |
| 67 |  |  | 0.58 |
| 68 |  |  | 0.49 |
| 69 | 6.19 | 2.09 | 0.84 |
| 70 |  |  | 0.39 |
| 71 |  |  | 0.18 |
| 72 |  |  | 0.38 |
| 73 | 2.97 | 1.57 | 0.84 |
| 74 |  | 0.52 | 0.40 |
| 75 |  | 0.55 | 0.37 |
| 76 |  | 2.04 | 0.60 |
| 77 | 2.33 | 0.78 | 0.33 |
| 78 |  |  | 0.08 |
| 79 | 0.42 | 0.13 | 0.06 |
| 80 |  |  | 0.13 |
| 81 |  | 0.32 | 0.13 |
| 82 |  |  | 0.84 |
| 83 |  | 1.19 | 0.21 |
| 84 |  |  | 0.16 |
| 85 |  |  | 0.11 |
| 86 |  |  | 0.23 |
| 87 |  |  | 0.28 |
| 88 |  |  | 0.13 |
| 89 |  |  | 0.12 |
| 90 |  |  | 0.26 |
| 91 |  |  | 0.25 |
| 92 |  |  | 0.24 |
| 93 |  |  | 0.62 |
| 94 |  | 3.06 | 0.17 |
| 95 |  |  | 0.26 |
| 96 |  |  | 0.18 |
| 97 |  |  |  |
| 98 |  |  | 0.16 |
| 99 |  |  | 0.22 |
| 100 |  |  | 0.47 |
| 101 |  |  | 1.01 |
| 102 |  |  | 0.22 |
| 103 | 1.31 | 0.47 | 0.09 |
| 104 |  |  | 0.10 |
| 105 |  |  | 0.37 |
| 106 |  |  | 0.47 |
| 107 |  |  | 0.32 |
| 108 |  |  | 0.72 |
| 109 |  |  | 0.60 |
| 110 |  | 2.05 | 0.13 |
| 111 |  | 0.43 | 0.18 |
| 112 |  | 1.05 | 0.37 |
| 113 | 1.66 | 0.88 | 0.69 |
| 114 | 0.12 | 0.10 | 0.02 |
| 115 | 0.24 | 0.20 | 0.05 |
| 116 | 0.79 | 0.78 | 0.10 |
| 117 |  |  |  |
| 118 |  | 1.06 | 0.92 |
| 119 |  |  | 0.78 |
| 120 | 0.26 | 0.43 | 0.08 |
| 121 |  | 0.39 | 0.11 |
| 122 | 0.66 | 0.25 | 0.08 |
| 123 | 0.68 | 0.73 | 0.16 |
| 124 |  | 0.82 | 0.14 |
| 125 |  | 0.73 | 0.17 |
| 126 |  | 0.76 | 0.19 |
| 127 | 3.29 | 2.43 | 0.49 |
| 128 |  | 0.25 | 0.04 |
| 129 | 0.29 | 0.30 | 0.07 |
| 130 |  | 0.48 | 0.12 |
| 131 | 0.77 | 0.77 | 0.16 |
| 132 |  | 1.46 | 0.99 |
| 133 |  | 1.83 | 0.59 |
| 134 |  |  | 1.39 |
| 135 | 5.17 |  | 2.24 |
| 136 | 0.07 | 0.14 | 0.02 |
| 137 |  |  | 2.43 |
| 138 |  | 2.34 | 0.39 |
| 139 |  | 2.64 | 0.68 |
| 140 |  | 3.85 | 0.97 |
| 141 | 0.42 | 0.33 | 0.05 |
| 142 | 0.38 | 0.16 | 0.04 |
| 143 | 0.53 | 0.20 | 0.05 |
| 144 |  | 0.51 | 0.15 |
| 145 | 1.59 | 0.79 | 0.28 |
| 146 |  | 0.58 | 0.27 |
| 147 |  | 1.32 | 0.46 |
| 148 | 2.42 | 0.49 | 0.26 |
| 149 |  | 2.05 | 0.53 |
| 150 |  | 7.19 | 0.71 |
| 151 | 1.12 | 0.30 | 0.06 |
| 152 | 0.45 | 0.29 | 0.05 |
| 153 | 0.92 | 0.53 | 0.04 |
| 154 |  | 0.54 | 0.14 |
| 155 |  |  | 0.45 |
| 156 |  | 0.68 | 0.64 |
| 157 |  | 3.68 | 2.12 |
| 158 |  | 4.06 | 0.86 |
| 159 |  | 3.47 | 0.87 |
| 160 |  |  | 1.32 |
| 161 |  | 0.24 | 0.05 |
| 162 |  | 2.24 | 1.25 |
| 163 |  | 0.47 | 0.16 |
| 164 |  | 0.33 | 0.28 |
| 165 |  | 0.46 | 0.39 |
| 166 |  | 3.63 | 1.30 |
| 167 |  | 3.81 | 1.67 |
| 168 |  | 0.66 | 0.24 |
| 169 |  | 2.34 | 0.66 |
| 170 |  | 2.23 | 0.81 |
| 171 |  | 0.31 | 0.09 |
| 172 |  | 1.92 | 1.28 |
| 173 |  | 3.07 | 1.63 |
| 174 |  | 0.32 | 0.28 |
| 175 |  | 2.58 | 1.48 |
| 176 |  | 0.28 | 0.09 |

| Example # | HEK human IDO-1 (IC50, uM) | LLE_IDO_ABS_DR (IC50, uM) | Hela Kyurenine (IC50, uM) |
|---|---|---|---|
| 177 | | 0.42 | 0.20 |
| 178 | | 1.74 | 0.89 |
| 179 | | | 0.21 |
| 180 | | 0.27 | 0.15 |
| 181 | | 0.74 | 0.09 |
| 182 | | | 1.05 |
| 183 | | | 0.69 |
| 184 | | | 1.10 |
| 185 | | 0.68 | 0.16 |
| 186 | | | 1.13 |
| 187 | | 2.33 | 0.86 |
| 188 | | 1.83 | 0.87 |
| 189 | | 1.24 | 0.36 |
| 190 | | 0.45 | 0.17 |
| 191 | | 1.21 | 0.34 |
| 192 | | 1.44 | 0.37 |
| 193 | | 1.16 | 0.25 |
| 194 | | | |
| 195 | | 1.86 | |
| 196 | | | |
| 197 | | 0.20 | |
| 198 | | 1.49 | |
| 199 | | 0.09 | |
| 200 | | | 1.52 |
| 201 | | 8.15 | 0.78 |
| 202 | | | 1.69 |
| 203 | | | 0.50 |
| 204 | | | 1.25 |
| 205 | | | 0.85 |
| 206 | | 3.35 | 0.85 |
| 207 | | | 1.23 |
| 208 | | | |
| 209 | | | 1.74 |
| 210 | | | 1.54 |
| 211 | | | 1.63 |
| 212 | | | 1.07 |
| 213 | | 2.56 | 0.93 |
| 214 | | | 0.15 |
| 215 | | 1.83 | 0.30 |
| 216 | | | 1.09 |
| 217 | | | 1.25 |
| 218 | | | 0.65 |
| 219 | | | |
| 220 | | | 0.93 |
| 221 | | | 1.01 |
| 222 | | | 1.63 |
| 223 | 7.50 | | 2.64 |
| 224 | 7.50 | | 1.02 |
| 225 | 7.65 | 2.90 | 0.57 |
| 226 | 9.19 | | 0.79 |
| 227 | | 10.00 | 0.93 |
| 228 | null | | 0.42 |
| 229 | 7.50 | | 1.89 |
| 230 | 7.50 | | 1.81 |
| 231 | | | 0.72 |
| 232 | 7.50 | | 1.80 |
| 233 | 7.50 | | 2.89 |
| 234 | | | 1.85 |
| 235 | | | 1.43 |
| 236 | | | |
| 237 | | | 0.80 |
| 238 | | 10.00 | 0.44 |
| 239 | | | 1.02 |
| 240 | | | 0.54 |
| 241 | | | 1.04 |
| 242 | | | 1.15 |
| 243 | | | 1.82 |
| 244 | | | 0.84 |
| 245 | 6.58 | 2.25 | 0.25 |
| 246 | | 3.94 | 0.70 |
| 247 | | | 1.34 |
| 248 | | | 1.49 |
| 249 | | | 2.55 |
| 250 | | | 1.06 |
| 251 | | | 0.74 |
| 252 | | | 0.66 |
| 253 | | | 1.10 |
| 254 | 1.62 | 1.16 | 0.35 |
| 255 | | | 0.37 |
| 256 | | | 0.31 |
| 257 | | 1.25 | 0.44 |
| 258 | | | 2.25 |
| 259 | | | 2.21 |
| 260 | | | 5.59 |
| 261 | | | 0.42 |
| 262 | | | 4.56 |
| 263 | | | |
| 264 | | | 0.58 |
| 265 | | | 3.46 |
| 266 | | 2.15 | |
| 267 | | 0.39 | |
| 268 | | 0.69 | |
| 269 | | 1.10 | |
| 270 | | 0.02 | |
| 271 | | 0.03 | |
| 272 | | 0.10 | |
| 273 | | 0.04 | |
| 274 | | 3.51 | |
| 275 | | 1.74 | |
| 276 | | 0.69 | |
| 277 | | 0.03 | |
| 278 | | 0.04 | |
| 279 | | 0.65 | |
| 280 | | 0.19 | |
| 281 | | 0.82 | |
| 282 | | 1.38 | |
| 283 | 0.06 | 0.03 | |
| 284 | 6.49E−03 | 5.56E−03 | |
| 285 | | 0.14 | |
| 286 | | 0.47 | |
| 287 | 4.49E−03 | 3.25E−03 | |
| 288 | 0.02 | 7.26E−03 | |
| 289 | 0.05 | 9.83E−03 | |
| 290 | | 1.49 | |
| 291 | | 0.73 | |
| 292 | | 3.35 | |
| 293 | | 4.88 | |
| 294 | | 0.52 | |
| 295 | | 0.05 | |
| 296 | | | |
| 297 | 0.09 | 0.05 | |
| 298 | 0.03 | 0.03 | |
| 299 | | 0.10 | |
| 300 | | 0.14 | |
| 301 | | 0.21 | |
| 302 | | 0.10 | |
| 303 | | 0.16 | |
| 304 | | 0.14 | |
| 305 | | 0.82 | |
| 306 | | 5.45 | |
| 307 | | 0.04 | |
| 308 | | 0.86 | |
| 309 | | 0.09 | |
| 310 | | 1.72 | |
| 311 | | 0.20 | |
| 312 | | 0.08 | |
| 313 | 0.61 | 0.09 | |
| 314 | | 2.36 | |
| 315 | | 0.08 | |
| 316 | 0.04 | 0.04 | |
| 317 | | 0.33 | |
| 318 | | 0.32 | |
| 319 | 0.09 | 0.05 | |
| 320 | | 0.22 | |
| 321 | 0.03 | 0.01 | |
| 322 | | 0.46 | |
| 323 | 0.06 | 0.04 | |
| 324 | | 1.07 | |
| 325 | | 2.97 | |
| 326 | | 0.13 | |

-continued

| Example # | HEK human IDO-1 (IC50, uM) | LLE_IDO_ABS_DR (IC50, uM) | Hela Kyurenine (IC50, uM) |
|---|---|---|---|
| 327 | | 0.31 | |
| 328 | | 0.13 | |
| 329 | | 1.66 | |
| 330 | | 0.29 | |
| 331 | | 0.81 | 0.52 |
| 332 | | 0.18 | |
| 333 | | 1.48 | 1.03 |
| 334 | | 16.67 | 0.38 |
| 335 | | | 0.34 |
| 336 | | 1.11 | 0.76 |
| 337 | 7.50 | | 2.26 |
| 338 | | | 87.93 |
| 339 | 6.18 | | 2.42 |

What is claimed is:

1. A compound of Formula (I)

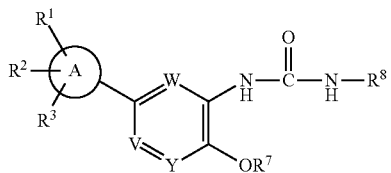

wherein:
W is $CR^4$ or N;
V is $CR^5$ or N, and
Y is $CR^6$ or N;
Ⓐ is optionally substituted phenyl or optionally substituted 5 to 7-membered monocyclic heteroaryl;
$R^1$ is COOH, tetrazol-5-yl, —$NHSO_2R^{20}$,

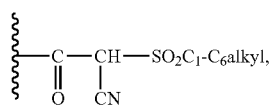

—$CONHSO_2R^{21}$, —$CONHCOOR^{22}$, or —$SO_2NHCOR^{23}$;
$R^2$ and $R^3$ are independently H, hydroxy, optionally substituted $C_1$-$C_6$ alkyl, halo, N($C_1$-$C_6$ alkyl)$_2$ or optionally substituted $C_1$-$C_6$ alkoxy;
$R^4$, $R^5$ and $R^6$ are independently H, optionally substituted $C_1$-$C_6$ alkyl, optionally substituted aryl, $C_1$-$C_6$ alkanoyl, halo, CN, $C_2$-$C_6$ alkenyl, $C_2$-$C_6$ alkynyl, $C_2$-$C_6$ alkenyl, optionally substituted $C_3$-$C_8$ cycloalkyl, $C_2$-$C_6$-alken-dienyl, dihydroindenyl, optionally substituted $C_1$-$C_6$ alkoxy, or OH,
wherein the optional substituents, where possible, are 1-3 groups selected from halo, $C_3$-$C_8$ cycloalkyl, aryl, optionally substituted $C_1$-$C_6$ alkyl, $C_1$-$C_6$ alkoxy, di-$C_1$-$C_6$-alkylamino or cyano;
$R^7$ is H, optionally substituted aryl, optionally substituted bicyclic carbocyclyl, optionally substituted 5- to 7-membered monocyclic heteroaryl, optionally substituted 5- to 7-membered monocyclic heterocyclic, optionally substituted $C_1$-$C_6$ alkoxy, optionally substituted arylalkyl, optionally substituted $C_1$-$C_9$ alkyl, optionally substituted $C_2$-$C_6$ alkenyl, optionally substituted $C_2$-$C_6$ alkynyl, optionally substituted $C_3$-$C_8$ cycloalkyl, or optionally substituted $C_5$-$C_8$ cycloalkenyl,
wherein the optional substituents, where possible, are 1-3 groups selected from H, $C_1$-$C_6$ alkyl, aryl, $C_2$-$C_6$ alkenyl, $C_2$-$C_6$ alkynyl, $C_3$-$C_8$ cycloalkyl, 5- to 7-membered monocyclic heterocyclic, $C_2$-$C_6$ alkynyloxy($C_1$-$C_6$ alkyl)$_{0-1}$, halo, halo-substituted aryl, oxo, trihalo-$C_1$-$C_6$-alkyl, or $OR^{19}$,
where $R^{19}$ is H, $C_1$-$C_6$ alkyl, $C_2$-$C_6$ alkyl, or $C_2$-$C_6$ alkynyl;
$R^8$ is optionally substituted aryl, optionally substituted $C_3$-$C_8$ cycloalkyl, optionally substituted $C_1$-$C_6$ alkyl, optionally substituted 5- to 7-membered monocyclic heterocyclic, optionally substituted 5- to 7-membered monocyclic heteroaryl, optionally substituted 8- to 10-membered bicyclic heteroaryl, optionally substituted $C_1$-$C_6$ alkoxycarbonyl 5- to 7-membered monocyclic heteroaryl, $R^{24}CO$—, optionally substituted $C_2$-$C_6$ alkenyl, optionally substituted $C_2$-$C_6$ alkynyl or optionally substituted $C_5$-$C_8$ cycloalkenyl,
wherein the optional substituents, where possible, are 1-2 groups selected from H, optionally substituted $C_1$-$C_6$ alkyl, $C_2$-$C_6$ alkenyl, $C_2$-$C_6$ alkynyl, $C_3$-$C_8$ cycloalkyl, halo, optionally substituted $C_1$-$C_6$-alkoxy, cyano, 5 to 7-membered monocyclic heteroaryl, $NH_2CO$—, di-$C_1$-$C_6$-alkylamino, aminosulfonyl, 5 to 7-membered monocyclic heterocyclo, hydroxy, $C_1$-$C_6$ alkylsulfonyl, azido, or aryl;
$R^{19}$ is H, $C_1$-$C_6$ alkyl, $C_2$-$C_6$ alkenyl, or $C_2$-$C_6$ alkynyl;
$R^{20}$ is optionally substituted $C_1$-$C_6$ alkyl, optionally substituted phenyl, $CF_3$, $CF_2CF_3$ or $CH_2CF_3$;
$R^{21}$ is optionally substituted $C_1$-$C_6$ alkyl, or optionally substituted $C_3$-$C_8$ cycloalkyl;
$R^{22}$ is $C_1$-$C_6$ alkyl, $C_3$-$C_8$ cycloalkyl, $C_2$-$C_6$ alkenyl, or $C_2$-$C_6$ alkynyl;
$R^{23}$ is $C_1$-$C_6$ alkyl, $C_3$-$C_8$ cycloalkyl, $C_2$-$C_6$ alkenyl, or $C_2$-$C_6$ alkynyl;
$R^{24}$ is optionally substituted aryl-$C_1$-$C_6$-alkyl, $C_1$-$C_6$ alkylaryl, aryl-$C_1$-$C_6$-alkyl(hydroxy), or optionally substituted $C_1$-$C_6$ alkyl;
and/or a stereoisomer, a tautomer or a pharmaceutically acceptable salt thereof.

2. The compound as defined in claim 1 wherein:
W is $CR^4$;
V is $CR^5$;
Y is $CR^6$ or N;
$R^4$ is H;
$R^5$ is H; and
$R^6$ is H, halo, optionally substituted $C_1$-$C_6$-alkyl, optionally substituted $C_2$-$C_6$-alkenyl, optionally substituted $C_2$-$C_6$ alken-dienyl, $C_3$-$C_8$ cycloalkyl or $C_3$-$C_8$-cycloalkyl-$C_1$-$C_6$-alkyl;
and/or a stereoisomer, a tautomer or a pharmaceutically acceptable salt thereof.

3. The compound as defined in claim 1 wherein Ⓐ is phenyl, and/or a stereoisomer, a tautomer or a pharmaceutically acceptable salt thereof.

4. The compound as defined in claim 1 wherein:
$R^1$ is COOH, tetrazol-5-yl, —$NHSO_2R^{20}$ or $CONHSO_2R^{21}$;
$R^2$ is H, halo, hydroxy, optionally substituted $C_1$-$C_6$-alkyl or $C_1$-$C_6$ alkoxyl; and
$R^3$ is H or $C_1$-$C_6$ alkoxy;
and/or a stereoisomer, a tautomer or a pharmaceutically acceptable salt thereof.

5. The compound as defined in claim 1 wherein:
$R^7$ is aryl, optionally substituted $C_1$-$C_9$-alkyl, optionally substituted $C_1$-$C_6$ alkylaryl, $C_3$-$C_8$-cycloalkyl-$C_1$-$C_6$-alkyl, $C_3$-$C_8$ cycloalkylaryl, optionally substituted $C_3$-$C_8$-cycloalkyl or optionally substituted aryl $C_1$-$C_6$-alkyl, and/or a stereoisomer, a tautomer or a pharmaceutically acceptable salt thereof.

6. The compound as defined in claim 1 wherein:
$R^8$ is optionally substituted $C_1$-$C_6$ alkylaryl, optionally substituted aryl, optionally substituted $C_3$-$C_8$ cycloalkylaryl, optionally substituted $C_3$-$C_8$-cycloalkyl-$C_1$-$C_6$ alkyl, optionally substituted 5- to 7-membered heterocyclic, optionally substituted $C_1$-$C_6$ alkyl, optionally substituted aryl-$C_1$-$C_6$-alkyl, $C_1$-$C_6$ alkoxyaryl, $C_1$-$C_6$-alkoxy($C_1$-$C_6$-alkyl)aryl, $C_3$-$C_8$ cycloalkyl, optionally substituted $C_1$-$C_6$-alkyl-$C_3$-$C_8$-cycloalkyl, optionally substituted $C_1$-$C_6$ alkanoyl, di-$C_1$-$C_6$-alkylaminophenyl or $C_2$-$C_6$ alkenyl, and/or a stereoisomer, a tautomer or a pharmaceutically acceptable salt thereof.

7. A compound of Formula (II)

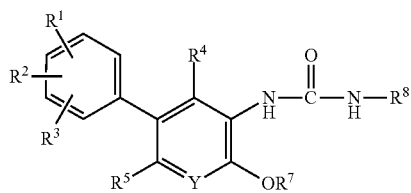

wherein:
Y is $CR^6$ or N;
$R^1$ is COOH, tetrazol-5-yl,

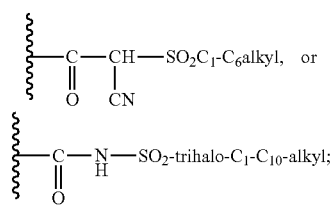

$R^2$ is H, optionally substituted $C_1$-$C_6$ alkyl, OH, optionally substituted $C_1$-$C_6$ alkoxy or $CF_3$;
$R^3$ is H, $C_1$-$C_6$ alkyl, or $C_1$-$C_6$ alkoxy;
$R^4$ is H;
$R^5$ is H;

$R^6$ is H, optionally substituted aryl $C_1$-$C_6$-alkyl, optionally substituted aryl-$C_2$-$C_6$-alkenyl, optionally substituted $C_1$-$C_6$ alkyl, optionally substituted $C_2$-$C_6$ alkenyl or optionally substituted $C_2$-$C_6$-alken-dienyl,
$R^7$ is selected from optionally substituted aryl, optionally substituted $C_1$-$C_6$ alkylaryl, optionally substituted $C_3$-$C_8$ cycloalkyl, optionally substituted $C_1$-$C_8$ alkyl, optionally substituted aryl-$C_1$-$C_6$-alkyl, $C_3$-$C_8$ cycloalkylaryl, 2,2-$C_1$-$C_6$-dialkyldihydrobenzofuran

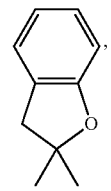

optionally substituted $C_1$-$C_6$-alkyl(aryl)-$C_1$-$C_6$-alkyl, $C_2$-$C_6$ alkynyloxy($C_1$-$C_6$ alkyl)aryl, optionally substituted 5 to 7-membered monocyclic heterocyclic or optionally substituted $C_3$-$C_8$-cycloalkyl-$C_1$-$C_6$-alkyl;

$R^8$ is optionally substituted $C_1$-$C_6$ alkylaryl, optionally substituted $C_1$-$C_6$ alkyl, optionally substituted aryl, optionally substituted aryl-$C_1$-$C_6$-alkyl, optionally substituted $C_1$-$C_6$ alkoxyaryl, optionally substituted $C_1$-$C_6$-alkoxy($C_1$-$C_6$-alkyl)aryl, optionally substituted $C_3$-$C_8$ cycloalkyl, optionally substituted $C_3$-$C_8$ cycloalkylaryl, optionally substituted $C_3$-$C_8$-cycloalkyl-$C_1$-$C_6$-alkyl, optionally substituted 5- to 7-membered monocyclic heterocyclic, optionally substituted $C_1$-$C_6$-alkyl-$C_3$-$C_8$-cycloalkyl, optionally substituted $C_1$-$C_6$ alkanoylaryl, $C_1$-$C_6$ dialkylaminoaryl, dihydroindenyl, optionally substituted $C_2$-$C_6$ alkenyl, or optionally substituted $C_2$-$C_6$ alkynyl;

and/or a pharmaceutically acceptable salt thereof, a tautomer thereof, or a stereoisomer thereof.

8. The compound as defined in claim 7 wherein:
$R^1$ is COOH, tetrazol-5-yl, $CONHSO_2CH_3$ or $-NHSO_2CH_3$;
$R^2$ is H, Cl, F, OH, or $CH_3O$; and
$R^3$ is H or $CH_3O$;

and/or a pharmaceutically acceptable salt thereof, a tautomer thereof, or a stereoisomer thereof.

9. The compound according to claim 1 wherein the $IC_{50}$ in the HEK Human IDO-1 assay is <10 nM.

10. A pharmaceutical composition comprising one or more compounds according to claim 1 and a pharmaceutically acceptable carrier or diluent.

11. A method of inhibiting activity of indoleamine 2,3-dioxygenase comprising contacting said indoleamine 2,3-dioxygenase with a compound according to claim 1, or a pharmaceutically acceptable salt thereof.

* * * * *